US008933074B2

(12) United States Patent
Ripka et al.

(10) Patent No.: US 8,933,074 B2
(45) Date of Patent: *Jan. 13, 2015

(54) 1,2-DISUBSTITUTED HETEROCYCLIC COMPOUNDS

(71) Applicant: FORUM Pharmaceuticals Inc., Watertown, MA (US)

(72) Inventors: Amy Ripka, Reading, MA (US); Gideon Shapiro, Gainesville, FL (US); Richard Chesworth, Boston, MA (US)

(73) Assignee: FORUM Pharmaceuticals Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/919,320

(22) Filed: Jun. 17, 2013

(65) Prior Publication Data

US 2014/0011808 A1      Jan. 9, 2014

Related U.S. Application Data

(63) Continuation of application No. 13/290,527, filed on Nov. 7, 2011, now Pat. No. 8,466,148, which is acontinuation of application No. 12/490,808, filed on Jun. 24, 2009, now Pat. No. 8,071,595.

(60) Provisional application No. 61/075,594, filed on Jun. 25, 2008, provisional application No. 61/109,162, filed on Oct. 28, 2008, provisional application No. 61/138,866, filed on Dec. 18, 2008, provisional application No. 61/176,413, filed on May 7, 2009.

(51) Int. Cl.

| *A61K 31/5377* | (2006.01) |
|---|---|
| *A61K 31/4709* | (2006.01) |
| *C07D 413/14* | (2006.01) |
| *C07D 417/14* | (2006.01) |
| *C07D 405/12* | (2006.01) |
| *C07D 405/14* | (2006.01) |
| *C07D 401/12* | (2006.01) |
| *C07D 401/14* | (2006.01) |
| *C07D 401/04* | (2006.01) |

(52) U.S. Cl.
CPC ............ *C07D 401/12* (2013.01); *C07D 401/04* (2013.01); *C07D 405/12* (2013.01); *C07D 417/14* (2013.01); *C07D 413/14* (2013.01); *C07D 405/14* (2013.01); *C07D 401/14* (2013.01)

USPC ........ 514/235.2; 514/314; 514/278; 544/128; 546/167; 546/15

(58) Field of Classification Search
USPC ................. 514/235.2, 314, 278; 546/167, 15; 544/128
See application file for complete search history.

(56) References Cited

U.S. PATENT DOCUMENTS

| 8,071,595 B2 | 12/2011 | Ripka et al. |
|---|---|---|
| 8,466,148 B2 | 6/2013 | Ripka et al. |
| 2003/0032579 A1 | 2/2003 | Lebel et al. |
| 2010/0292238 A1 | 11/2010 | Ripka et al. |
| 2011/0053905 A1 | 3/2011 | Guo et al. |
| 2011/0183976 A1 | 7/2011 | Ripka et al. |
| 2012/0040979 A1 | 2/2012 | Falco et al. |
| 2012/0046320 A1 | 2/2012 | Kc et al. |
| 2012/0053202 A1 | 3/2012 | De Peretti et al. |

FOREIGN PATENT DOCUMENTS

| EP | 1541149 A1 | 6/2005 |
|---|---|---|
| WO | WO-2006072828 A2 | 7/2006 |
| WO | WO-2007077490 A2 | 7/2007 |
| WO | WO-2007129183 A2 | 11/2007 |
| WO | WO-2008/033455 A2 | 3/2008 |
| WO | WO-2009158393 A1 | 12/2009 |
| WO | WO-2009158473 A1 | 12/2009 |

OTHER PUBLICATIONS

Davis, J.M et al. "Dose response and dose equivalence of antipsychotics." Journal of Clinical Psychopharmacology, Apr. 2004, 24 (2),192-208.

Fernandez et al "Treatment of psychosis in Parkinson's disease: Safety considerations." Drug Safety, 2003, 26 (9), 643-659.

Fujishige et al. "Cloning and characterization of a novel human phosphodiesterase that hydrolyzes both cAMP and cGMP (PDE10A)" J. Biol. Chem. Jun. 1999,274, 18438-18445.

Handa et al. "Crystal structure of the GAF-B domain from human phosphodiesterase 10A complexed with its ligand, cAMP" J Biol. Chem. Jul. 2008, pp. 19657-19664.

Kostowski et. al "Papaverine drug induced stereotypy and catalepsy and biogenic aminesin the brain of the rat" Pharmacol. Biochem. Behav. Jul. 1976, 5, 15-17.

Lazorthes et al. "Advances in Drug Delivery Systems and Applications in Neurosurgery." Advances and Technical Standards in Neurosurgery, vol. 18, 1991. 143-192.

Loughney et al. "Isolation and characterization of PDE10A, a novel human 3',5'-cyclicnucleotide phosphodiesterase" Gene, Jun. 1999, vol. 234, No. 1. pp. 109-117.

Meyer et al "The Clinical Antipsychotic Trials of Intervention Effectiveness (CATIE) Schizophrenia Trial: clinical comparison of subgroups with and without the metabolic syndrome." Schizophrenia Research, 2005, 80 (1), 9-43.

Minto, J. et al., Pharmacokinetics and Pharmacodynamics of Nandrolone Esters in Oil Vehicle: Effects of Ester, Injection Site and Injection Volume, Pharmcol. Exp. Ther. vol. 291, No. 1. Apr. 1997. pp. 93-102.

Navidpour et al., Design and synthesis of new water-soluble tetrazolide derivatives of celecoxib and refecoxib as selective cyclooxygenase-2 (COX-2) inhibitors, 2006, Bioorganic & Medicinal Chemistry Letters, 16, 4483-4487.

Ommaya et al. "Implantable Devices for Chronic Access and Drug Delivery to the Central Nervous System", Cancer Drug Delivery, vol. 1, No. 2, 1984. pp. 169-179.

Patani et al., Bioisosterism: A Rational Approach in Drug Design, 1996, Chem. Rev., vol. 96, No. 8. pp. 3147-3176.

Soderling and Beavo "Regulation of cAMP and cGMP signaling: New phosphodiesterases and new functions," Curr. Opin. Cell Biol., Apr. 2000, vol. 12, No. 2. pp. 174-179.

Soderling et al. "Isolation and characterization of a dual-substrate phosphodiesterase gene family: PDE10A" Proc. Natl Sci. Jun. 8, 1999, vol. 96, No. 12. pp. 7071-7076.

*Primary Examiner* — Kristin Vajda
(74) *Attorney, Agent, or Firm* — Wilmer Cutler Pickering Hale and Dorr LLP

(57) ABSTRACT

1,2-disubstituted heterocyclic compounds which are inhibitors of phosphodiesterase 10 are described. Also described are processes, pharmaceutical compositions, pharmaceutical preparations and pharmaceutical use of the compounds in the treatment of mammals, including human(s) for central nervous system (CNS) disorders and other disorders which may affect CNS function. Among the disorders which may be treated are neurological, neurodegenerative and psychiatric disorders including, but not limited to, those associated with cognitive deficits or schizophrenic symptoms.

16 Claims, No Drawings

1,2-DISUBSTITUTED HETEROCYCLIC COMPOUNDS

This application is a continuation of U.S. patent application Ser. No. 13/290,527, filed on Nov. 7, 2011, now U.S. Pat. No. 8,466,148, which is a continuation of U.S. patent application Ser. No. 12/490,808 filed on Jun. 24, 2009, now U.S. Pat. No. 8,071,595 and claims priority to U.S. Provisional Application No. 61/176,413 filed on May 7, 2009, U.S. Provisional Application No. 61/138,866 filed on Dec. 18, 2008, U.S. Provisional Application No. 61/109,162 filed on Oct. 28, 2008 and U.S. Provisional Application No. 61/075,594 filed on Jun. 25, 2008, the disclosures each of which are hereby incorporated by reference in their entirety.

The disclosure relates to 1,2-disubstituted heterocyclic compounds which are inhibitors of phosphodiesterase 10. The disclosure further relates to processes, pharmaceutical compositions, pharmaceutical preparations and pharmaceutical use of the compounds in the treatment of mammals, including human(s) for central nervous system (CNS) disorders and other disorders which may affect CNS function. The disclosure also relates to methods for treating neurological, neurodegenerative and psychiatric disorders including but not limited to those comprising cognitive deficits or schizophrenic symptoms.

BACKGROUND

Cyclic phosphodiesterases are intracellular enzymes which, through the hydrolysis of cyclic nucleotides cAMP and cGMP, regulate the levels of these mono phosphate nucleotides which serve as second messengers in the signaling cascade of G-protein coupled receptors. In neurons, PDEs also play a role in the regulation of downstream cGMP and cAMP dependent kinases which phosphorylate proteins involved in the regulation of synaptic transmission and homeostasis. To date, eleven different PDE families have been identified which are encoded by 21 genes. The PDEs contain a variable N-terminal regulatory domain and a highly conserved C-terminal catalytic domain and differ in their substrate specificity, expression and localization in cellular and tissue compartments, including the CNS.

The discovery of a new PDE family, PDE10, was reported simultaneously by three groups in 1999 (Soderling et al. "Isolation and characterization of a dual-substrate phosphodiesterase gene family: PDE10A" *Proc. Natl. Sci.* 1999, 96, 7071-7076; Loughney et al. "Isolation and characterization of PDE10A, a novel human 3',5'-cyclic nucleotide phosphodiesterase" *Gene* 1999, 234, 109-117; Fujishige et al. "Cloning and characterization of a novel human phosphodiesterase that hydrolyzes both cAMP and cGMP (PDE10A)" *J. Biol. Chem.* 1999, 274, 18438-18445). The human PDE10 sequence is highly homologous to both the rat and mouse variants with 95% amino acid identity overall, and 98% identity conserved in the catalytic region.

PDE10 is primarily expressed in the brain (caudate nucleus and putamen) and is highly localized in the medium spiny neurons of the striatum, which is one of the principal inputs to the basal ganglia. This localization of PDE10 has led to speculation that it may influence the dopaminergic and glutamatergic pathways both which play roles in the pathology of various psychotic and neurodegencrative disorders.

PDE10 hydrolyzes both cAMP ($K_m$=0.05 uM) and cGMP ($K_m$=3 uM) (Soderling et al. "Isolation and Characterization of a dual-substrate phosphodiesterase gene family: PDE10." *Proc. Natl Sci. USA* 1999, 96(12), 7071-7076). In addition, PDE10 has a five-fold greater $V_{max}$ for cGMP than for cAMP and these in vitro kinetic data have lead to the speculation that PDE10 may act as a cAMP-inhibited cGMP phosphodiesterase in vive (Soderling and Beavo "Regulation of cAMP and cGMP signaling: New phosphodiesterases and new functions," *Curr. Opin. Cell Biol.*, 2000, 12, 174-179).

PDE10 is also one of five phosphodiesterase members to contain a tandem GAF domain at their N-terminus. It is differentiated by the fact that the other GAF containing PDEs (PDE2, 5, 6, and 11) bind cGMP while recent data points to the tight binding of cAMP to the GAF domain of PDE10 (Handa et al. "Crystal structure of the GAF-B domain from human phosphodiesterase 10A complexed with its ligand, cAMP" *J. Biol. Chem.* 2008, May 13th, ePub).

PDE10 inhibitors have been disclosed for the treatment of a variety of neurological and psychiatric disorders including Parkinson's disease, schizophrenia, Huntington's disease, delusional disorders, drug-induced psychoses, obsessive compulsive and panic disorders (US Patent Application 2003/0032579). Studies in rats (Kostowski et. al "Papaverine drug induced stereotypy and catalepsy and biogenic amines in the brain of the rat" *Pharmacol. Biochem. Behav.* 1976, 5, 15-17) have showed that papaverine, a selective PDE10 inhibitor, reduces apomorphine induced stereotypes and rat brain dopamine levels and increases haloperidol induced catalepsy. This experiment lends support to the use of a PDE10 inhibitor as an antipsychotic since similar trends are seen with known, marketed antipsychotics.

Antipsychotic medications are the mainstay of current treatment for schizophrenia. Conventional or classic antipsychotics, typified by haloperidol, were introduced in the mid-1950s and have a proven track record over the last half century in the treatment of schizophrenia. While these drugs are effective against the positive, psychotic symptoms of schizophrenia, they show little benefit in alleviating negative symptoms or the cognitive impairment associated with the disease. In addition, drugs such as haloperidol have extreme side effects such as extrapyramidal symptoms (EPS) due to their specific dopamine D2 receptor interaction. An even more severe condition characterized by significant, prolonged, abnormal motor movements known as tardive dyskinesia also may emerge with prolonged classic antipsychotic treatment.

The 1990s saw the development of several new drugs for schizophrenia, referred to as atypical antipsychotics, typified by risperidone and olanzapine and most effectively, clozapine. These atypical antipsychotics are generally characterized by effectiveness against both the positive and negative symptoms associated with schizophrenia, but have little effectiveness against cognitive deficiencies and persisting cognitive impairment remain a serious public health concern (Davis, J. M et al. "Dose response and dose equivalence of antipsychotics." *Journal of Clinical Psychopharmacology*, 2004, 24 (2), 192-208; Friedman, J. H. et al "Treatment of psychosis in Parkinson's disease: Safety considerations." *Drug Safety*, 2003, 26 (9), 643-659). In addition, the atypical antipsychotic agents, while effective in treating the positive and, to some degree, negative symptoms of schizophrenia, have significant side effects. For example, clozapine which is one of the most clinically effective antipsychotic drugs shows agranulocytosis in approximately 1.5% of patients with fatalities due to this side effect being observed. Other atypical antipsychotic drugs have significant side effects including metabolic side effects (type 2 diabetes, significant weight gain, and dyslipidemia), sexual dysfunction, sedation, and potential cardiovascular side effects that compromise their clinically effectiveness. In the large, recently published NIH sponsored CATIE study, (Lieberman et al "The Clinical Antipsychotic Trials Of Intervention Effectiveness (CATIE) Schizophrenia Trial: clinical comparison of subgroups with and without the metabolic syndrome." *Schizophrenia Research,* 2005, 80 (1), 9-43) 74% of patients discontinued use of their antipsychotic medication within 18 months due to a number of factors including poor tolerability or incomplete efficacy. Therefore, a substantial clinical need still exists for more effective and better tolerated antipsychotic mediations possibly through the use of PDE10 inhibitors.

BRIEF SUMMARY

Described herein are 1,2-disubstituted heterocyclic compounds of Formulas (I), (II) or (III) that are inhibitors of at least one phosphodiesterase 10 (e.g., human PDE-10A):

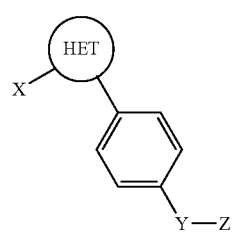
(I)

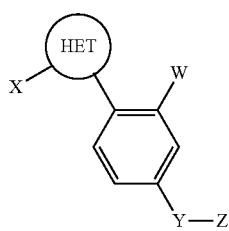
(II)

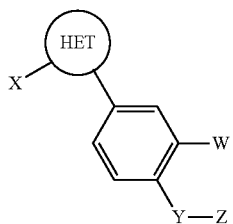
(III)

Wherein:

HET is a heterocyclic ring selected from Formulas A1-A26 and A29-42 below

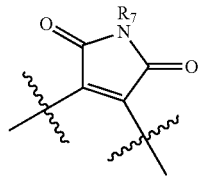
A1, A2

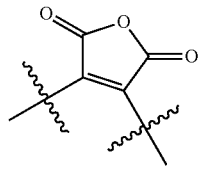
A3

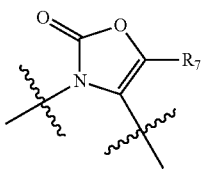
A4

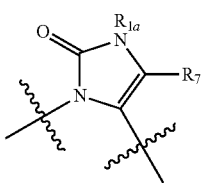
A5

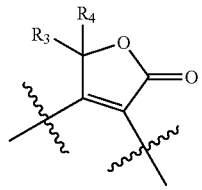
A6

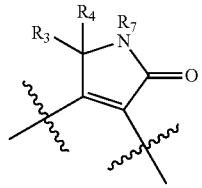
A7, A8

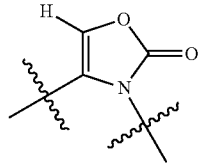
A9

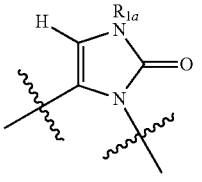
A10

-continued
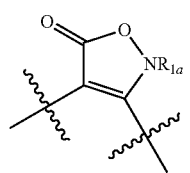 A11
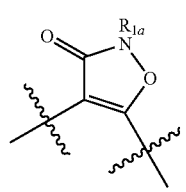 A12
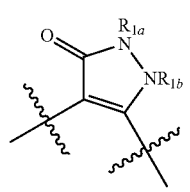 A13
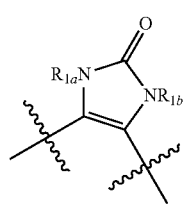 A14
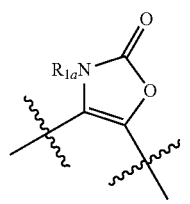 A15
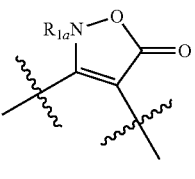 A16
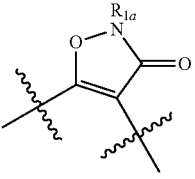 A17
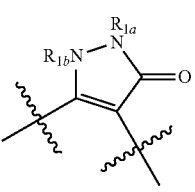 A18
-continued
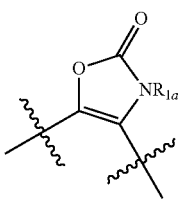 A19
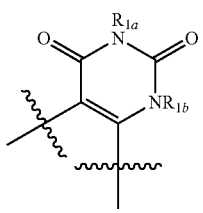 A20
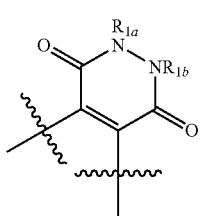 A21
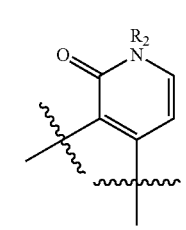 A22
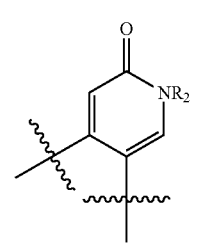 A23
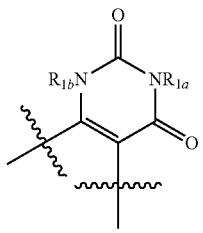 A24
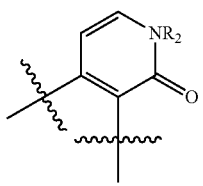 A25

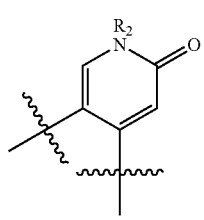 A26
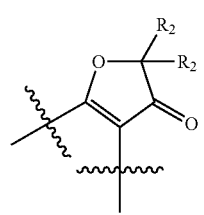 A29
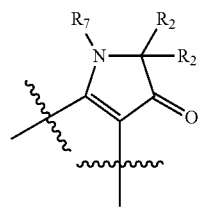 A30
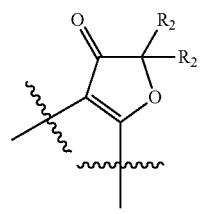 A31
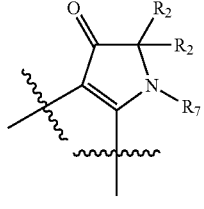 A32
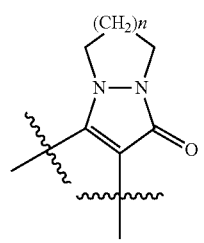 A33
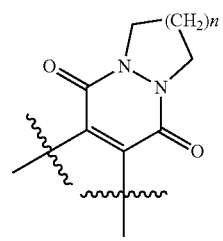 A34
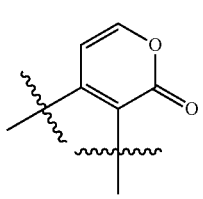 A35
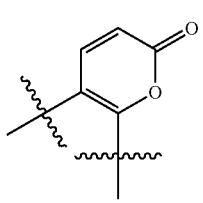 A36
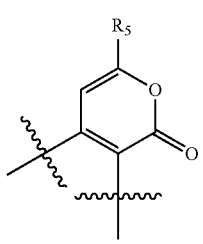 A37
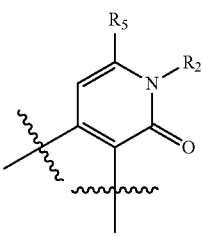 A38
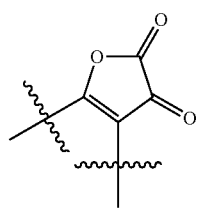 A39
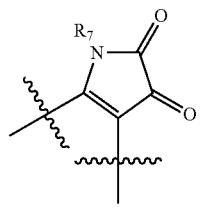 A40
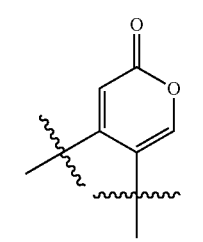 A41

-continued

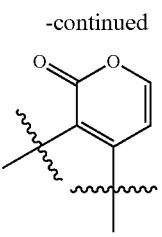
A42 and the left most radical is connected to the X group;
W is selected from halogen, cyano, nitro, alkoxy, amino, alkylamino, dialkylamino, carboxy, amido, alkylamido, and dialkylamido;
X is selected from $C_3$-$C_8$ alkyl, optionally substituted cycloalkyl, optionally substituted cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl;
Y is a bond or a divalent linker group selected from —$CH_2$—, —O—, —$SO_2$—, —$CH_2O$—, —$OCH_2$— and —$CH_2CH_2$— with the rightmost radical of the Y group connected to the Z substituent;
Z is optionally substituted heteroaryl;
$R_{1a}$ is selected from alkyl, optionally substituted cycloalkyl, optionally substituted cycloalkylalkyl and optionally substituted alkoxyalkyl;
$R_{1b}$ is selected from alkyl, optionally substituted cycloalkyl, optionally substituted cycloalkylalkyl and optionally substituted alkoxyalkyl;
Each $R_2$ is independently selected from alkyl, optionally substituted cycloalkyl, optionally substituted cycloalkylalkyl and optionally substituted alkoxyalkyl; or two $R_2$ groups taken together form a 3-6 membered cycloalkyl ring;
$R_3$ and $R_4$ are independently selected from $C_1$-$C_4$ alkyl, $CF_3$, optionally substituted cycloalkyl; or $R_3$ and $R_4$ taken together form a 3-6 membered cycloalkyl ring;
$R_5$ is selected from alkyl, optionally substituted cycloalkyl, optionally substituted cycloalkylalkyl and optionally substituted alkoxyalkyl;
n is independently selected from 1 and 2;
$R_7$ is selected from hydrogen, alkyl, optionally substituted cycloalkyl, optionally substituted cycloalkylalkyl and optionally substituted alkoxyalkyl;

In one embodiment, alkyl groups are fully saturated whether present on their own or as part of another group (e.g., alkylamino).

In certain embodiments, substituent groups are not further substituted. In other embodiments, substituent groups are not further substituted.

In various embodiments, any group that is defined as being optionally substituted can be independently singly or multiply optionally substituted.

In various embodiments, a group that is defined as being optionally substituted is not substituted.

In one embodiment, a compound of Formula (I) is selected.

In another embodiment, a compound of Formula (II) is selected.

In another embodiment, a compound of Formula (III) is selected.

In one embodiment, HET is selected from Formulas A1, A2, A7, A8, A14, A15, A19, A25, A29, A30, A31, A32, A35, A37, A38, A39, A40.

In one embodiment, HET is selected from Formulas A7, A8, A25, A29, A30, A31, A32, A35, A37 and A38.

In another embodiment, HET is selected from Formulas A7, A8, A25, A29, A30, A35, A37 and A38.

In another embodiment, HET is selected from Formulas A7, A8, A17 A18, A25, A29, A30 and A34.

In a further embodiment, HET is selected from Formulas A1, A2, A7, A8, A14, A15 and A19.

In another embodiment, HET is selected from Formulas A5, A6, A9 A10, A20 and A24.

In an additional embodiment, HET is selected from Formulas A1, A2, A7 and A8.

In another embodiment, HET is selected from Formulas A22, A23, A25 and A26.

In another embodiment, HET is selected from Formulas A29, A30, A31 and A32.

In another embodiment, HET is selected from Formulas A7, A8, A29 and A30.

In another embodiment, HET is selected from Formulas A25, A26, A35 and A36.

In another embodiment, HET is selected from Formulas A25, A29, A35 and A38.

In a further embodiment, HET is selected from Formulas A7, A8, A29 and A31.

In another embodiment, HET is selected from Formulas A29, A31, A37 and A38.

In another embodiment, HET is selected from Formulas A25, A35, A37 and A38.

In another embodiment, HET is selected from Formulas A25, A29, A30 and A35.

In another embodiment, HET is selected from Formulas A7 and A8.

In another embodiment, HET is selected from Formulas A25 and A26.

In another embodiment, HET is selected from Formulas A29 and A30.

In another embodiment, HET is selected from Formulas A35 and A36.

In another embodiment, HET is selected from Formulas A29 and A31.

In a further embodiment, HET is selected from Formulas A31 and A32.

In another embodiment, HET is selected from Formulas A37 and A38.

In another embodiment, HET is Formula A1.
In another embodiment, HET is Formula A2.
In another embodiment, HET is Formula A3.
In another embodiment, HET is Formula A4.
In another embodiment, HET is Formula A5.
In another embodiment, HET is Formula A6.
In another embodiment, HET is Formula A7.
In another embodiment, HET is Formula A8.
In another embodiment, HET is Formula A9.
In another embodiment, HET is Formula A10.
In another embodiment, HET is Formula A11.
In another embodiment, HET is Formula A12.
In another embodiment, HET is Formula A13.
In another embodiment, HET is Formula A14.
In another embodiment, HET is Formula A15.
In another embodiment, HET is Formula A16.
In another embodiment, HET is Formula A17.
In another embodiment, HET is Formula A18.
In another embodiment, HET is Formula A19.
In another embodiment, HET is Formula A20.
In another embodiment, HET is Formula A21.
In another embodiment, HET is Formula A22.
In another embodiment, HET is Formula A23.
In another embodiment, HET is Formula A24.
In another embodiment, HET is Formula A25.

In another embodiment, HET is Formula A26.
In another embodiment, HET is Formula A29.
In another embodiment, HET is Formula A30.
In another embodiment, HET is Formula A31.
In another embodiment, HET is Formula A32.
In another embodiment, HET is Formula A33.
In another embodiment, HET is Formula A34.
In another embodiment, HET is Formula A35.
In another embodiment, HET is Formula A36.
In another embodiment, HET is Formula A37.
In another embodiment, HET is Formula A38.
In another embodiment, HET is Formula A39.
In another embodiment, HET is Formula A40.
In another embodiment, HET is Formula A41.
In another embodiment, HET is Formula A42.

In one embodiment, W is selected from nitro, carboxy, amido, alkylamido, and dialkylamido.

In another embodiment, W is selected from amino, alkylamino and dialkylamino.

In another embodiment, W is selected from halogen, cyano and alkoxy.

In an additional embodiment, W is selected from halogen and cyano.

In another embodiment, W is halogen.

In a further embodiment, W is cyano.

In an additional embodiment, W is alkoxy.

In one embodiment, X is selected from $C_3$-$C_8$ alkyl, cycloalkyl and cycloalkylalkyl.

In a further embodiment X is selected from cycloalkyl and cycloalkylalkyl. Examples include, but are not limited to, cyclohexyl and cyclohexylmethyl.

In another embodiment X is $C_3$-$C_8$ alkyl. Examples include, but are not limited to, isopropyl, t-butyl and isopentyl.

In an additional embodiment, X is heterocycloalkyl.

In a further embodiment X is heterocycloalkyl having only 6 ring atoms. Examples include, but are not limited to, morpholinyl, piperidinyl, piperazinyl N-Me-piperazinyl and pyranyl.

In another embodiment X is heterocycloalkyl having only 5 ring atoms. Examples include, but are not limited to, tetrahydrofuranyl and pyrrolidinyl.

In another embodiment, X is a heterocycloalkyl group selected from Formulas B1-B16 depicted below:

B1
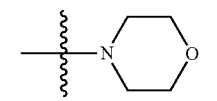

B2
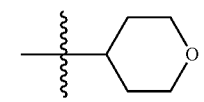

B3
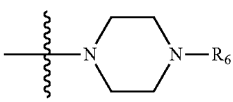

B4
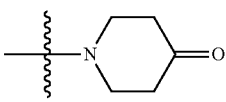

-continued

B5
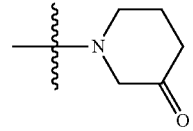

B6
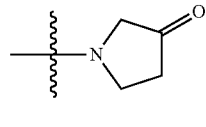

B7
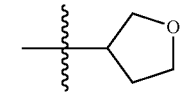

B8
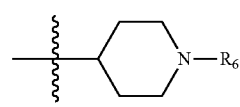

B9
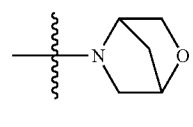

B10
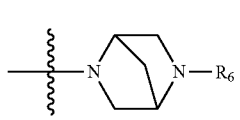

B11

B12
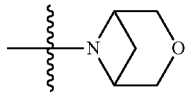

B13
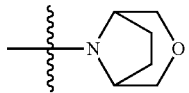

B14
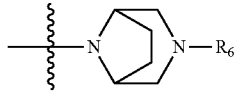

B15

B16 wherein $R_6$ is selected from hydrogen and $C_1$-$C_6$ alkyl, $C_3$-$C_6$ cycloalkyl and $C_4$-$C_7$ cycloalkylalkyl, all of which can be optionally substituted.

In another embodiment X is selected from morpholinyl, pyranyl and tetrahydrofuranyl.

In another embodiment X is selected from morpholinyl (having Formula B1) and 4-pyranyl (having Formula B2).

In another embodiment X is heteroaryl.

In another embodiment, X is selected from a monocyclic aromatic ring having 5 ring atoms selected from C, O, S and N provided the total number of ring heteroatoms is less than or equal to four and where no more than one of the total number of heteroatoms is oxygen or sulfur, and a monocyclic aromatic ring having 6 atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl, 1,2,3-triazinyl, 1,2,4-triazinyl, 1,3,5-triazinyl, pyridinyl, pyrazinyl, pyridazinyl and pyrimidinyl.

In a further embodiment, X is a monocyclic aromatic ring having 6 ring atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1,2,3-triazinyl, 1,2,4-triazinyl, 1,3,5-triazinyl, pyridinyl, pyrazinyl, pyridazinyl and pyrimidinyl.

In a further embodiment, X is a monocyclic aromatic ring having 5 ring atoms selected from C, O, S, and N, provided the total number of ring heteroatoms is less than or equal to four and where no more than one of the total number of heteroatoms is oxygen or sulfur and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl.

In a further embodiment, X is selected from 2-pyridinyl, 3-pyridinyl and 4-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen and cyano.

In a further embodiment, X is 3-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen and cyano.

In a further embodiment, X is 4-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen and cyano.

In a further embodiment, X is selected from 3-pyridinyl and 4-pyridinyl.

In a further embodiment, X is 3-pyridinyl.
In another embodiment, X is 2-methoxy-5-pyridinyl.
In a further embodiment, X is 4-pyridinyl.
In another embodiment, X is 2-methoxy-4-pyridinyl.

In another embodiment X is a heterobicyclic ring system.
In another embodiment X is a heterobicyclic ring system where one ring is aromatic.
In a further embodiment, X is a heterobicyclic ring system where both rings are aromatic.
In another embodiment, X is a heterobicyclic ring system containing exactly 9 ring atoms.
In another embodiment, X is a heterobicyclic ring system containing exactly 10 ring atoms.
In another embodiment X is selected from benzo[d]oxazoyl, benzo[c][1,2,5]oxadiazyl, benzo[c][1,2,5]thiadiazolyl, benzo[d]isoxazolyl, 1H-benzo[d]imidazoyl, benzo[d]thiazoyl, benzo[c]isothiazolyl, benzo[d]isothiazolyl, benzo[c]isoxazolyl, imidazo[1,2-a]pyridinyl and imidazo[1,5-a]pyridinyl.
In another embodiment X is selected from benzo[c][1,2,5]oxadiazyl and benzo[c][1,2,5]thiadiazolyl.
In a further embodiment, X is selected from benzo[d]oxazoyl, 1H-benzo[d]imidazoyl and benzo[d]thiazoyl.
In a further embodiment, X is benzo[d]oxazoyl.
In a further embodiment, X is 1H-benzo[d]imidazoyl.
In a further embodiment, X is benzo[d]thiazoyl.
In another embodiment X is benzo[c][1,2,5]oxadiazoyl.
In a further embodiment X is benzo[c][1,2,5]thiadiazolyl.
In a further embodiment, X is benzo[d]isoxazolyl.
In another embodiment, X is benzo[d]isothiazolyl.
In another embodiment, X is benzo[c]isothiazolyl.
In another embodiment, X is benzo[c]isoxazolyl.
In another embodiment, X is imidazo[1,2-a]pyridinyl.
In another embodiment, X is imidazo[1,5-a]pyridinyl.
In an additional embodiment, X is aryl.
In another embodiment, X is selected from phenyl and pyridinyl.
In a further embodiment, X is phenyl.
In another embodiment, X is phenyl optionally substituted with one or more substituents selected from F, Cl, CN, $NO_2$, $CP_3$, $OCF_3$, $OCHF_2$, $CH_2CF_3$ and OMe.
In another embodiment, X is restricted phenyl.
In a further embodiment, X is selected from a 3,4-disubstituted phenyl, 3-substituted phenyl and 4-substituted phenyl.
In another embodiment, X is selected from 3,4-disubstituted phenyl and 4-substituted phenyl.
In another embodiment, X is 3-chloro-4-methoxyphenyl
In another embodiment, X is 3-cyano-4-methoxyphenyl
In a further embodiment, X is 3-chloro-4-difluoromethoxyphenyl
In a further embodiment, X is 3-cyano-4-difluoromethoxyphenyl
In an additional embodiment, X is 4-substituted phenyl.
In another embodiment, X is 4-nitrophenyl.
In a further embodiment, X is 4-methoxyphenyl.
In another embodiment, X is 4-chlorophenyl.
In another embodiment, X is 4-cyanophenyl.
In another embodiment, X is 4-trifluoromethylphenyl.
In a further embodiment, X is 4-trifluoromethoxyphenyl.
In a further embodiment, X is 3-substituted phenyl.
In another embodiment, X is 3-nitrophenyl.
In a further embodiment, X is 3-trifluoromethoxyphenyl.
In a further embodiment, X is 3-methoxyphenyl.
In another embodiment, X is 3-chlorophenyl.
In another embodiment, X is 3-cyanophenyl.
In another embodiment, X is 3-trifluoroethylphenyl.
In a further embodiment, X is 3-trifluoromethoxyphenyl.
In one embodiment, Y is —$CH_2O$— or —$OCH_2$— with the rightmost radical connected to the Z substituent.

In another embodiment, Y is —CH$_2$CH$_2$— with the rightmost radical connected to the Z substituent.

In an additional embodiment, Y is —CH$_2$O— with the rightmost radical connected to the Z substituent.

In a further embodiment, Y is —OCH$_2$— with the rightmost radical connected to the Z substituent.

In one embodiment, Z is selected from heteroaryl having only 6 ring atoms and a heterobicyclic ring system.

In another embodiment, Z is a heterobicyclic ring system.

In another embodiment, Z is a heterobicyclic ring system where one ring is aromatic.

In a further embodiment, Z is a heterobicyclic ring system where both rings are aromatic.

In another embodiment, Z is a heterobicyclic ring system containing exactly 9 ring atoms.

In another embodiment, Z is a heterobicyclic ring system containing exactly 10 ring atoms.

In an additional embodiment, Z is selected from benzimidazolyl, quinolinyl, tetrahydroquinolyl, imidazo[1,2-a]pyridin-2-yl, tetrahydroisoquinolyl, 5-methylpyridin-2-yl, 3,5-dimethylpyridin-2-yl, 6-fluoroquinolyl and isoquinolinyl, all of which may be optionally substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from benzimidazolyl, quinolinyl, tetrahydroquinolyl, tetrahydroisoquinolyl and isoquinolinyl, all of which may be optionally substituted with up to 3 substituents independently selected from alkyl, alkoxy, cycloalkyl, cycloalkyloxy, cycloalkylalkyl, cycloalkylalkoxy, halogen, alkylsulfonyl, cyano and nitro.

In an additional embodiment, Z is selected from quinolinyl, imidazo[1,2-a]pyridin-2-yl, 5-methylpyridin-2-yl, 3,5-dimethylpyridin-2-yl and 6-fluoroquinolin-2-yl, all of which may be optionally substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from quinolinyl and isoquinolinyl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is selected from 2-quinolinyl and 2-benzimidazolyl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 2-quinolinyl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 6-fluoroquinolin-2-yl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 3,5-dimethylpyridin-2-yl substituted with up to 2 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 5-methylpyridin-2-yl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from 2-quinolinyl and 2-benzimidazolyl.

In an additional embodiment, Z is selected from 2-quinolinyl and 5-methylpyridin-2-yl.

In an additional embodiment, Z is selected from 2-quinolinyl and 3,5-dimethylpyridin-2-yl.

In an additional embodiment, Z is selected from 2-quinolinyl and 6-fluoroquinolin-2-yl.

In an additional embodiment, Z is 2-quinolinyl.

In another embodiment, Z is heteroaryl consisting of 6 ring atoms selected from C and N provided the total number of ring nitrogens is less than or equal to two; said ring is optionally substituted with up to 2 substituents independently selected from alkyl, alkoxy, cycloalkyl, cycloalkyloxy, cycloalkylalkyl, cycloalkylalkoxy, halogen, alkylsulfonyl and cyano and nitro.

In another embodiment, Z is heteroaryl consisting of 6 ring atoms selected from C and N provided the total number of ring nitrogens is less than or equal to two.

In a further embodiment, Z is pyridinyl optionally substituted with up to 2 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 2-pyridinyl optionally substituted with up to 2 substituents independently selected from alkyl, alkoxy, cycloalkyl, cycloalkyloxy, cycloalkylalkyl, cycloalkylalkoxy, halogen, alkylsulfonyl, cyano and nitro.

In a further embodiment, any Z is substituent may be unsubstituted.

In one embodiment, $R_{1a}$ is selected from cycloalkyl and alkyl.

In an additional embodiment, $R_{1a}$ is cycloalkyl.

In another embodiment, $R_{1a}$ is alkyl.

In another embodiment, $R_{1a}$ is fully saturated $C_1$-$C_4$ alkyl.

In one embodiment, $R_{1b}$ is selected from cycloalkyl and alkyl.

In another embodiment, $R_{1b}$ is cycloalkyl.

In a further embodiment, $R_{1b}$ is alkyl.

In another embodiment, $R_{1b}$ is fully saturated $C_1$-$C_4$ alkyl.

In one embodiment, each $R_2$ is independently selected from cycloalkyl, alkyl or two $R_2$ groups taken together form a 3-6 membered cycloalkyl ring.

In another embodiment, each $R_2$ is independently selected from cycloalkylalkyl and alkoxyalkyl.

In an additional embodiment, each $R_2$ is independently selected from cycloalkyl and alkyl.

In another embodiment, each $R_2$ is independently selected from cycloalkyl.

In another embodiment, each $R_2$ is independently selected from alkyl.

In another embodiment, each $R_2$ is independently selected from fully saturated $C_1$-$C_4$ alkyl.

In another embodiment, two $R_2$ groups taken together form a 3-6 membered cycloalkyl ring.

In another embodiment, two $R_2$ groups taken together form a three membered ring.

In one embodiment, $R_3$ and $R_4$ are independently selected from $C_1$-$C_4$ alkyl or $R_3$ and $R_4$ taken together form a $C_3$-$C_6$ cycloalkyl ring.

In another embodiment, $R_3$ and $R_4$ are independently selected from $C_1$-$C_4$ alkyl and cycloalkyl.

In another embodiment, $R_3$ and $R_4$ are independently selected from $C_1$-$C_4$ alkyl and $CF_3$.

In an additional embodiment, $R_3$ and $R_4$ taken together form a $C_3$-$C_6$ cycloalkyl ring.

In an additional embodiment, $R_3$ and $R_4$ taken together form a $C_3$ cycloalkyl ring.

In a further embodiment, $R_3$ and $R_4$ are $C_1$-$C_4$ alkyl.

In a further embodiment, $R_3$ and $R_4$ are methyl.

In one embodiment, $R_5$ is selected from cycloalkylalkyl and alkoxyalkyl.

In another embodiment, $R_5$ is cycloalkyl.

In another embodiment, $R_5$ is alkyl.

In an additional embodiment, $R_5$ is selected from cycloalkyl and alkyl.

In one embodiment n is 1.

In another embodiment n is 2.

In one embodiment, $R_7$ is selected from hydrogen, alkyl, cycloalkyl, cycloalkylalkyl and alkoxyalkyl.

In another embodiment, $R_7$ is selected from alkyl, cycloalkyl, cycloalkylalkyl and alkoxyalkyl.

In another embodiment, $R_7$ is selected from hydrogen, alkyl, cycloalkyl and cycloalkylalkyl.

In another embodiment, $R_7$ is selected from alkyl, cycloalkyl and cycloalkylalkyl.

In another embodiment, $R_7$ is selected from cycloalkyl and cycloalkylalkyl.

In another embodiment, $R_7$ is selected from alkyl and cycloalkyl.

In another embodiment, $R_7$ is alkyl.

In another embodiment, $R_7$ is cycloalkyl.

In another embodiment, $R_7$ is cycloalkylalkyl.

In a further embodiment, $R_7$ is hydrogen.

Compounds of the disclosure may contain asymmetric centers and exist as different enantiomers or diastereomers or a combination of these therein. All enantiomeric, diastereomeric forms of Formulas (I), (II) and (III) are embodied herein.

Compounds in the disclosure may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include lithium, sodium, potassium, magnesium, calcium and zinc. Salts derived from organic bases include ammonia, primary, secondary and tertiary amines, and amino acids. Salts derived from inorganic acids include sulfuric, hydrochloric, phosphoric, hydrobromic. Salts derived from organic acids include $C_{1-6}$ alkyl carboxylic acids, di-carboxylic acids and tricarboxylic acids such as acetic acid, proprionic acid, fumaric acid, malcic acid, succinic acid, tartaric acid, adipic acid and citric acid, and alkyl-sulfonic acids such as methanesulphonic, and aryl sulfonic acids such as para-tolouene sulfonic acid and benzene sulfonic acid.

Compounds in the disclosure may be in the form of a solvate. This occurs when a compound of Formulas (I) or (II) or (III) has an energetically favorable interaction with a solvent, crystallizes in a manner that it incorporates solvent molecules into the crystal lattice or a complex is formed with solvent molecules in the solid or liquid state. Examples of solvents forming solvates are water (hydrates), MeOH, EtOH, iPrOH, and acetone.

Compounds in the disclosure may exist in different crystal forms known as polymorphs. Polymorphism is the ability of a substance to exist in two or more crystalline phases that have different arrangements and/or conformations of the molecule in the crystal lattice.

Compounds in the disclosure may exist as isotopically labeled compounds of Formulas (I) or (II) or (III) where one or more atoms are replaced by atoms having the same atomic number but a different atomic mass from the atomic mass which is predominantly seen in nature. Examples of isotopes include, but are not limited to hydrogen isotopes (deuterium, tritium), carbon isotopes ($^{11}C$, $^{13}C$, $^{14}C$) and nitrogen isotopes ($^{13}N$, $^{15}N$). For example, substitution with heavier isotopes such as deuterium ($^{2}H$) may offer certain therapeutic advantages resulting from greater metabolic stability which could be preferable and lead to longer in vivo half-life or dose reduction in a mammal or human.

Prodrugs of compounds embodied by Formulas (I) or (II) or (III) are also within the scope of this disclosure. Particular derivatives of compounds of Formulas (I) or (II) or (III) which may have little to negligible pharmacological activity themselves, can, when administered to a mammal or human, be converted into compounds of Formulas (I) or (II) or (III) having the desired biological activity.

Compounds in the disclosure and their pharmaceutically acceptable salts, prodrugs, as well as metabolites of the compounds, may also be used to treat certain eating disorders, obesity, compulsive gambling, sexual disorders, narcolepsy, sleep disorders, diabetes, metabolic syndrome, neurodegenerative disorders and CNS disorders/conditions as well as in smoking cessation treatment.

In one embodiment the treatment of CNS disorders and conditions by the compounds of the disclosure can include Huntington's disease, schizophrenia and schizo-affective conditions, delusional disorders, drug-induced psychoses, panic and obsessive compulsive disorders, post-traumatic stress disorders, age-related cognitive decline, attention deficit/hyperactivity disorder, bipolar disorders, personality disorders of the paranoid type, personality disorders of the schizoid type, psychosis induced by alcohol, amphetamines, phencyclidine, opioids hallucinogens or other drug-induced psychosis, dyskinesia or choreiform conditions including dyskinesia induced by dopamine agonists, dopaminergic therapies, psychosis associated with Parkinson's disease, psychotic symptoms associated with other neurodegenerative disorders including Alzheimer's disease, dystonic conditions such as idiopathic dystonia, drug-induced dystonia, torsion dystonia, and tardive dyskinesia, mood disorders including major depressive episodes, post-stroke depression, minor depressive disorder, premenstrual dysphoric disorder, dementia including but not limited to multi-infarct dementia, AIDS-related dementia, and neurodegenerative dementia, In another embodiment, compounds of the disclosure may be used for the treatment of eating disorders, obesity, compulsive gambling, sexual disorders, narcolepsy, sleep disorders as well as in smoking cessation treatment.

In a further embodiment, compounds of the disclosure may be used for the treatment of obesity, schizophrenia, schizo-affective conditions, Huntington's disease, dystonic conditions and tardive dyskinesia.

In another embodiment, compounds of the disclosure may be used for the treatment of schizophrenia, schizo-affective conditions, Huntington's disease and obesity.

In a further embodiment, compounds of the disclosure may be used for the treatment of schizophrenia and schizo-affective conditions.

In an additional embodiment, compounds of the disclosure may be used for the treatment of Huntington's disease.

In another embodiment, compounds of the disclosure may be used for the treatment of obesity and metabolic syndrome.

Compounds of the disclosure may also be used in mammals and humans in conjunction with conventional antipsychotic medications including but not limited to Clozapine, Olanzapine, Risperidone, Ziprasidone, Haloperidol, Aripiprazole, Sertindole and Quetiapine. The combination of a compound of Formula (I) or (II) or (III) with a subtherapeutic dose of an aforementioned conventional antipsychotic medication may afford certain treatment advantages including improved side effect profiles and lower dosing requirements.

DEFINITIONS

Alkyl is meant to denote a linear or branched saturated or unsaturated aliphatic $C_1$-$C_8$ hydrocarbon which can be optionally substituted with up to 3 fluorine atoms. Unsaturation in the form of a double or triple carbon-carbon bond may be internal or terminally located and in the case of a double bond both cis and trans isomers are included. Examples of alkyl groups include but are not limited to methyl, trifluoromethyl, ethyl, trifluoroethyl, isobutyl, neopentyl, cis- and trans-2-butenyl, isobutenyl, propargyl. $C_1$-$C_4$ alkyl is the subset of alkyl limited to a total of up to 4 carbon atoms.

In each case in which a size range for the number of atoms in a ring or chain is disclosed, all subsets are disclosed. Thus, $C_x$-$C_y$ includes all subsets, e.g., $C_1$-$C_4$ includes $C_1$-$C_2$, $C_2$-$C_4$, $C_1$-$C_3$ etc.

Acyl is an alkyl-C(O)— group wherein alkyl is as defined above. Examples of acyl groups include acetyl and proprionyl.

Alkoxy is an alkyl-O— group wherein alkyl is as defined above. $C_1$-$C_4$ alkoxy is the subset of alkyl-O— where the subset of alkyl is limited to a total of up to 4 carbon atoms. Examples of alkoxy groups include methoxy, trifluoromethoxy, ethoxy, trifluoroethoxy, and propoxy Alkoxyalkyl is an alkyl-O—($C_1$-$C_4$ alkyl)- group wherein alkyl is as defined above. Examples of alkoxyalkyl groups include methoxymethyl and ethoxymethyl.

Alkoxyalkyloxy is an alkoxy-alkyl-O— group wherein alkoxy and alkyl are as defined above. Examples of alkoxyalkyloxy groups include methoxymethyloxy ($CH_3OCH_2O$—) and methoxyethyloxy ($CH_3OCH_2CH_2O$—) groups.

Alkylthio is alkyl-S— group wherein alkyl is as defined above.

Alkylsulfonyl is alkyl-$SO_2$— wherein alkyl is as defined above.

Alkylamino is alkyl-NH— wherein alkyl is as defined above.

Dialkylamino is (alkyl)$_2$-N— wherein alkyl is as defined above.

Amido is $H_2NC(O)$—

Alkylamido is alkyl-NHC(O)— wherein alkyl is as defined above.

Dialkylamido is (alkyl)$_2$-NC(O)— wherein alkyl is as defined above.

Aromatic is heteroaryl or aryl wherein heteroaryl and aryl are as defined below.

Aryl is a phenyl or napthyl group. Aryl groups may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —OC(O)$R_a$, —OC(O)O$R_a$, —OC(O)NH$R_a$, —OC(O)N($R_a$), —S$R_a$, —S(O)$R_a$, —$NH_2$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)C(O)NH($R_b$), —N($R_a$)C(O)NH($R_b$)$_2$, —C(O)$NH_2$, —C(O)NH$R_a$, —C(O)N($R_a$)($R_b$), —$CO_2$H, —$CO_2R_a$, —COR$_a$, wherein $R_a$ and $R_b$ are independently chosen from alkyl, alkoxyalkyl, —$CH_2CH_2$OH, —$CH_2CH_2$OMe, cycloalkyl, cycloalkylalkyl, aryl, arylalkyl, heteroaryl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Arylalkyl is an aryl-alkyl- group wherein aryl and alkyl are as defined above.

Aryloxy is an aryl-O— group wherein aryl is as defined above.

Arylalkoxy is an aryl-($C_1$-$C_4$ alkyl)-O— group wherein aryl is as defined above.

Carboxy is a $CO_2$H or $CO_2R_c$ group wherein $R_c$ is independently chosen from, alkyl, $C_1$-$C_4$ alkyl, cycloalkyl, arylalkyl, cycloalkylalkyl, $CF_3$, and alkoxyalkyl, wherein alkyl is as defined above.

Cycloalkyl is a $C_3$-$C_7$ cyclic non-aromatic hydrocarbon which may contain a single double bond and is optionally and independently substituted with up to three groups selected from alkyl, alkoxy, hydroxyl and oxo. Examples of cycloalkyl groups include cyclopropyl, cyclobutyl, cyclopentyl, cyclohexyl, cyclopentenyl and cyclohexanonyl.

Cycloalkyloxy is a cycloalkyl-O— group wherein cycloalkyl is as defined above. Examples include cyclopropyloxy, cyclobutyloxy and cyclopentyloxy. $C_3$-$C_6$ cycloalkyloxy is the subset of cycloalkyl-O— where cycloalkyl contains 3-6 carbon atoms.

Cycloalkylalkyl is a cycloalkyl-($C_1$-$C_4$ alkyl)- group. Examples include cyclopropylmethyl, cyclopropylethyl, cyclohexylmethyl and cyclohexylethyl.

Cycloalkylalkoxy is a cycloalkyl-($C_1$-$C_4$ alkyl)-O— group wherein cycloalkyl and alkyl are as defined above. Examples of cycloalkylalkoxy groups include cyclopropylmethoxy, cyclopentylmethoxy and cyclohexylmethoxy.

Halogen is F, Cl, Br or I.

Heteroaryl is a tetrazole, 1,2,3,4-oxatriazole, 1,2,3,5-oxatriazole, a mono or bicyclic aromatic ring system, or a heterobicyclic ring system with one aromatic ring having 5 to 10 ring atoms independently selected from C, N, O and S, provided that not more than 3 ring atoms in any single ring are other than C. Examples of heteroaryl groups include but are not limited to thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, 1,3,4-triazolyl, pyrimidinyl, pyrazinyl, indolyl, quinolyl, tetrahydroquinolyl, isoquinolyl, tetrahydroisoquinolyl, indazolyl, benzthiadiazololyl, benzoxadiazolyl and benzimidazolyl. Heteroaryl groups may be optionally and independently substituted with up to 3 substituents independently selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —OC(O)$R_a$, —OC(O)O$R_a$, —OC(O)NH$R_a$, —OC(O)N($R_a$), —S$R_a$, —S(O)$R_a$, —$NH_2$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)C(O)NH($R_b$), —N($R_a$)C(O)NH($R_b$)$_2$, —C(O)$NH_2$, —C(O)NH$R_a$, —C(O)N($R_a$)($R_b$), —$CO_2$H, —$CO_2R_a$, —COR$_a$, wherein $R_a$ and $R_b$ are independently chosen from alkyl, alkoxyalkyl, —$CH_2CH_2$OH, —$CH_2CH_2$OMe, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Heteroarylalkyl is a heteroaryl-($C_1$-$C_4$ alkyl)- group wherein heteroaryl and alkyl are as defined above. Examples of heteroarylalkyl groups include 4-pyridinylmethyl and 4-pyridinylethyl.

Heteroaryloxy is a heteroaryl-O group wherein heteroaryl is as defined above.

Heteroarylalkoxy is a heteroaryl-($C_1$-$C_4$ alkyl)-O— group wherein heteroaryl and alkoxy are as defined above. Examples of heteroarylalkyl groups include 4-pyridinylmethoxy and 4-pyridinylethoxy.

Heterobicyclic ring system is a ring system having 8-10 atoms independently selected from C, N, O and S, provided that not more than 3 ring atoms in any single ring are other than carbon and provided that at least one of the rings is aromatic; said bicyclic ring may be optionally and independently substituted with up to 3 substituents independently selected from alkyl, alkoxy, cycloalkyl, $C_3$-$C_6$ cycloalkyloxy, cycloalkylalkyl, halogen, nitro, alkylsulfonyl and cyano. Examples of 8-10 membered heterobicyclic ring systems include but are not limited to 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl, tetrahydroquinoxalinyl, benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl, [1,2,4]triazolo[4,3-a]pyridinyl, benzo[b]thienyl, benzo[c][1,2,5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl, 3H-imidazo[4,5-c]pyridinyl, benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridinyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl.

Heterocycloalkyl is a non-aromatic, monocyclic or bicyclic saturated or partially unsaturated ring system comprising 5-10 ring atoms selected from C, N, O and S, provided that not more than 2 ring atoms in any single ring are other than C. In the case where the heterocycloalkyl group contains a nitrogen atom the nitrogen may be substituted with an alkyl, acyl, —C(O)O-alkyl, —C(O)NH(alkyl) or a —C(O)N(alkyl)$_2$ group. Heterocycloalkyl groups may be optionally and independently substituted with hydroxy, alkyl and alkoxy groups and may contain up to two oxo groups. Heterocycloalkyl groups may be linked to the rest of the molecule via either carbon or nitrogen ring atoms. Examples of heterocycloalkyl groups include tetrahydrofuranyl, tetrahydrothienyl, tetrahydro-2H-pyran, tetrahydro-2H-thiopyranyl, pyrrolidinyl, pyrrolidonyl, succinimidyl, piperidinyl, piperazinyl, N-methylpiperazinyl, morpholinyl, morpholin-3-one, thiomorpholinyl, thiomorpholin-3-one, 2,5-diazabicyclo[2.2.2]octanyl, 2,5-diazabicyclo[2.2.1]heptanyl, octahydro-1H-pyrido[1,2-a]pyrazine, 3-thia-6-azabicyclo[3.1.1]heptane and 3-oxa-6-azabicyclo[3.1.1]heptanyl Heterocycloalkylalkyl is a heterocycloalkyl-($C_1$-$C_4$ alkyl)-group wherein heterocycloalkyl is as defined above.

Heterocycloalkyloxy is a heterocycloalkyl-O— group wherein heterocycloalkyl is as defined above.

Heterocycloalkylalkoxy is a heterocycloalkyl-($C_1$-$C_4$ alkyl)-O— group wherein heterocycloalkyl is as defined above.

Oxo is a —C(O)— group.

Phenyl is a benzene ring which may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —OCH$_2$CH$_2$OCH$_3$, —OC(O)R$_a$, —OC(O)OR$_a$, —OC(O)NHR$_a$, —OC(O)N(R$_a$), SR$_a$, —S(O)R$_a$, —NH$_2$, —NHR$_a$, —N(R$_a$)(R$_b$), —NHC(O)R$_a$, —N(R$_a$)C(O)R$_b$, —NHC(O)OR$_a$, —N(R$_a$)C(O)OR$_b$, —N(R$_a$)C(O)NH(R$_b$), —N(R$_a$)C(O)NH(R$_b$)$_2$, —C(O)NH$_2$, —C(O)NHR$_a$, —C(O)N(R$_a$)(R$_b$), —CO$_2$H, —CO$_2$R$_a$, —COR$_a$ wherein R$_a$ and R$_b$ are independently chosen from alkyl, alkoxyalkyl, —CH$_2$CH$_2$OH, —CH$_2$CH$_2$OMe, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, NO$_2$, NH$_2$, CF$_3$, NHMe, NMe$_2$, OMe, OCF$_3$, each of which are attached via carbon-carbon or carbon-nitrogen or carbon-oxygen single bonds; or R$_a$ and R$_b$ taken together with the atom(s) to which they are attached form a 5-6 membered ring.

Restricted phenyl is a benzene ring which may be optionally and independently substituted with up to three groups selected from halogen, CF$_3$, CN, alkoxy, alkoxyalkyl, aryloxy, alkoxyalkyloxy, heterocycloalkyl, heterocycloalkyloxy, heteroaryl, heteroaryloxy, —OCH$_2$CH$_2$OCH$_3$, —OC(O)R$_a$, —OC(O)OR$_a$, —OC(O)N(R$_a$), —N(R$_a$)(R$_b$), —NHC(O)R$_a$, —N(R)C(O)R$_b$, —NHC(O)OR$_a$, —N(R$_a$)C(O)OR$_b$, —C(O)N(R$_a$)(R$_b$), —COR$_a$ wherein R$_a$ and R$_b$ are independently chosen from alkyl, alkoxyalkyl, —CH$_2$CH$_2$OH, —CH$_2$CH$_2$OMe, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$, and $R_b$ taken together with the atom(s) to which they are attached form a 5-6 membered ring.

Abbreviations used in the following examples and preparations include:

Ac Acyl (Me-C(O)—)
AcN Acetonitrile
BINAP 2,2'-bis(diphenylphosphino)-1,1'-binaphthyl
Bn Benzyl
Celite® Diatomaceous earth
DBU 1,8-Diazabicyclo[5.4.0]undec-7-ene
DCC N,N', Dicyclohexylcarbodiimide
DCM Dichloromethane
DIEA Di-isopropylethyl amine
DIPEA Di-isopropylethyl amine
DMAP 4-Dimethylaminopyridine
DMF Dimethylformamide
DMP Dess Martin Periodinane
DMSO Dimethyl sulfoxide
Dppf 1,4-Bis(diphenylphosenylphino) ferrocene
EDC  1-(3-Dimethylaminopropyl)-3-ethylcarbodiimide Hydrochloride
$Et_3N$ Triethylamine
g gram(s)
h Hour(s)
hr Hour(s)
HATU 2-(7-Aza-1H-benzotriazole-1-yl)-1,1,3,3-tetrumethyluronium hexafluorophosphate
HMDS Hexamethyldisilazide
HOBt 1-Hydroxybenzotriazole
HPLC High Pressure Liquid Chromatography
HRMS High resolution mass spectrometry
i.v. Intravenous
KHMDS Potassium Hexamethydisilazide
LDA Lithium Di-isopropylamide
m Multiplet
m- meta
MEM Methoxyethoxymethyl
MeOH Methyl Alcohol or Methanol
min Minute(s)
mmol millimoles
mmole millimoles
Ms Mesylate
MS Mass Spectrometry
MW Molecular Weight
NBS N-Bromosuccinamide
NIS N-Iodosuccinamide
NMR Nuclear Magnetic Resonance
NMM N-Methyl Morpholine
NMP N-Methyl-2-pyrrolidone
o ortho
o/n overnight
p para
PCC Pyridinium Chlorochromate
PEPPSI 1,3-Bis(2,6-diisopropylphenyl)imidazolidene)(3-chloropyridinyl) palladium(II) dichloride
$PhNTf_2$ 1,1,1-trifluoro-N-phenyl-N-(trifluoromethylsulfonyl)methanesulfonamide
POPd Dihydrogen dichlorobis(di-tert-butylphosphinito-kp) palladate (2-)
p.s.i. Pounds per square inch
PPA Polyphosphoric acid
PPAA 1-Propanephosphonic Acid Cyclic Anhydride
PTSA p-Toluenesulfonic acid
PyBOP® Benzotriazol-1-yl-oxytripyrrolidinophosphonium hexafluorophosphate
RT (or rt) room temperature (about 20-25° C.)
s Singlet
sat. Saturated
t Triplet
TBAF Tetra-butyl ammonium fluoride
TEA Triethylamine
TFA Trifluoroacetic Acid
THF Tetrahydrofuran
TLC Thin layer chromatography
TMS Trimethylsilyl
Tf Triflate
T of-MS Time of Flight Mass Spectrometry
Ts Tosylate
v/v volume/volume
wt/v weight/volume

DETAILED DESCRIPTION OF THE DISCLOSURE

The 1,2 disubstituted heterocyclic compounds of Formula I may be prepared from multi-step organic synthesis routes from commercially available starting materials by one skilled in the art of organic synthesis using established organic synthetic procedures. Non-commercially available phenyl acetic acids can be made from commercially available starting materials via methods known by one skilled in the art of organic synthesis. Such methods include synthesis from the corresponding aryl acids via. the Wolff rearrangement using diazomethane.

Compounds of the disclosure where HET is A3, A5, A7, A5, A9, A14, A15, A16, A18, A19, A24, A29, A30, A31, A35 and A39 may be prepared generally as depicted in Schemes 1-18 below. Compounds of the disclosure where HET is A1, A2, A4, A6, A10, A11, A12, A13, A17, A20, A21, A22, A23, A25, A26, A32, A33, A34, A36, A37, A38, A40, A41 and A42 may be prepared by methods known to one skilled in the art of organic synthesis.

Compounds of the disclosure of Formulas (I), (II) or (III) in which X=phenyl, restricted phenyl, aryl, heteroaryl or a heterobicyclic ring are as described previously and thus having general Formula XIV may be prepared generally as depicted in Scheme 1.

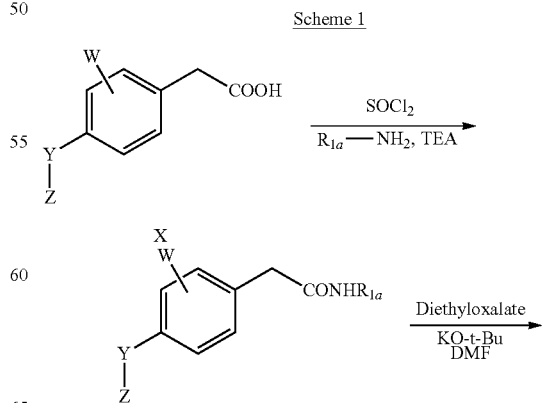

Scheme 1

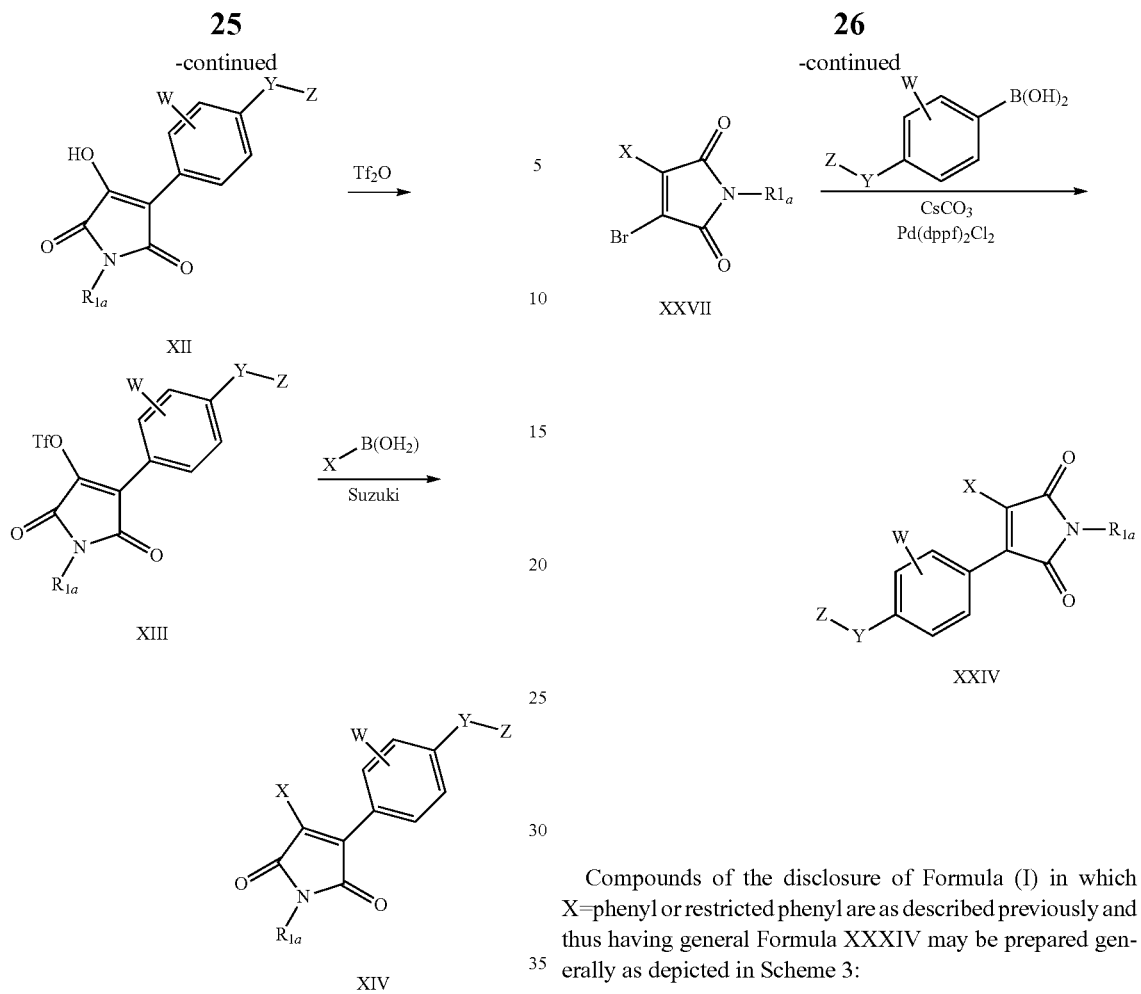

Compounds of the disclosure of Formulas (I), (II) or (III) in which X=heterocycloalkyl are as described previously and thus having general Formula XXIV may be prepared generally as depicted in Scheme 2.

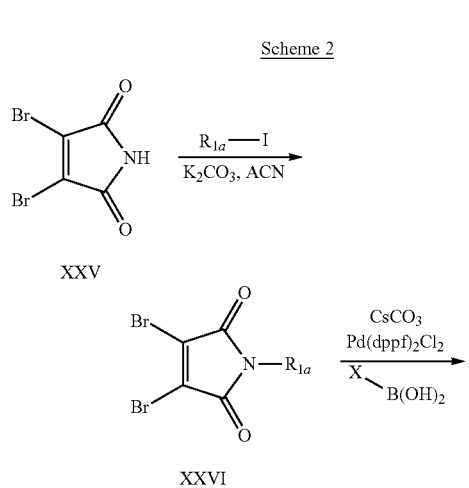

Compounds of the disclosure of Formula (I) in which X=phenyl or restricted phenyl are as described previously and thus having general Formula XXXIV may be prepared generally as depicted in Scheme 3:

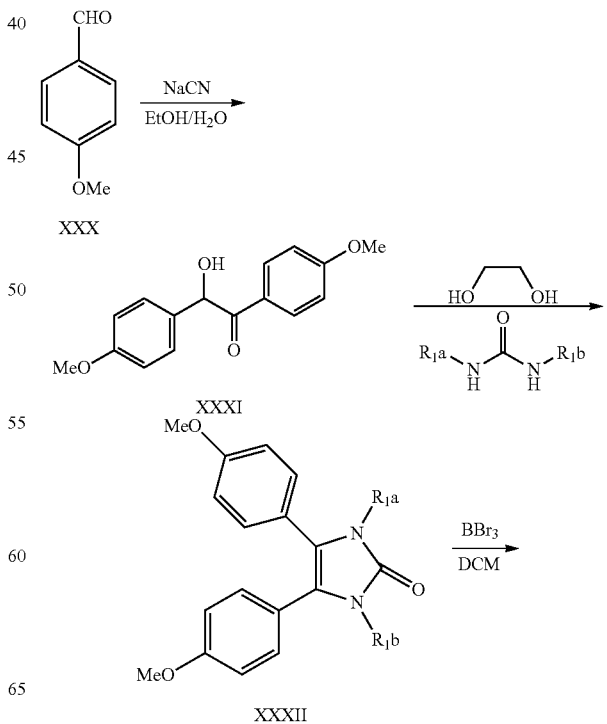

-continued

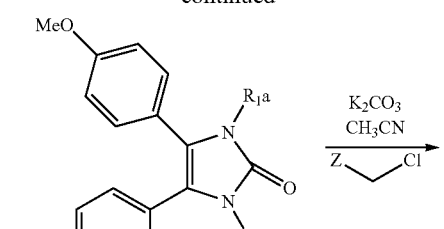

XXXIII

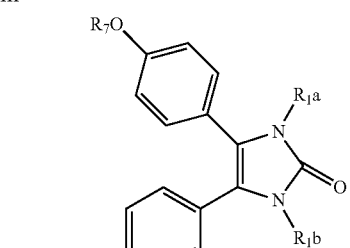

XXXIV

Compounds of the disclosure of Formulas (I), (II) or (III) in which X=phenyl, restricted phenyl or heteroaryl are as described previously and thus having general Formula XLIV and XLV may be prepared generally as depicted in Scheme 4:

Scheme 4

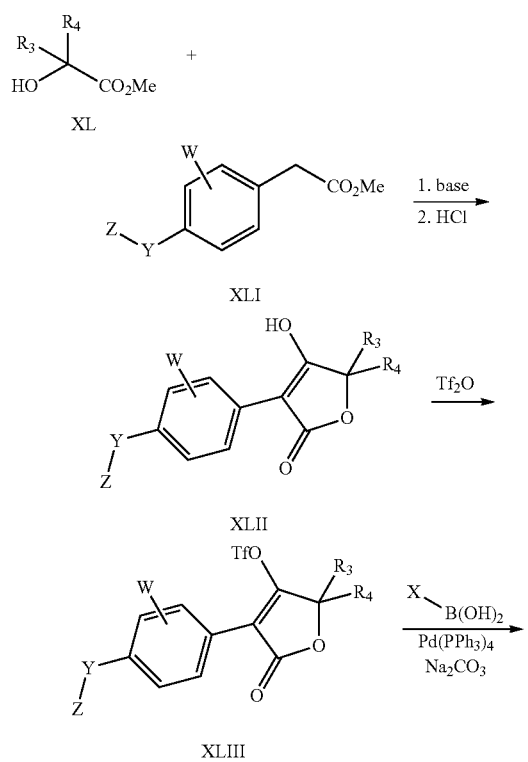

-continued

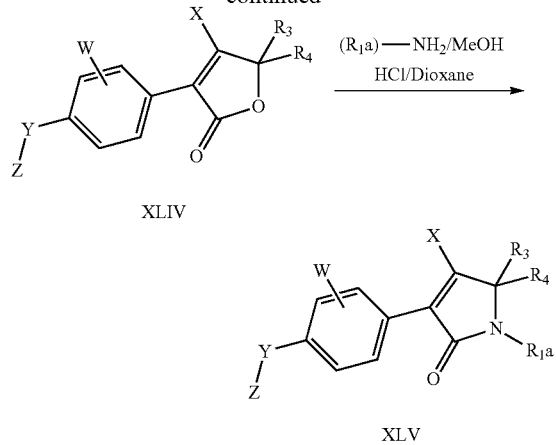

Compounds of the disclosure of Formulas (I), (II) or (III) in which X=phenyl, restricted phenyl, aryl or heteroaryl are as described previously and thus having general Formula LIV may be prepared generally as depicted in Scheme 5:

Scheme 5

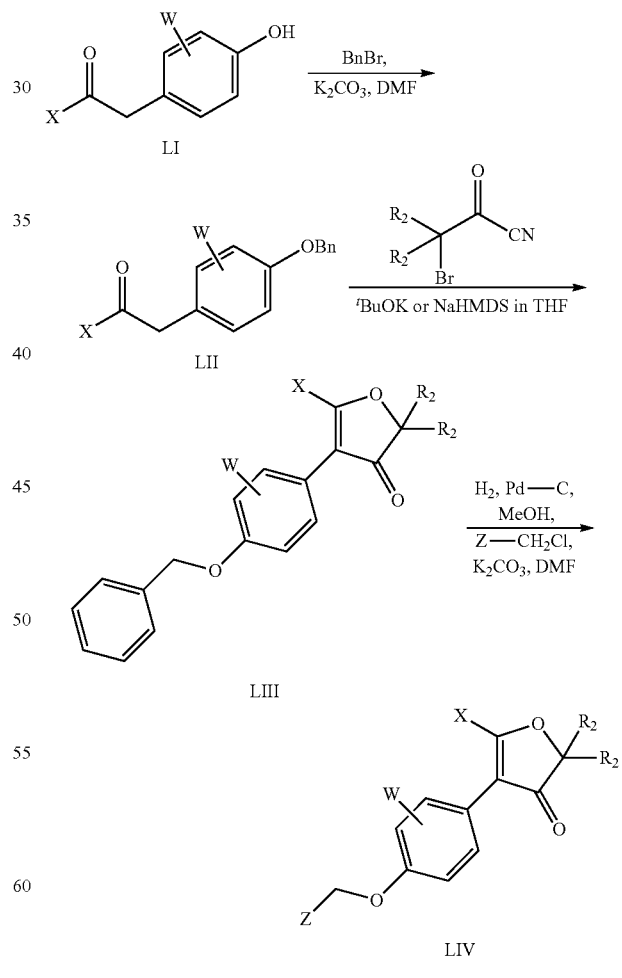

Compounds of the disclosure of Formula I in which X=phenyl, restricted phenyl. aryl, heteroaryl, heterocycloalkyl or a heterobicyclic ring are as described previously and thus having general Formula LXV may be prepared generally as depicted in Scheme 6:

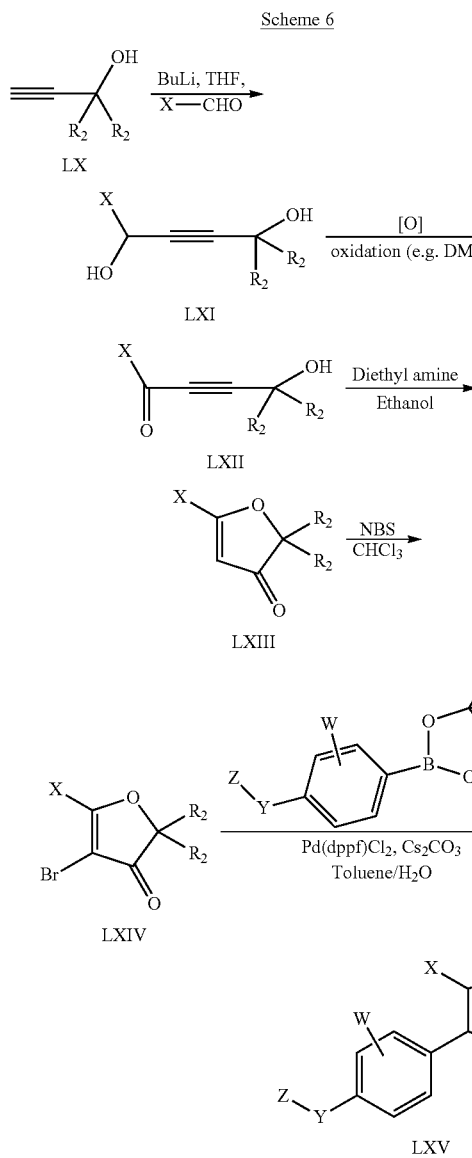

Compounds of the disclosure of Formulas (I), (II) and (II) in which X=phenyl or heteroaryl are as described previously and thus having general Formula LXXIV may be prepared generally as depicted in Scheme 7:

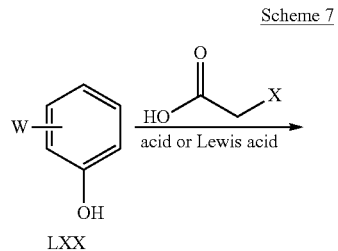

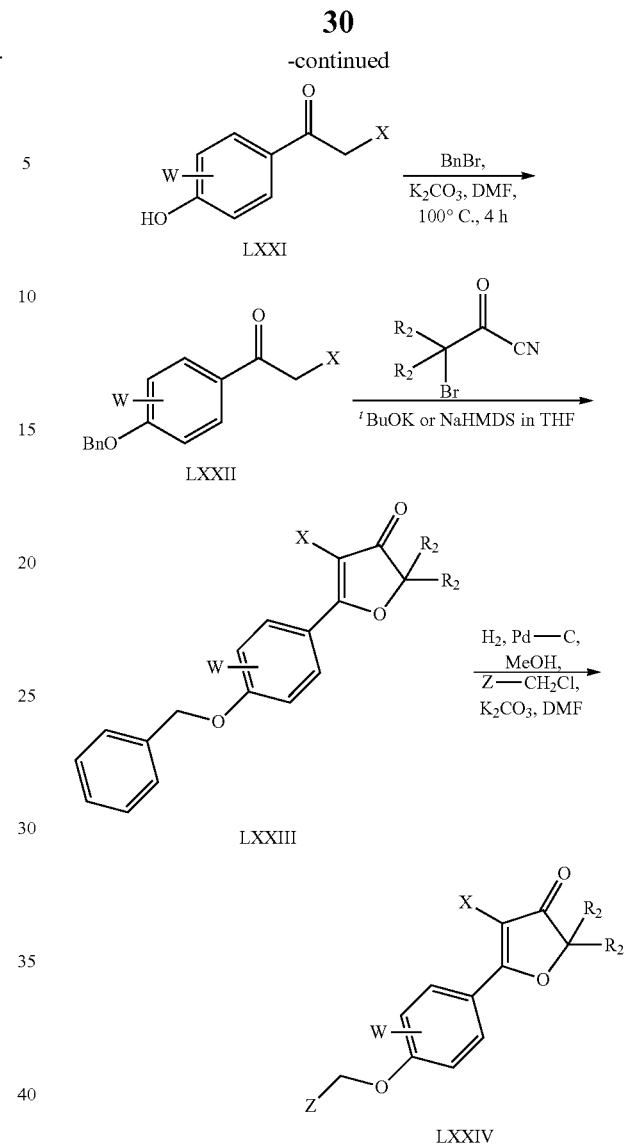

Compounds of the disclosure of Formulas (I), (II) and (III) in which X=aryl, phenyl or heteroaryl are as described previously and thus having general Formula LXXXIV may be prepared generally as depicted in Scheme 8:

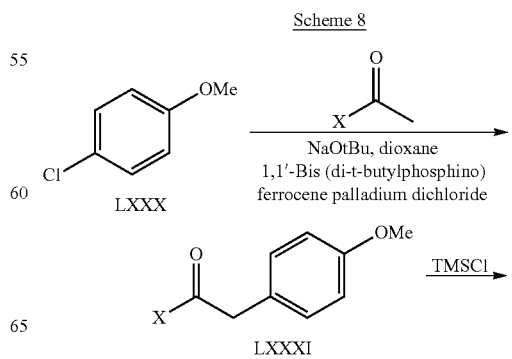

-continued

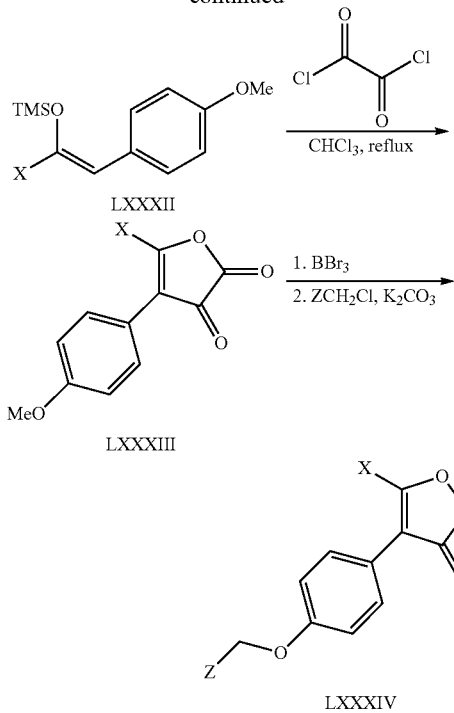

Compounds of the disclosure of Formula (I), (II) or (III) in which X=aryl, heteroaryl or heterocycloalkyl are as described previously and thus having general Formula XCIII may be prepared generally as depicted in Scheme 9:

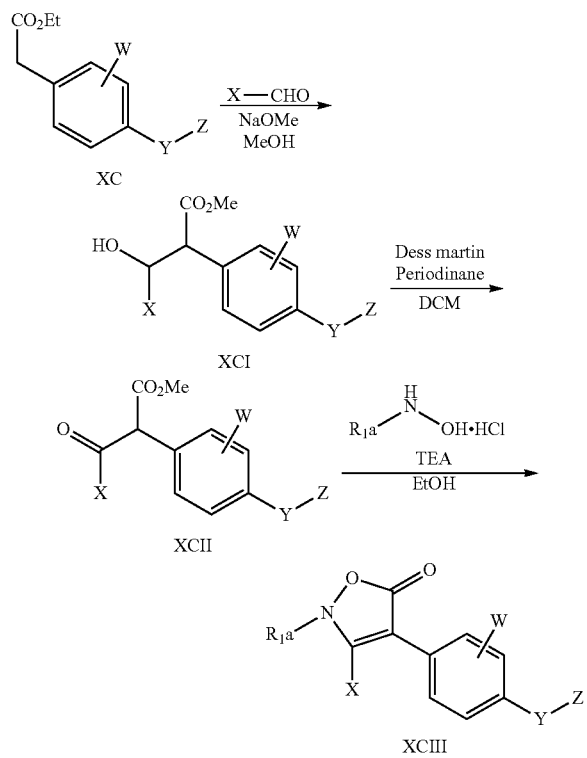

Compounds of the disclosure of Formula (I), (II) or (II) in which X=phenyl, heteroaryl or heterocycloalkyl are as described previously and thus having general Formula CIII may be prepared generally as depicted in Scheme 10:

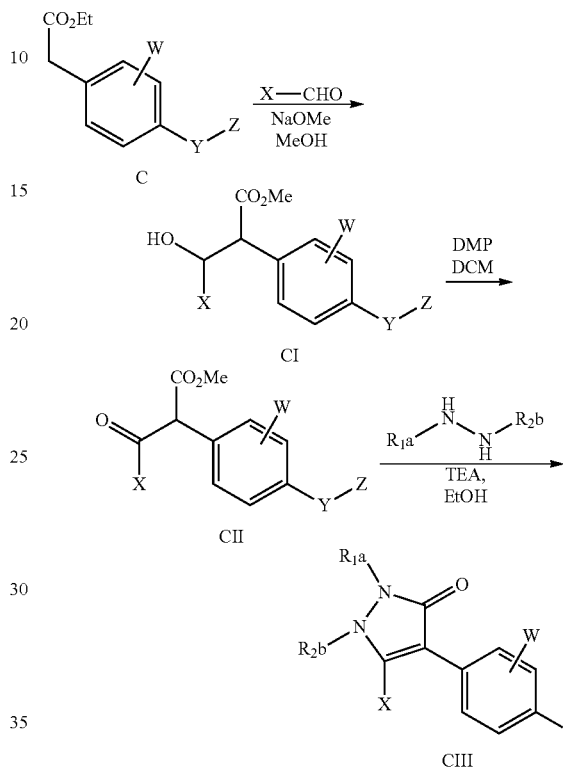

Compounds of the disclosure of Formula (I), (II) or (III) in which X=phenyl or heteroaryl are as described previously and thus having general Formula CXII may be prepared generally as depicted in Scheme 11:

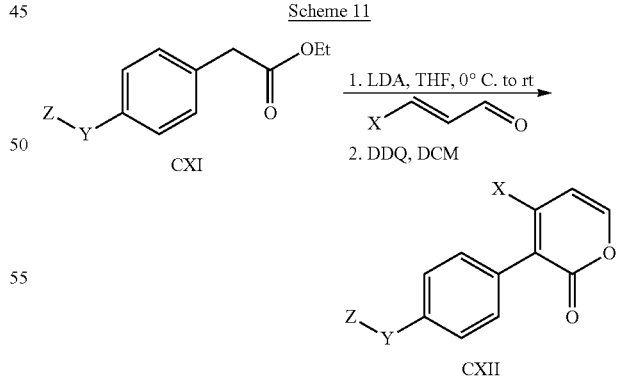

Compounds of the disclosure of Formula (I) in which X=aryl or phenyl are as described previously and thus having general Formula CXXIII may be prepared generally as depicted in Scheme 12. Other compounds of Formula CXXIII may be synthesized by further modification of the OMe group into other functional groups via methods standard in the art of organic chemistry.

Scheme 12

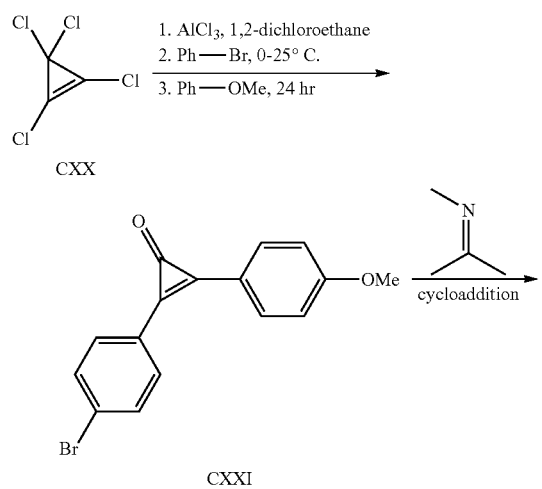

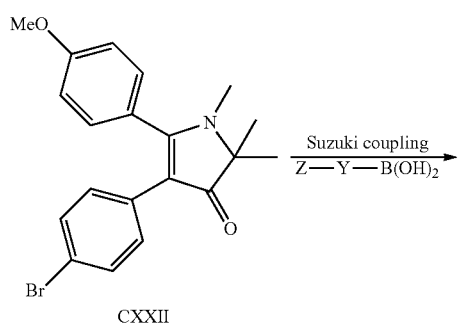

Compounds of the disclosure of Formula (I) in which X=aryl or heteroaryl are as described previously and thus having general Formula CXXXIII may be prepared generally as depicted in Scheme 13.

Scheme 13

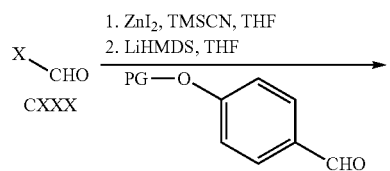

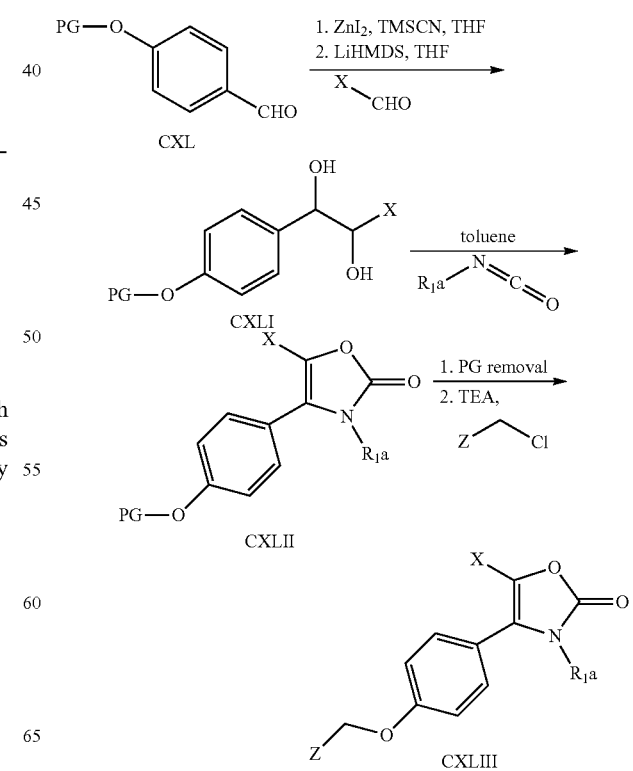

PG: MEM, etc.
PG removal: PTSA etc.

Compounds of the disclosure of Formula (I) in which X=aryl or heteroaryl are as described previously and thus having general Formula CXLIII may be prepared generally as depicted in Scheme 14.

Scheme 14

PG: MEM, etc.
PG removal:PTSA etc.

Compounds of the disclosure of Formula (I) in which X=aryl or heteroaryl are as described previously and thus having general Formula CLIV may be prepared generally as depicted in Scheme 15.

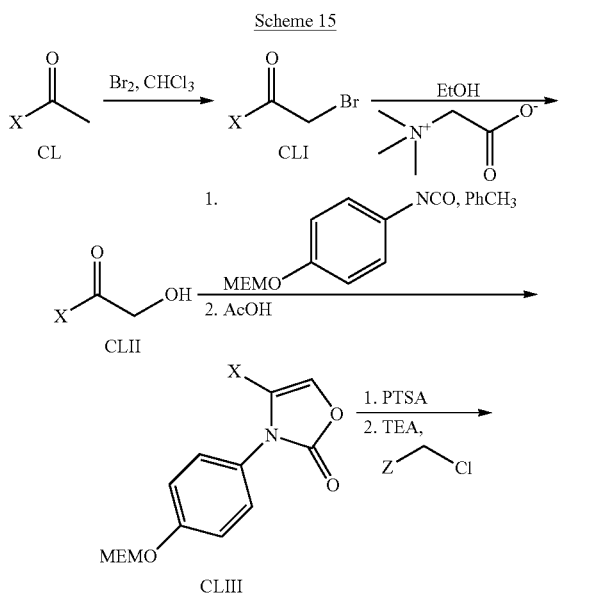

Compounds of the disclosure of Formula (I) in which X=aryl or heteroaryl and R$_7$ is hydrogen are as described previously and thus having general Formula CLXIV may be prepared generally as depicted in Scheme 16.

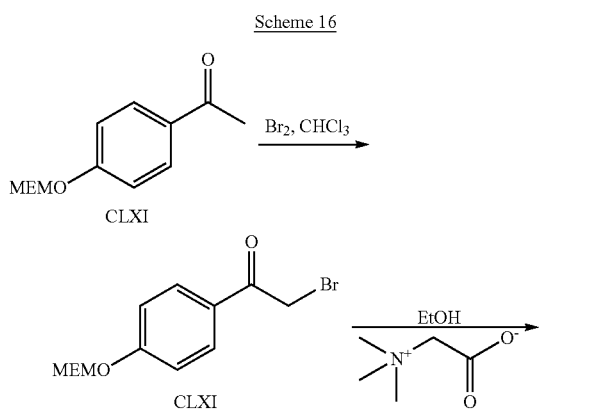

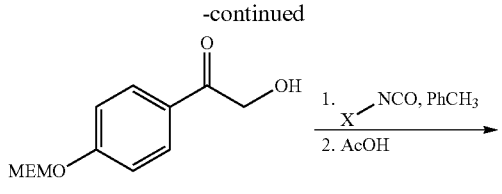

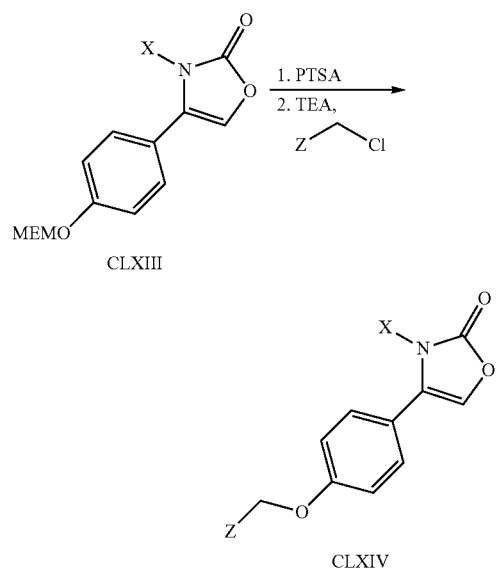

Compounds of the disclosure of Formula (I) in which X=aryl or heteroaryl are as described previously and thus having general Formula CLXXIV may be prepared generally as depicted in Scheme 17.

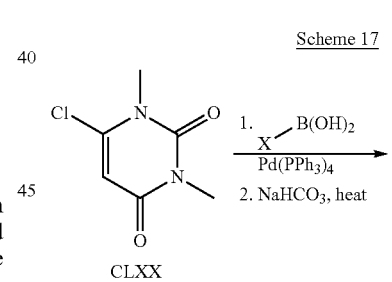

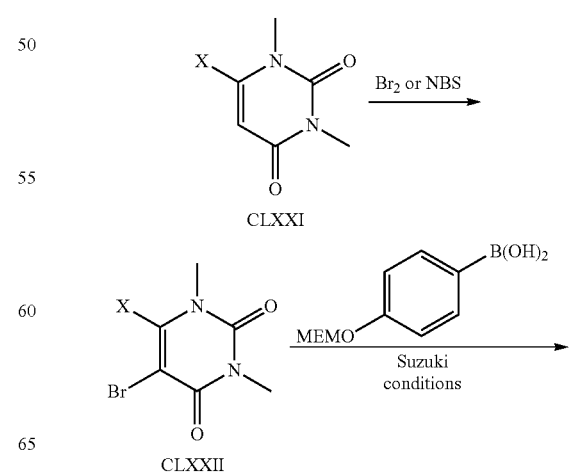

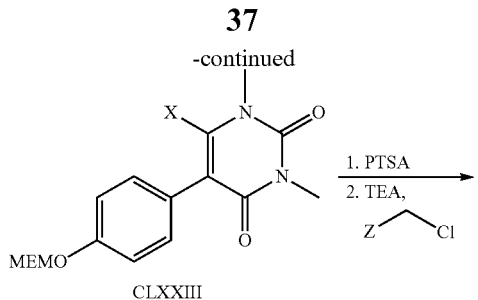

CLXXIII

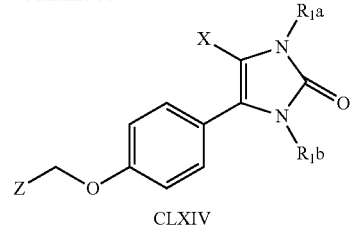

CLXIV

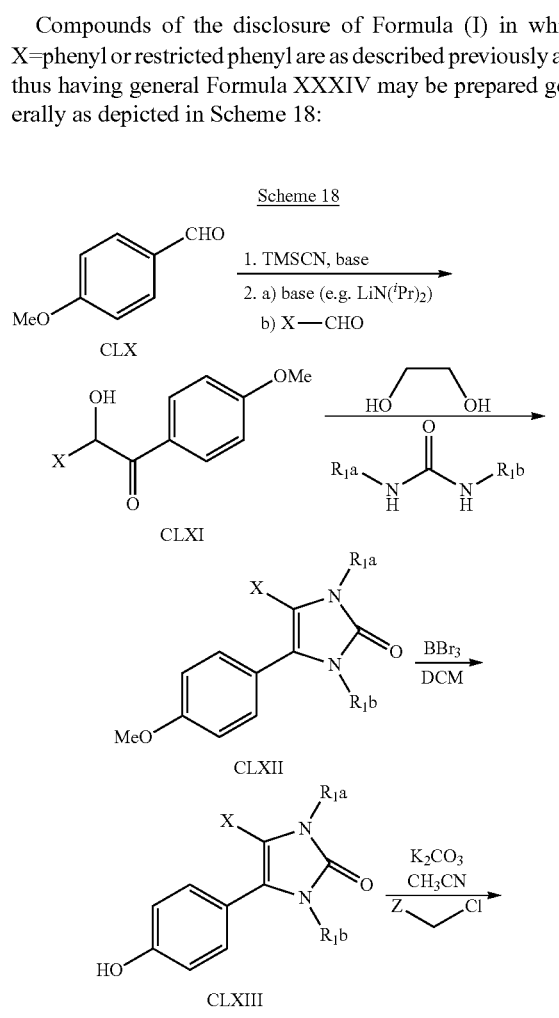

Compounds of the disclosure of Formula (I) in which X=phenyl or restricted phenyl are as described previously and thus having general Formula XXXIV may be prepared generally as depicted in Scheme 18:

Reactive groups not involved in the above processes can be protected with standard protecting groups during the reactions and removed by standard procedures (T. W. Greene & P. G. M. Wuts, Protecting Groups in Organic Synthesis, Third Edition, Wiley-Interscience) known to those of ordinary skill in the art. Presently preferred protecting groups include methyl, benzyl, MEM, acetate and tetrahydropyranyl for the hydroxyl moiety, and BOC, Cbz, trifluoroacetamide and benzyl for the amino moiety, methyl, ethyl, tert-butyl and benzyl esters for the carboxylic acid moiety.

EXPERIMENTAL PROCEDURES

The synthesis of N-methoxy-N-methylcarboxamides from their corresponding carboxylic acids is known by those of ordinary skill in the art. A representative procedure is described below, where is selected from

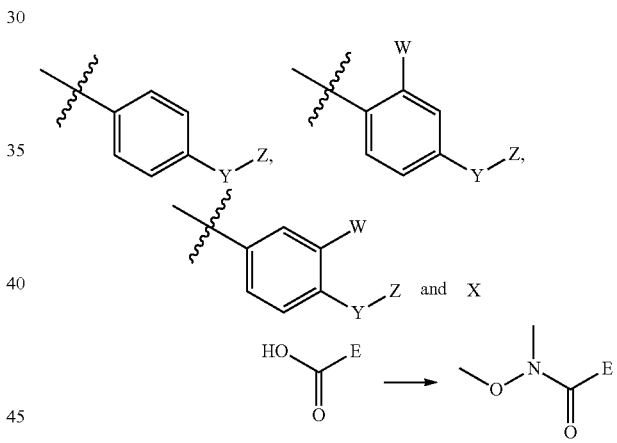

To a stirred solution of carboxylic acid (1 eq., 3 mmol) in DCM (50 mL) was added HATU (1.5 eq, 4.5 mmol), N-methoxy methylamine (1.5 eq, 4.5 mmol) and TEA (3 eq., 9 mmol) at RT under nitrogen atmosphere. The reaction mixture was then stirred at RT for 3 h. The reaction mixture was diluted with water and the aqueous layer was extracted with DCM (3×50 mL). The combined organic extracts were washed with water (50 mL), brine (20 mL), dried over anhydrous $Na_2SO_4$, filtered and evaporated under reduced pressure to afford the corresponding N-methoxy-N-methylcarboxamide.

HPLC Conditions
Condition-A:
Column: Hypersil BDS C8 250×4.6 mm, 5 um (SHCL06E001)
Mobile Phase AcN (A): 0.1% TFA in Water. (B).
Flow rate: 1.5 ml/min (Gradient)
Condition-B:
Column: Zobrax SB-C18 250×4.6 mm, 5 um
Mobile Phase AcN (A): 0.1% TFA in Water. (B).
Flow rate: 1.5 ml/min (Gradient)

Condition-C:
Column: Targa C-18 250×4.6 mm, 5 um
Mobile Phase AcN (A): 0.1% TFA in Water. (B).
Flow rate: 1.5 ml/min (Gradient)
Condition-D:
Column: Targa C18 250×4.6 mm, 5 um (SHCL-12)
Mobile Phase AcN (A): 5M Ammonium Acetate in Water. (B).
Flow rate: 1.0 ml/min (Gradient
Condition-E:
Column: Higgins-C18 250×4.6 mm, 5um
Mobile Phase AcN (A): 0.1% TFA in Water. (B).
Flow rate: 1.5 ml/min (Gradient)
Condition-F:
Column: Chiralpak AD
Mobile Phase: n-Hexane:Ethanol (50:50)
Flow rate: 0.6 ml/min (Gradient)
Condition-G:
Column: Venusil C8, 250×4.6 mm, 5 um.
Mobile Phase: AcN (A): 0.1% TFA in Water. (B).
Flow rate: 1.5 ml/min (Gradient)
Condition-H:
Column: Eclipse XDB-C18, 150×4.6 mm, 5 um.
Mobile Phase: 0.1% TFA in Water. (A).ACN (B)
Flow rate: 1.5 ml/min (Gradient)
Condition-I:
Column: Acquity BEH-C18, (50×2.1 mm, 1.7 um.)
Mobile Phase AcN (B)
Flow rate: 0.5 ml/min (Gradient)
Condition-J:
Column: Zobrax C18, (150×4.6 mm, 5 um.)
Mobile Phase AcN (A): 0.1% TFA in Water. (B).
Flow rate: 1.0 ml/min (Gradient)

Synthesis of 1-Methyl-3-(pyridin-4-yl-4-(4-(quinolin-2-ylmethoxy)phenyl)-1H-pyrrole-2,5-dione (Example 11)

Ethyl 2-(4-(quinolin-2-ylmethoxy)phenyl)acetate

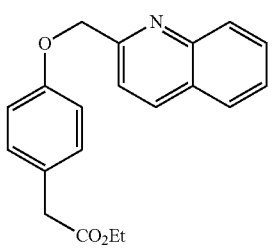

To a stirred solution of ethyl 2-(4-hydroxyphenyl)acetate (30 g, 0.16 mol) in acetonitrile (300 mL) was added $K_2CO_3$ (114.9 g, 0.83 mol) and 2-(chloromethyl) quinoline (42.7 g, 0.19 mol) at RT. The reaction mixture was refluxed for 16 h. The reaction mixture was then filtered and the solid residue was extracted with EtOAc (2×100 mL). The combined organic layers were washed with water, dried over $Na_2SO_4$ and concentrated in vacuo to afford ethyl 2-(4-(quinolin-2-ylmethoxy)phenyl)acetate (50 g, 93.4%) as a solid.

2-(4-(Quinolin-2-ylmethoxy)phenyl)acetic acid

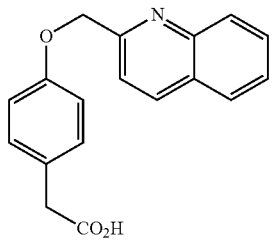 [SMILES: O=C(O)Cc1ccc(OCc2ccc3ccccc3n2)cc1]

To a solution of ethyl 2-(4-(quinolin-2-ylmethoxy)phenyl) acetate (8 g, 0.02 mol) in MeOH: THF (300 mL; 1:1) was added $LiOH.H_2O$ (5.21 g, 0.124 mol) and the mixture was stirred at RT for 1 h. The reaction mixture was then concentrated in vacuo to obtain the crude compound. The crude material was acidified with HCl (1N), filtered and dried in vacuo to afford 2-(4-(quinolin-2-ylmethoxy)phenyl)acetic acid (7.0 g, 95%) as a solid.

2-Bromo-1-(pyridin-4-yl)ethanone hydro bromide

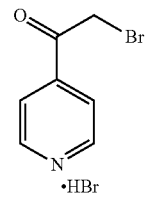

To a stirred solution of 1-(pyridin-4-yl)-ethanone (10 g, 0.08 mol) in $CCl_4$ (150 mL) was added $Br_2$ (3.99 mL, 0.02 mol) dropwise at 0° C. and the mixture was then refluxed for 1 h. The reaction mixture was filtered and dried in vacuo to afford 2-bromo-1-(pyridin-4-yl)-ethanone hydrobromide (22 g, 94%) as a solid.

4-(Pyridin-4-yl)-3-(4-(quinolin-2-ylmethoxy)phenyl) furan-2(5H)-one

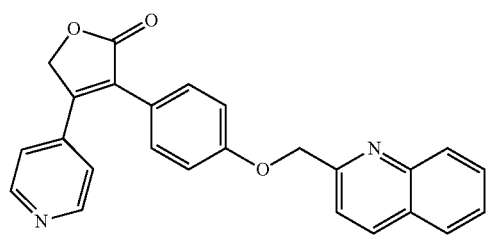 [SMILES: O=C1OCC(c2ccncc2)=C1c1ccc(OCc2ccc3ccccc3n2)cc1]

To a solution of 2-(4-(quinolin-2-ylmethoxy)phenyl)acetic acid (3.0 g, 0.01 mol) in acetonitrile (40 mL) were added TEA (1.3 mL, 0.01 mol) and 2-bromo-1-(pyridin-4-yl)ethanone hydrobromide (2.86 g, 0.01 mol) at RT under an inert atmosphere. The reaction mixture was stirred for 1 h followed by addition of DBU (46.6 g, 0.03 mol) at 0° C. and stirring was continued for another 2 h at 0° C. The reaction mixture was quenched with HCl (1 N), aqueous layer was basified with NaHCO₃ solution and extracted with DCM (2×50 mL). The combined organic layers were washed with water, dried over Na₂SO₄ and concentrated in vacuo to obtain the crude product. The crude product was purified via silica gel column chromatography eluting with 25% EtOAc in hexanes to afford 4-(pyridin-4-yl)-3-(4-(quinolin-2-ylmethoxy)phenyl) furan-2(5H)-one (600 mg, 15%) as a solid.

(Z)-4-Hydroxy-N-methyl-3-(pyridin-4-yl)-2-(4-quinolin-2-ylmethoxy)phenyl) but-2-enamide

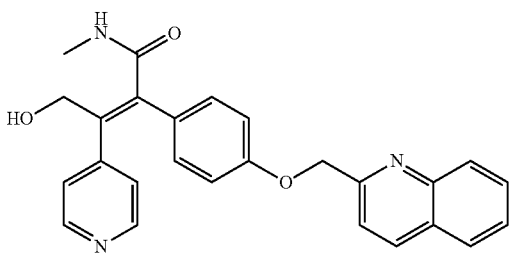 [SMILES: CNC(=O)/C(=C(\CO)c1ccncc1)c1ccc(OCc2ccc3ccccc3n2)cc1]

A solution of 4-(pyridin-4-yl)-3-(4-(quinolin-2-ylmethoxy)phenyl) furan-2(5H)-one (1.0 g, 0.002 mol) and MeNH₂ in MeOH (25 mL) was refluxed for 1 h. The reaction mixture was concentrated in vacuo to afford (Z)-4-hydroxy-N-methyl-3-(pyridin-4-yl)-2-(4-(quinolin-2-ylmethoxy)-phenyl) but-2-enamide (920 mg, 86%) as a solid.

1-Methyl-4-(pyridin-4-yl)-3-(4-(quinolin-2-ylmethoxy)phenyl)-1H-pyrrol-2(5H)-one

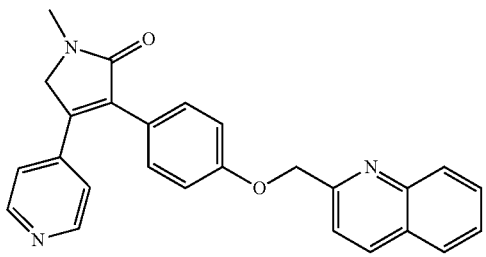 [SMILES: CN1CC(c2ccncc2)=C(c2ccc(OCc3ccc4ccccc4n3)cc2)C1=O]

To a solution of (Z)-4-hydroxy-N-methyl-3-(pyridin-4-yl)-2-(4-(quinolin-2-ylmethoxy)phenyl)-but-2-enamide (430 mg, 1.01 mmol) in Ether. DCM (20 mL; 1:1) was added PBr₃ (0.114 mL, 1.21 mol) dropwise at 0° C. The reaction mixture was stirred at RT for 2 h. The reaction mixture was then diluted with DCM and basified with NaHCO₃ solution. The organic layer was separated, washed with water, dried over Na₂SO₄ and concentrated in vacuo to obtain the crude product. The crude material was purified via silica gel column chromatography to afford 1-methyl-4-(pyridin-4-yl)-3-(4-(quinolin-2-ylmethoxy)phenyl)-1H-pyrrol-2(5H)-one (350 mg, 85%) as a solid. ¹H NMR (500 MHz, CD₃OD): δ 8.81 (d, J=7.8 Hz, 2H), 8.24-8.19 (m, 2H), 8.11-7.94 (m, 3H), 7.85-7.80 (m, 1H), 7.59 (d, J=7.2 Hz, 2H), 7.44 (s, 2H), 7.21 (d, J=7.2 Hz, 2H), 5.61 (s, 2H), 3.38 (s, 2H), 3.09 (s, 3H). MS: M⁺H: m/z=408.2. HPLC: 89%, (Condition-B).

1-Methyl-3-(pyridin-4-yl)-4-(4-(quinolin-2-ylmethoxy)phenyl)-1H-pyrrole-2,5-dione (Example 11)

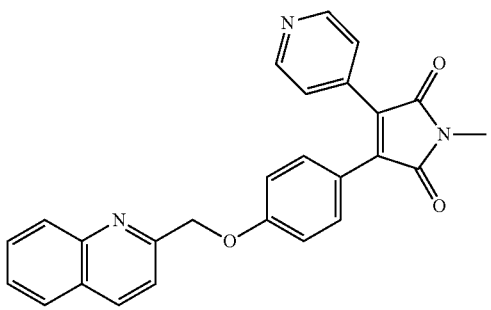 [SMILES: CN1C(=O)C(c2ccncc2)=C(c2ccc(OCc3ccc4ccccc4n3)cc2)C1=O]

To a stirred solution of 1-methyl-4-(pyridin-4-yl)-3-(4-(quinolin-2-ylmethoxy)phenyl)-1H-pyrrol-2(5H)-one (200 mg, 0.49 mmol) in AcN (10 mL) was added DBU (224.5 mg, 1.47 mmol) dropwise and then the reaction mixture was stirred for 6 h under a continuous flow of oxygen. The reaction mixture was quenched with 1N HCl and extracted with EtOAc (2×20 mL). The organic layer was washed with brine, dried over anhydrous Na₂SO₄, and concentrated in vacuo to afford 1-methyl-3-(pyridin-4-yl)-4-(4-(quinolin-2-ylmethoxy)phenyl)-1H-pyrrole-2,5-dione (100 mg, 48%) as a solid. ¹H NMR (500 MHz, CDCl₃): δ 8.18-8.09 (m, 1H), 8.0-7.95 (m, 3H), 7.65-7.59 (m, 3H), 7.48-7.39 (m, 1H), 7.28-7.18 (m, 4H), 7.1-7.09 (m, 2H), 5.25 (s, 2H), 2.86 (s, 3H); MS: M⁻H: m/z=420.1.

Synthesis of 4-(4-methoxyphenyl)-5,5-dimethyl-3-(4-(quinolin-2-ylmethoxy)phenyl) furan-2(5H)-one (Example 33)

4-Hydroxy-5,5-dimethyl-3-(4-(quinolin-2-ylmethoxy)phenyl)furan-2(5H)-one

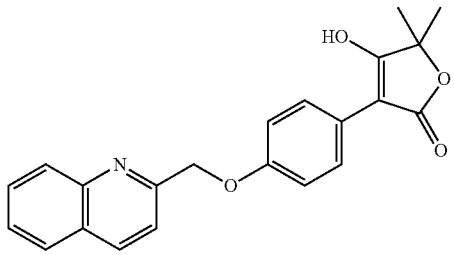 [SMILES: CC1(C)OC(=O)C(c2ccc(OCc3ccc4ccccc4n3)cc2)=C1O]

To a solution of ethyl 2-(4-(quinolin-2-ylmethoxy)phenyl) acetate (2.0 g, 0.006 mol) in THF (10 mL), were added methyl 2-hydroxy-2-methylpropanoate (1.4 g, 0.012 mol) and t-BuOK (1 N, 50 mL) at RT under an inert atmosphere. The mixture was then stirred for 16 h at RT. The reaction mixture was diluted with water, acidified with HCl (1N), and extracted with EtOAc (2×200 mL). The combined organic layers were washed with water, dried over Na₂SO₄ and concentrated in vacuo to afford 4-hydroxy-5,5-dimethyl-3-(4-(quinolin-2-ylmethoxy)phenyl)furan-2(5H)-one (1.0 g, 45%) as a yellow solid.

2,2-Dimethyl-5-oxo-4-(4-(quinolin-2-ylmethoxy)phenyl)-2,5-dihydrofuran-3-yl trifluoromethanesulfonate

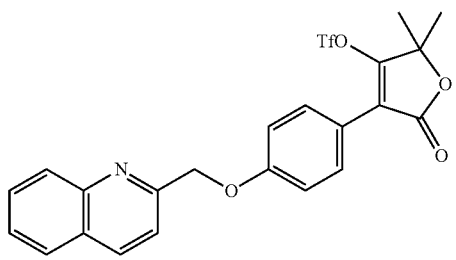 [SMILES: CC1(C)OC(=O)C(c2ccc(OCc3ccc4ccccc4n3)cc2)=C1OS(=O)(=O)C(F)(F)F]

To a solution of 4-hydroxy-5,5-dimethyl-3-(4-(quinolin-2-ylmethoxy)phenyl)furan-2(5H)-one (500 mg, 1.3 mmol) in DCM (50 mL) were added TEA (410 mg, 4.1 mmol) and triflic anhydride (780 mg, 2.7 mmol) at 0° C. under an inert atmosphere. The mixture was then stirred for 2 h at 0° C. The reaction mixture was diluted with water and extracted with DCM (2×100 mL). The combined organic layers were washed with water, dried over $Na_2SO_4$ and concentrated in vacuo to afford 2,2-dimethyl-5-oxo-4-(4-(quinolin-2-ylmethoxy)phenyl)-2,5-dihydrofuran-3-yl trifluoromethanesulfonate (250 mg, 37%) as a white solid.

4-(4-Methoxyphenyl)-5,5-dimethyl-3-(4-(quinolin-2-ylmethoxy)phenyl) furan-2(5H)-one (Example 33)

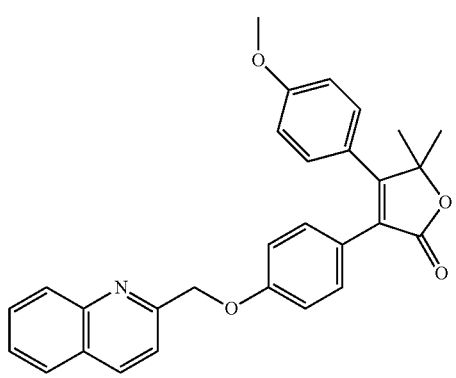 [SMILES: COc1ccc(C2=C(c3ccc(OCc4ccc5ccccc5n4)cc3)C(=O)OC2(C)C)cc1]

To a stirred solution of 2,2-dimethyl-5-oxo-4-(4-(quinolin-2-ylmethoxy)phenyl)-2,5-dihydrofuran-3-yl trifluoromethanesulfonate (250 mg, 0.5 mol) in 1,4-Dioxane (10 mL) were added 4-methoxyphenylboronic acid (92 mg, 0.6 mmol), $Na_2CO_3$ (127 mg, 1.5 mol) and water (4 mL) at RT under an inert atmosphere. The mixture was stirred for 30 min followed by addition of $Pd(PPh_3)_4$ (58 mg, 0.05 mol) and then refluxed for 16 h. The reaction mixture was diluted with water and extracted with EtOAc (2×100 mL). The combined organic layers were washed with water and brine, and then dried over $Na_2SO_4$ and concentrated in vacuo to afford 4-(4-methoxyphenyl)-5,5-dimethyl-3-(4-(quinolin-2-ylmethoxy)phenyl) furan-2(5H)-one- (40 mg, 18%) as a yellow solid. $^1$H NMR (500 MHz, $d_6$-DMSO): δ 8.43-8.41 (m, 1H), 8.02-7.98 (m, 2H), 7.78 (t, J=7.8 Hz, 1H), 7.68-7.52 (m, 2H), 7.25-7.21 (m, 4H), 7.02-6.98 (m, 4H), 5.40 (s, 2H), 5.25 (s, 2H), 3.79 (s, 3H). MS: $M^+H$: m/z=452.2; $M^+Na$: m/z=474.3. HPLC: 91%, (Condition-B).

Synthesis of 5,5-dimethyl-4-(pyridin-4-yl)-3-(4-(quinolin-2-ylmethoxy)phenyl) furan-2(5H)-one (Example 23)

5,5-dimethyl-4-(pyridin-4-yl)-3-(4-(quinolin-2-ylmethoxy)phenyl) furan-2(5H)-one (Example 23)

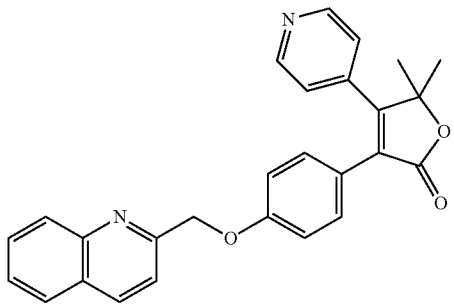 [SMILES: CC1(C)OC(=O)C(c2ccc(OCc3ccc4ccccc4n3)cc2)=C1c1ccncc1]

Following the procedure for the preparation of 4-(4-methoxyphenyl)-5,5-dimethyl-3-(4-(quinolin-2-ylmethoxy)phenyl) furan-2(5H)-one (Example 33) using pyridine-4-yl boronic acid provided the title compound.

Yield: 76%. $^1$H NMR (500 MHz, $d_6$-DMSO): δ 8.68 (d, J=7.2 Hz, 2H), 8.40 (d, J=7.6 Hz, 1H), 8.06-7.95 (m, 2H), 7.62-7.58 (m, 2H), 7.38 (d, J=7.8 Hz, 2H), 7.33 (d, J=7.6 Hz, 2H), 7.0-6.96 (m, 3H), 5.39 (s, 2H), 1.54 (s, 6H). MS: $M^+H$: m/z=423.1. HPLC: 99%, (Condition-B).

Synthesis of 5,5-dimethyl-4-(pyridin-4-yl)-3-(4-(quinolin-2-ylmethoxy)phenyl)-1H-pyrrol-2(5H)-one (Example 63)

Methyl 2-amino-2-methylpropanoate

To a solution of 2-amino-2-methylpropanoic acid (5.0 g) in MeOH (15 mL) was added $SOCl_2$ (4 mL) at 0° C. under an inert atmosphere. The mixture was then stirred for 2 h. The reaction mixture was concentrated in vacuo and washed with ether to afford methyl 2-amino-2-methylpropanoate (4.8 g, 82.7%) as a white solid.

2-(4-(Quinolin-2-ylmethoxy)phenyl)acetic acid

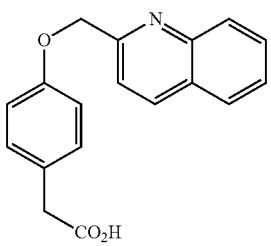 [SMILES: O=C(O)Cc1ccc(OCc2ccc3ccccc3n2)cc1]

To a solution of ethyl 2-(4-(quinolin-2-ylmethoxy)phenyl) acetate (25 g, 0.07 mol) in 1:1 (MeOH:THFi) (400 mL) were added LiOH.H₂O (6.3 g, 0.38 mol) and water (50 mL). The mixture was then stirred at RT for 1 h. The reaction mixture was then concentrated in vacuo. The residue was then acidified with aqueous HCl (1N) and extracted with EtOAc (2×300 mL). The combined organic layers were washed with water, dried over Na₂SO₄ and concentrated in vacuo to afford 2-(4-(quinolin-2-ylmethoxy)phenyl)acetic acid (9.0 g, 40%) as a solid.

Methyl 2-methyl-2-(2-(4-(quinolin-2-ylmethoxy) phenyl)acetamido)propanoate

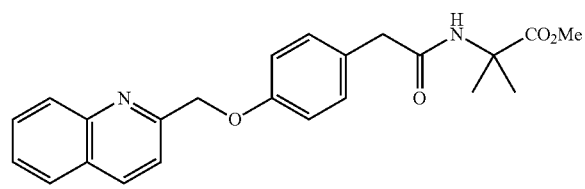 [SMILES: COC(=O)C(C)(C)NC(=O)Cc1ccc(OCc2ccc3ccccc3n2)cc1]

To a stirred solution of 2-(4-(quinolin-2-ylmethoxy)phenyl)acetic acid (5.0 g, 0.017 mol) in DCM (50 mL) were added DIPEA (6.6 g, 0.05 mol), HOBT (3.4 g, 0.02 mol) and EDC (4.9 g, 0.02 mol) at RT under an inert atmosphere. After 10 minutes, 2-amino-2-methylpropanoate (3.9 g, 0.02 mol) was added to the reaction mixture and stirring was continued for 4 h. The reaction mixture was diluted with water and extracted with DCM (2×200 mL). The combined organic layers were washed with water and brine, and then dried over Na₂SO₄. Evaporation of organic solvents in vacuo afforded methyl 2-methyl-2-(2-(4-(quinolin-2-ylmethoxy)phenyl)acetamido)propanoate (5.0 g, 74%) as a white solid.

4-Hydroxy-5,5-dimethyl-3-(4-(quinolin-2-ylmethoxy)phenyl)-1H-pyrrol-2(5H)-one

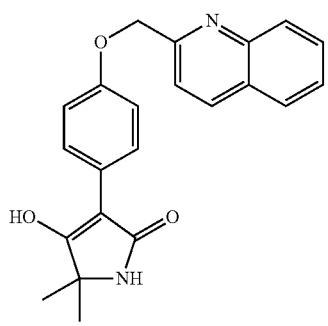 [SMILES: CC1(C)NC(=O)C(c2ccc(OCc3ccc4ccccc4n3)cc2)=C1O]

To a stirred solution of methyl 2-methyl-2-(2-(4-(quinolin-2-ylmethoxy)phenyl)acetamido)propanoate (5.0 g, 0.01 mol) in DMF (100 mL) was added NaH (913 mg, 0.03 mmol) at 0° C. under an inert atmosphere. The reaction mixture was then stirred for 2 h, diluted with ice water and then extracted with EtOAc (2×200 mL). The combined organic layers were washed with water and brine, and then dried over Na₂SO₄ and concentrated in vacuo to afford 4-hydroxy-5,5-dimethyl-3-(4-(quinolin-2-ylmethoxy)phenyl)-H-pyrrol-2(5H)-one (2.0 g, 44%) as a white solid.

2,2Dimethyl-5-oxo-4-(4-(quinolin-2-ylmethoxy) phenyl)-2,5-dihydro-1H-pyrrol-3-yl trifluoromethanesulfonate

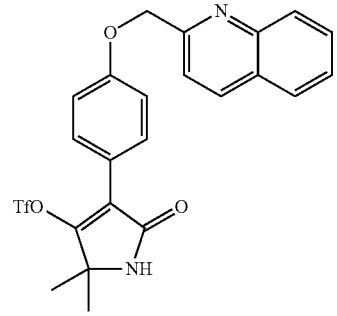 [SMILES: CC1(C)NC(=O)C(c2ccc(OCc3ccc4ccccc4n3)cc2)=C1OS(=O)(=O)C(F)(F)F]

To a solution of 4-hydroxy-5,5-dimethyl-3-(4-(quinolin-2-ylmethoxy)phenyl)-1H-pyrrol-2(5H)-one (500 mg, 1.3 mmol) in DCM (15 mL) were added TEA (422 mg, 4.1 mmol) and triflic anhydride (785 mg, 2.7 mol) at 0° C. under an inert atmosphere. The mixture as then stirred for 2 h., diluted with water and extracted with DCM (2×50 mL). The combined organic layers were washed with water, dried over Na₂SO₄ and then concentrated in vacuo to afford 2,2-dimethyl-5-oxo-4-(4-(quinolin-2-ylmethoxy)phenyl)-2,5-dihydro-1H-pyrrol-3-yl trifluoromethanesulfonate (400 mg, 58%) as a white solid.

5,5-Dimethyl-4-(pyridin-4-yl)-3-(4-(quinolin-2-ylmethoxy)phenyl)-1H-pyrrol-2(5H)-one (Example 63)

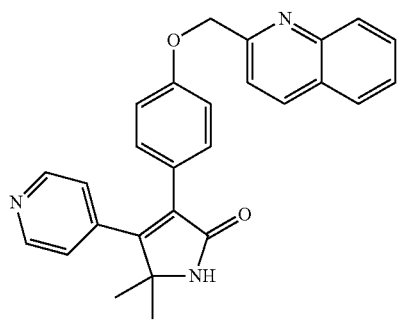 [SMILES: CC1(C)NC(=O)C(c2ccc(OCc3ccc4ccccc4n3)cc2)=C1c1ccncc1]

To a solution of 2,2-dimethyl-5-oxo-4-(4-(quinolin-2-ylmethoxy)phenyl)-2,5-dihydro-1H-pyrrol-3-yl trifluoromethanesulfonate (2.0 g, 0.004 mol) in 1,4-dioxane (50 mL) were added pyridin-4-yl boronic acid (598 mg, 4.8 mol), Na₂CO₃ (1.0 g, 0.012 mol) and water (20 mL) at RT under an inert atmosphere. The mixture was stirred for 30 min and then Pd(PPh₃)₄ (468 mg, 0.4 mol) was added. The mixture was then heated at 80° C. for 16 h, diluted with water, and extracted with EtOAc (2×200 mL). The combined organic layers were washed with water and brine, and then dried over Na₂SO₄ and concentrated in vacuo to afford 5,5-dimethyl-4-(pyridin-4-yl)-3-(4-(quinolin-2-ylmethoxy)phenyl)-1H-pyrrol-2(5H)-one (250 mg, 15%) as a white solid. ¹H NMR (500 MHz, d₆-DMSO): δ 8.74-8.68 (m, 1H), 8.66-8.56 (m, 2H), 8.06-7.94 (m, 2H), 7.78 (t, J=7.2 Hz, 1H), 7.66-7.56 (m, 3H), 7.30-7.18 (m, 4H), 6.98-6.88 (m, 3H), 5.36 (s, 2H), 1.36 (s, 6H). MS: M⁺H: m/z=422.1; M⁺Na: m/z=444.1. HPLC: 89%, (Condition-I).

Synthesis of 4-(4-Methoxphenyl)-5,5-dimethyl-3-(4-(quinolin-2-ylmethoxy) phenyl)-1H-pyrrol-2(5H)-one (Example 823)

4-(4-Methoxyphenyl)-5,5-dimethyl-3-(4-(quinolin-2-ylmethoxy)phenyl)-1H-pyrrol-2(5H)-one (Example 823)

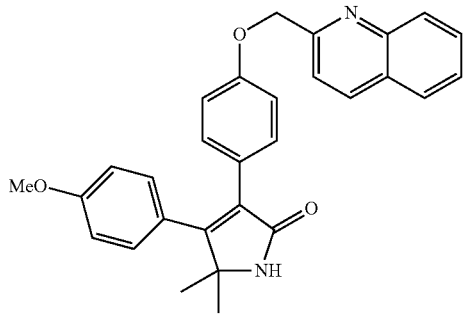 [SMILES: COc1ccc(C2=C(c3ccc(OCc4ccc5ccccc5n4)cc3)C(=O)NC2(C)C)cc1]

To a stirred solution of 2,2-dimethyl-5-oxo-4-(4-(quinolin-2-ylmethoxy)phenyl)-2,5-dihydro-1H-pyrrol-3-yl trifluoromethanesulfonate (500 mg, 1.01 mmol) in 1,4-dioxane (20 mL) were added 4-methoxyphenylboronic acid (185 mg, 1.2 mmol), $Na_2CO_3$ (256 mg, 3.04 mmol) and water (4 mL) at RT under an inert atmosphere. The mixture was stirred for 30 min and then $Pd(PPh_3)_4$ (117 mg, 0.1 mmol) was added. Stirring was continued at 80° C. for 16 h. The reaction mixture was then diluted with water and extracted with EtOAc (2×200 mL). The combined organic layers were washed with water and brine, and then dried over $Na_2SO_4$ and concentrated in vacuo to afford 4-(4-methoxyphenyl)-5,5-dimethyl-3-(4-(quinolin-2-ylmethoxy)phenyl)-1H-pyrrol-2(5H)-one (30 mg, 7%) as a white solid. $^1H$ NMR (500 MHz, $CDCl_3$): δ 8.20-8.01 (m, 2H), 7.87-7.62 (m, 2H), 7.61-7.51 (m, 2H), 7.38-7.30 (m, 2H), 7.16-7.09 (m, 2H), 6.91 6.80 (m, 4H), 5.96 (bs, 1H), 5.39 (s, 2H), 3.81 (s, 3H), 1.43 (s, 6H). MS: $M^+H$: m/z=451.2 and HPLC: 94%, (Condition-I).

Synthesis 4-(4-methoxyphenyl-1,5,5-trimethyl-3-(4-quinolin-2-ylmethoxy)phenyl)-1H-pyrrol-2(5H)-one (Example 73)

4-(4-Methoxyphenyl)-1,5,5-trimethyl-3-(4-(quinolin-2-ylmethoxy)phenyl)-1H-pyrrol-2(5H)-one (Example 73)

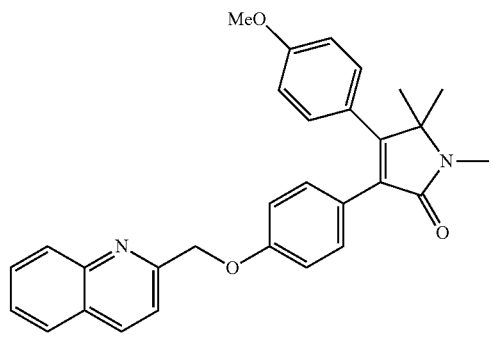 [SMILES: COc1ccc(C2=C(c3ccc(OCc4ccc5ccccc5n4)cc3)C(=O)N(C)C2(C)C)cc1]

To a solution of 4-(4-methoxyphenyl)-5,5-dimethyl-3-(4-(quinolin-2-ylmethoxy)phenyl)-1H-pyrrol-2(5H)-one (150 mg, 0.35 mmol) in DMF (10 mL) were added NaH (15 mg, 0.7 mmol) and $CH_3I$ (100 mg, 0.7 mmol) at 0° C. under an inert atmosphere. The mixture was then stirred for 4 h, diluted with cold water and filtered. The resulting residue was dried to afford 4-(4-methoxyphenyl)-1,5,5-trimethyl-3-(4-(quinolin-2-ylmethoxy)phenyl)-1H-pyrrol-2(5H)-one (50 mg, 37%) as a white solid. $^1H$ NMR (500 MHz, $d_6$-DMSO): δ 8.04 (d, J=7.2 Hz, 1H), 8.02-7.98 (m, 2H), 7.81-7.78 (m, 1H), 7.62-7.58 (m, 2H), 7.31-7.28 (m, 2H), 7.19-7.16 (m, 2H), 6.99-6.84 (m, 4H), 5.36 (s, 2H), 3.89 (s, 3H), 2.96 (s, 3H), 1.24 (s, 6H). MS: $M^+H$: m/z=465.2; $M^+Na$: m/z=487.2. HPLC: 92%, (Condition-I).

Synthesis 4-(4-methoxyphenyl)-2,2-dimethyl-5-(4-(quinolin-2-ylmethoxy)phenyl) furan-3(2H)-one (Example 262)

Ethyl 2-(4-methoxyphenyl)acetate

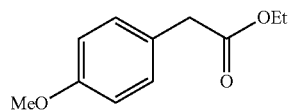 [SMILES: CCOC(=O)Cc1ccc(OC)cc1]

To a stirred solution of ethyl 2-(4-hydroxyphenyl)acetate (10 g, 0.05 mol) in acetonitrile (100 mL) were added $K_2CO_3$ (15.3 g, 0.11 mol) and dimethyl sulfate (8.4 g, 0.06 mol) under an inert atmosphere. The reaction mixture was stirred at 80° C. for 2 h and then extracted with EtOAc (2×300 mL), The combined organic layers were washed with water, dried over $Na_2SO_4$ and concentrated in vacuo to afford ethyl 2-(4-methoxyphenyl)acetate (8 g, 74%) as a white solid.

2-(4-Methoxyphenyl)acetic acid

To a solution of ethyl 2-(4-methoxyphenyl)acetate (12 g, 0.06 mol) in MeOH (150 mL) was added dropwise a solution of NaOH (9.8 g, 0.24 mol) in water (50 mL). The mixture was then stirred at RT for 1 h and concentrated in vacuo, the residue was acidified with HCl (IN) and extracted with EtOAc (2×400 mL). The combined organic layers were washed with water, dried over $Na_2SO_4$ and concentrated in vacuo to afford 2-(4-methoxyphenyl)acetic acid (10 g, 67%) as a yellow oil.

1-(4-Hydroxyphenyl)-2-(4-methoxyphenyl)ethanone

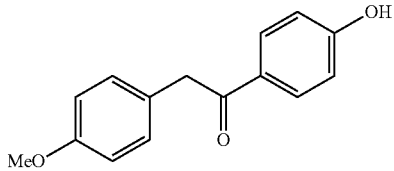 [SMILES: COc1ccc(CC(=O)c2ccc(O)cc2)cc1]

To a solution of 2-(4-methoxyphenyl)acetic acid (10 g, 0.06 mol) in PPA (20 mL) was added dropwise phenol (5.6 g, 0.06 mol) under an inert atmosphere. The mixture was then stirred at 80° C. for 1 h, quenched with cold water and extracted with EtOAc (2×300 mL). The combined organic layers were dried over Na$_2$SO$_4$ and concentrated in vacuo to obtain the crude product which was purified via silica gel column chromatography to afford 1-(4-hydroxyphenyl)-2-(4-methoxyphenyl)-ethanone (3 g, 20%) as a pale yellow solid

1-(4-(Benzyloxy)phenyl)-2-(4-methoxyphenyl)ethanone

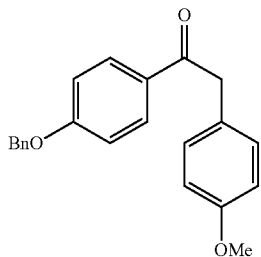 [SMILES: COc1ccc(CC(=O)c2ccc(OCc3ccccc3)cc2)cc1]

To a 0° C. solution of 1-(4-hydroxyphenyl)-2-(4-methoxyphenyl)ethanone (3.0 g, 0.01 mol) in acetonitrile (60 mL) under an inert atmosphere was added potassium carbonate (3.4 g, 0.02 mol) followed by benzyl chloride (1.8 mL, 0.014 mol). The reaction mixture was brought to 80° C. and stirred for 2 h. The reaction was quenched with cold water, filtered and the filtrate was extracted with DCM (2×100 mL). The combined organic layers were dried over Na$_2$SO$_4$ and concentrated in vacuo to afford 1-(4-(benzyloxy)phenyl)-2-(4-methoxyphenyl)ethanone (1.0 g, 24%) as a white solid.

5-(4-(Benzyloxy)phenyl)-4-(4-methoxyphenyl)-2,2-dimethylfuran-3(2H)-one

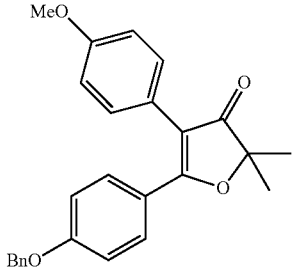 [SMILES: COc1ccc(C2=C(c3ccc(OCc4ccccc4)cc3)OC(C)(C)C2=O)cc1]

To a pre-cooled 0° C. solution of 1-(4-(benzyloxy)phenyl)-2-(4-methoxyphenyl)-ethanone (2 g, 6.02 mmol) in THF (20 mL) under an inert atmosphere was added t-BuOK (8 mL, 1.0 N solution in THF). The mixture was then stirred for 30 minutes. 2-Bromo-2-methylpropanoyl cyanide (2 g, 12 mmol) was then added to then reaction mixture and stirring was continued for an additional 16 h. The reaction mixture was then quenched with cold water (10 mL) and extracted with EtOAc (2×50 mL). The combined organic layers were washed with water (30 mL) and brine (30 mL), and then dried over Na$_2$SO$_4$ concentrated and purified via silica gel column chromatography (10-15% Ethyl acetate in hexanes) to afford 5-(4-(benzyloxy)phenyl)-4-(4-methoxyphenyl)-2,2-dimethylfuran-3(2H)-one (100 mg) as a white solid.

5-(4-Hydroxyphenyl)-4-(4-methoxyphenyl)-2,2-dimethylfuran-3(2H)-one

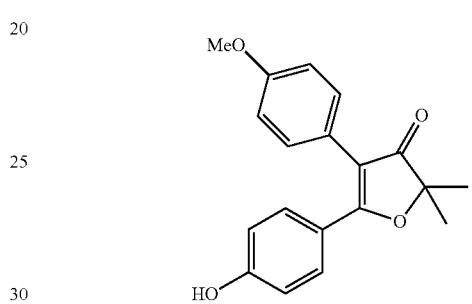

To a stirred solution of 5-(4-(benzyloxy)phenyl)-4-(4-methoxyphenyl)-2,2-dimethylfuran-3(2H)-one (1.0 g, 3.0 mmol) in methanol (50 mL) was added Pd(OH)$_2$ (150 mg, 1.07 mmol) at RT under an inert atmosphere. The reaction mixture was stirred under an atmosphere of hydrogen for 1 h. The reaction mixture was filtered through a pad of Celite® and the filtrate was concentrated in vacuo to afford 5-(4-hydroxyphenyl)-4-(4-methoxyphenyl)-2,2-dimethylfuran-3(2H)-one (600 mg, 64%) as a pale yellow solid

4-(4-Methoxyphenyl)-2,2-dimethyl-5-(4-(quinolin-2-ylmethoxy)phenyl) furan-3(2H)-one (Example 262)

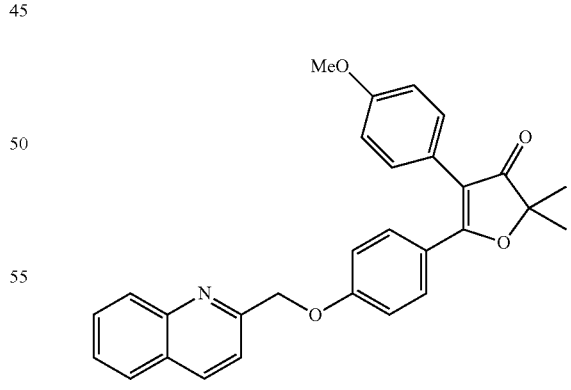

To a stirred solution of 5-(4-hydroxyphenyl)-4-(4-methoxyphenyl)-2,2-dimethylfuran-3(2H)-one (600 mg, 1.93 mol) in acetonitrile (50 mL) was added K$_2$CO$_3$ (800 mg, 5.8 mol). 2-Chloromethyl quinoline (500 mg, 2.32 mol) was added dropwise under an inert atmosphere. The reaction mixture was stirred at 80° C. for 16 h and then partitioned between water and EtOAc (200 mL). The organic layer was separated, washed with water, dried over Na₂SO₄ and then concentrated in vacuo to obtain a residue. The residue was purified via silica gel column chromatography to afford 4-(4-methoxyphenyl)-2,2-dimethyl-5-(4-(quinolin-2-ylmethoxy)phenyl) furan-3(2H)-one (0.51 g, 58%) as a white solid. ¹H NMR (500 MHz, d₆-DMSO): δ 8.45 (d, J=7.2 Hz, 1H), 8.02-7.97 (m, 2H), 7.85-7.77 (m, 1H), 7.76-7.68 (m, 2H), 7.59-7.51 (m, 2H), 7.19-7.11 (m, 4H), 6.95 (d, J=7.4 Hz, 2H), 5.41 (s, 2H), 3.75 (s, 3H), 1.45 (s, 6H). MS: M⁺H: m/z=452.1. HPLC: 97%, (Condition-I).

Synthesis of 2,2-Dimethyl-5-(pyridin-4-yl)-4-(4-(quinolin-2-ylmethoxy)phenyl) furan-3(2H-one (Example 125)

Trimethyl(2-methylbut-3-yl)-2-yloxy) silane

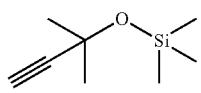

To a stirred solution of 2-methylbut-3-yn-2-ol (20 g, 0.23 mol) in HMDS (42.3 g, 0.261 mol) was added LiClO₄ (38.03 g, 0.35 mol) at RT. The reaction mixture was then stirred for additional 30 minutes, diluted with water (100 mL) and then extracted with ether (3×200 mL). The combined ether layers were washed with water (100 mL) and brine (100 mL), dried over Na₂SO and filtered. The ether was distilled off at 80° C. to afford trimethyl (2-methylbut-3-yn-2-yloxy) silane (25 g) as an oil.

4-Methyl-1-(pyridin-4-yl)-4-(trimethylsilyloxy)pent-2-yn-1-one

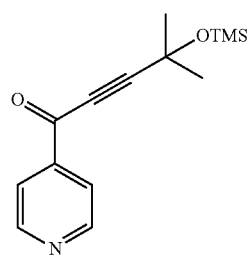

To a pre-cooled-78° C. stirred solution of trimethyl (2-methylbut-3-yn-2-yloxy) silane (5.0 g, 0.03 mol) in dry THF (150 mL), n-BuLi (23.82 mL, 0.03 mol, 1.6 M in hexane) was added dropwise over a period of 10 minutes under an inert atmosphere. The reactions was stirred for 30 minutes at −78° C. and then a solution of N-methoxy-N-methylisonicotinamide (6.34 g, 0.03 mol) in dry THF (30 mL) was added to the reaction mixture and stirring was continued for an additional 40 min at −78° C. The reaction mixture was quenched with a saturated NH₄Cl solution and extracted with EtOAc (2×100 mL). The combined organic layers were washed with water (100 mL) and brine (100 mL), dried over Na₂SO₄, filtered and finally concentrated in vacuo to obtain a residue. The residue was purified via silica gel column chromatography eluting with 5% EtOAc in hexanes to afford 4-methyl-1-(pyridin-4-yl)-4-(trimethylsilyloxy)pent-2-yl)-1-one (2.2 g, 27%) as oil.

4-Hydroxy-4-methyl-1-(pyridin-4-yl) pent-2-yn-1-one

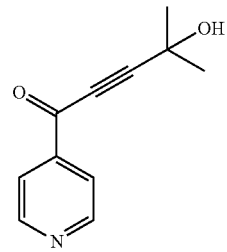

To a stirred solution of 4-methyl-1-(pyridin-4-yl)-4-(trimethylsilyloxy)pent-2-yl)-1-one (0.5 g, 1.915 mmol) in DCM (10 mL) was added PTSA (0.47 g, 2.49 mmol) at RT and the reaction mixture was stirred for 2 h. The reaction mixture was diluted with DCM (50 mL). The organic layers were washed with a saturated NaHCO₃ solution and water, dried over Na₂SO₄, filtered and then concentrated in vacuo to afford 4-hydroxy-4-methyl-1-(pyridin-4-yl) pent-2-yl)-1-one (0.35 g, 96%) as an oil.

2,2-Dimethyl-5-(pyridin-4-yl) furan-3(2H)-one

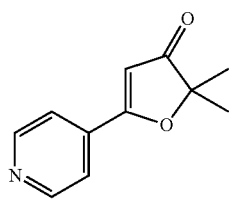

To a stirred solution of 4-hydroxy-4-methyl-1-(pyridin-4-yl) pent-2-yl)-1-one (1.49 g, 0.007 mol) in ethanol (15 mL), diethylamine (0.511 g, 0.007 mol) in EtOH (15 mL) was added dropwise at RT. The mixture was then stirred for additional 40 min. The EtOH was evaporated and the mixture was diluted with EtOAc (100 mL). The organic layers were washed with water (50 mL) and brine (20 mL), dried over Na₂SO₄, filtered and concentrated in vacuo to afford 2,2-dimethyl-5-(pyridin-4-yl)furan-3(2H)-one (1.4 g).

4-Bromo-2,2-dimethyl-5-(pyridin-4-yl) furan-3(2H)-one

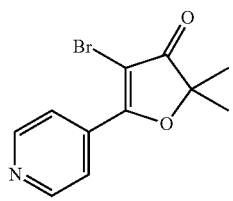

To a stirred solution of 2,2-dimethyl-5-(pyridin-4-yl) furan-3(2H)-one (0.81 g, 4.28 mmol) in CHCl₃ (20 mL), NBS (1.3 g, 7.28 mmol) was added portionwise at RT. The reaction mixture was then stirred for 2 h and diluted with DCM (100 mL). The organic layers were washed with water (50 mL) and brine (50 mL), dried over Na₂SO₄, filtered, and then concentrated in vacuo to obtain the crude product. The crude material was purified via silica gel column chromatography to afford 4-bromo-2,2-dimethyl-5-(pyridin-4-yl) furan-3(2H)-one (0.25 g, 21%) as a solid 2,2-Dimethyl-5-(pyridin-4-yl)-4-(4-(quinolin-2-ylmethoxy)phenyl) furan-3(2H)-one (Example 125)

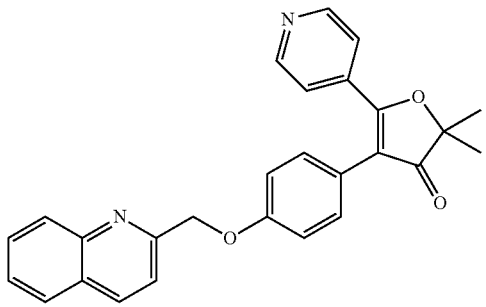 [SMILES: CC1(C)OC(c2ccncc2)=C(c2ccc(OCc3ccc4ccccc4n3)cc2)C1=O]

A mixture of 4-bromo-2,2-dimethyl-5-(pyridin-4-yl)-furan-3(2H)-one (0.25 g, 0.93 mmol), 2-((4-(4,4,5,5-tetramethyl-1,3,2-dioxaborolan-2-yl)phenoxy)methyl)quinoline (0.37 g, 1.026 mmol), and Cs₂CO₃ (1.52 g, 4.664 mmol) in 5:1 toluene/water (12 mL) was degassed. Pd(dppf)Cl₂ (152.2 mg, 0.18 mmol) was then added under an inert atmosphere and the mixture was again degassed. The reaction mixture was refluxed for 3 h, filtered through a pad of Celite® and the filtrate was diluted with EtOAc (100 mL). The combined organic layers were washed with water (50 mL) and brine (50 mL), dried over Na₂SO₄, filtered and concentrated in vacuo to obtain the crude product. The crude material was purified via silica gel column chromatography to afford 2,2-dimethyl-5-(pyridin-4-yl)-4-(4-(quinolin-2-ylmethoxy)phenyl) furan-3(2H)-one (0.29 g, 74%) as a solid. $^1$H NMR (500 MHz, CDCl₃): δ 8.78 (d, J=7.2 Hz, 1H), 8.56-8.50 (m, 2H), 8.15-8.05 (m, 2H), 7.78-7.72 (m, 1H), 7.63-7.59 (m, 1H), 7.56-7.47 (m, 2H); 7.18-7.09 (m, 2H), 7.02-6.96 (m, 3H), 5.40 (s, 2H), 1.50 (s, 6H). MS: M⁺H: m/z=423.1. LC MS: 98%, Column: Eclipse XDB-C18, 150×4.6 mm, 5 um. Mobile Phase: 0.1% TFA in Water (A), AcN (B), Flow rate: 1.5 ml/min (Gradient)

Synthesis of 5-(4-methoxyphenyl)-2,2-dimethyl-4-(4-(quinolin-2-ylmethoxy)phenyl) furan-3(2H)-one (Example 138)

1-(4-Methoxyphenyl)-4-methylpent-2-yne-1,4-diol

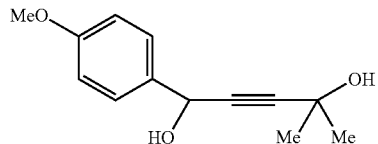

To a pre-cooled, −78° C. stirred solution of 2-methylbut-3-yn-2-ol (4.3 g, 0.04 mol) in dry THF (150 mL) n-BuLi (39.9 mL, 0.03 mol, 1.6 M in hexane) was added dropwise over 10 minutes under an inert atmosphere. The mixture was stirred for 30 min at −78° C., and then a solution of 4-methoxybenzaldehyde (5 g, 0.037 mol) in dry THF (30 mL) was added to reaction mixture and stirring was continued for an additional 40 min at −78° C. The reaction mixture was then quenched with a saturated NH₄Cl solution and extracted with EtOAc (2×100 mL). The combined organic layers were washed with water (100 mL) and brine (100 mL), dried over Na₂SO₄, filtered and concentrated in vacuo to obtain crude material. The crude material was purified via silica gel column chromatography eluting with 5% EtOAc in hexanes to afford 1-(4-methoxyphenyl)-4-methylpent-2-yne-1,4-diol (6.3 g, 78%) as an oil.

4-Hydroxy-1-(4-methoxyphenyl)-4-methylpent-2-yn-1-one

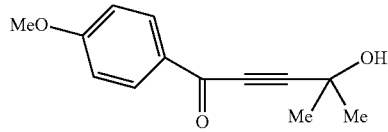 [SMILES: COc1ccc(C(=O)C#CC(C)(C)O)cc1]

To a room temperature, stirred solution of 1-(4-methoxyphenyl)-4-methylpent-2-yne-1,4-diol (6.3 g, 0.029 mol) in DCM (50 mL), Dess Martin periodinane (31.2 g, 0.07 mol) was added and the reaction mixture was stirred for 3 h. The reaction mixture was then diluted with DCM (50 mL) and the combined organic layers were washed with a saturated NaHCO₃ solution and water, dried over Na₂SO₄, filtered and then concentrated in vacuo to afford 4-hydroxy-1-(4-methoxyphenyl)-4-methylpent-2-yn-1-one (6 g, 96%) as an oil.

5-(4-Methoxyphenyl)-2,2-dimethylfuran-3(2H)-one

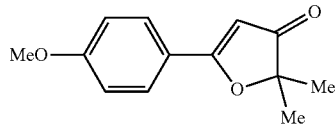 [SMILES: COc1ccc(C2=CC(=O)C(C)(C)O2)cc1]

To a stirred solution of 4-hydroxy-1-(4-methoxyphenyl)-4-methylpent-2-yn-1-one (6 g, 0.027 mol) in ethanol (100 mL) diethyl amine (2.86 g, 0.027 mol) in EtOH (15 mL) was added dropwise at RT and the reaction mixture was stirred for additional 4 h. The EtOH was then removed and the mixture diluted with EtOAc (100 mL). The combined organic layers were washed with water (50 mL) and brine (20 mL), dried over Na₂SO₄, filtered and concentrated in vacuo to afford 5-(4-methoxyphenyl)-2,2-dimethylfuran-3(2H)-one (5.5 g, 92%).

4-Bromo-5-(4-methoxyphenyl)-2,2-dimethylfuran-3(2H)-one

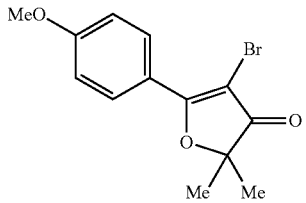 [SMILES: COc1ccc(C2=C(Br)C(=O)C(C)(C)O2)cc1]

To a stirred solution of 5-(4-methoxyphenyl)-2,2-dimethylfuran-3(2H)-one (5.5 g, 0.025 mol) in CHCl₃ (100 mL) NBS (6.733 g, 0.038 mol) was added portionwise at RT and the reaction mixture was stirred for 2 h. The mixture was then diluted with DCM (100 mL), washed with water (50 mL) and brine (50 mL), dried over Na₂SO₄, filtered and then concentrated in vacuo to obtain the crude product. The crude material was purified via silica gel column chromatography to afford 4-bromo-5-(4-methoxyphenyl)-2,2-dimethylfuran-3(2H)-one (4.6 g, 65%) as a solid.

5-(4-Methoxyphenyl)-2,2-dimethyl-4-(4-(quinolin-2-ylmethoxy)phenyl) furan-3(2H)-one (Example 138)

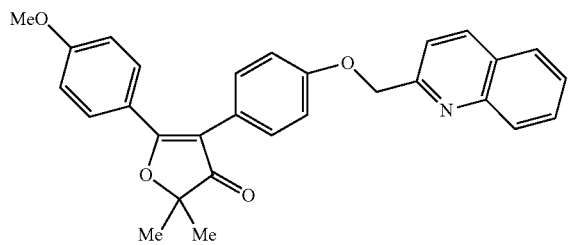 [SMILES: COc1ccc(C2=C(c3ccc(OCc4ccc5ccccc5n4)cc3)C(=O)C(C)(C)O2)cc1]

A mixture of 4-bromo-5-(4-methoxyphenyl)-2,2-dimethylfuran-3(2H)-one (2 g, 0.0067 mol), 2-((4-(4,4,5,5-tetramethyl-1,3,2-dioxaborolan-2-yl)phenoxy)methyl)quinoline (2.43 g, 0.0067 mol), and $Cs_2CO_3$ (11 g, 0.034 mol) in toluene (25 mL) and water (8 mL) was degassed. $Pd(dppf)Cl_2$ (0.1 g, 0.0013 mol) was then added under an inert atmosphere and the mixture was degassed again. The reaction mixture was refluxed for 3 h, filtered through a pad of Celite®. The filtrate was diluted with EtOAc (100 mL), washed with water (50 mL) and brine (50 mL), dried over $Na_2SO_4$, filtered and concentrated in vacuo to obtain the crude product. The crude material was purified via silica gel column chromatography to afford 5-(4-methoxyphenyl)-2,2-dimethyl-4-(4-(quinolin-2-ylmethoxy)phenyl) furan-3(2H)-one (2.3 g, 74%) as solid. $^1$H NMR (500 MHz, $d_6$-DMSO): δ 8.42 (d, J=7.6 Hz, 1H), 8.06-7.99 (m, 2H), 7.95 (t, J=7.2 Hz, 1H), 7.72 (t, J=7.2 Hz, 1H), 7.63 (t, J=7.8 Hz, 1H), 7.56 (d, J=7.2 Hz, 2H); 7.18 (d, J=7.4 Hz, 2H), 7.12 (d, J=7.2 Hz, 2H), 6.89 (d, J=7.2 Hz, 2H), 5.38 (s, 2H), 3.79 (s, 3H), 1.42 (s, 6H). MS: M$^+$H: m/z=452.1; M$^+$Na: m/z=474.2. HPLC: 96%, Column: Eclipse XDB-C18, 150×4.6 mm, 5 um. Mobile Phase: 0.1% TFA in Water (A), AcN (B), Flow rate: 1.5 ml/min (Gradient)

Synthesis of 5-(4-hydroxyphenyl)-2,2-dimethyl-4-(4-(quinolin-2-ylmethoxy)phenyl)furan-3(2H)-one (Example 813)

5-(4-hydroxyphenyl)-2,2-dimethyl-4-(4-(quinolin-2-ylmethoxy)phenyl)furan-3(2H)-one (Example 813)

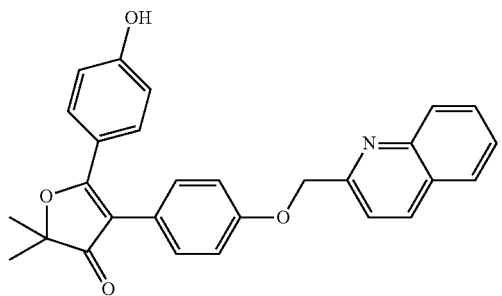 [SMILES: CC1(C)OC(c2ccc(O)cc2)=C(c2ccc(OCc3ccc4ccccc4n3)cc2)C1=O]

To a stirred 0° C. solution of 5-(4-methoxyphenyl)-2,2-dimethyl-4-(4-(quinolin-2-ylmethoxy)phenyl)furan-3(2H)-one (1.0 g, 2.61 mmol) in THF (10 mL), aqueous HBr (908 mg, 5.2 mmol) was added under a nitrogen atmosphere. The reaction mixture was then stirred for 12 h at RT, diluted with water and extracted with hexane (2×50 mL).

The organic layers were concentrated in vacuo to afford 5-(4-hydroxyphenyl)-2,2-dimethyl-4-(4-(quinolin-2-ylmethoxy)phenyl)furan-3(2H)-one (100 mg) as a white solid. $^1$H NMR (500 MHz, $d_6$-DMSO): δ 10.25 (s, 1H), 8.48 (d, J=7.8 Hz, 1H), 8.16-8.00 (m, 2H), 7.95 (t, J=7.8 Hz, 1H), 7.72 (t, J=7.8 Hz, 1H), 7.63 (t, J=7.2 Hz, 1H), 7.56 (d, J=7.2 Hz, 2H); 7.18 (d, J=7.2 Hz, 2H), 7.12 (d, J=7.2 Hz, 2H), 6.89 (d, J=7.6 Hz, 2H), 5.32 (s, 2H), 1.37 (s, 6H). MS: M$^+$H: m/z=438.2; and LC MS: 88%, (Condition-H).

Synthesis of 7-(pyridin-4-yl)-6-(4-(quinolin-2-ylmethoxy)phenyl)-4-oxaspiro[2.4]hept-6-en-5-one (Example 26)

Methyl 1-(2-(4-(quinolin-2-ylmethoxy)phenyl)acetoxy)cyclopropane carboxylate

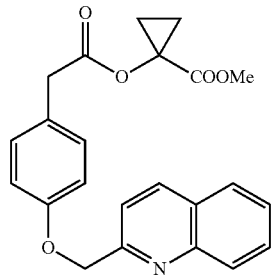 [SMILES: COC(=O)C1(OC(=O)Cc2ccc(OCc3ccc4ccccc4n3)cc2)CC1]

To a stirred solution of 2-(4-(quinolin-2-ylmethoxy)phenyl)acetyl chloride (2.0 g, 6.557 mmol) in DCM (50 mL), DMAP (1.4 g, 13.114 mmol) was added followed by methyl 1-hydroxycyclopropanecarboxylate (1.1 g, 9.836 mmol) under a nitrogen atmosphere at RT and the mixture was stirred for 14 h. After complete consumption of the starting material (by TLC), the reaction mixture was quenched with water (10 mL) and the aqueous layer was extracted with DCM (2×50 mL). The combined organic layers were washed with a saturated $NaHCO_3$ solution (20 mL) and brine (20 mL), dried over anhydrous $Na_2SO_4$, filtered, and concentrated in vacuo to afford crude methyl 1-(2-(4-(quinolin-2-ylmethoxy)phenyl)acetoxy)cyclopropanecarboxylate (2.0 g,) as a solid.

7-Hydroxy-6-(4-(quinolin-2-ylmethoxy)phenyl)-4-oxaspiro[2.4]hept-6-en-5-one

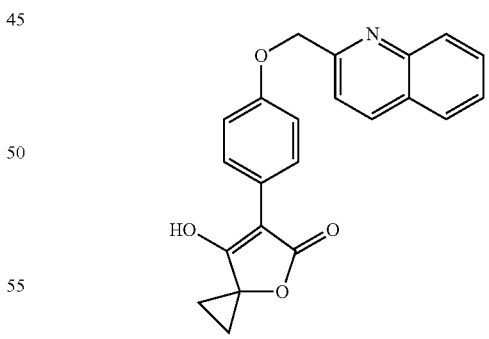

To a 0° C. solution of methyl 1-(2-(4-(quinolin-2-ylmethoxy)phenyl)acetoxy)cyclopropanecarboxylate (2.0 g, 6.825 mmol) in DMF (20 mL) NaI (49 mg, 20.477 mol) was added and the mixture stirred at RT for 12 h. After complete consumption of the starting material (by TLC), the reaction mixture was quenched with ice water (3 mL) and the aqueous layer was extracted with EtOAc (2×50 mL). The combined organic layers were washed with water (30 mL) and brine (20 mL), dried over anhydrous $Na_2SO_4$, filtered, and concentrated in vacuo to afford crude 7-hydroxy-6-(4-(quinolin-2-ylmethyl)phenyl)-4-oxaspiro[2.4]hept-6-en-5-one (2.0 g, 83%) as a light yellow color solid.

5-Oxo-6-(4-(quinolin-2-ylmethoxy)phenyl)-4-oxaspiro[2.4]hept-6-en-7-yl trifluoromethanesulfonate

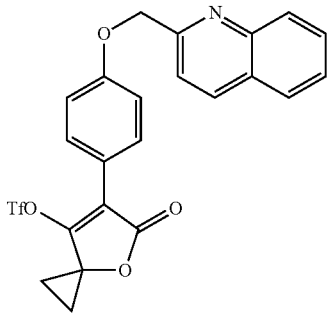 [SMILES: O=C1OC2(CC2)C(OS(=O)(=O)C(F)(F)F)=C1c1ccc(OCc2ccc3ccccc3n2)cc1]

To a 0° C. solution of 7-hydroxy-6-(4-(quinolin-2-ylmethoxy)-phenyl)-4-oxaspiro[2.4]hept-6-en-5-one (400 mg, 1.1 mmol) in DCM (15 mL) TEA (226 mg, 3.36 mmol) and triflic anhydride (631 mg, 2.2 mol) were added under an inert atmosphere and the reaction mixture was stirred for 2 h at 0° C. The reaction mixture was then diluted with water and extracted with DCM (2×50 mL). The combined organic layers were washed with water, dried over $Na_2SO_4$ and concentrated in vacuo to afford 5-oxo-6-(4-(quinolin-2-ylmethoxy)phenyl)-4-oxaspiro[2.4]hept-6-en-7-yl trifluoromethanesulfonate (400 mg, 73%) as an ash-colored solid.

7-(Pyridin-4-yl)-6-(4-(quinolin-2-ylmethoxy)phenyl)-4-oxaspiro[2.4]hept-6-en-5-one (Example 26)

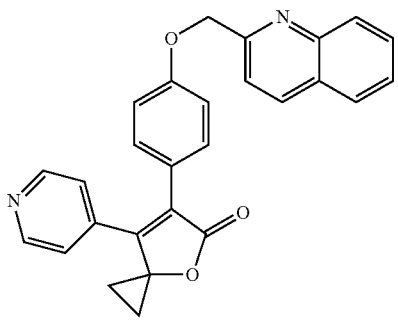 [SMILES: O=C1OC2(CC2)C(c2ccncc2)=C1c1ccc(OCc2ccc3ccccc3n2)cc1]

To a stirred solution of 5-oxo-6-(4-(quinolin-2-ylmethhoxy)phenyl)-4-oxaspiro[2.4]hept-6-en-7-yl trifluoromethanesulfonate (200 mg, 0.4 mmol) in 1,4-dioxane (10 mL) were added pyridin-4-ylboronic acid (74 mg, 0.6 mmol), $Na_2CO_3$ (102 mg, 1.2 mmol) and water (4 mL) at RT under an inert atmosphere. The mixture was stirred for 30 minutes, and then $Pd(PPh_3)_4$ (46 mg, 0.04 mmol) was added and the reaction mixture was then refluxed for 16 h, diluted with water and extracted with EtOAc (2×40 mL). The combined organic layers were washed with water and brine, dried over $Na_2SO_4$ and concentrated in vacuo to afford 7-(pyridin-4-yl)-6-(4-(quinolin-2-ylmethoxy)phenyl)-4-oxaspiro[2.4]hept-6-en-5-one (30 mg, 18%) as white solid. $^1$H NMR (500 MHz, $d_6$-DMSO): δ 8.64-8.61 (m, 2H), 8.40 (d, J=7.2 Hz, 1H),
8.02-7.99 (m, 2H), 7.81-7.77 (m, 1H), 7.67-7.51 (m, 3H), 7.38-7.24 (m, 5H), 5.36 (s, 2H), 1.88-1.85 (m, 2H), 1.24-1.21 (m, 2H). MS: $M^+H$: m/z=421.2; $M^+Na$: m/z=443.2. HPLC: 92%, (Condition-I).

Synthesis of 7-(4-methoxyphenyl)-6-(4-(quinolin-2-ylmethoxy)phenyl)-4-oxaspiro[2.4]hept-6-en-5-one (Example 885)

7-(4-Methoxyphenyl)-6-(4-(quinolin-2-ylmethoxy)phenyl)-4-oxaspiro[2.4]hept-6-en-5-one (Example 885)

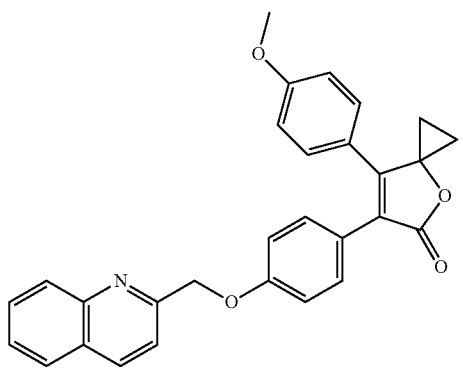 [SMILES: COc1ccc(C2=C(c3ccc(OCc4ccc5ccccc5n4)cc3)C(=O)OC23CC3)cc1]

Following the procedure for the preparation of 7-(pyridin-4-yl)-6-(4-(quinolin-2-ylmethoxy)phenyl)-4-oxaspiro[2.4]hept-6-en-5-one (Example 26) using 4-methoxyphenylboronic acid provided the title compound.

Yield: 18%. $^1$H NMR (500 MHz, $d_6$-DMSO): δ 8.38 (d, J=7.8 Hz, 1H), 8.16-8.0 (m, 2H), 7.73 (t, J=7.8 Hz, 1H), 7.66 (d, J=7.2 Hz, 2H), 7.28 (d, J=7.2 Hz, 2H), 7.22 (d, J=7.2 Hz, 2H), 6.99-6.92 (m, 4H), 5.36 (s, 2H), 3.76 (s, 3H), 1.72-1.66 (m, 2H), 1.25-1.18 (m, 2H). MS: $M^+H$: m/z=450.2; $M^+Na$: m/z=472.1. HPLC: 96%, (Condition-I).

Synthesis of 4-(4-methoxyphenyl)-1,3-dimethyl-5-(4-(quinolin-2-ylmethoxy)phenyl)-1H-imidazol-2(3H)-one (Example 822)

2-Hydroxy-1,2-bis(4-methoxyphenyl)ethanone

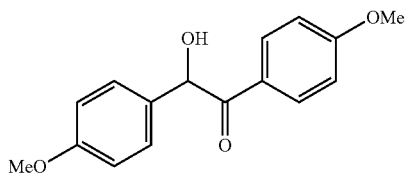 [SMILES: COc1ccc(C(=O)C(O)c2ccc(OC)cc2)cc1]

To a stirred solution of 4-methoxybenzaldehyde (2 g, 14.6 mmol) in EtOH (50 mL) was added a solution of NaCN (0.8 g, 16.3 mmol) in water (5 mL) and the reaction mixture was refluxed for 16 h. The reaction mixture was diluted with water and extracted with EtOAc (2×50 mL). The combined organic layers were washed with water, dried over $Na_2SO_4$, filtered and then concentrated in vacuo to yield a crude material which was purified via silica gel column chromatography eluting with 40% EtOAc in hexanes to afford 2-hydroxy-1,2-bis(4-methoxyphenyl)ethanone (1.3 g, 65%) as a solid.

4,5-bis(4-methoxyphenyl)-1,3-dimethyl-1H-imidazol-2(3H)-one

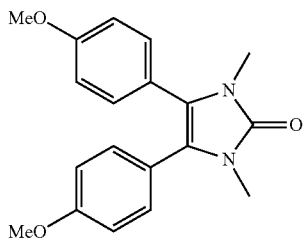 [SMILES: COc1ccc(-c2c(-c3ccc(OC)cc3)n(C)c(=O)n2C)cc1]

A mixture of 2-hydroxy-1,2-bis(4-methoxyphenyl)ethanone (1 g, 3.6 mmol) and 1,3-dimethylurea (1.29 g, 14.7 mmol) in ethylene glycol (10 mL) was refluxed at 180° C. for 2 h. The reaction mixture was diluted with water and extracted with EtOAc (2×50 mL). The combined organic layers were washed with water, dried over Na₂SO₄, filtered and then concentrated in vacuo. The crude material was purified via silica gel column chromatography eluting with 80% EtOAc in hexanes to afford 4,5-bis(4-methoxyphenyl)-1,3-dimethyl-1H-imidazol-2(3H)-one (0.8 g, 67%) as a solid.

4-(4-hydroxyphenyl)-5-(4-methoxyphenyl)-1,3-dimethyl-1H-imidazol-2(3H)-one

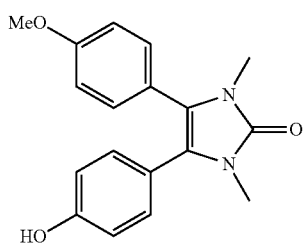 [SMILES: COc1ccc(-c2c(-c3ccc(O)cc3)n(C)c(=O)n2C)cc1]

To a stirred −40° C. solution of 4,5-bis(4-methoxyphenyl)-1,3-dimethyl-1H-imidazol-2(3H)-one (0.6 g, 1.84 mmol) in DCM (10 mL), BBr₃ (0.7 mL, 7.38 mmol) was added dropwise and the reaction mixture was then stirred for 48 h at RT, quenched with 6 N HCl and washed with water. The combined organic layers were then dried over Na₂SO₄, filtered and then concentrated in vacuo to afford 4-(4-hydroxyphenyl)-5-(4-methoxyphenyl)-1,3-dimethyl-1H-imidazol-2(3H)-one (0.38 mg, 66%) as a solid.

4-(4-Methoxyphenyl)-1,3-dimethyl-5-(4-(quinolin-2-ylmethoxy)phenyl)-1H-imidazol-2(3H)-one (Example 822)

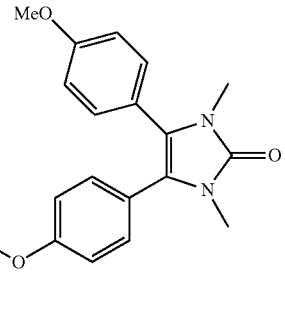

To a stirred solution of 4-(4-hydroxyphenyl)-5-(4-methoxyphenyl)-1,3-dimethyl-1H-imidazol-2(3H)-one (0.35 g, 1.12 mmol) in AcN (20 mL) was added K₂CO₃ (0.46 g, 3.3 mmol) at RT. The reaction mixture was heated to 80° C. for 30 min, and then 2-(chloromethyl)quinoline hydrochloride (0.29 g, 1.35 mmol) was added and the mixture stirred for an additional 3 h at 80° C. Then the mixture was concentrated in vacuo and the residue was dissolved in EtOAc (30 mL). The organic layer was washed with water, dried over Na₂SO₄, filtered, and then concentrated in vacuo to obtain the crude product. The crude material was purified via silica gel column chromatography eluting with 80% EtOAc/20% hexanes to afford 4-(4-methoxyphenyl)-1,3-dimethyl-5-(4-(quinolin-2-ylmethoxy)phenyl)-1H-imidazol-2(3H)-one (0.2 g, 39%) as a solid. $^1$H NMR (500 MHz, CDCl₃): δ 8.21 (d, J=7.2 Hz, 1H), 8.05 (d, J=8.4 Hz, 1H), 7.84 (d, J=7.2 Hz, 1H), 7.74-7.72 (m, 1H), 7.64 (d, J=7.6 Hz, 1H), 7.59-7.56 (m, 1H), 7.11-7.05 (m, 4H), 6.93 (d, J=7.2 Hz, 2H), 6.82 (d, J=7.6 Hz, 2H), 5.39 (s, 2H), 3.81 (s, 3H), 3.19 (s, 6H). MS: M⁺H: m/z=452.2 and HPLC: 97%, (Condition-H).

Synthesis of 2,2-dimethyl-4-(pyridin-4-yl)-5-(4-(quinolin-2-ylmethoxy)phenyl) furan-3(2H)-one (Example 249)

1-(4-(Benzyloxy)phenyl)-4-methylpent-2-yne-1,4-diol

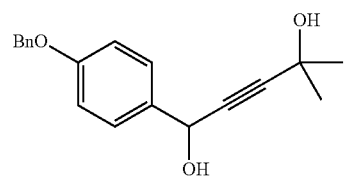 [SMILES: CC(C)(O)C#CC(O)c1ccc(OCc2ccccc2)cc1]

To a precooled −78° C. solution of 2-methylbut-3-yn-2-ol (4.71 g, 0.05 mol) in THF (250 mL), n-BuLi (51.2 mL, 0.08 mol) was added under an inert atmosphere, and the mixture stirred for 30 min. Then, 4-(benzyloxy)benzaldehyde (8.0 g, 0.037 mol) in THF was added and the mixture was stirred for an additional 3 h at RT, quenched with a saturated NH₄Cl solution and concentrated in vacuo. The residue was acidified with HCl (1 N) and extracted with DCM (3×200 mL). The combined organic layers were washed with water, dried over Na₂SO₄ and concentrated in vacuo to obtain the crude product. The crude material was purified via silica gel column chromatography to afford 1-(4-(benzyloxy)phenyl)-4-methylpent-2-yne-1,4-diol (6 g, 54%) as a solid.

1-(4-(Benzyloxy)phenyl)-4-hydroxy-4-methylpent-2-yn-1-one

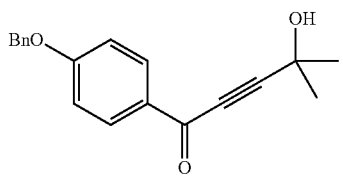 [SMILES: CC(C)(O)C#CC(=O)c1ccc(OCc2ccccc2)cc1]

To a solution of 1-(4-(benzyloxy)phenyl)-4-methylpent-2-yne-1,4-diol (3.0 g, 0.01 mol) in DCM (30 mL) were added Celitc® (1.0 g) followed by PCC (2.61 g, 0.01 mol) at RT. The reaction mixture was stirred for 1 h, filtered through a pad of Celite® and the filtrate was concentrated in vacuo to obtain the crude product. The crude material was purified via silica gel column chromatography to afford 1-(4-(benzyloxy)phenyl)-4-hydroxy-4-methylpent-2-yn-1-one (1.5 g, 51%) as a solid.

5-(4-(Benzyloxy)phenyl)-2,2-dimethylfuran-3(2H)-one

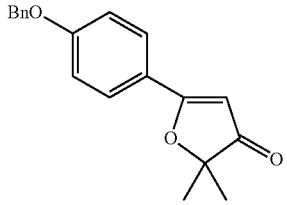 [SMILES: CC1(C)OC(c2ccc(OCc3ccccc3)cc2)=CC1=O]

To a RT solution of 1-(4-(benzyloxy)phenyl)-4-hydroxy-4-methylpent-2-yn-1-one (15 g, 0.005 mol) in EtOH (10 mL) was added a solution of Et₂NH (0.86 mL) in EtOH (10 mL) under an inert atmosphere. The reaction mixture was stirred for 1 hr and then concentrated in vacuo to obtain the crude product. The crude material was partitioned between water and DCM and the organic layer was separated, washed with water, dried over Na₂SO₄ and then concentrated in vacuo to afford 5-(4-(benzyloxy)phenyl)-2,2-dimethylfuran-3(2H)-one (1.4 g, 98%) as a solid.

5-(4-(Benzyloxy)phenyl)-4-bromo-2,2-dimethylfuran-3(2H)-one

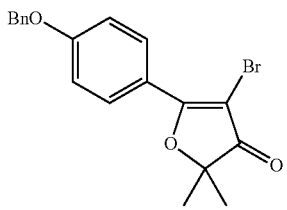 [SMILES: CC1(C)OC(c2ccc(OCc3ccccc3)cc2)=C(Br)C1=O]

To a room temperature solution of 5-(4-(benzyloxy)phenyl)-2,2-dimethylfuran-3(2H)-one (1.5 g, 0.005 mol) in CHCl₃ (50 mL), NBS (1.37 g, 0.007 mol) was added portionwise. The reaction mixture was stirred for 2 h at RT and then concentrated in vacuo to obtain the crude product. The residue was partitioned between water and DCM. The organic layer was separated, washed with water, dried over Na₂SO₄, and concentrated in vacuo to afford 5-(4-(benzyloxy)phenyl)-4-bromo-2,2-dimethylfuran-3(2H)-one (2.0 g) as a solid. This material was used in the next step without further purification.

5-(4-(Benzyloxy)phenyl)-2,2-dimethyl-4-(pyridin-4-yl) furan-3(2H)-one

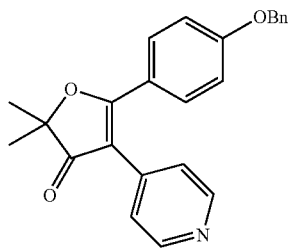 [SMILES: CC1(C)OC(c2ccc(OCc3ccccc3)cc2)=C(c2ccncc2)C1=O]

To a solution of 5-(4-(benzyloxy)phenyl)-4-bromo-2,2-dimethylfuran-3(2H)-one (1.0 g, 2.67 mmol) in toluene (10 mL) were added pyridin-4-ylboronic acid (362 mg, 2.94 mmol), Cs₂CO₃ (4.3 g, 13.3 mmol) followed by water (5 mL) under an inert atmosphere. The reaction mixture was stirred for 15 minutes and then Pd(dppf)Cl₂ (430 mg, 0.0005 mmol) was added. This mixture was refluxed for 16 h and then filtered through a pad of Celite®. The filtrate was extracted with EtOAc (2×40 mL) and the combined organic layers were washed with water, dried over Na₂SO₄, and concentrated in vacuo to obtain the crude product. The crude material was purified via silica gel column chromatography eluting with 40% EtOAc in hexanes to afford 5-(4-(benzyloxy)phenyl)-2,2-dimethyl-4-(pyridin-4-yl) furan-3(2H)-one (620 mg, 62%).

5-(4-Hydroxyphenyl)-2,2-dimethyl-4-(pyridin-4-yl) furan-3(2H)-one

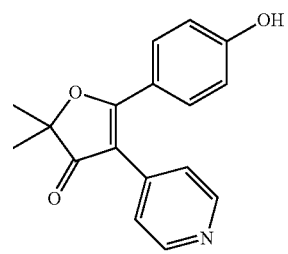 [SMILES: CC1(C)OC(c2ccc(O)cc2)=C(c2ccncc2)C1=O]

To a stirred solution of 5-(4-(benzyloxy)phenyl)-2,2-dimethyl-4-(pyridin-4-yl) furan-3(2H)-one (620 mg, 0.001 mmol) in MeOH (15 mL) was added Pd (OH)₂ (120 mg, 0.85 mmol) at RT under an inert atmosphere. The reaction mixture was stirred under a hydrogen atmosphere for 1 h. The reaction mixture was then filtered through a pad of Celite® and the filtrate was concentrated in vacuo to obtain the crude product. The crude material was purified via silica gel column chromatography to afford 5-(4-hydroxyphenyl)-2,2-dimethyl-4-(pyridin-4-yl) furan-3(2H)-one (280 mg, 60%) as a solid.

2,2-dimethyl-4-(pyridin-4-yl)-5-(4-(quinolin-2-yl-methoxy)phenyl) furan-3(2H)-one (Example 249)

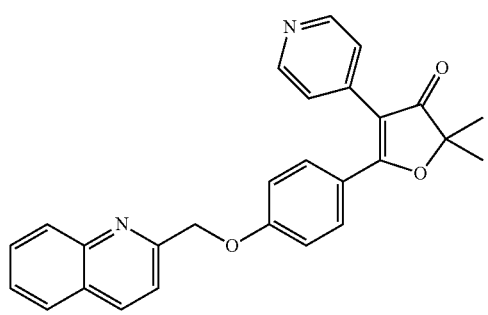 [SMILES: CC1(C)OC(c2ccc(OCc3ccc4ccccc4n3)cc2)=C(c2ccncc2)C1=O]

To a room temperature solution of 5-(4-hydroxyphenyl)-2,2-dimethyl-4-(pyridin-4-yl) furan-3(2H)-one (280 mg, 0.9 mol) in DMF (5 mL), K$_2$CO$_3$ (413 mg, 2.98 mol) was added and the reaction mixture was stirred for 30 min. 2-Chloro methyl quinoline (235 mg, 1.09 mol) was then added to the reaction and stirring was continued for 2 h at 85° C. The reaction mixture was then quenched with cold water and extracted with EtOAc (2×50 mL). The combined organic layers were washed with water, dried over Na$_2$SO$_4$ and concentrated in vacuo to obtain the crude product. The crude material was purified via silica gel column chromatography to afford 2,2-dimethyl-4-(pyridin-4-yl)-5-(4-(quinolin-2-yl-methoxy)phenyl) furan-3(2H)-one (240 mg, 57%) as a solid. $^1$H NMR (500 MHz, d$_6$-DMSO): δ 8.58-8.54 (m, 2H), 8.42 (d, J=7.8 Hz, 1H), 8.04-7.98 (m, 2H), 7.80 (t, J=7.6 Hz, 1H), 7.68 (d, J=7.4 Hz, 1H), 7.64 (t, J=7.6 Hz, 1H), 7.58 (d, J=7.4 Hz, 2H), 7.30-7.24 (m, 2H), 7.19 (d, J=7.2 Hz, 2H), 5.43 (s, 2H), 1.50 (s, 6H). MS: M$^+$H: m/z=423.0. HPLC: 96%, (Condition-1).

Synthesis of 5-(4-methoxyphenyl)-2,2-dimethyl-4-(4-(quinolin-2-ylmethoxy)phenyl) furan-3(2H)-one (Example 138)

Ethyl 2-(4-(quinolin-2-ylmethoxy)phenyl)acetate

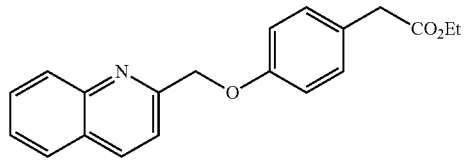 [SMILES: CCOC(=O)Cc1ccc(OCc2ccc3ccccc3n2)cc1]

To a stirred solution of ethyl 2-(4-hydroxyphenyl)acetate (10 g, 0.05 mol) in acetonitrile (150 mL) were added K$_2$CO$_3$ (23 g, 0.16 mol) and 2-(chloromethyl) quinoline (14.2 g, 0.06 mol) under an inert atmosphere. The reaction mixture was then heated at 80° C. for 16 h, diluted with water (50 mL) and extracted with EtOAc (3×100 mL). The combined organic layers were washed with water (100 mL) and brine (100 mL), dried over Na$_2$SO$_4$, filtered, and concentrated in vacuo to afford ethyl 2-(4-(quinolin-2-ylmethoxy)phenyl)acetate (19 g, 95%) as an oil.

2-(4-(Quinolin-2-ylmethoxy)phenyl)acetic acid

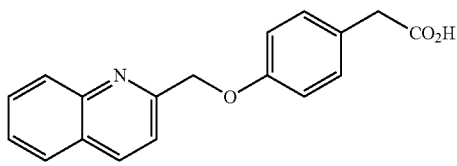 [SMILES: O=C(O)Cc1ccc(OCc2ccc3ccccc3n2)cc1]

To a stirred solution of ethyl 2-(4-(quinolin-2-ylmethoxy)phenyl)acetate (20 g, 0.05 mol) in MeOH (200 mL), a solution of KOH (12.6 g, 0.22 mol) in water (50 mL) was added dropwise and the reaction mixture was stirred for 1 h at RT. The methanol was then removed, and the reaction mixture was washed with EtOAc (2×100 mL) and acidified to pH ~3 with 1 N HCl at 0° C. The precipitated solid was filtered and dried to afford 2-(4-(quinolin-2-ylmethoxy)phenyl)acetic acid (15 g, 92%) as a white solid.

2-(4-(Quinolin-2-ylmethoxy)phenyl)acetyl chloride

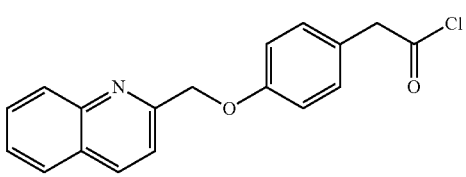 [SMILES: O=C(Cl)Cc1ccc(OCc2ccc3ccccc3n2)cc1]

A mixture of acid 2-(4-(quinolin-2-ylmethoxy)phenyl) acetic acid (2.0 g, 6.8 mmol) in SOCl$_2$ (10 mL) was stirred at RT for 2 h under an inert atmosphere. The reaction was concentrated in vacuo to afford 2-(4-(quinolin-2-ylmethoxy) phenyl)acetyl chloride (2.0 g, 95%) as a light yellow solid.

1-(4-Methoxyphenyl)-2-(4-(quinolin-2-ylmethoxy)phenyl)ethanone

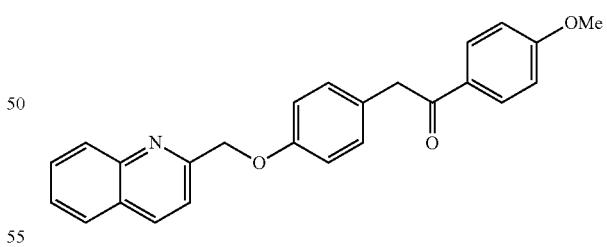

To a stirred solution of PPA (2.0 g, 20 mmol) were added 2-(4-(quinolin-2-ylmethoxy)phenyl)acetyl chloride (2.0 g, 5.0 mmol) and anisole (1.0 g, 10 mmol) at RT under an inert atmosphere. The reaction mixture was then heated at 80° C. for 3 h, quenched with ice cold water and stirred for another 10 minutes. The precipitated solid was filtered, and then the solid was stirred in 10% NaOH solution for 1 h, extracted with DCM (2×50 mL). The combined organic layers were washed with water (2×10 mL) and brine, concentrated, and dried under vacuum to afford 1-(4-methoxyphenyl)-2-(4-(quinolin-2-ylmethoxy)phenyl)ethanone (1.85 g, 90%) as a solid.

2-Bromo-2-methylpropanoyl chloride

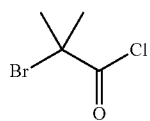

A stirred solution of 2-bromo-2-methylpropanoic acid (3.0 g, 17.9 mmol) in $SOCl_2$ (20 mL) was refluxed for 3 h. The reaction was concentrated in vacuo to afford 2-bromo-2-methylpropanoyl chloride (2.5 g, 76%) as a colorless oil.

2-Bromo-2-methylpropanoyl cyanide

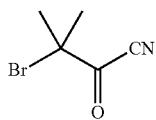

A stirred solution of 2-bromo-2-methylpropanoyl chloride (2.5 g, 13.5 mmol) in trimethylsilanecarbonitrile (3.0 mL) was stirred at RT for 3 h under an inert atmosphere. The reaction mixture was concentrated in vacuo to afford 2-bromo-2-methylpropanoyl cyanide (1.8 g, 76%) as a black oil.

5-(4-Methoxyphenyl)-2,2-dimethyl-4-(4-(quinolin-2-ylmethoxy)phenyl) furan-3(2H)-one (Example 138)

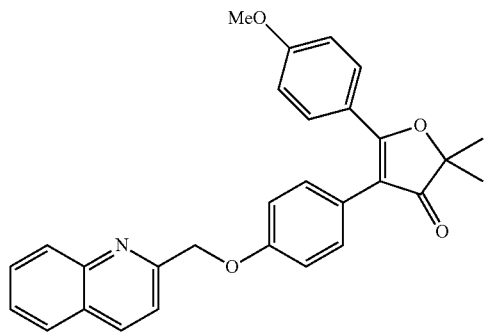 [SMILES: COc1ccc(C2=C(c3ccc(OCc4ccc5ccccc5n4)cc3)C(=O)C(C)(C)O2)cc1]

To a room temperature, stirred solution of 1-(4-methoxyphenyl)-2-(4-(quinolin-2-ylmethoxy)phenyl)ethanone (100 mg, 0.26 mmol) in THF (5 mL), t-BuOK (1.0 mL, 1.0 N solution in THF) was added under an inert atmosphere and the resulting mixture was stirred for 30 min. 2-Bromo-2-methylpropanoyl cyanide (90 mg, 0.5 mmol) was then added to the reaction mixture and stirring was continued for an additional 16 h. The reaction mixture was quenched with cold water (10 mL) and extracted with EtOAc (2×50 mL). The combined organic layers were washed with water (30 mL) and brine (30 mL), dried over $Na_2SO_4$, filtered, concentrated and purified by column chromatography (10-15% ethyl acetate in hexanes) to afford 5-(4-methoxyphenyl)-2,2-dimethyl-4-(4-(quinolin-2-ylmethoxy)phenyl) furan-3(2H)-one (10 mg) as a solid.

$^1$H NMR (500 MHz, $d_6$-DMSO): δ 8.42 (d, J=7.6 Hz, 1H), 8.06-7.99 (m, 2H), 7.95 (t, J=7.2 Hz, 1H), 7.72 (t, J=7.2 Hz, 1H), 7.63 (t, J=7.8 Hz, 1H), 7.56 (d, J=7.2 Hz, 2H); 7.18 (d, J=7.4 Hz, 2H), 7.12 (d, J=7.2 Hz, 2H), 6.89 (d, J=7.2 Hz, 2H), 5.38 (s, 2H), 3.79 (s, 3H), 1.42 (, 6H). MS: M$^+$H: m/z=452.1; M$^+$Na: m/z=474.2. HPLC: 96%, Column: Eclipse XDB-C18, 150×4.6 mm, 5 um. Mobile Phase: 0.1% TFA in Water (A), AcN (B), Flow rate: 1.5 ml/min (Gradient).

Synthesis of 2,2-Dimethyl-5-(pyridin-4-yl)-4-(4-(quinolin-2-ylmethoxy)phenyl furan-3(2H)-one (Example 125)

Trimethyl(2-methylbut-3-yn-2-yloxy)silane

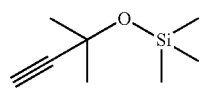

To a room temperature, stirred solution of 2-methylbut-3-yn-2-ol (20 g, 0.23 mol) in HMDS (42.3 g, 0.261 mol), $LiClO_4$ (38.03 g, 0.35 mol) was added and the mixture was stirred for additional 30 min. The reaction mixture was then diluted with water (100 mL) and extracted with ether (3×200 mL). The combined organic layers were washed with water (100 mL) and brine (100 mL), dried over $Na_2SO_4$ and filtered. The ether was distilled off at 80° C. to afford trimethyl (2-methylbut-3-yn-2-yloxy) silane (25 g) as an oil.

4-Methyl-1-(pyridin-4-yl)-4-(trimethylsilyloxy)pent-2-yn-1-one

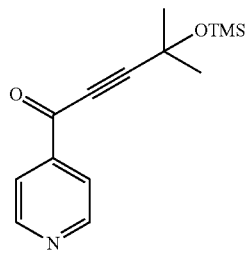

To a stirred −78° C. solution of trimethyl (2-methylbut-3-yn-2-yloxy) silane (5.0 g, 0.03 mol) in dry THF (150 mL), n-BuLi (23.82 mL, 0.03 mol, 1.6 M in hexane) was added dropwise over 10 minutes under an inert atmosphere. After stirring for 30 min at −78° C., a solution of N-methoxy-N-methylisonicotinamide (6.34 g, 0.03 mol) in dry THF (30 mL) was added to the reaction mixture and stirring was continued for an additional 40 min at −78° C. The reaction mixture was quenched with a saturated $NH_4Cl$ solution and extracted with EtOAc (2×100 mL). The combined organic layers were washed with water (100 mL) and brine (100 mL), dried over $Na_2SO_4$, filtered and concentrated in vacuo to obtain the crude product. The crude material was purified via silica gel column chromatography eluting with 5% EtOAc in hexanes to afford 4-methyl-1-(pyridin-4-yl)-4-(trimethylsilyloxy)pent-2-yn-1-one (2.2 g, 27%) as an oil.

4-Hydroxy-4-methyl-1-(pyridin-4-yl) pent-2-yn-1-one

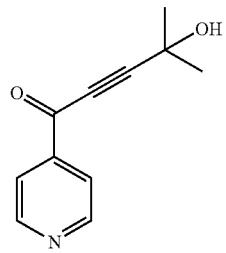

To a room temperature, stirred solution of 4-methyl-1-(pyridin-4-yl)-4-(trimethylsilyloxy)pent-2-yn-1-one (0.5 g, 1.915 mmol) in DCM (10 mL) was added PTSA (0.47 g, 2.49 mmol). The reaction mixture was stirred for 2 h and then diluted with DCM (50 mL). The combined organic layers were washed with a saturated NaHCO$_3$ solution and water, dried over Na$_2$SO$_4$, filtered, and then concentrated in vacuo to afford 4-hydroxy-4-methyl-1-(pyridin-4-yl) pent-2-yn-1-one (0.35 g, 97%) as an oil.

2,2-Dimethyl-5-(pyridin-4-yl) furan-3(2H)-one

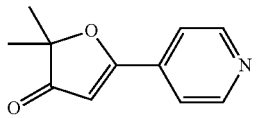

To a room temperature, stirred solution of 4-hydroxy-4-methyl-1-(pyridin-4-yl) pent-2-yn-1-one (1.49 g, 0.007 mol) in ethanol (15 mL), a solution of diethylamine (0.511 g, 0.007 mol) in EtOH (15 mL) was added dropwise and the reaction mixture was stirred for additional 40 min. The ethanol was removed, and the mixture was then diluted with EtOAc (100 mL). The combined organic layers were washed with water (50 mL) and brine (20 mL), dried over Na$_2$SO$_4$, filtered and concentrated in vacuo to afford 2,2-dimethyl-5-(pyridin-4-yl) furan-3(2H)-one (1.4 g).

4-Bromo-2,2-dimethyl-5-(pyridin-4-yl) furan-3(2H)-one

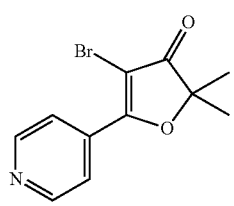

To a room temperature, stirred solution of 2,2-dimethyl-5-(pyridin-4-yl) furan-3(2H)-one (0.81 g, 4.28 mmol) in CHCl$_3$ (20 mL), NBS (1.3 g, 7.28 mmol) was added portionwise. The reaction mixture was then stirred for 2 h and diluted with DCM (100 mL). The combined organic layers were washed with water (50 mL) and brine (50 mL), dried over Na$_2$SO$_4$, filtered, and then concentrated in vacuo to obtain the crude product. The crude material was purified via silica gel column chromatography to afford 4-bromo-2,2-dimethyl-5-(pyridin-4-yl) furan-3(2H)-one (0.25 g, 22%) as a solid.

2,2-Dimethyl-5-(pyridin-4-yl)-4-(4-(quinolin-2-ylmethoxy)phenyl) furan-3(2B)-one (Example 125)

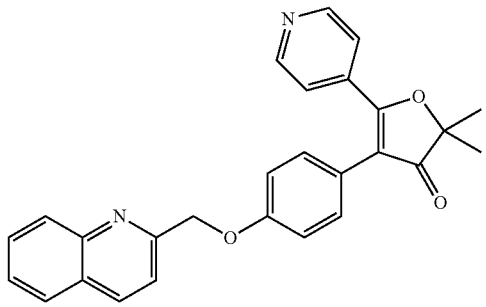 [SMILES: CC1(C)OC(c2ccncc2)=C(c2ccc(OCc3ccc4ccccc4n3)cc2)C1=O]

A solution of 4-bromo-2,2-dimethyl-5-(pyridin-4-yl)furan-3(2H)-one (0.25 g, 0.93 mmol), 2-((4-(4,4,5,5-tetramethyl-1,3,2-dioxaborolan-2-yl)phenoxy)methyl)quinoline (0.37 g, 1.026 mmol), and Cs$_2$CO$_3$ (1.52 g, 4.664 mmol) in 5:1 toluene/water (12 mL) was degassed. Then, Pd(dppf)Cl$_2$ (152.2 mg, 0.18 mmol) was added under an inert atmosphere and the solution was degassed again. The reaction mixture was then refluxed for 3 h, filtered through a pad of Celite® and the filtrate was diluted with EtOAc (100 mL). The combined organics were washed with water (50 mL) and brine (50 mL), dried over Na$_2$SO$_4$, filtered, and concentrated in vacuo to obtain the crude product. The crude material was purified via silica gel column chromatography to afford 2,2-dimethyl-5-(pyridin-4-yl)-4-(4-(quinolin-2-ylmethoxy)phenyl) furan-3(2H)-one (0.29 g, 74%) as a solid. $^1$H NMR (500 MHz, CDCl$_3$): δ 8.78 (d, J=7.2 Hz, 1H), 8.56-8.50 (m, 2H), 8.15-8.05 (m, 2H), 7.78-7.72 (m, 1H), 7.63-7.59 (m, 1H), 7.56-7.47 (m, 2H); 7.18-7.09 (m, 2H), 7.02-6.96 (m, 3H), 5.40 (s, 2H), 1.50 (s, 6H). MS: M$^+$H: m/z=423.1. LC-MS: 98%, Column: Eclipse XDB-C18, 150×4.6 mm, 5 um. Mobile Phase: 0.1% TFA in Water (A), AcN (B), Flow rate: 1.5 ml/min (Gradient).

Synthesis of 7-(pyridin-4-yl)-6-(4-(quinolin-2-ylmethoxy)phenyl)-4-oxaspiro[2.4]hept-6-en-5-one (Example 26)

Ethyl 2-(4-(quinolin-2-ylmethoxy)phenyl)acetate

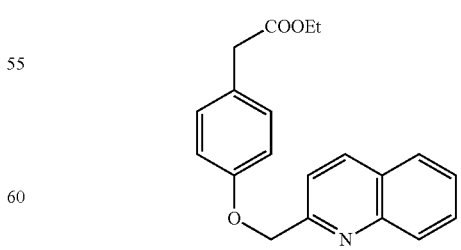

To a stirred solution of ethyl 2-(4-hydroxyphenyl)acetate (20 g, 111.10 mmol) in AcN (200 mL) were added K$_2$CO$_3$ (145.9 g, 333.30 mmol) and 2-(chloromethyl) quinoline (28.50 g, 133.32 mmol) at RT. The reaction mixture was heated at 90° C. for 12 h and then cooled to RT and filtered. The filtrate was concentrated in vacuo. The residue was then diluted with water (100 mL) and extracted with EtOAc (3×100 mL). The combined organic layers were washed with water, a saturated NH₄Cl solution, and then dried over anhydrous Na₂SO₄, filtered and concentrated in vacuo to afford ethyl 2-(4-(quinolin-2-ylmethoxy)phenyl)acetate (38.0 g, 89%) as a solid.

2-(4-(Quinolin-2-ylmethoxy)phenyl)acetic acid

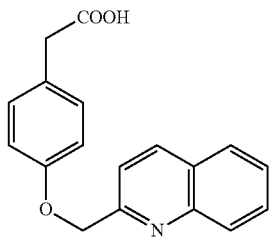 [SMILES: O=C(O)Cc1ccc(OCc2ccc3ccccc3n2)cc1]

To a stirred solution of ethyl 2-(4-(quinolin-2-ylmethoxy)phenyl)acetate (38.0 g, 106.741 mmol) in ethanol (200 mL) and water (100 mL) was added KOH (23.9 g, 426.964 mmol) at room temperature. The mixture was stirred at RT for 4 h and after complete consumption of starting material as monitored by TLC, the reaction mixture was diluted with water (50 mL) and acidified using 1 N HCl at 0° C. The aqueous layer was extracted with EtOAc (2×150 mL) and the combined organic extracts were washed with water (50 mL) and brine (50 mL), dried over anhydrous Na₂SO₄, and evaporated in vacuo to afford 2-(4-(quinolin-2-ylmethoxy)phenyl)acetic acid (30.0 g, 95%) as a white solid.

2-(4-(Quinolin-2-ylmethoxy)phenyl)acetyl chloride

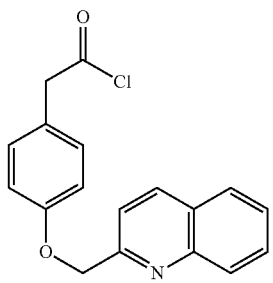 [SMILES: O=C(Cl)Cc1ccc(OCc2ccc3ccccc3n2)cc1]

To a stirred solution of 2-(4-(quinolin-2-ylmethoxy)phenyl)acetic acid (2.0 g, 6.825 mmol) in CHCl₃ (6 mL) was added SOCl₂ (10 mL) at 0° C. and the reaction mixture was stirred at RT for 2 h. The reaction was concentrated in vacuo and the residue was re-dissolved in ether (50 mL). The mixture was concentrated in vacuo again to afford 2-(4-(quinolin-2-ylmethoxy)phenyl)acetyl chloride (2.0 g, 95%) as a light yellow oil.

Methyl 1-(2-(4-(quinolin-2-ylmethoxy)phenyl)acetoxy)cyclopropanecarboxylate

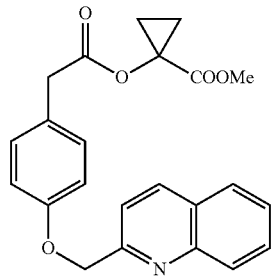 [SMILES: COC(=O)C1(OC(=O)Cc2ccc(OCc3ccc4ccccc4n3)cc2)CC1]

To a stirred solution of 2-(4-(quinolin-2-ylmethoxy)phenyl)acetyl chloride (2.0 g, 6.557 mmol) in DCM (50 mL) was added DMAP (1.4 g, 13.11 mmol) followed by methyl 1-hydroxycyclopropanecarboxylate (1.1 g, 9.836 mmol) under a nitrogen atmosphere at RT. The reaction mixture was stirred for 14 h and after complete consumption of the starting material (by TLC), the reaction mixture was quenched with water (10 mL) and the aqueous layer was extracted with DCM (2×50 mL). The combined organic layers were washed with a saturated NaHCO₃ solution (20 mL) and brine (20 mL), dried over anhydrous Na₂SO₄, filtered and concentrated in vacuo to afford crude methyl 1-(2-(4-(quinolin-2-ylmethoxy)phenyl)acetoxy)cyclopropanecarboxylate (2.0 g) as a solid.

7-Hydroxy-6-(4-(quinolin-2-ylmethoxy)phenyl)-4-oxaspiro[2.4]hept-6-en-5-one

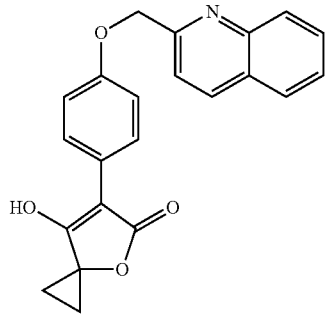 [SMILES: O=C1OC2(CC2)C(O)=C1c1ccc(OCc2ccc3ccccc3n2)cc1]

To a 0° C. solution of methyl 1-(2-(4-(quinolin-2-ylmethoxy)phenyl)acetoxy)cyclopropanecarboxylate (2.0 g, 6.825 mmol) in DMF (20 mL), NaH (49 mg, 20.477 mol) was added and the mixture was stirred at RT for 12 h. After complete consumption of the starting material (monitored by TLC), the reaction mixture was quenched with ice water (3 mL) and the aqueous layer was extracted with EtOAc (2×50 mL). The combined organic layer were washed with water (30 mL) and brine (20 mL), dried over anhydrous Na₂SO₄, filtered and concentrated in vacuo to afford crude 7-hydroxy-6-(4-(quinolin-2-ylmethoxy)phenyl)-4-oxaspiro[2.4]hept-6-en-5-one (2.0 g, 83%) as a light yellow solid.

5-Oxo-6-(4-(quinolin-2-ylmethoxy)phenyl)-4-oxaspiro[2.4]hept-6-en-7-yl trifluoromethanesulfonate

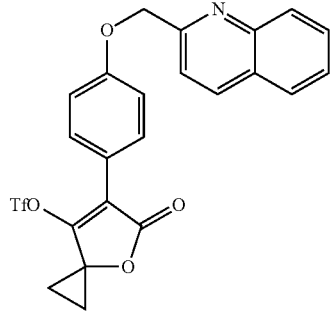 [SMILES: O=C1OC2(CC2)C(OS(=O)(=O)C(F)(F)F)=C1c1ccc(OCc2ccc3ccccc3n2)cc1]

To a 0° C. solution of 7-hydroxy-6-(4-(quinolin-2-ylmethoxy)phenyl)-4-oxaspiro[2.4]hept-6-en-5-one (400 mg, 1.1 mmol) in DCM (15 mL) were added TEA (226 mg, 3.36 mmol) and triflic anhydride (631 mg, 2.2 mol) under an inert atmosphere. The reaction mixture was stirred for 2 h at 0° C., diluted with water and then extracted with DCM (2×50 mL). The combined organic layers were washed with water, dried over Na$_2$SO$_4$ and concentrated in vacuo to afford 5-oxo-6-(4-(quinolin-2-ylmethoxy)phenyl)-4-oxaspiro[2.4]hept-6-en-7-yl trifluoromethanesulfonate (400 mg, 73%) as an ash-colored solid.

7-(Pyridin-4-yl)-6(4-(quinolin-2-ylmethoxy)phenyl)-4-oxaspiro[2.4]hept-6-en-5-one (Example 26)

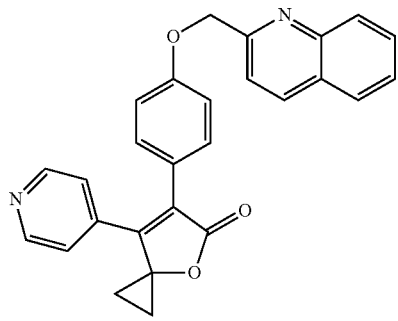 [SMILES: O=C1OC2(CC2)C(c2ccncc2)=C1c1ccc(OCc2ccc3ccccc3n2)cc1]

To a room temperature, stirred solution of 5-oxo-6-(4-(quinolin-2-ylmethoxy)phenyl)-4-oxaspiro[2.4]hept-6-en-7-yl trifluoromethanesulfonate (200 mg, 0.4 mmol) in 1,4-dioxane (10 mL) were added pyridin-4-ylboronic acid (74 mg, 0.6 mmol), Na$_2$CO$_3$ (102 mg, 1.2 mmol) and water (4 mL) under an inert atmosphere. The mixture was stirred for 30 minutes and then Pd(PPh$_3$)$_4$ (46 mg, 0.04 mmol) was added and the mixture refluxed for 16 h. The reaction mixture was then diluted with water and extracted with EtOAc (2×40 mL). The combined organic layers were washed with water, brine, dried over Na$_2$SO$_4$ and concentrated in vacuo to afford 7-(pyridin-4-yl)-6-(4-(quinolin-2-ylmethoxy)phenyl)-4-oxaspiro[2.4]hept-6-en-5-one (30 mg, 18%) as a white solid. $^1$H NMR (500 MHz, d$_6$-DMSO): δ 8.64-8.61 (m, 2H), 8.40 (d, J=7.2 Hz, 1H), 8.02-7.99 (m, 2H), 7.81-7.77 (m, 1H), 7.67-7.51 (m, 3H), 7.38-7.24 (m, 5H), 5.36 (s, 2H), 1.88-1.85 (m, 2H), 1.24-1.21 (m, 2H). MS: M$^+$H: m/z=421.2; M$^+$Na: m/z=443.2. HPLC: 92%, (Condition-I).

Synthesis of 1-methyl-3-morpholino-4-(4-(quinolin-2-ylmethoxy)phenyl)-1H-pyrrole-2,5-dione (Example 812)

3-Bromo-1-methyl-4-morpholino-1H-pyrrole-2,5-dione

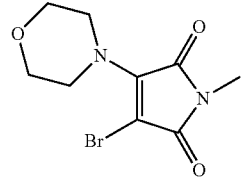

To a room temperature, stirred solution of 2,3-dibromo-N-methylmaleimide (1 g, 0.004 mol) in DMF (10 mL) was added Cs$_2$CO$_3$ (1.34 g, 0.004 mol) followed by morpholine (360 mg, 0.004 mol) under N$_2$ atmosphere. The reaction mixture was then stirred for 30 minutes, quenched with ice water, and extracted with EtOAc (2×50 mL). The combined organic layers were washed with water, dried over anhydrous Na$_2$SO$_4$, filtered and concentrated in vacuo to afford 3-bromo-1-methyl-4-morpholino-1H-pyrrole-2,5-dione (0.87 g, 85%) as a solid.

1-Methyl-3-morpholino-4-(4-(quinolin-2-ylmethoxy)phenyl)-1H-pyrrole-2,5-dione (Example 812)

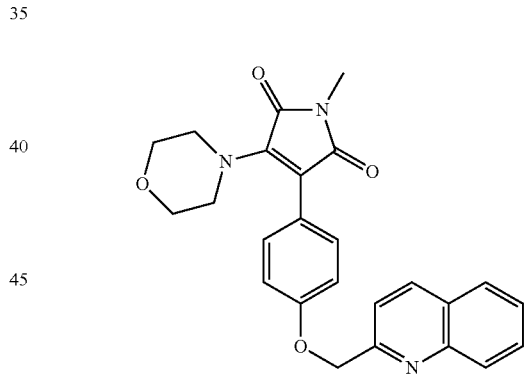

To a stirred solution of 3-bromo-1-methyl-4-morpholino-1H-pyrrole-2,5-dione (100 mg, 0.36 mol) in DMF (40 mL) were added Cs$_2$CO$_3$ (415 mg, 1.27 mmol), water (5 mL), and Pd(Ph$_3$P)$_4$ (84 mg, 0.072 mmol). 2-((4-(4,4,5,5-tetramethyl-1,3,2-dioxaborolan-2-yl)phenoxy)methyl)quinoline (138 mg, 0.38 mmol) was then added and the reaction mixture was heated at 80° C. for 3 h, filtered through a pad of Celite® and the filtrate was then concentrated in vacuo to obtain the crude product. The crude material was purified via silica gel column chromatography eluting with 60% EtOAc in hexanes to afford 1-methyl-3-morpholino-4-(4-(quinolin-2-ylmethoxy)phenyl)-1H-pyrrole-2,5-dione (70 mg, 45%). $^1$H NMR (500 MHz, d$_6$-DMSO): δ 8.42 (d, J=7.2 Hz, 1H), 8.1 (t, J=7.2 Hz, 2H) 7.78 (t, J=7.8 Hz, 1H), 7.70 (d, J=7.2 Hz, 1H), 7.64 (t, J=7.2 Hz, 1H), 7.28 (d, J=7.4 Hz, 2H), 7.12 (d, J=7.4 Hz, 2H), 5.38 (s, 2H), 3.62-3.58 (m, 4H), 3.45-3.39 (m, 4H), 2.96 (s, 3H); MS: M$^+$H: m/z=430.2 HPLC: 96%, (Condition-C).

Synthesis of 1-methyl-3-(4-oxopiperidin-1-yl)-4-(4-(quinolin-2-ylmethoxy)phenyl)-1H-pyrrole-2,5-dione (Example 820)

3-Bromo-1-methyl-4-(4-oxopiperidin-1-yl)-1H-pyrrole-2,5-dione

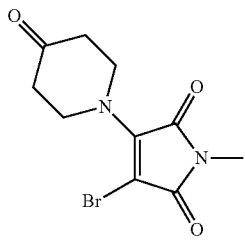 [SMILES: CN1C(=O)C(Br)=C(N2CCC(=O)CC2)C1=O]

To a stirred solution of 3,4-dibromo-1-methyl-1H-pyrrole-2,5-dione (100 mg, 0.373 mmol) in AcN (20 mL) was added piperidin-4-one hydrochloride (101 mg, 0.746 mmol) at room temperature followed by K$_2$CO$_3$ (102 mg, 7.46 mol). The reaction mixture was then refluxed for 2 h, diluted with water, extracted with EtOAc (2×20 mL). The combined organic layers were washed with brine, dried over anhydrous Na$_2$SO$_4$, filtered, and concentrated in vacuo. The crude material was purified via silica gel column chromatography eluting with 30% EtOAc in hexanes to afford 3-bromo-1-methyl-4-(4-oxopiperidin-1-yl)-1H-pyrrole-2,5-dione (100 mg, 99%) as a pale yellow solid.

1-Methyl-3-(4-oxopiperidin-1-yl)-4-(4-(quinolin-2-ylmethoxy)phenyl)-1H-pyrrole-2,5-dione (Example 820)

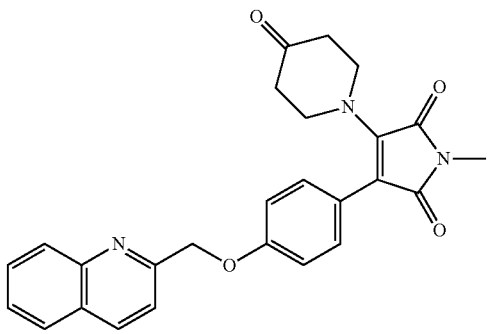 [SMILES: CN1C(=O)C(c2ccc(OCc3ccc4ccccc4n3)cc2)=C(N2CCC(=O)CC2)C1=O]

To a room temperature, stirred solution of 3-bromo-1-methyl-4-(4-oxopiperidin-1-yl)-1H-pyrrole-2,5-dione (100 mg, 0.34 mmol) in 1,4-dioxane (10 mL) was added 2-((4-(4,4,5,5-tetramethyl-1,3,2-dioxaborolan-2-yl)phenoxy)methyl)quinoline (151 mg, 0.41 mol) under a N$_2$ atmosphere. The reaction mixture was stirred for 30 minutes and then Na$_2$CO$_3$ (87 mg, 1.04 mmol), water (4 mL) and Pd(PPh$_3$)$_4$ (40 mg, 0.03 mmol) were added also under a N$_2$ atmosphere. The resulting mixture was then refluxed for 16 h, diluted with water and extracted with EtOAc (2×20 mL). The combined organic layers were washed with brine, dried over anhydrous Na$_2$SO$_4$, filtered, and concentrated in vacuo. The crude material was purified via silica gel column chromatography eluting with 60% EtOAc in hexanes to afford 1-methyl-3-(4-oxopiperidin-1-yl)-4-(4-(quinolin-2-ylmethoxy)phenyl)-1H-pyrrole-2,5-dione (80 mg, 52%) as a solid. $^1$H NMR (500 MHz, d$_6$-DMSO): δ 8.45 (d, J=7.4 Hz, 1H), 8.12 (t, J=7.2 Hz, 2H) 7.79 (t, J=7.2 Hz, 1H), 7.72 (d, J=7.8 Hz, 1H), 7.64 (t, J=7.6 Hz, 1H), 7.18 (d, J=7.2 Hz, 2H), 7.12 (d, J=7.2 Hz, 2H), 5.38 (s, 2H), 3.62-3.58 (m, 4H), 2.96-2.85 (m, 4H), 2.56 (s, 4H). MS: M$^+$: m/z=441.6; M$^+$H: m/z=442.7. HPLC: 97%, (Condition-B).

Synthesis of 2,2-dimethyl-5-(4-nitrophenyl)-4-(4-(quinolin-2-ylmethoxy)phenyl) furan-3(2H)-one (Example 164)

4-Methyl-1-(4-nitrophenyl) pent-2-yne-1,4-diol

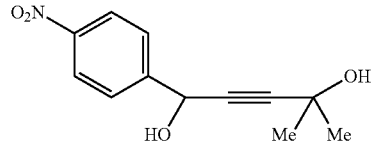 [SMILES: CC(C)(O)C#CC(O)c1ccc([N+](=O)[O-])cc1]

To a stirred −78° C. solution of 2-methylbut-3-yn-2-ol (6.1 mL, 63.5 mmol, 1.2 eq) in dry THF (250 mL), n-BuLi (62 mL, 2.3 M in hexane, 142 mmol, 2.7 eq) was added dropwise over 10 minutes under an inert atmosphere. After being stirred for 40 min at −78° C., a solution of 4-nitrobenzaldehyde (8 g, 52.9 mmol, 1 eq) in dry THF (50 mL) was added to the reaction mixture and stirring was continued for an additional 1 h at −78° C. The reaction mixture was then quenched with a saturated NH$_4$Cl solution and extracted with EtOAc (2×200 mL). The combined organic layers were washed with water (200 mL) and brine (100 mL), dried over Na$_2$SO$_4$, filtered, and concentrated in vacuo. The resulting residue was purified by column chromatography (30% ethyl acetate in hexanes) to afford 4-methyl-1-(4-nitrophenyl)pent-2-yne-1,4-diol (8 g, 65%) as a yellow solid.

4-Hydroxy-4-methyl-1-(4-nitrophenyl)pent-2-yn-1-one

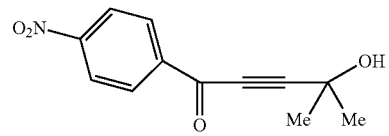 [SMILES: CC(C)(O)C#CC(=O)c1ccc([N+](=O)[O-])cc1]

To a room temperature solution of 4-methyl-1-(4-nitrophenyl) pent-2-yne-1,4-diol (2 g, 8.51 mmol, 1 eq) in dry DCM (100 mL) was added NaHCO$_3$ (680 mg, 8.51 mmol, 1 eq) followed by Dess Martin Periodinane (9.2 g, 21.27 mmol, 2.5 eq). The reaction mixture was stirred at RT for 16 h. After completion of the reaction (as monitored by TLC), the reaction mixture was quenched with a saturated sodium bisulfite solution and extracted with DCM (2×100 mL). The combined organic layers were washed with water (100 mL) and brine (100 mL), dried over Na$_2$SO$_4$, filtered, and concentrated in vacuo to obtain the crude product. The crude material was purified via silica gel column chromatography eluting with 20% EtOAc in hexanes to afford 4-hydroxy-4-methyl-1-(4-nitrophenyl) pent-2-yn-1-one (1.7 g, 86%) as an oil.

2,2-Dimethyl-5-(4-nitrophenyl) furan-3(2H)-one

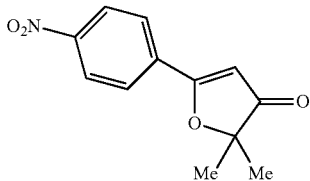 [SMILES: CC1(C)OC(c2ccc([N+](=O)[O-])cc2)=CC1=O]

To a stirred solution of 4-hydroxy-4-methyl-1-(4-nitrophenyl) pent-2-yn-1-one (1.74 g, 7.46 mmol, 1 eq) in ethanol (30 mL), a solution of diethylamine (778 mg, 7.46 mmol, 1 eq) in EtOH (5 mL) was added dropwise at RT. The reaction mixture was then stirred for additional 90 min. The ethanol was removed, and the mixture was then diluted with EtOAc (100 mL). The combined organic layers were washed with water (50 mL) and brine (20 mL), dried over $Na_2SO_4$, filtered, and concentrated in vacuo to afford 2,2-dimethyl-5-(4-nitrophenyl) furan-3(2H)-one (1.6 g, 92%) which was used in the next step without further purification.

4-Bromo-2,2-dimethyl-5-(4-nitrophenyl) furan-3(2H)-one

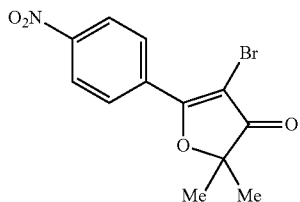 [SMILES: CC1(C)OC(c2ccc([N+](=O)[O-])cc2)=C(Br)C1=O]

To a 0° C. stirred solution of crude 2,2-dimethyl-5-(4-nitrophenyl) furan-3(2H)-one (170 mg, 0.73 mmol, 1 eq) in $CHCl_3$ (10 mL) was added NBS (259 mg, 1.45 mmol, 2 eq), and the reaction mixture was then stirred at RT for 2 h. The chloroform was removed and the crude material was then purified via silica gel column chromatography eluting with 10% EtOAc in hexanes to afford 4-bromo-2,2-dimethyl-5-(4-nitrophenyl) furan-3(2H)-one (100 mg, 44%) as a yellow solid.

2,2-Dimethyl-5-(4-nitrophenyl)-4-(4-(quinolin-2-ylmethoxy)phenyl) furan-3(2H)-one (Example 164)

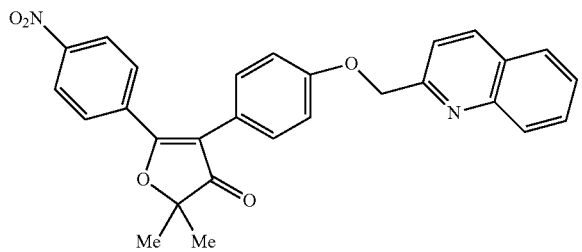 [SMILES: CC1(C)OC(c2ccc([N+](=O)[O-])cc2)=C(c2ccc(OCc3ccc4ccccc4n3)cc2)C1=O]

A solution of 4-bromo-2,2-dimethyl-5-(4-nitrophenyl) furan-3(2H)-one (100 mg, 0.32 mmol, 1 eq), 2-((4-(4,4,5,5-tetramethyl-1,3,2-dioxaborolan-2-yl)phenoxy)methyl) quinoline (115 mg, 0.32 mmol, 1 eq), and $Cs_2CO_3$ (521 mg, 1.6 mmol, 5 eq) in toluene (7 mL) and water (2.5 mL) was degassed. Then Pd (dppf)$Cl_2$ (52 mg, 0.06 mmol, 0.2 eq) was added under an inert atmosphere and the solution was again degassed. The reaction mixture was then refluxed for 3 h, filtered through a pad of Celite®, and the filtrate was diluted with EtOAc (30 mL). The combined organic layers were washed with water (20 mL) and brine (10 mL), dried over $Na_2SO_4$, filtered, and concentrated in vacuo to obtain the crude product. The crude material was purified via silica gel column chromatography (10% ethyl acetate in hexanes) to afford 2,2-dimethyl-5-(4-nitrophenyl)-4-(4-(quinolin-2-ylmethoxy)phenyl) furan-3(2H)-one (80 mg, 54%) as a solid. $^1$H NMR (400 MHz, $d_6$-DMSO): δ 8.42 (d, J=8.5 Hz, 1H), 8.27 (d, J=8.5 Hz, 2H), 8.00 (t, J=7.9 Hz, 2H), 7.82-7.76 (m, 3H), 7.68 (d, J=8.5 Hz, 1H), 7.61 (t, J=7.2 Hz, 1H), 7.18 (d, J=8.7 Hz, 2H), 7.10 (d, J=8.7 Hz, 2H), 5.38 (s, 2H), 1.48 (s, 6H). MS: [M+H]: m/z=467.1. HPLC: 89%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of 5-(4-chlorophenyl)-2,2-dimethyl-4-(4-(quinolin-2-ylmethoxy)phenyl) furan-3(2H)-one (Example 147)

1-(4-Chlorophenyl)-4-methyl-4-(trimethylsilyloxy) pent-2-yn-1-one

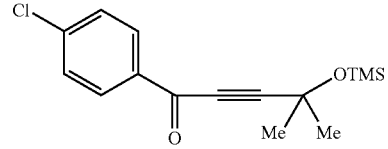

To a −78° C. stirred solution of trimethyl (2-methylbut-3-yn-2-yloxy) silane (11.79 g, 75.15 mmol) in dry THF (100 mL), n-BuLi (14.08 mL, 22.54 mmol, 1.6 M in hexane) was added dropwise over 10 minutes under an inert atmosphere. After being stirred for 30 min at −78° C., a solution of 4-chloro-N-methoxy-N-methylbenzamide (5.0 g, 25.0 mmol) in dry THF (10 mL) was added to reaction mixture and stirring was continued for an additional 1 h at −78° C. The reaction mixture was quenched with a saturated $NH_4C$ solution and extracted with EtOAc (2×100 mL). The combined organic layers were washed with water (50 mL) and brine (50 mL), dried over $Na_2SO_4$, filtered and concentrated in vacuo to obtain the crude product. The crude material was purified via silica gel column chromatography elating with 5-7% EtOAc in hexanes to afford 1-(4-chlorophenyl)-4-methyl-4-(trimethylsilyloxy)pent-2-yn-1-one (3.8 g, 57%) as a light green oil.

1-(4-Chlorophenyl)-4-hydroxy-4-methylpent-2-yn-1-one

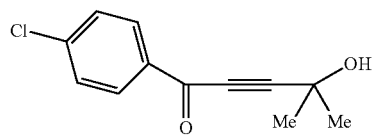 [SMILES: CC(C)(O)C#CC(=O)c1ccc(Cl)cc1]

To a stirred solution of 1-(4-chlorophenyl)-4-methyl-4-(trimethylsilyloxy)pent-2-yn-1-one (3.7 g, 12.50 mmol) in DCM (20 mL) was added PTSA (2.87 g, 15.01 mmol) at RT. The reaction mixture was stirred for 1 h and diluted with water (10 mL). The combined organic layers were washed with a saturated NaHCO$_3$ solution and water, dried over Na$_2$SO$_4$, filtered, and then concentrated in vacuo to afford 1-(4-chlorophenyl)-4-hydroxy-4-methylpent-2-yn-1-one (2.40 g) as a pale red oil.

5-(4-Chlorophenyl)-2,2-dimethylfuran-3(2H)-one

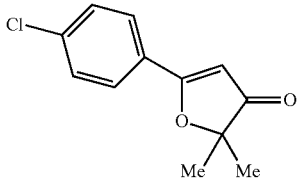 [SMILES: CC1(C)OC(c2ccc(Cl)cc2)=CC1=O]

To a stirred solution of 1-(4-chlorophenyl)-4-hydroxy-4-methylpent-2-yn-1-one (2.4 g, 10.70 mmol) in ethanol (20 mL), a solution of diethyl amine (1.34 mL, 12.90 mmol) in EtOH (5 mL) was added dropwise at RT. The reaction mixture was then stirred for additional 30 min. The ethanol was then removed and the mixture was diluted with EtOAc (50 mL). The combined organic layers were then washed with water (10 mL), and brine (10 mL), dried over Na$_2$SO$_4$, filtered, and concentrated in vacuo to afford 5-(4-chlorophenyl)-2,2-dimethylfuran-3(2H)-one (2.1 g) as a light green gummy oil.

4-Bromo-5-(4-chlorophenyl)-2,2-dimethylfuran-3(2H)-one

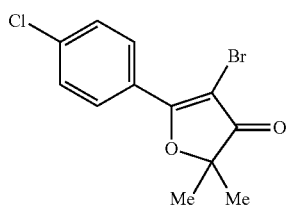 [SMILES: CC1(C)OC(c2ccc(Cl)cc2)=C(Br)C1=O]

To stirred solution of crude 5-(4-chlorophenyl)-2,2-dimethylfuran-3(2H)-one (2.1 g, 13.0 mmol) in CHCl$_3$ (15 mL), NBS (3.93 g, 22.10 mmol) was added portionwise at RT. The reaction mixture was stirred for 1 h and then diluted with DCM (100 mL). The combined organic layers were washed with water (50 mL) and brine (30 mL), dried over Na$_2$SO$_4$, filtered, and then concentrated in vacuo to obtain the crude product. The crude material was purified via silica gel column chromatography to afford 4-bromo-5-(4-chlorophenyl)-2,2-dimethylfuran-3(2H)-one (2.0 g, 51% over three steps) as an off-white solid.

5-(4-Chlorophenyl)-2,2-dimethyl-4-(4-(quinolin-2-ylmethoxy)phenyl) furan-3(2H)-one (Example 147)

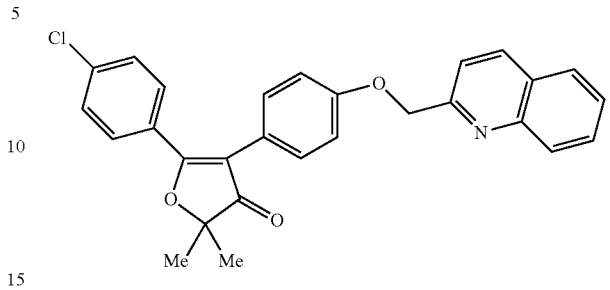

A solution of 4-bromo-5-(4-chlorophenyl)-2,2-dimethylfuran-3(2H)-one (1.0 g, 3.30 mmol), 2-((4-(4,4,5,5-tetramethyl-1,3,2-dioxaborolan-2-yl)phenoxy)methyl)quinoline (1.30 g, 3.60 mmol), and Cs$_2$CO$_3$ (5.37 g, 16.50 mmol) in toluene (10 mL) and water (5 mL) was degassed. Then, Pd(dppf)C$_2$ (0.54 g, 0.601 mmol) was added under an inert atmosphere and the solution was degassed again. The reaction mixture was then refluxed for 2 h, filtered through a pad of Celite®, and the filtrate was diluted with EtOAc (40 mL). The combined organic layers were washed with water (20 mL) and brine (20 mL), dried over Na$_2$SO$_4$, filtered, and concentrated in vacuo to obtain the crude product. The crude material was purified via silica gel column chromatography to afford 5-(4-chlorophenyl)-2,2-dimethyl-4-(4-(quinolin-2-ylmethoxy)phenyl) furan-3(2H)-one (520 mg, 35%) as a pale yellow solid. $^1$H NMR (500 MHz, d$_6$-DMSO): δ 8.44 (d, J=8.5 Hz, 1H), 8.02 (t, J=7.9 Hz, 2H), 7.81 (t, J=8.4 Hz, 1H), 7.70 (d, J=8.2 Hz, 1H), 7.63 (t, J=8.2 Hz, 1H), 7.58 (d, J=8.5 Hz, 2H), 7.52 (d, J=8.5 Hz, 2H), 7.18 (d, J=7.4 Hz, 2H), 7.11 (d, J=7.5 Hz, 2H), 5.39 (s, 2H), 1.44 (s, 6H). MS: [M+Na]: m/z=478.1, [M+H]: m/z=456.1. HPLC: 97%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of 4-(5,5-dimethyl-4-oxo-3-(4-(quinolin-2-ylmethoxy)phenyl)-4,5-dihydrofuran-2-yl)benzonitrile (Example 141)

4-Cyano-N-methoxy-N-methylbenzamide

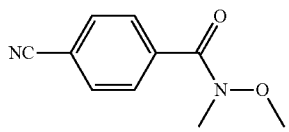

To a stirred solution of 4-cyanobenzoic acid (5.0 g, 34.0 mmol) in DCM (75 mL) were added HATU (19.40 g, 51.0 mmol), N-methoxy, N-methylamine (4.90 g, 51.0 mmol) and TEA (14.30 mL, 102.0 mmol) at RT under a nitrogen atmosphere. The reaction mixture was then stirred at RT for 3 h, diluted with water and the aqueous layer was extracted with DCM (3×100 mL). The combined organic extracts were washed with water (60 mL) and brine (30 mL), dried over anhydrous Na$_2$SO$_4$, filtered and evaporated under reduced pressure to afford 4-cyano-N-methoxy-N-methylbenzamide (6.2 g, 96%) as a yellow color oil.

4-(4-Methyl-4-(trimethylsilyloxy)pent-2-ynoyl)benzonitrile

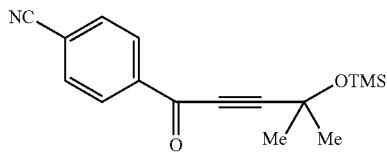

To a −78° C. stirred solution of trimethyl (2-methylbut-3-yn-2-yloxy) silane (3.3 g, 20.00 mmol) in dry THF (45 mL), n-BuLi (4.1 mL, 9.00 mmol, 1.6 M in hexane) was added dropwise over 10 minutes under an inert atmosphere. The reaction mixture was stirred for 30 min at −78° C., and then a solution of 4-cyano-N-methoxy-N-methylbenzamide (2.0 g, 10.00 mmol) in dry THF (15 mL) was added to the reaction mixture and stirring was continued for an additional 1 h at −78° C. The reaction mixture was quenched with a saturated NH$_4$Cl solution and extracted with EtOAc (2×100 mL). The combined organic layers were washed with water (50 mL) and brine (50 mL), dried over Na$_2$SO$_4$, filtered, and concentrated in vacuo to obtain the crude product. The crude material was purified via silica gel column chromatography eluting with 15% EtOAc in hexanes to afford 4-(4-methyl-4-(trimethylsilyloxy)pent-2-ynoyl)benzonitrile (3.8 g, 68%) as a yellow oil.

4-(4-Hydroxy-4-methylpent-2-ynoyl)benzonitrile

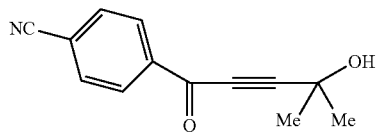 [SMILES: CC(C)(O)C#CC(=O)c1ccc(C#N)cc1]

To a stirred solution of 4-(4-methyl-4-(trimethylsilyloxy)pent-2-ynoyl)benzonitrile (1.7 g, 5.00 mmol) in DCM (15 mL) was added PTSA (1.70 g, 8.90 mmol) at RT and the reaction mixture was stirred for 30 min. The reaction mixture was diluted with water (10 mL) and extracted with DCM (2×50 mL). The combined organic layers were washed with a saturated NaHCO$_3$ solution and water, dried over Na$_2$SO$_4$, filtered, and then concentrated in vacuo to afford 4-(4-hydroxy-4-methylpent-2-ynoyl)benzonitrile (1.20 g) as a yellow oil.

4-(5,5-Dimethyl-4-oxo-4,5-dihydrofuran-2-yl)benzonitrile

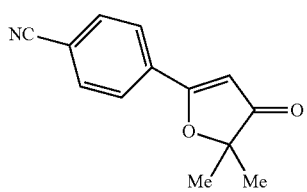 [SMILES: CC1(C)OC(c2ccc(C#N)cc2)=CC1=O]

To a stirred solution of crude 4-(4-hydroxy-4-methylpent-2-ynoyl)benzonitrile (1.2 g, 5.60 mmol) in ethanol (12 mL), a solution of diethyl amine (0.58 mL, 5.60 mmol) in EtOH (5 mL) was added dropwise at RT. The reaction mixture was then stirred for additional 1 h. The ethanol was removed and the mixture then diluted with EtOAc (50 mL). The combined organic layers were washed with water (10 mL), brine (10 mL), dried over Na$_2$SO$_4$, filtered, and concentrated in vacuo to afford crude 4-(5,5-dimethyl-4-oxo-4,5-dihydrofuran-2-yl)benzonitrile (1.2 g) as a light green semi solid which was taken on to the next step without further purification.

4-(3-Bromo-5,5-dimethyl-4-oxo-4,5-dihydrofuran-2-yl)benzonitrile

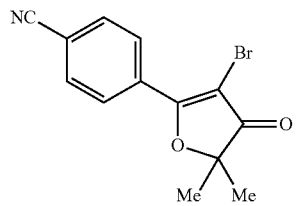 [SMILES: CC1(C)OC(c2ccc(C#N)cc2)=C(Br)C1=O]

To a stirred solution of 4-(5,5-dimethyl-4-oxo-4, 5-dihydrofuran-2-yl)benzonitrile (1.2 g, 5.60 mmol) in CHCl$_3$ (12 mL), NBS (1.1 g, 6.00 mmol) was added portionwise at RT.

The reaction mixture was then stirred for 3 h and diluted with DCM (100 mL). The combined organic layers were washed with water (30 mL) and brine (30 mL), dried over Na$_2$SO$_4$, filtered, and then concentrated in vacuo to obtain the crude product. The crude material was purified via silica gel column chromatography to afford 4-(3-bromo-5,5-dimethyl-4-oxo-4,5-dihydrofuran-2-yl)benzonitrile (0.50 g, 31%) as an off white solid.

4-(5,5-Dimethyl-4-oxo-3-(4-(quinolin-2-ylmethoxy)phenyl)-4,5-dihydrofuran-2-yl)benzonitrile (Example 141)

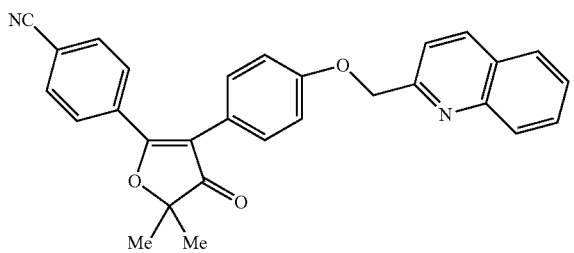 [SMILES: CC1(C)OC(c2ccc(C#N)cc2)=C(c2ccc(OCc3ccc4ccccc4n3)cc2)C1=O]

A solution of 4-(3-bromo-5,5-dimethyl-4-oxo-4,5-dihydrofuran-2-yl)benzonitrile (0.3 g, 1.03 mmol), 2-((4-(4,4,5,5-tetramethyl-1,3,2-dioxaborolan-2-yl)phenoxy)methyl)quinoline (0.374 g, 1.03 mmol), and Cs$_2$CO$_3$ (1.70 g, 5.14 mmol) in toluene (7 mL) and water (2.5 mL) was degassed. Then, Pd(dppf)Cl$_2$ (0.17 g, 0.20 mmol) was added under an inert atmosphere and the solution was again degassed. Then the reaction was refluxed for 2 h. The reaction mixture was then filtered through a pad of Celitc® and the filtrate was diluted with EtOAc (40 mL). The combined organic layers were washed with water (20 mL) and brine (20 mL), dried over Na$_2$SO$_4$, filtered, and concentrated in vacuo to obtain the crude product. The crude material was purified via silica gel column chromatography to afford 4-(5,5-dimethyl-4-oxo-3-

(4-(quinolin-2-ylmethoxy)phenyl)-4,5-dihydrofuran-2-yl)benzonitrile (280 mg, 61%) as a pale yellow solid. ¹H NMR (400 MHz, d₆-DMSO): δ 8.42 (d, J=8.5 Hz, 1H), 8.01 (t, J=7.9 Hz, 2H), 7.90 (d, J=8.4 Hz, 2H), 7.78 (t, J=8.3 Hz, 1H), 7.72-7.67 (m, 3H), 7.62 (t, J=8.3 Hz, 1H), 7.16 (d, J=8.8 Hz, 2H), 7.10 (d, J=8.8 Hz, 2H), 5.38 (s, 2H), 1.46 (s, 6H). MS: [M+H]: m/z=447.5. HPLC: 98%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of 5-Benzo[c][1,2,5]oxadiazol-5-yl)-2,2-dimethyl-4-(4-(quinolin-2-ylmethoxy)phenyl)furan-3(2H)-one (Example 166)

4-Bromo-2-nitroaniline

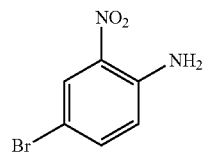 [SMILES: Nc1ccc(Br)cc1[N+](=O)[O-]]

To a stirred solution of 2-nitroaniline (10.0 g, 72.462 mmol) in AcOH (50 mL) was added NBS (12.0 g, 72.463 mmol) at 0° C. under a N₂ atmosphere. The reaction mixture was stirred at 40° C. for 30 min. After completion of starting material (monitored by TLC), reaction mixture was diluted with water and a white precipitate was formed. After filtration, the crude solid was recrystalised from n-hexanes to afford 4-bromo-2-nitroaniline (12 g, 76%), as a brown solid.

5-Bromobenzo[c][1,2,5]oxadiazole 1-oxide

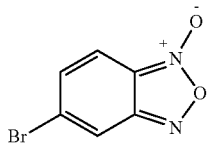

To a room temperature, stirred solution of 4-bromo-2-nitroaniline (8.0 g, 37.037 mmol) in EtOH (80 mL) was added KOH (6.20 g, 111.111 mmol) and the reaction mixture was stirred at 60° C. for 2 h. The reaction was then cooled to 0° C. and NaOCl (80 mL) was added. The reaction mixture was then stirred at RT for another 2 h. After consumption of starting material (monitored by TLC), the reaction mixture was filtered, washed with water, and dried in vacuo to afford 5-bromobenzo[c][1,2,5]oxadiazole 1-oxide (7.0 g, 88%) as a light yellow solid.

5-Bromobenzo[c][1,2,5]oxadiazole

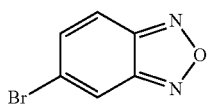

To a stirred solution of 5-bromobenzo[c][1,2,5]oxadiazole 1-oxide (6.0 g, 28.436 mmol) in ethanol (60 mL) was added triethyl phosphite (6.2 mL, 34.123 mmol) at RT under an inert atmosphere. The reaction mixture was then heated at 60° C. for 1 h., cooled to RT, diluted with hexane (100 mL) and stirred for 10 min. The precipitated solid was filtered off and the filtrate was concentrated in vacuo to obtain the crude product. The crude material was purified via silica gel column chromatography to afford 5-bromobenzo[c][1,2,5]oxadiazole (4.0 g, 71%) as a light yellow solid.

Benzo[c][1,2,5]oxadiazole-5-carbonitrile

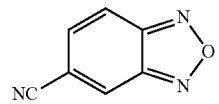 [SMILES: N#Cc1ccc2nonc2c1]

To a stirred solution of 5-bromobenzo[c][1, 2, and 5]oxadiazole (2.0 g, 10.050 mmol) in DMF (50 mL) was added CuCN (1.79 g, 230.10 mmol) at RT under an inert atmosphere. The reaction mixture was then heated at 140° C. for 24 h., cooled to RT, diluted with water (10 mL) and stirred for 10 min. The precipitated solid was filtered off and the filtrate was concentrated in vacuo to obtain the crude product. The crude material was purified via silica gel column chromatography to afford benzo[c][1,2,5]oxadiazole-5-carbonitrile (0.7 g, 48%) as a yellow solid.

Ethyl benzo[c][1,2,5]oxadiazole-5-carboxylate

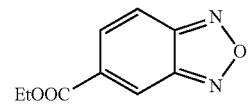

To a solution of benzo[c][1,2,5]oxadiazole-5-carbonitrile (700 mg, 1.33 mol) in EtOH (100 mL) was added H₂SO₄ (20 mL) and the reaction mixture was refluxed for 14 h. The reaction was concentrated in vacuo and the residue was diluted with water (50 mL), and extracted with DCM (2×100 mL). The combined organic layers were dried over magnesium sulfate, filtered, and then concentrated in vacuo to afford ethyl benzo[c][1,2,5]oxadiazole-5-carboxylate (0.7 g, 75%) as a yellow, sticky solid.

Benzo[c][1,2,5]oxadiazole-5-carboxylic acid

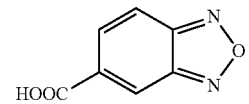 [SMILES: O=C(O)c1ccc2nonc2c1]

To a room temperature, stirred solution of ethyl benzo[c][1,2,5]oxadiazole-5-carboxylate (0.7 g, 3.626 mmol) in MeOH (30 mL) was added 10% NaOH solution (6 mL) and the reaction mixture was then stirred at 40° C. for 3 h. The

N-Methoxy-N-methylbenzo[c][1,2,5]oxadiazole-5-carboxamide

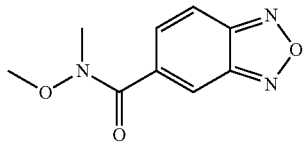

To a stirred solution of benzo[c][1,2,5]oxadiazole-5-carboxylic acid (0.49 g, 2.987 mmol) in DCM (50 mL) were added HATU (1.7 g, 4.481 mmol), N-methoxy, N-methylamine (0.44 g, 4.481 mmol) and TEA (914 mg, 8.963 mmol) at RT under a nitrogen atmosphere. The reaction mixture was then stirred at RT for 3 h, diluted with water and the aqueous layer was extracted with DCM (3×50 mL). The combined organic extracts were washed with water (50 mL) and brine (20 mL), dried over anhydrous $Na_2SO_4$, filtered, and evaporated under reduced pressure to afford N-methoxy-N-methylbenzo[c][1,2,5]oxadiazole-5-carboxamide (0.49 g, 79%) as a yellow oil.

1-(Benzo[c][1,2,5]oxadiazol-5-yl)-4-methyl-4-(trimethylsilyloxy)pent-2-yn-1-one

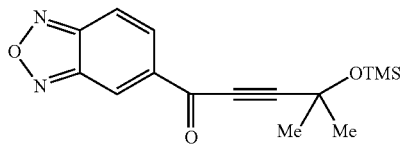

To a −78° C. stirred solution of trimethyl(2-methylbut-3-yn-2-yloxy)silane (0.49 g, 2.367 mmol) in dry THF (20 mL), n-BuLi (3.70 mL, 5.917 mmol, 1.6 M in hexane) was added dropwise over 10 minutes under an inert atmosphere. The reaction mixture was stirred for 30 min at −78° C., and then a solution of N-methoxy-N-methylbenzo[c][1,2,5]oxadiazole-5-carboxamide (0.557 g, 3.550 mmol) in dry THF (10 mL) was added to reaction mixture and stirring was continued for an additional 3 h at −78° C. The reaction mixture was quenched with a saturated $NH_4Cl$ solution and extracted with EtOAc (2×20 mL). The combined organic layers were washed with water (10 mL) and brine (10 mL), dried over $Na_2SO_4$, filtered and concentrated in vacuo to obtain the crude product. The crude material was purified via silica gel column chromatography eluting with 5% EtOAc in hexanes to afford 1-(benzo[c][1,2,5]oxadiazol-5-yl)-4-methyl-4-(trimethylsilyloxy)pent-2-yn-1-one (0.45 g, 63%) as a colorless oil.

1-(Benzo[c][1,2,5]oxadiazol-5-yl)-4-hydroxy-4-methylpent-2-yn-1-one

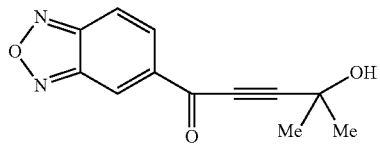 [SMILES: CC(C)(O)C#CC(=O)c1ccc2nonc2c1]

To a stirred solution of 1-(benzo[c][1,2,5]oxadiazol-5-yl)-4-methyl-4-(trimethylsilyloxy)pent-2-yn-1-one (0.45 g, 1.490 mmol) in DCM (15 mL) was added p-TSA (0.341 g, 1.790 mmol) at RT and the reaction mixture was stirred for 3 h. The reaction mixture was then diluted with water (5 mL) and the layers were separated. The combined organic layers were washed with a saturated $NaHCO_3$ solution and water, dried over $Na_2SO_4$, filtered, and then concentrated in vacuo to afford 1-(benzo[c][1,2,5]oxadiazol-5-yl)-4-hydroxy-4-methylpent-2-yn-1-one (0.3 g, 87%) as an oil.

5-(Benzo[c][1,2,5]oxadiazol-5-yl)-2,2-dimethylfuran-3(2H)-one

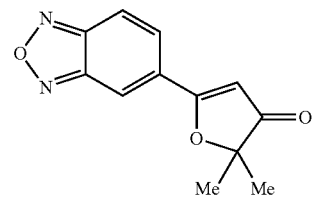 [SMILES: CC1(C)OC(c2ccc3nonc3c2)=CC1=O]

To a stirred solution of 1-(benzo[c][1,2,5]oxadiazol-5-yl)-4-hydroxy-4-methylpent-2-yn-1-one (0.3 g, 1.304 mmol) in ethanol (15 mL), a solution of diethyl amine (0.095 g, 1.304 mmol) in EtOH (5 mL) was added dropwise at RT. The reaction mixture was then stirred for 2 h. The ethanol was then removed, and the mixture was diluted with EtOAc (10 mL). The combined organic layers were washed with water (5 mL) and brine (10 mL), dried over $Na_2SO_4$, filtered, and concentrated in vacuo to afford 5-(benzo[c][1,2,5]oxadiazol-5-yl)-2,2-dimethylfuran-3(2H)-one (0.25 g, 83%) as a black oil.

5-(Benzo[c][1,2,5]oxadiazol-5-yl)-4-bromo-2,2-dimethylfuran-3(2H)-one

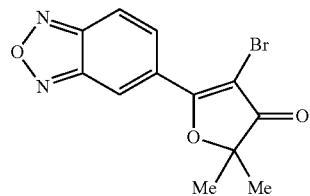

To a stirred solution of 5-(benzo[c][1,2,5]oxadiazol-5-yl)-2,2-dimethylfuran-3(2H)-one (0.25 g, 1.086 mmol) in $CHCl_3$ (15 mL), NBS (0.29 g, 1.630 mmol) was added portionwise at RT. The reaction mixture was then stirred for 3 h and diluted with DCM (10 mL). The organic layer was then washed with water (5 mL) and brine (10 mL), dried over $Na_2SO_4$, filtered, and then concentrated in vacuo to obtain the crude product. The crude material was purified via silica gel column chromatography to afford 5-(benzo[c][1,2,5]oxadiazol-5-yl)-4-bromo-2,2-dimethylfuran-3(2H)-one (0.2 g, 60%) as a yellow solid.

5-(Benzo[c][1,2,5]oxadiazol-5-yl)-2,2-dimethyl-4-(4-(quinolin-2-ylmethoxy)phenyl)furan-3(2H)-one (Example 166)

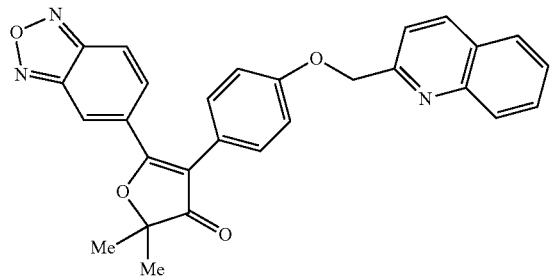 [SMILES: CC1(C)OC(c2ccc3nonc3c2)=C(c2ccc(OCc3ccc4ccccc4n3)cc2)C1=O]

A solution of 5-(Benzo[c][1,2,5]oxadiazol-5-yl)-4-bromo-2,2-dimethylfuran-3(2H)-one (0.2 g, 0.645 mmol), 2-((4-(4,4,5,5-tetramethyl-1,3,2-dioxaborolan-2-yl)phenoxy)methyl)quinoline (0.256 g, 0.709 mmol), and $Cs_2CO_3$ (1.0 g, 3.220 mmol) in toluene (10 mL) and water (5 mL) was degassed. Then, Pd(dppf)$Cl_2$ (0.105 g, 0.129 mmol) was added under an inert atmosphere and the solution was again degassed. Then the reaction mixture was refluxed for 12 h, filtered through a pad of Celite® and the filtrate was diluted with EtOAc (20 mL). The combined organic layers were washed with water (10 mL) and brine (10 mL), dried over $Na_2SO_4$, filtered, and concentrated in vacuo to obtain the crude product. The crude material was purified via silica gel column chromatography to afford 5-(benzo[c][1,2,5]oxadiazol-5-yl)-2,2-dimethyl-4-(4-(quinolin-2-ylmethoxy)phenyl)furan-3(2H)-one (170 mg, 57%) as a yellow color solid. $^1$H NMR (500 MHz, $d_6$-DMSO): δ 8.44 (d, J=8.5 Hz, 1H), 8.39 (s, 1H), 8.07-8.00 (m, 3H), 7.81 (t, J=8.4 Hz, 1H), 7.70 (d, J=8.2 Hz, 1H), 7.64 (t, J=8.2 Hz, 1H), 7.48 (d, J=8.5 Hz, 2H), 7.25 (d, J=8.3 Hz, 2H), 7.12 (d, J=8.4 Hz, 2H), 5.39 (s, 2H), 1.49 (s, 6H). MS: [M+H]: m/z=464.2. HPLC: 93%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of 5-(benzo[c][1,2,5]thiadiazol-5-yl)-2,2-dimethyl-4-(4-(quinolin-2-ylmethoxy)phenyl)furan-3 (2H)-one (Example 167)

N-Methoxy-N-methylbenzene[c][1,2,5]thiadiazole-5-carboxamide

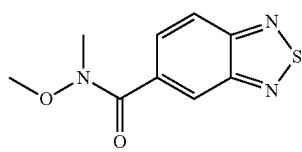

To a stirred solution of benzo[c][1,2,5]thiadiazole-5-carboxylic acid (1.0 g, 5.556 mmol) in DCM (20 mL) were added HATU (3.1 g mg, 8.334 mmol), N-methoxy methylamine (0.58 g, 8.334 mmol) and TEA (1.7 g, 16.666 mmol) at RT under a nitrogen atmosphere. The reaction mixture was then stirred at RT for 3 h, diluted with water and the aqueous layer was extracted with DCM (3×50 mL). The combined organic extracts were washed with water (50 mL) and brine (20 mL), dried over anhydrous $Na_2SO_4$, filtered, and evaporated under reduced pressure to afford N-methoxy-N-methylbenzene[c][1,2,5]thiadiazole-5-carboxamide (1.14 g, 95%) as a light yellow solid.

1-(benzo[c][1,2,5]thiadiazol-5-yl)-4-methyl-4-(trimethylsilyloxy)pent-2-yn-1-one

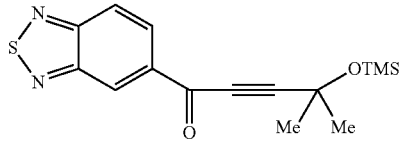

To a −78° C. stirred solution of trimethyl(2-methylbut-3-yn-2-yloxy)silane (0.557 g, 3.636 mmol) in dry THF (50 mL), n-BuLi (5.0 mL, 4.484 mmol, 1.6 M in hexane) was added dropwise over 10 minutes under an inert atmosphere. The reaction mixture was stirred for 30 min at −78° C., and then a solution N-methoxy-N-methylbenzene[c][1,2,5]thiadiazole-5-carboxamide (1.0 g, 2.242 mmol) in dry THF (10 mL) was added to the reaction mixture and stirring was continued for an additional 3 h at −78° C. The reaction mixture was quenched with a saturated $NH_4Cl$ solution and extracted with EtOAc (2×40 mL). The combined organic layers were washed with water (20 mL) and brine (20 mL), dried over $Na_2SO_4$, filtered, and concentrated in vacuo to obtain the crude product. The crude material was purified via silica gel column chromatography eluting with 5% EtOAc in hexanes to afford 1-(benzo[c][1,2,5]thiadiazol-5-yl)-4-methyl-4-(trimethylsilyloxy)pent-2-yn-1-one (1.0 g, 76%) as a yellow oil.

1-(Benzo[c][1,2,5]thiadiazol-5-yl)-4-hydroxy-4-methylpent-2-yn-1-one

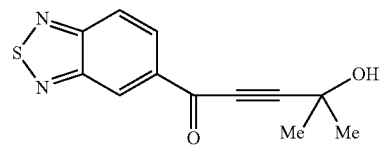 [SMILES: CC(C)(O)C#CC(=O)c1ccc2nsnc2c1]

To a stirred solution of 1-(benzo[c][1,2,5]thiadiazol-5-yl)-4-methyl-4-(trimethylsilyloxy)pent-2-yn-1-one (0.80 g, 2.515 mmol) in DCM (15 mL) was added p-TSA (0.574 g, 3.018 mmol) at RT. The reaction mixture was stirred for 2 h and diluted with water (5 mL). The combined organic layers were washed with a saturated $NaHCO_3$ solution and water, dried over $Na_2SO_4$, filtered, and then concentrated in vacuo to afford 1-(benzo[c][1,2,5]thiadiazol-5-yl)-4-hydroxy-4-methylpent-2-yn-1-one (0.6 g, 100%) as a colorless oil.

5-(Benzo[c][1,2,5]thiadiazol-5-yl)-2,2-dimethylfuran-3(2H)-one

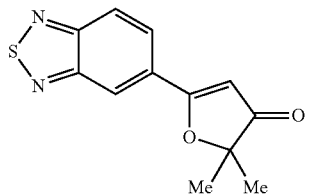 [SMILES: CC1(C)OC(c2ccc3nsnc3c2)=CC1=O]

To a stirred solution of 1-(benzo[c][1,2,5]thiadiazol-5-yl)-4-hydroxy-4-methylpent-2-yn-1-one (0.6 g, 2.597 mmol) in ethanol (10 mL), a solution of diethyl amine (0.189 g, 2.597 mmol) in EtOH (5 mL) was added dropwise at RT. The reaction mixture was then stirred for additional 3 h. The ethanol was then removed, and the mixture further diluted with EtOAc (10 mL). The combined organic layers were washed with water (5 mL) and brine (10 mL), dried over $Na_2SO_4$, filtered, and concentrated in vacuo to afford 5-(benzo[c][1,2,5]thiadiazol-5-yl)-2,2-dimethylfuran-3(2H)-one (0.5 g, 83%) as a light yellow solid.

5-(Benzo[c][1,2,5]thiadiazol-5-yl)-4-bromo-2,2-dimethylfuran-3(2H)-one

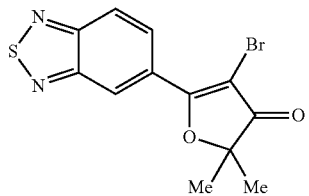 [SMILES: CC1(C)OC(c2ccc3nsnc3c2)=C(Br)C1=O]

To a stirred solution of 5-(benzo[c][1,2,5]thiadiazol-5-yl)-2,2-dimethylfuran-3(2H)-one (0.5 g, 2.164 mmol) in $CHCl_3$ (15 mL), NBS (0.462 g, 2.590 mmol) was added portionwise at RT. The reaction mixture was then stirred for 2 h and diluted with DCM (10 mL). The combined organic layers were washed with water (5 mL) and brine (10 mL), dried over $Na_2SO_4$, filtered, and then concentrated in vacuo to obtain the crude product. The crude material was purified via silica gel column chromatography to afford 5-(benzo[c][1,2,5]thiadia-zol-5-yl)-4-bromo-2,2-dimethylfuran-3(2H)-one (0.45 g, 69%) as a yellow oil.

5-(Benzo[c][1,2,5]thiadiazol-5-yl)-2,2-dimethyl-4-(4-(quinolin-2-ylmethoxy)phenyl)furan-3(2H)-one (Example 167)

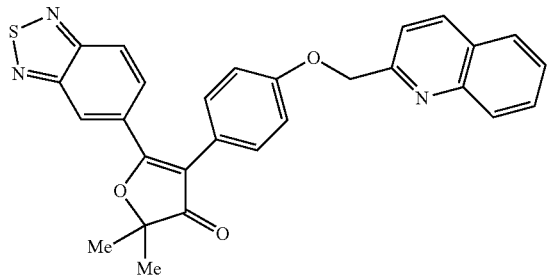 [SMILES: CC1(C)OC(c2ccc3nsnc3c2)=C(c2ccc(OCc3ccc4ccccc4n3)cc2)C1=O]

A solution of 5-(benzo[c][1,2,5]thiadiazol-5-yl)-4-bromo-2,2-dimethylfuran-3(2H)-one (0.45 g, 1.465 mmol), 2-((4-(4,4,5,5-tetramethyl-1,3,2-dioxaborolan-2-yl)phenoxy)methyl) quinoline (0.634 g, 1.759 mmol), and $Cs_2CO_3$ (2.3 g, 7.329 mmol) in toluene (10 mL) and water (5 mL) was degassed. Then, $Pd(dppf)Cl_2$ (0.24 g, 0.293 mmol) was added under an inert atmosphere and the solution was again degassed. The reaction was then refluxed for 12 h, filtered through a pad of Celite® and the filtrate was diluted with EtOAc (20 mL). The combined organic layers were washed with water (10 mL) and brine (10 mL), dried over $Na_2SO_4$, filtered, and concentrated in vacuo to obtain the crude product. The crude material was purified via silica gel column chromatography to afford 5-(benzo[c][1,2,5]thiadiazol-5-yl)-2,2-dimethyl-4-(4-(quinolin-2-ylmethoxy)phenyl)furan-3(2H)-one (65 mg) as a yellow solid. $^1$H NMR (500 MHz, $d_6$-DMSO): δ 8.44 (d, J=8.5 Hz, 1H), 8.35 (s, 1H), 8.12 (d, J=8.2 Hz, 1H), 8.02 (t, J=7.4 Hz, 2H), 7.79 (t, J=8.4 Hz, 1H), 7.73-7.69 (m, 2H), 7.63 (t, J=8.2 Hz, 1H), 7.24 (d, J=8.3 Hz, 2H), 7.12 (d, J=8.4 Hz, 2H), 5.39 (s, 2H), 1.49 (s, 6H). MS: [M+Na]: m/z=502.2, [M+H]: m/z=480.1. HPLC: 98%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of 5-(5,5-dimethyl-4-oxo-3-(4-(quinolin-2-ylmethoxy)phenyl)-4,5-dihydrofuran-2-yl)-2-methoxybenzonitrile (Example 137)

Methyl 3-bromo-4-hydroxybenzoate

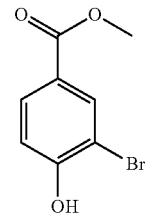

To a stirred solution of methyl 4-hydroxybenzoate (10.0 g, 84.935 mmol) in $CCl_4$ (30 mL) was added AcOH (20 mL, 2 Vol). $Br_2$ (1.80 mL, 71.428 mmol) was then added slowly at 0° C. After the addition was completed, the reaction mixture was brought to RT and stirred for 8 h. Reaction mixture was quenched with water (50 mL), neutralized with saturated $NaHCO_3$ solution and extracted with EtOAc (2×150 mL). The combined organic layers were washed with water (2×50 mL) and brine (50 mL), dried over anhydrous $Na_2SO_4$, filtered, and concentrated in vacuo to obtain crude product. The crude material was purified via silica gel column chromatography eluting with 5% EtOAc-95% hexanes to afford methyl 3-bromo-4-hydroxybenzoate (10.0 g, 66%) as a brown solid.

Methyl 3-cyano-4-hydroxybenzoate

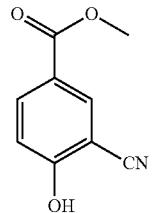

To a stirred solution of methyl 3-bromo-4-hydroxybenzoate (2.50 g, 10.775 mmol) in NMP (7.5 mL) was added CuCN (1.05 g, 11.853 mmol) at RT under an inert atmosphere.

The reaction mixture was then heated at 200° C. for 4 h., cooled to RT, diluted with water (10 mL) and stirred for 10 min. The precipitated solid was filtered off and the filtrate was concentrated in vacuo to obtain the crude product. The crude material was purified via silica gel column chromatography to afford methyl 3-cyano-4-hydroxybenzoate (1.50 g, 78%) as a yellow solid.

Methyl 3-cyano-4-methoxybenzoate

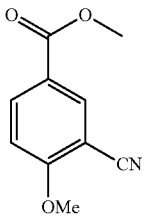

To a stirred solution of methyl 3-cyano-4-hydroxybenzoate (2.0 g, 11.20 mmol) in DMF (20 mL) were added CH$_3$I (2.40 g, 16.01 mmol) and K$_2$CO$_3$ (2.30 g, 16.01 mmol) at 0° C. under a N$_2$ atmosphere. The reaction mixture was stirred at 80° C. for 2 h. After completion of starting material (monitored by TLC), reaction mixture was diluted with water and extracted with EtOAc (2×100 mL). The combined organic layers were washed with water (2×50 mL), brine and dried over anhydrous Na$_2$SO$_4$. After filtration and evaporation in vacuo, the crude material was purified by silica gel column chromatography to afford methyl 3-cyano-4-methoxybenzoate (1.1 g, 52%), as a pale yellow solid.

3-Cyano-4-methoxybenzoic acid

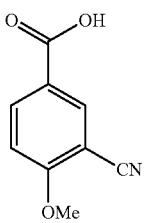 [SMILES: COc1ccc(C(=O)O)cc1C#N]

To a stirred solution of methyl 3-cyano-4-methoxybenzoate (1.1 g, 5.70 mmol) in a mixture of THF (70 mL), MeOH (70 mL) and water (5 mL) was added LiOH (0.97 g, 23.01 mmol) at RT and the reaction mixture was then stirred at RT for 1 h. The reaction mixture was acidified to pH ~2 with 2 N HCl and the aqueous layer was extracted with DCM (3×100 mL). The combined organic extracts were washed with water (50 mL) and brine (50 mL), dried over anhydrous Na$_2$SO$_4$, filtered and evaporated under reduced pressure to afford 3-cyano-4-methoxybenzoic acid (1.0 g, 100%) as a solid.

3-Cyano-N,4-dimethoxy-N-methylbenzamide

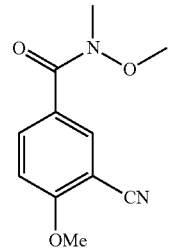 [SMILES: COc1ccc(C(=O)N(C)OC)cc1C#N]

To a stirred solution of 3-cyano-4-methoxybenzoic acid (1.0 g, 5.60 mmol) in DCM (30 mL) were added HATU (3.20 g, 8.01 mmol), N-methoxy,N-methylamine (0.82 g, 8.01 mmol) and TEA (2.3 mL, 17.01 mmol) at RT under a nitrogen atmosphere. The reaction mixture was then stirred at RT for 2 h, diluted with water and the aqueous layer was extracted with DCM (3×50 mL). The combined organic extracts were washed with water (50 mL) and brine (20 mL), dried over anhydrous Na$_2$SO$_4$, filtered, and evaporated under reduced pressure to afford 3-cyano-N,4-dimethoxy-N-methylbenzamide (1.3 g, 100%) as a white solid.

2-Methoxy-5-(4-methyl-4-(trimethylsilyloxy)pent-2-ynoyl)benzonitrile

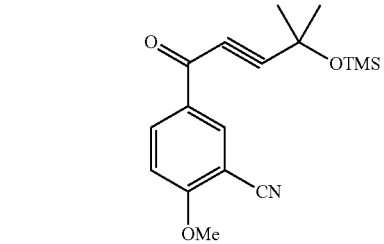

To a −78° C. stirred solution of trimethyl(2-methylbut-3-yn-2-yloxy)silane (1.9 g, 12.501 mmol) in dry THF (25 mL), n-BuLi (2.80 mL, 4.50 mmol, 1.6 M in hexane) was added dropwise over 10 minutes under an inert atmosphere. The reaction was stirred for 30 min at −78° C., and then a solution of 3-cyano-N,4-dimethoxy-N-methylbenzamide (1.10 g, 5.01 mmol) in dry THF (10 mL) was added to reaction mixture and stirring was continued for an additional 3 h at −78° C. The reaction mixture was quenched with a saturated NH$_4$Cl solution and extracted with EtOAc (2×50 mL). The combined organic layers were washed with water (20 mL) and brine (20 mL), dried over Na$_2$SO$_4$, filtered and concentrated in vacuo to obtain the crude product. The crude material was purified via silica gel column chromatography eluting with 5% EtOAc in hexanes to afford 2-methoxy-5-(4-methyl-4-(trimethylsilyloxy)pent-2-ynoyl)benzonitrile (0.8 g, 56%) as a pale yellow oil.

5-(4-Hydroxy-4-methylpent-2-ynoyl)-2-methoxybenzonitrile

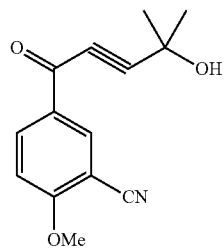 [SMILES: COc1ccc(C(=O)C#CC(C)(C)O)cc1C#N]

To a stirred solution of 2-methoxy-5-(4-methyl-4-(trimethylsilyloxy)pent-2-ynoyl)benzonitrile (1.2 g, 3.01 mmol) in DCM (20 mL) was added PTSA (1.08 g, 5.60 mmol) at RT. The reaction mixture was stirred for 30 minutes and diluted with water (5 mL). The combined organic layers were then washed with a saturated NaHCO$_3$ solution and water, dried over Na$_2$SO$_4$, filtered, and then concentrated in vacuo to afford 5-(4-hydroxy-4-methylpent-2-ynoyl)-2-methoxybenzonitrile (0.9 g, 97%) as a semi-solid.

5-(5,5-Dimethyl-4-oxo-4,5-dihydrofuran-2-yl)-2-methoxybenzonitrile

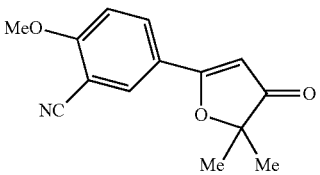 [SMILES: COc1ccc(C2=CC(=O)C(C)(C)O2)cc1C#N]

To a stirred solution of 5-(4-hydroxy-4-methylpent-2-ynoyl)-2-methoxybenzonitrile (0.9 g, 3.70 mmol) in ethanol (10 mL), a solution of diethyl amine (0.38 mL, 3.70 mmol) in EtOH (2.0 mL) was added dropwise at RT and the reaction mixture was stirred for additional 1 h. The ethanol was then was removed, and the mixture diluted with EtOAc (40 mL). The combined organic layers were washed with water (5 mL) and brine (10 mL), dried over Na$_2$SO$_4$, filtered, and concentrated in vacuo to afford 5-(5,5-dimethyl-4-oxo-4,5-dihydrofuran-2-yl)-2-methoxybenzonitrile (0.9 g, 100%) as a yellow semi solid.

5-(3-Bromo-5,5-dimethyl-4-oxo-4,5-dihydrofuran-2-yl)-2-methoxybenzonitrile

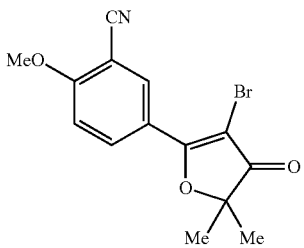 [SMILES: COc1ccc(C2=C(Br)C(=O)C(C)(C)O2)cc1C#N]

To a stirred solution of 5-(5,5-dimethyl-4-oxo-4,5-dihydrofuran-2-yl)-2-methoxybenzonitrile (0.9 g, 3.70 mmol) in CHCl$_3$ (10 mL), NBS (1.1 g, 6.29 mmol) was added portionwise at RT. The reaction mixture was then stirred for 1 h and diluted with DCM (50 mL). the combined organic layers were washed with water (20 mL) and brine (15 mL), dried over Na$_2$SO$_4$, filtered, and then concentrated in vacuo to obtain the crude product. The crude material was purified via silica gel column chromatography to afford 5-(3-bromo-5,5-dimethyl-4-oxo-4,5-dihydrofuran-2-yl)-2-methoxybenzonitrile (0.5 g, 42%) as a yellow solid.

5-(5,5-Dimethyl-4-oxo-3-(4-(quinolin-2-ylmethoxy)phenyl)-4,5-dihydrofuran-2-yl)-2-methoxybenzonitrile (Example 137)

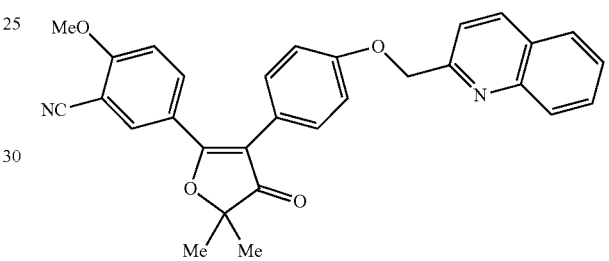

A solution of 5-(3-bromo-5,5-dimethyl-4-oxo-4,5-dihydrofuran-2-yl)-2-methoxybenzonitrile (0.15 g, 0.465 mmol), 2-((4-(4,4,5,5-tetramethyl-1,3,2-dioxaborolan-2-yl)phenoxy)methyl)quinoline (0.17 g, 0.465 mmol), and Cs$_2$CO$_3$ (0.75 g, 2.32 mmol) in toluene (6 mL) and water (3 mL) was degassed. Then, Pd(dppf)Cl$_2$ (0.76 g, 0.090 mmol) was added under an inert atmosphere and the solution was again degassed. The reaction was then refluxed for 2 h, filtered through a pad of Celite® and the filtrate was diluted with EtOAc (40 mL). The combined organic layers were washed with water (20 mL) and brine (20 mL), dried over Na$_2$SO$_4$, filtered, and concentrated in vacuo to obtain the crude product. The crude material was purified via silica gel column chromatography to afford 5-(5,5-dimethyl-4-oxo-3-(4-(quinolin-2-ylmethoxy)phenyl)-4,5-dihydrofuran-2-yl)-2-methoxybenzonitrile (125 mg, 58%) as a pale yellow solid. $^1$H NMR (500 MHz, d$_6$-DMSO): δ 8.43 (d, J=8.5 Hz, 1H), 8.02 (t, J=7.9 Hz, 2H), 7.90 (s, 1H), 7.81-7.77 (m, 2H), 7.70 (d, J=8.2 Hz, 1H), 7.62 (t, J=8.2 Hz, 1H), 7.32 (d, J=8.1 Hz, 1H), 7.19 (d, J=7.4 Hz, 2H), 7.12 (d, J=7.5 Hz, 2H), 5.40 (s, 2H), 3.95 (s, 3H), 1.46 (s, 6H). MS: [M+Na]: m/z=499.3, [M+H]: m/z=477.2. HPLC: 98%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of 5-(3-chloro-4-methoxyphenyl)-2,2-dimethyl-4-(4-(quinolin-2-ylmethoxy)phenyl)furan-3(2H)-one (Example 135)

3-Chloro-4-hydroxybenzaldehyde

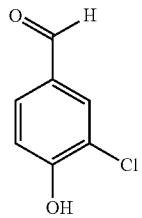

To a stirred solution of 4-hydroxybenzaldehyde (5.0 g, 40.0 mmol) in DCM (50 mL) $SOCl_2$ (3.30 mL, 40.0 mmol) was added slowly at 0° C. After the addition was completed, the reaction mixture was brought to RT and stirred for 14 h. The reaction mixture was then quenched with water (50 mL), neutralized with a saturated $NaHCO_3$ solution and extracted with EtOAc (2×100 mL). The combined organic layers were washed with water and brine, dried over anhydrous $Na_2SO_4$, filtered, and concentrated in vacuo to obtain crude product. The crude material was purified via silica gel column chromatography to afford 3-chloro-4-hydroxybenzaldehyde (5.0 g, 77%) as a brown solid.

3-Chloro-4-methoxybenzaldehyde

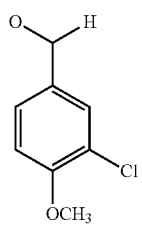

To a stirred solution of 3-chloro-4-hydroxybenzaldehyde (2.9 g, 18.412 mmol) in DMF (30 mL) was added $K_2CO_3$ (7.6 g, 55.238 mmol). $CH_3I$ (7.80 g, 55.238 mmol) was then added slowly at RT under an inert atmosphere. After addition was completed, the reaction mixture was brought to 80° C. and stirred for 1 h. The reaction mixture was quenched with water (20 mL) and extracted with EtOAc (2×50 mL). The combined organic layers were washed with water and brine, dried over anhydrous $Na_2SO_4$, filtered and concentrated in vacuo to obtain crude product. The crude material was purified via silica gel column chromatography to afford 3-chloro-4-methoxybenzaldehyde (2.78 g, 93%) as a yellow solid.

1-(3-Chloro-4-methoxyphenyl)-4-methylpent-2-yne-1,4-diol

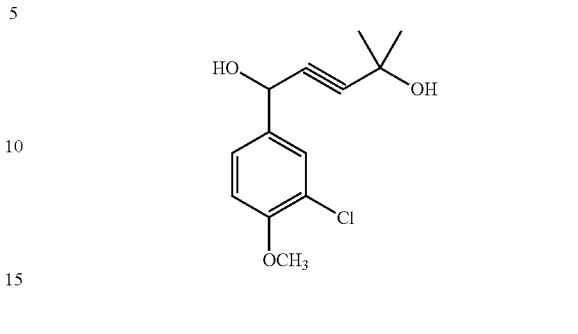

To a −78° C. stirred solution of 2-methylbut-3-yn-2-ol (0.89 g, 10.710 mmol) in dry THF (50 mL), n-BuLi (16.0 mL, 27.001 mmol, 1.6 M in hexane) was added dropwise over 5 minutes under an inert atmosphere. The reaction mixture was stirred for 30 min at −78° C., and then a solution of 3-chloro-4-methoxybenzaldehyde (1.8 g, 10.710 mmol) in dry THF (10 mL) was added and stirring was continued for an additional 3 h at RT. The reaction mixture was then quenched with a saturated $NH_4Cl$ solution and extracted with EtOAc (2×50 mL). The combined organic layers were washed with water (20 mL) and brine (20 mL), dried over $Na_2SO_4$, filtered, and concentrated in vacuo to obtain the crude product. The crude material was purified via silica gel column chromatography eluting with 2-4% EtOAc in hexanes to afford 1-(3-chloro-4-methoxyphenyl)-4-methylpent-2-yne-1,4-diol (0.69 g, 26%) as a yellow syrup.

1-(3-Chloro-4-methoxyphenyl)-4-hydroxy-4-methylpent-2-yn-1-one

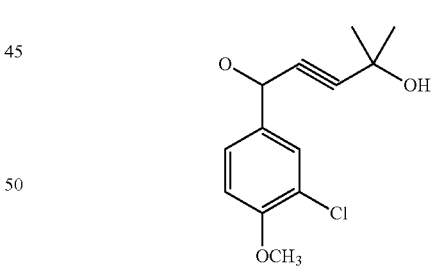

To a stirred solution of 1-(3-chloro-4-methoxyphenyl)-4-methylpent-2-yne-1,4-diol (0.69 g, 2.716 mmol) in DCM (20 mL) was added DMP (2.36 g, 5.430 mmol) at RT. The reaction mixture was stirred for 1 h and diluted with water (10 mL). The combined organic layers were washed with a saturated $NaHCO_3$ solution and water, dried over $Na_2SO_4$, filtered, and then concentrated in vacuo to afford 1-(3-chloro-4-methoxyphenyl)-4-hydroxy-4-methylpent-2-yn-1-one (0.45 g, 65%) as a brown oil.

5-(3-Chloro-4-methoxyphenyl)-2,2-dimethylfuran-3(2H)-one

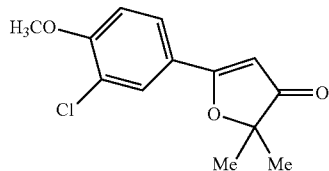 [SMILES: COc1ccc(C2=CC(=O)C(C)(C)O2)cc1Cl]

To a stirred solution of 1-(3-chloro-4-methoxyphenyl)-4-hydroxy-4-methylpent-2-yn-1-one (0.7 g, 2.75 mmol) in ethanol (5 mL), a solution of diethyl amine (0.20 g, 2.75 mmol) in EtOH (7 mL) was added dropwise at RT. The reaction mixture was then stirred for additional 30 min. The ethanol was removed, and the reaction mixture diluted with EtOAc (10 mL). The combined organic layers were then washed with water (5 mL) and brine (5 mL), dried over $Na_2SO_4$, filtered, and concentrated in vacuo to afford 5-(3-chloro-4-methoxyphenyl)-2,2-dimethylfuran-3(2H)-one (0.7 g, 100%) as a semi solid.

4-Bromo-5-(3-chloro-4-methoxyphenyl)-2,2-dimethylfuran-3(2H)-one

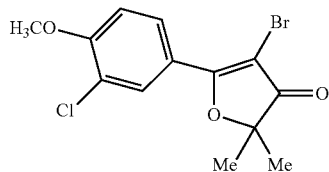 [SMILES: COc1ccc(C2=C(Br)C(=O)C(C)(C)O2)cc1Cl]

To a stirred solution of afford 5-(3-chloro-4-methoxyphenyl)-2,2-dimethylfuran-3(2H)-one (0.7 g, 2.77 mmol) in $CHCl_3$ (10 mL), NBS (0.84 g, 4.72 mmol was added portionwise at RT. The reaction mixture was then stirred for 1 h. and diluted with DCM (20 mL). The combined organic layers were washed with water (5 mL) and brine (10 mL), dried over $Na_2SO_4$, filtered, and then concentrated in vacuo to obtain the crude product. The crude material was purified via silica gel column chromatography to afford 4-bromo-5-(3-chloro-4-methoxyphenyl)-2,2-dimethylfuran-3(2H)-one (340 mg, 37%) as a thick syrup.

5-(3-Chloro-4-methoxyphenyl)-2,2-dimethyl-4-(4-(quinolin-2-ylmethoxy)phenyl) furan-3(2H)-one (Example 135)

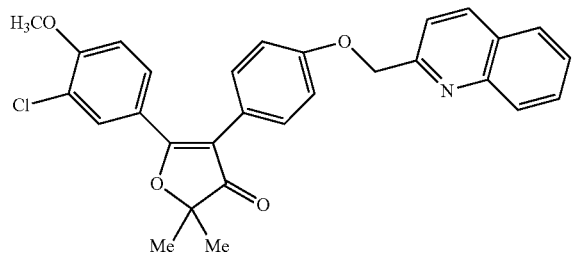 [SMILES: COc1ccc(C2=C(c3ccc(OCc4ccc5ccccc5n4)cc3)C(=O)C(C)(C)O2)cc1Cl]

A solution of 4-bromo-5-(3-chloro-4-methoxyphenyl)-2,2-dimethylfuran-3(2H)-one 0.34 g, 1.021 mmol), 2-((4-(4,4,5,5-tetramethyl-1,3,2-dioxaborolan-2-yl)phenoxy)methyl)quinoline (0.37 g, 1.021 mmol), and $Cs_2CO_3$ (1.67 g, 5.130 mmol) in toluene (6 mL) and water (3 mL) was degassed. Then, $Pd(dppf)Cl_2$ (0.167 g, 0.204 mmol) was added under an inert atmosphere and the solution was again degassed. Then the reaction mixture was refluxed for 1 h, filtered through a pad of Celite® and the filtrate was diluted with EtOAc (20 mL). The combined organic layers were washed with water (5 mL) and brine (5 mL), dried over $Na_2SO_4$, filtered, and concentrated in vacuo to obtain the crude product. The crude material was purified via silica gel column chromatography to afford 5-(3-chloro-4-methoxyphenyl)-2,2-dimethyl-4-(4-(quinolin-2-ylmethoxy)phenyl)furan-3(2H)-one (122 mg, 23%) as a solid. $^1$H NMR (500 MHz, d-DMSO): δ 8.42 (d, J=8.5 Hz, 1H), 8.02 (t, J=7.9 Hz, 2H), 7.79 (t, J=7.4 Hz, 1H), 7.70 (d, J=8.2 Hz, 1H), 7.65-7.59 (m, 2H), 7.51 (d, J=8.1 Hz, 1H), 7.22-7.18 (m, 3H), 7.12 (d, J=7.5 Hz, 2H), 5.40 (s, 2H), 3.91 (s, 3H), 1.46 (s, 6H). MS: [M+Na]: m/z=508.2, [M+H]: m/z=486.2. HPLC: 96%, Column: Acquity BEH-C-18, 50×2.1 mm, 1.7 um. Mobile Phase: 0.025% TFA in Water (A), AcN (B), Flow rate: 0.5 ml/min (Gradient).

Synthesis of Example 810, 4-(4-((6-fluoroquinolin-2-yl)methoxy)phenyl)-2,2-dimethyl-5-(pyridin-4-yl)furan-3(2H)-one

N-methoxy-N-methylisonicotinamide

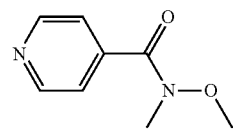

To a stirred solution of isonicotinic acid (20.0 g, 162 mmol) in DCM (400 mL) were added HATU (92.6 g, 243 mmol), N-methoxy methylamine (17.24 g, 178 mmol) and TEA (68.7 mL, 487 mmol) at RT under nitrogen atmosphere. The reaction mixture was then stirred at RT for 12 h. The reaction mixture was diluted with water and the aqueous layer was extracted with DCM (3×500 mL). The combined organic extracts were washed with water (150 mL), brine (150 mL), dried over anhydrous $Na_2SO_4$, filtered and concentrated in vacuo to obtain the crude product. The crude material was purified via silica gel column chromatography eluting with 30-40% EtOAc in Hexane to afford to afford N-methoxy-N-methylisonicotinamide (15.0 g, 55%) as an oil.

4-Methyl-1-(pyridin-4-yl)-4-(trimethylsilyloxy)pent-2-yn-1-one

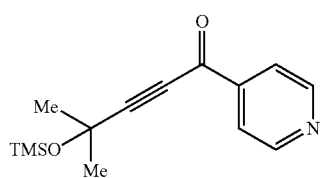

To a stirred solution of trimethyl(2-methylbut-3-yn-2-yloxy)silane (4.22 g, 25.4 mmol) in dry THF (100 mL) was added n-BuLi (17.9 mL, 28.7 mmol, 1.6 M in hexane) dropwise at −78° C. under an inert atmosphere for a period of 10 min. After being stirred for 30 min at −78° C., a solution of N-methoxy-N-methylisonicotinamide (5.0 g, 31.8 mmol) in dry THF (15 mL) was added to reaction mixture and stirring was continued for an additional 2 h at −78° C. The reaction mixture was quenched with a saturated NH₄Cl solution and extracted with EtOAc (2×100 mL). The combined organic layers were washed with water (80 mL), brine (50 mL), dried over Na₂SO₄, filtered and concentrated in vacuo to obtain the crude product. The crude material was purified via silica gel column chromatography eluting with 2-3% EtOAc in Hexane to afford 4-methyl-1-(pyridin-4-yl)-4-(trimethylsilyloxy)pent-2-yn-1-one (4.8 g, 57%) as an oil.

4-Hydroxy-4-methyl-1-(pyridin-4-yl)pent-2-yn-1-one

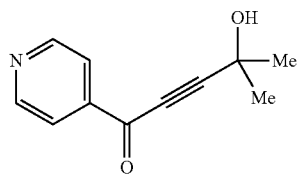 [SMILES: CC(C)(O)C#CC(=O)c1ccncc1]

To a stirred solution of 4-methyl-1-(pyridin-4-yl)-4-(trimethylsilyloxy)pent-2-yn-1-one (3.0 g, 11.0 mmol) in DCM (60 mL) was added PTSA (2.62 g, 13.0 mmol) at RT and the reaction mixture was stirred for 1 h. The reaction mixture was diluted with water (10 mL), the organic layer was washed with a saturated NaHCO₃ solution, water, dried over Na₂SO₄, filtered and then concentrated in vacuo to afford 4-hydroxy-4-methyl-1-(pyridin-4-yl) pent-2-yn-1-one (1.5 g, 69%) as an oil.

2,2-Dimethyl-5-(pyridin-4-yl) furan-3(2H)-one

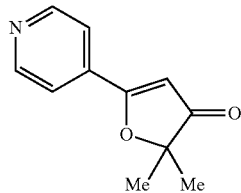 [SMILES: CC1(C)OC(c2ccncc2)=CC1=O]

To a stirred solution of 4-hydroxy-4-methyl-1-(pyridin-4-yl) pent-2-yn-1-one (1.8 g, 9.50 mmol) in ethanol (18 mL) was added diethyl amine (1.04 g, 14.0 mmol) in EtOH (1 mL) dropwise at RT and the reaction mixture was stirred for additional 1 h. The reaction mixture was concentrated, diluted with EtOAc (20 mL), washed with water (10 mL), brine (10 mL), dried over Na₂SO₄, filtered and concentrated in vacuo to afford crude 2,2-dimethyl-5-(pyridin-4-yl) furan-3(2H)-one (1.3 g) as an oil.

4-Bromo-2,2-dimethyl-5-(pyridin-4-yl) furan-3(2H)-one

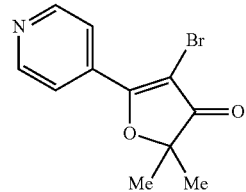 [SMILES: CC1(C)OC(c2ccncc2)=C(Br)C1=O]

To a stirred solution of 2,2-dimethyl-5-(pyridin-4-yl) furan-3(2H)-one (1.3 g, 6.80 mmol) in CHCl₃ (13 mL) was added NBS (2.08 g, 11.6 mmol) portionwise at RT and the reaction mixture was stirred for 3 h. The reaction mixture was diluted with DCM (30 mL), washed with water (10 mL), brine (10 mL), dried over Na₂SO₄, filtered and then concentrated in vacuo to obtain the crude product. The crude material was purified via silica gel column chromatography to afford 4-bromo-2,2-dimethyl-5-(pyridin-4-yl) furan-3(2H)-one (1.2 g) as an oil.

6-Fluoro-2-((4-(4,4,5,5-tetramethyl-1,3,2-dioxaborolan-2-yl)phenoxy)methyl)quinoline

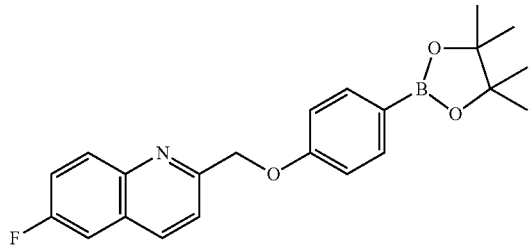 [SMILES: CC1(C)OB(c2ccc(OCc3ccc4cc(F)ccc4n3)cc2)OC1(C)C]

6-Fluoro-2-((4-(4,4,5,5-tetramethyl-1,3,2-dioxaborolan-2-yl)phenoxy)methyl)quinoline may be prepared in manner analogous to 2-((4-(4,4,5,5-tetramethyl-1,3,2-dioxaborolan-2-yl)phenoxy)methyl)quinoline using 2-(chloromethyl)-6-fluoroquinoline instead of 2-(chloromethyl)quinoline.

Example 810

4-(4-((6-Fluoroquinolin-2-yl)methoxy)phenyl)-2,2-dimethyl-5-(pyridin-4-yl) furan-3(2H)-one

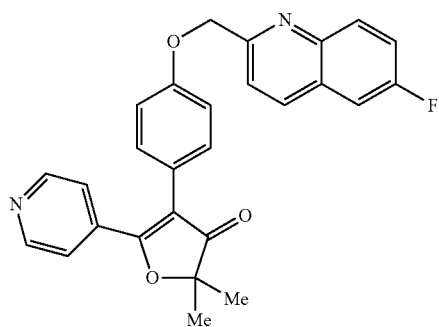 [SMILES: CC1(C)OC(c2ccncc2)=C(c2ccc(OCc3ccc4cc(F)ccc4n3)cc2)C1=O]

A mixture of 4-bromo-2,2-dimethyl-5-(pyridin-4-yl) furan-3(2H)-one (0.085 g, 0.32 mmol), 6-Fluoro-2-((4-(4,4,5,5-tetramethyl-1,3,2-dioxaborolan-2-yl)phenoxy)methyl) quinoline (0.12 g, 0.32 mmol), and Cs$_2$CO$_3$ (0.52 g, 1.58 mmol) in toluene (5 mL) and water (2 mL) was degassed, added Pd(dppf)Cl$_2$ (0.052 g, 0.06 mmol) under an inert atmosphere and degassed again. Then the reaction was refluxed for 2 h. The reaction mixture was filtered through a pad of Celite®, the filtrate was diluted with EtOAc (30 mL), washed with water (20 mL), brine (20 mL), dried over Na$_2$SO$_4$, filtered and concentrated in vacuo to obtain the crude product. The crude material was purified via silica gel column chromatography to afford 4-(4-((6-fluoroquinolin-2-yl)methoxy)phenyl)-2,2-dimethyl-5-(pyridin-4-yl) furan-3(2H)-one (35 mg, 25%) as a pale yellow solid. $^1$H NMR (500 MHz, d$_6$-DMSO): δ 8.71 (d, J=8.5 Hz, 2H), 8.42 (t, J=7.9 Hz, 1H), 8.1 (t, J=8.4 Hz, 1H), 7.70-7.61 (m, 3H), 7.44 (d, J=8.5 Hz, 2H), 7.18 (d, J=7.4 Hz, 2H), 7.11 (d, J=7.5 Hz, 2H), 5.40 (s, 2H), 1.44 (s, 6H). MS: [M+H]: m/z=441.1. HPLC: 90.1% (RT-2.39 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 808, 2,2-dimethyl-4-(4-((5-methylpyridin-2-yl)methoxy)phenyl)-5-(pyridin-4-yl) furan-3(2H)one 5-Methyl-2-((4-(4,4,5,5-tetramethyl-1,3,2-dioxaborolan-2-yl)phenoxy)methyl)pyridine

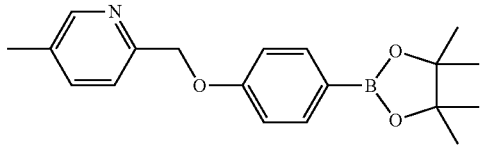

5-Methyl-2-((4-(4,4,5,5-tetramethyl-1,3,2-dioxaborolan-2-yl)phenoxy)methyl)pyridine may be prepared in a manner analogous to 2-((4-(4,4,5,5-tetramethyl-1,3,2-dioxaborolan-2-yl)phenoxy)methyl)quinoline using 2-(chloromethyl)-5-methylpyridine instead of 2-(chloromethyl)quinoline.

Example 808

2,2-dimethyl-4-(4-((5-methylpyridin-2-yl)methoxy) phenyl)-5-(pyridin-4-yl) furan-3(2H)-one

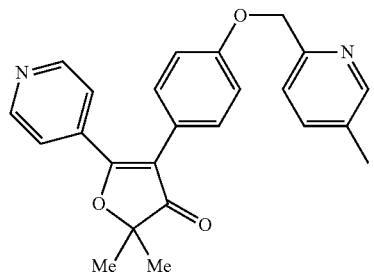 [SMILES: Cc1ccc(COc2ccc(C3=C(c4ccncc4)OC(C)(C)C3=O)cc2)nc1]

A mixture of 4-bromo-2,2-dimethyl-5-(pyridin-4-yl) furan-3(2H)-one (0.11 g, 0.34 mmol), 5-methyl-2-((4-(4,4,5,5-tetramethyl-1,3,2-dioxaborolan-2-yl) phenoxy)methyl)pyridine (0.1 g, 0.37 mmol), and Cs$_2$CO$_3$ (0.55 g, 1.86 mmol) in toluene (7 mL) and water (3 mL) was degassed, Pd(dppf)Cl$_2$ (0.058 g, 0.07 mmol) was added under an inert atmosphere and the mixture was degassed again. Then the reaction was refluxed for 2 h and was filtered through a pad of Celite®. The filtrate was diluted with EtOAc (50 mL), washed with water (20 mL), brine (20 mL), dried over Na$_2$SO$_4$, filtered and concentrated in vacuo to obtain the crude product. The crude material was purified via silica gel column chromatography to afford 2,2-dimethyl-4-(4-((5-methylpyridin-2-yl)methoxy)phenyl)-5-(pyridin-4-yl)furan-3(2H)-one (70 mg, 48%) as a solid. $^1$H NMR (500 MHz, d$_6$-DMSO): δ 8.72 (d, J=8.5 Hz, 2H), 8.42 (t, J=7.9 Hz, 1H), 7.70 (d, J=8.2 Hz, 2H), 7.63 (t, J=8.2 Hz, 1H), 7.52-7.43 (m, 3H), 7.18 (d, J=7.4 Hz, 2H), 7.11 (d, J=7.5 Hz, 2H), 5.18 (s, 2H), 2.35 (s, 3H), 1.54 (s, 6H). MS: [M+H]: m/z=387.0. HPLC: 91.4% (RT-1.73 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 809, 4-(4-((3,5-dimethylpyridin-2-yl)methoxy)phenyl)-2,2-dimethyl-5-(pyridin-4-yl) furan-3(2H)-one 3,5-Dimethyl-2-((4-(4,4,5,5-tetramethyl-1,3,2-dioxaborolan-2-yl)phenoxy)methyl)pyridine

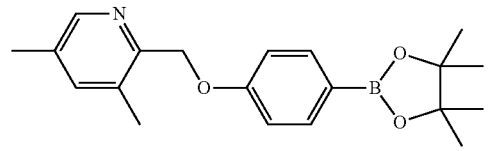

3,5-Dimethyl-2-((4-(4,4,5,5-tetramethyl-1,3,2-dioxaborolan-2-yl)phenoxy)methyl)pyridine may be prepared in a manner analogous to 2-((4-(4,4,5,5-tetramethyl-1,3,2-dioxaborolan-2-yl)phenoxy)methyl)quinoline using 2-(chloromethyl)-3,5-dimethylpyridine instead of 2-(chloromethyl) quinoline.

Example 809

4-(4-((3,5-Dimethylpyridin-2-yl) methoxy)phenyl)-2,2-dimethyl-5-(pyridin-4-yl) furan-3(2H)-one

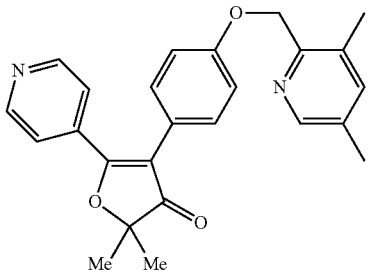 [SMILES: Cc1cnc(COc2ccc(C3=C(c4ccncc4)OC(C)(C)C3=O)cc2)c(C)c1]

A mixture of 4-bromo-2,2-dimethyl-5-(pyridin-4-yl)furan-3(2H)-one (0.28 g, 1.04 mmol), 3,5-dimethyl-2-((4-(4,4,5,5-tetramethyl-1,3,2-dioxaborolan-2-yl)phenoxy)methyl) pyridine (0.32 g, 0.94 mmol), and Cs$_2$CO$_3$ (1.3 g, 4.0 mmol) in toluene (10 mL) and water (3 mL) was degassed, Pd(dppf)

Cl₂ (0.14 g, 0.16 mmol) was added under an inert atmosphere and again degassed. Then the reaction was refluxed for 2 h and was filtered through a pad of Celite®. The filtrate was diluted with EtOAc (50 mL), washed with water (20 mL), brine (20 mL), dried over Na₂SO₄, filtered and concentrated in vacuo to obtain the crude product. The crude material was purified via silica gel column chromatography to afford 4-(4-((3,5-dimethylpyridin-2-yl)methoxy)phenyl)-2,2-dimethyl-5-(pyridin-4-yl) furan-3(2H)-one (90 mg, 24%) as an oil. ¹H NMR (500 MHz, d₆-DMSO): δ 8.72 (d, J=7.5 Hz, 2H), 8.24 (d, J=7.8 Hz, 1H), 7.50 (d, J=8.6 Hz, 3H), 7.23 (d, J=7.4 Hz, 2H), 7.08 (d, J=7.5 Hz, 2H), 5.18 (s, 2H), 2.35 (s, 3H), 2.25 (s, 3H), 1.52 (s, 6H). MS: [M+H]: m/z=401.1. HPLC: 95.2% (RT-1.78 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 824, 2-(pyridin-4-yl)-3-(4-(quinolin-2-ylmethoxy)phenyl)-1-oxaspiro[4.4]non-2-en-4-one 1-(Pyrdin-4-yl)-3-(1-trimethylsilyloxy)cyclopentyl) prop-2-yn-1-one

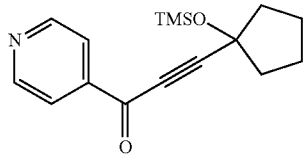

To a stirred solution of (1-ethynylcyclopentyloxy)trimethylsilane (2.0 g, 11.0 mmol) in dry THF (50 mL) was added n-BuLi (20.0 mL, 20.0 mmol, 1.6 M in hexane) drop wise at −78° C. under an inert atmosphere for a period of 10 min. After being stirred for 30 min at −78° C., a solution of compound N-methoxy-N-methylisonicotinamide (2.1 g, 13.2 mmol) in dry THF (10 mL) was added to the reaction mixture and stirring was continued for an additional 2 h at −78° C. The reaction mixture was quenched with a saturated NH₄Cl solution and extracted with EtOAc (2×60 mL). The combined organic layers were washed with water (20 mL), brine (20 mL), dried over Na₂SO₄, filtered and concentrated in vacuo to obtain the crude product. The crude material was purified via silica gel column chromatography eluting with 5% EtOAc in Hexane to afford 1-(pyridin-4-yl)-3-(1-(trimethylsilyloxy)cyclopentyl) prop-2-yn-1-one (1.0 g, 32%) as an oil.

3-(1-Hydroxycyclopentyl)-1-(pyridin-4-yl) prop-2-yn-1-one

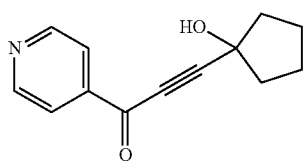 [SMILES: O=C(C#CC1(O)CCCC1)c1ccncc1]

To a stirred solution of 1-(pyridin-4-yl)-3-(1-(trimethylsilyloxy)cyclopentyl) prop-2-yn-1-one (1.1 g, 3.8 mmol) in DCM (15 mL) was added PTSA (0.87 g, 4.6 mmol) at RT and the reaction mixture was stirred for 1 h. The reaction mixture was diluted with water (2 mL), the organic layer was washed with a saturated NaHCO₃ solution, water, dried over Na₂SO₄, filtered and then concentrated in vacuo to afford 3-(1-hydroxycyclopentyl)-1-(pyridin-4-yl) prop-2-yn-1-one (0.42 g, 51%) as an oil.

2-(Pyridin-4-yl)-1-oxaspiro[4.4]non-2-en-4-one

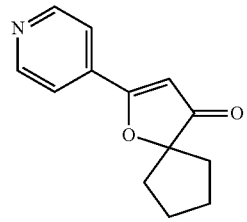 [SMILES: O=C1C=C(c2ccncc2)OC12CCCC2]

To a stirred solution of 3-(1-hydroxycyclopentyl)-1-(pyridin-4-yl) prop-2-yn-1-one (0.42 g, 1.95 mmol) in ethanol (10 mL) was added diethyl amine (0.21 g, 2.9 mmol) in EtOH (1 mL) dropwise at RT and the reaction mixture was stirred for additional 1 h. Then the EtOH was removed, diluted with EtOAc (20 mL), washed with water (10 mL), brine (10 mL), dried over Na₂SO₄, filtered and concentrated in vacuo to afford 2-(pyridin-4-yl)-1-oxaspiro[4.4]non-2-en-4-one (0.4 g) as an oil.

3-Bromo-2-(pyridin-4-yl)-1-oxaspiro[4.4]non-2-en-4-one

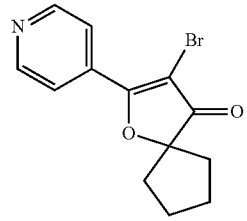 [SMILES: O=C1C(Br)=C(c2ccncc2)OC12CCCC2]

To a stirred solution of afford 2-(pyridin-4-yl)-1-oxaspiro[4.4]non-2-en-4-one (0.18 g, 0.84 mmol) in CHCl₃ (10 mL) was added NBS (0.22 g, 1.25 mmol) portionwise at RT and the reaction mixture was stirred for 1 h. The reaction mixture was diluted with DCM (30 mL), washed with water (10 mL), brine (10 mL), dried over Na₂SO₄, filtered and then concentrated in vacuo to obtain the crude product. The crude material was purified via silica gel column chromatography to afford 3-bromo-2-(pyridin-4-yl)-1-oxaspiro[4.4]non-2-en-4-one (0.18 g, 40%) as an oil.

Example 824

2-(Pyrdin-4-yl)-3-(4-(quinolin-2-ylmethoxy)phenyl)-1-oxaspiro[4.4]non-2-en-4-one

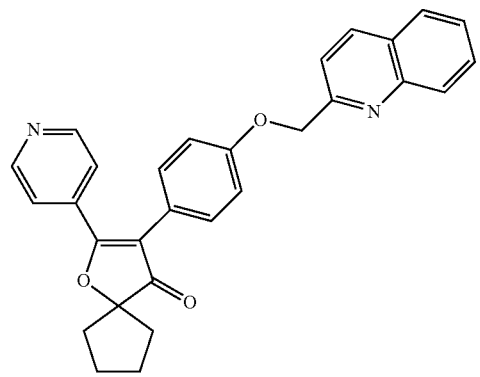 [SMILES: O=C1C(c2ccc(OCc3ccc4ccccc4n3)cc2)=C(c2ccncc2)OC12CCCC2]

A mixture of 3-bromo-2-(pyridin-4-yl)-1-oxaspiro[4.4]non-2-en-4-one (0.2 g, 0.68 mmol), 2-((4-(4,4,5,5-tetramethyl-1,3,2-dioxaborolan-2-yl)phenoxy)methyl) quinoline (0.25 g, 0.82 mmol), and $Cs_2CO_3$ (1.25 g, 6.68 mmol) in toluene (10 mL) and water (2 mL) was degassed, Pd(dppf)Cl$_2$ (0.05 g, 0.014 mmol) was added under an inert atmosphere and again degassed. Then the reaction was refluxed for 3 h. and was filtered through a pad of Celite®, the filtrate was diluted with EtOAc (50 mL), washed with water (20 mL), brine (20 mL), dried over $Na_2SO_4$, filtered and concentrated in vacuo to obtain the crude product. The crude material was purified via silica gel column chromatography to afford 2-(pyridin-4-yl)-3-(4-(quinolin-2-ylmethoxy)phenyl)-1-oxaspiro[4.4]non-2-en-4-one (20 mg, 5%) as a solid. $^1$H NMR (500 MHz, d$_6$-DMSO): δ 8.68 (d, J=8.5 Hz, 2H), 8.44 (d, J=7.9 Hz, 1H), 8.02 (t, J=8.4 Hz, 2H), 7.80 (t, J=8.2 Hz, 1H), 7.68 (d, J=8.2 Hz, 1H), 7.63 (t, J=8.5 Hz, 1H), 7.48 (d, J=8.5 Hz, 2H), 7.18 (d, J=7.4 Hz, 2H), 7.12 (d, J=7.5 Hz, 2H), 5.42 (s, 2H), 2.08-1.82 (m, 8H). MS: [M+H]: m/z=449.2. HPLC: 96.9% (RT-2.24 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 894, 5-(4-aminophenyl)-2,2-dimethyl-4-(4-(quinolin-2-ylmethoxy)phenyl) furan-3(2H)-one

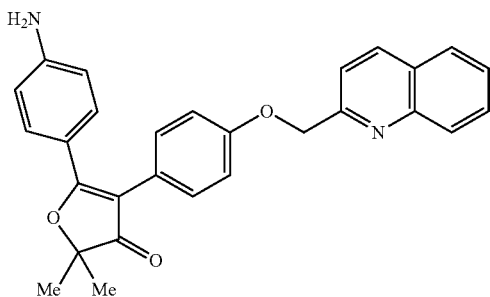 [SMILES: CC1(C)OC(c2ccc(N)cc2)=C(c2ccc(OCc3ccc4ccccc4n3)cc2)C1=O]

To a stirred solution of 2,2-dimethyl-5-(4-nitrophenyl)-4-(4-(quinolin-2-ylmethoxy)phenyl)furan-3(2H)-one (0.6 g, 1.28 mmol) in ethanol (10 mL) was added AcOH (1.28 mL) at RT under $N_2$ atmosphere. After being stirred for 10 min at RT, the reaction mixture was heated to 70° C. and Fe (0.524 g, 9.04 mmol) and FeCl$_3$ (0.062 g, 0.38 mmol) were added under $N_2$ atmosphere. The reaction mixture was stirred at 70° C. for 2 h. After completion of starting material (by TLC), reaction mixture was cooled to RT, and the volatiles were evaporated in vacuo to obtain the crude product. The crude product was extracted in EtOAc (25 mL), washed with water (2×10 mL), brine and dried over anhydrous $Na_2SO_4$. After filtration and evaporation, the crude material was purified by silica gel column chromatography to afford 5-(4-aminophenyl)-2,2-dimethyl-4-(4-(quinolin-2-ylmethoxy)phenyl) furan-3(2H)-one (400 mg, 71%), as a yellow solid.

Synthesis of Example 817, N-(4-(5,5-dimethyl-4-oxo-3-(4-(quinolin-2-ylmethoxy)phenyl)-4,5-dihydrofuran-2-yl)phenyl)acetamide

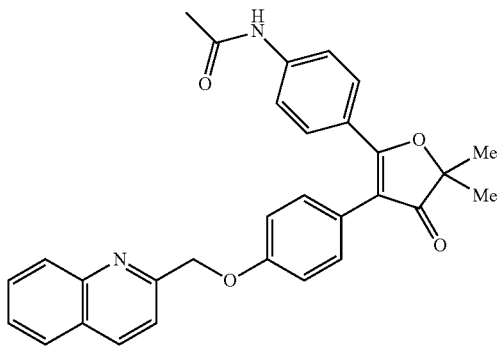 [SMILES: CC(=O)Nc1ccc(C2=C(c3ccc(OCc4ccc5ccccc5n4)cc3)C(=O)C(C)(C)O2)cc1]

To a stirred solution of 5-(4-aminophenyl)-2,2-dimethyl-4-(4-(quinolin-2-ylmethoxy)phenyl) furan-3(2H)-one (0.07 g, 0.16 mmol) in DCM (5 mL) were added Ac$_2$O (0.018 mL, 0.19 mmol) and TEA (0.04 mL, 0.32 mmol) at 0° C. under $N_2$ atmosphere. The reaction mixture was stirred at RT for 14 h. The reaction mixture was diluted with water and extracted with DCM (2×15 mL). Combined organic layers were washed with water (2×5 mL), brine and dried over anhydrous $Na_2SO_4$. After filtration and evaporation, the crude material was purified by silica gel column chromatography to afford N-(4-(5,5-dimethyl-4-oxo-3-(4-(quinolin-2-ylmethoxy)phenyl)-4,5-dihydrofuran-2-yl)phenyl)acetamide (20 mg, 26%), as an off white solid. $^1$H NMR (500 MHz, CDCl$_3$): δ 8.22 (d, J=8.5 Hz, 1H), 8.08 (d, J=7.9 Hz, 1H), 7.84 (d, J=8.4 Hz, 1H), 7.74 (t, J=8.2 Hz, 1H), 7.68 (d, J=8.2 Hz, 1H), 7.64 (d, J=8.2 Hz, 2H), 7.56 (t, J=8.5 Hz, 1H), 7.48 (d, J=7.4 Hz, 2H), 7.22 (d, J=7.5 Hz, 2H), 7.08 (d, J=8.9 Hz, 2H), 5.42 (s, 2H), 2.22 (s, 3H), 1.58 (s, 6H). MS: [M+Na]: m/z=501.3, [M+H]: m/z=479.3. HPLC: 95.9% (RT-2.32 min), Column: Acquity BEH-C-18, 50×2.1 mm, 1.7 um. Mobile Phase: 0.025% TFA in Water (A), ACN (B), Flow rate: 0.5 ml/min (Gradient).

Also isolated was Example 819, N-acetyl-N-(4-(5,5-dimethyl-4-oxo-3-(4-(quinolin-2-ylmethoxy)phenyl)-4,5-dihydrofuran-2-yl)phenyl)acetamide, (30 mg, 18.0%) as an off white solid

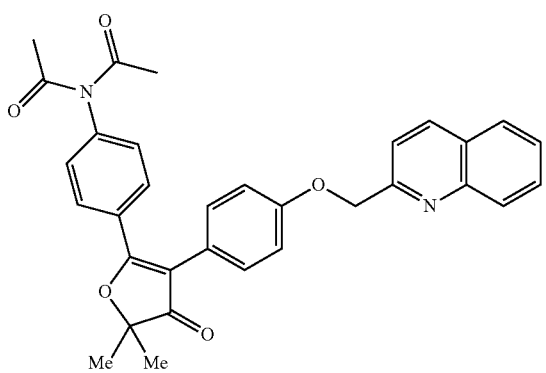 [SMILES: CC(=O)N(C(C)=O)c1ccc(C2=C(c3ccc(OCc4ccc5ccccc5n4)cc3)C(=O)C(C)(C)O2)cc1]

¹H NMR (500 MHz, CDCl₃): δ 8.22 (d, J=8.5 Hz, 1H), 8.08 (d, J=7.9 Hz, 1H), 7.78 7.68 (m, 5H), 7.64 (t, J=8.2 Hz, 1H), 7.28 (d, J=7.4 Hz, 2H), 7.12 (d, J=7.5 Hz, 2H), 7.06 (d, J=8.9 Hz, 2H), 5.42 (s, 2H), 2.32 (s, 6H), 1.44 (s, 6H). MS: [M+Na]: m/z=543.2, [M+H]: m/z=521.3. HPLC: 92.7% (RT-2.53 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 817, N-(4-(5,5-dimethyl-4-oxo-3-(4-(quinolin-2-ylmethoxy)phenyl)-4,5-dihydrofuran-2-yl)phenyl)-N-(methylsulfonyl)methane sulfonamide

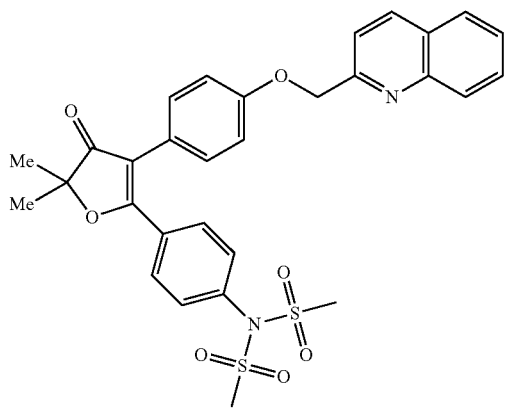 [SMILES: CC1(C)OC(c2ccc(N(S(C)(=O)=O)S(C)(=O)=O)cc2)=C(c2ccc(OCc3ccc4ccccc4n3)cc2)C1=O]

To a stirred solution of 5-(4-aminophenyl)-2,2-dimethyl-4-(4-(quinolin-2-ylmethoxy)phenyl) furan-3(2H)-one (60 mg, 0.13 mmol) in DCM (5 mL) were added methane sulfonyl chloride (0.012 g, 0.15 mmol) and TEA (0.04 mL, 0.27 mmol) at 0° C. under N₂ atmosphere. The reaction mixture was stirred at RT for 10 min. The reaction mixture diluted with water and extracted with DCM (2×10 mL). The combined organic layers were washed with water (2×5 mL), brine and dried over anhydrous Na₂SO₄. After filtration and evaporation, the crude material was purified by silica gel column chromatography to afford N-(4-(5,5-dimethyl-4-oxo-3-(4-(quinolin-2-ylmethoxy)phenyl)-4,5-dihydrofuran-2-yl)phenyl)-N-(methylsulfonyl)methane sulfonamide (25 mg, 30%), as a white color solid. ¹H NMR (500 MHz, CDCl₃): δ 8.22 (d, J=8.5 Hz, 1H), 8.10 (d, J=7.9 Hz, 1H), 7.76 (d, J=8.4 Hz, 1H), 7.80 (d, J=8.2 Hz, 2H), 7.74 (t, J=8.2 Hz, 1H), 7.70 (d, J=8.5 Hz, 1H), 7.56 (d, J=7.5 Hz, 1H), 7.28 (d, J=7.4 Hz, 2H), 7.12 (d, J=7.5 Hz, 2H), 7.08 (d, J=7.6 Hz, 2H), 5.42 (s, 2H), 3.42 (s, 6H), 1.58 (s, 6H). MS: [M+Na]: m/z=615.1, [M+H]: m/z=593.1. HPLC: 98.9% (RT-2.52 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 815, N-(4-(5,5-dimethyl-4-oxo-3-(4-(quinolin-2-ylmethoxy)phenyl)-4,5-dihydrofuran-2-yl)phenyl)methane sulfonamide

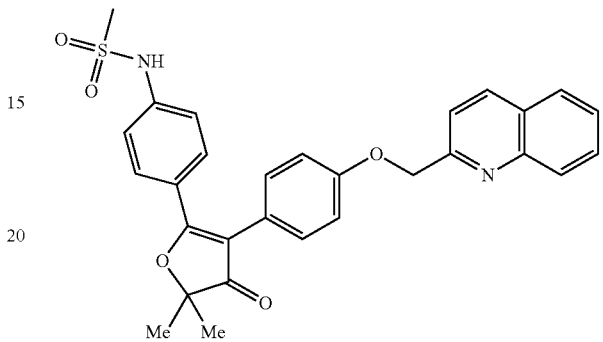

To a stirred solution of N-(4-(5,5-dimethyl-4-oxo-3-(4-(quinolin-2-ylmethoxy)phenyl)-4,5-dihydrofuran-2-yl)phenyl)-N-(methylsulfonyl)methane sulfonamide (40 mg, 0.06 mmol) in THF: H₂O (6 mL) was added 2N NaOH (1.0 mL) at 0° C. under N₂ atmosphere. The reaction mixture was stirred at 0° C. for 10 min. Upon complete consumption of the starting material (by TLC), the reaction mixture was diluted with water and extracted with EtOAc (2×15 mL). The combined organic layers were washed with water (2×5 mL), brine and dried over anhydrous Na₂SO₄. After filtration and evaporation, the crude material was purified by silica gel column chromatography to afford N-(4-(5,5-dimethyl-4-oxo-3-(4-(quinolin-2-ylmethoxy)phenyl)-4,5-dihydrofuran-2-yl)phenyl)methane sulfonamide (20 mg, 26%), as a pale yellow solid. ¹H NMR (500 MHz, CDCl₃): δ 8.45 (d, J=8.5 Hz, 1H), 8.12 (t, J=7.9 Hz, 1H), 7.78 (t, J=8.4 Hz, 1H), 7.70 (d, J=8.2 Hz, 1H), 7.64 (t, J=8.2 Hz, 1H), 7.44 (d, J=8.5 Hz, 2H), 7.18 (d, J=7.5 Hz, 2H), 7.10 (d, J=7.5 Hz, 2H), 6.98 (d, J=8.2 Hz, 2H), 5.42 (s, 2H), 2.85 (s, 3H), 1.44 (s, 6H). MS: [M+Na]: m/z=537.3, [M+H]: m/z=515.2 HPLC: 95.7% (RT-2.37 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 811, 2,2-dimethyl-5-phenyl-4-(4-(quinolin-2-ylmethoxy)phenyl) furan-3(2H)-one

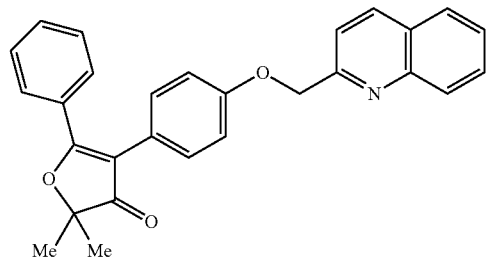 [SMILES: CC1(C)OC(c2ccccc2)=C(c2ccc(OCc3ccc4ccccc4n3)cc2)C1=O]

To a stirred solution of 5-(4-aminophenyl)-2,2-dimethyl-4-(4-(quinolin-2-ylmethoxy)phenyl) furan-3(2H)-one (80 mg, 0.18 mmol) in ACN: H₂O (6 mL, 1:1) was added conc HCl (0.2 mL) at 0° C. under N₂ atmosphere. The reaction mixture was stirred at 0° C. for 10 min. After being stirred for 5 min then added NaNO₂ in water and stirred for 40 min at 0° C. The reaction mixture was stirred at 70° C. for 2 h. After completion of starting material (by TLC), reaction mass was diluted with water and extracted with EtOAc (2×25 mL). Combined organic layers were washed with water (2×5 mL), brine and dried over anhydrous Na₂SO₄. After filtration and evaporation, the crude material was purified by silica gel column chromatography to afford 2,2-dimethyl-5-phenyl-4-(4-(quinolin-2-ylmethoxy)phenyl) furan-3(2H)-one (18 mg, 23%), as an off white solid. ¹H NMR (400 MHz, CDCl₃): δ 8.45 (d, J=8.5 Hz, 1H), 8.10 (d, J=7.9 Hz, 1H), 7.86 (d, J=8.4 Hz, 1H), 7.75-7.62 (m, 3H), 7.52 (t, J=8.2 Hz, 1H), 7.45 (d, J=8.5 Hz, 1H), 7.32 (d, J=7.5 Hz, 2H), 7.21 (d, J=7.4 Hz, 2H), 7.03 (d, J=7.5 Hz, 2H), 5.42 (s, 2H), 1.51 (s, 6H). MS: [M+Na]: m/z=444.1, [M+H]: m/z=422.1. HPLC: 98.72% (RT-2.83 min), Column: Acquity BEH-C-18, 50×2.1 mm, 1.7 um. Mobile Phase: 0.025% TFA in Water (A), ACN (B), Flow rate: 0.5 ml/min (Gradient).

Synthesis of Example 174, 2,2-dimethyl-4-(4-(quinolin-2-ylmethoxy)phenyl)-5-(thiazol-4-yl)furan-3(2H)-one 4-Methyl-1-(thiazol-4-yl)-4-(trimethylsilyloxy)pent-2-yn-1-one

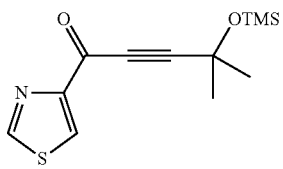

To a stirred solution of trimethyl (2-methylbut-3-yn-2-yloxy) silane (0.56 g, 3.57 mmol) in dry THF (10 mL) was added n-BuLi (1.3 mL, 2.1 mmol, 1.6 M in hexane) dropwise at −78° C. under an inert atmosphere for a period of 5 min. After being stirred for 30 min at −78° C., a solution of N-methoxy-N-methylthiazole-4-carboxamide (0.25 g, 1.78 mmol) in dry THF (5 mL) was added to reaction mixture and stirring was continued for an additional 1 h at −78° C. The reaction mixture was quenched with a saturated NH₄Cl solution and extracted with EtOAc (2×30 mL). The combined organic layers were washed with water (20 mL), brine (20 mL), dried over Na₂SO₄, filtered and concentrated in vacuo to obtain the crude product. The crude material was purified via silica gel column chromatography eluting with 2-4% EtOAc in Hexane to afford 4-methyl-1-(thiazol-4-yl)-4-(trimethylsilyloxy)pent-2-yn-1-one (0.15 g, 31.44%) as an oil.

4-Hydroxy-4-methyl-1-(thiazol-4-yl) pent-2-yn-1-one

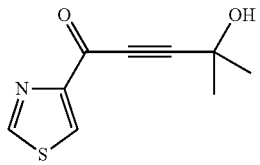

To a stirred solution of 4-methyl-1-(thiazol-4-yl)-4-(trimethylsilyloxy)pent-2-yn-1-one (0.15 g, 0.56 mmol) in DCM (3 mL) was added PTSA (0.16 g, 0.84 mmol) at RT and the reaction mixture was stirred for 1 h. The reaction mixture was diluted with water (10 mL), the organic layer was washed with a saturated NaHCO₃ solution, water, dried over Na₂SO₄, filtered and then concentrated in vacuo to afford 4-hydroxy-4-methyl-1-(thiazol-4-yl) pent-2-yn-1-one (0.12 g, crude) as an oil.

2,2-Dimethyl-5-(thiazol-4-yl) furan-3(2H)-one

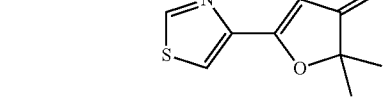

To a stirred solution of 4-hydroxy-4-methyl-1-(thiazol-4-yl) pent-2-yn-1-one (0.1 g, 0.53 mmol) in ethanol (1 mL) was added diethyl amine (0.057 mL, 0.59 mmol) in EtOH (0.5 mL) dropwise at RT and the reaction mixture was stirred for additional 45 min. Then the EtOH was removed, diluted with EtOAc (10 mL), washed with water (5 mL), brine (5 mL), dried over Na₂SO₄, filtered and concentrated in vacuo to afford 2,2-dimethyl-5-(thiazol-4-yl) furan-3(2H)-one (0.1 g) as an oil.

4-Bromo-2,2-dimethyl-5-(thiazol-4-yl) furan-3(2H)-one

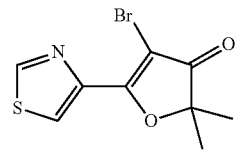

To a stirred solution of 2,2-dimethyl-5-(thiazol-4-yl) furan-3(2H)-one (90 mg, 0.46 mmol) in CHCl₃ (1.8 mL) was added NBS (0.12 g, 0.69 mmol) portionwise at RT and the reaction mixture was stirred for 1 h. The reaction mixture was diluted with DCM (10 mL), washed with water (5 mL), brine (10 mL), dried over Na₂SO₄, filtered and then concentrated in vacuo to obtain the crude product. The crude material was purified via silica gel column chromatography to afford 4-bromo-2,2-dimethyl-5-(thiazol-4-yl) furan-3(2H)-one (40 mg, 71%) as an off white solid.

Example 174

2,2-dimethyl-4-(4-(quinolin-2-ylmethoxy)phenyl)-5-(thiazol-4-yl)furan-3(2H)-one

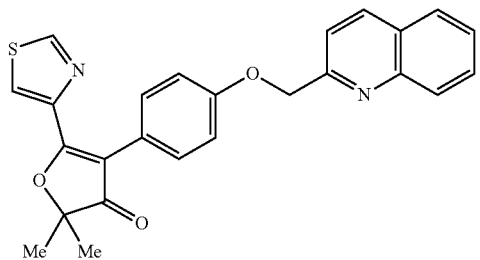 [SMILES: CC1(C)OC(c2cscn2)=C(c2ccc(OCc3ccc4ccccc4n3)cc2)C1=O]

A mixture of 4-bromo-2,2-dimethyl-5-(thiazol-4-yl)furan-3(2H)-one (0.1 g, 0.37 mmol), 2-((4-(4,4,5,5-tetramethyl-1,3,2-dioxaborolan-2-yl)phenoxy)methyl)quinoline (0.164 g, 0.454 mmol), and $Cs_2CO_3$ (0.673 g, 2.06 mmol) in toluene (1 mL) and water (1 mL) was degassed and Pd(dppf)$Cl_2$ (0.067 g, 0.082 mmol) was added under an inert atmosphere, and degassed once more. Then the reaction was refluxed for 2 h and was filtered through a pad of Celite®, the filtrate was diluted with EtOAc (10 mL), washed with water (5 mL), brine (5 mL), dried over $Na_2SO_4$, filtered and concentrated in vacuo to obtain the crude product. The crude material was purified via silica gel column chromatography to afford 2,2-dimethyl-4-(4-(quinolin-2-ylmethoxy)phenyl)-5-(thiazol-4-yl) furan-3(2H)-one (30 mg, 18%) as a solid. $^1$H NMR (500 MHz, $d_6$-DMSO): δ 9.17 (s, 1H), 8.43 (d, J=8.5 Hz, 1H), 8.30 (s, 1H), 8.02-7.98 (m, 2H), 7.80 (t, J=8.2 Hz, 1H), 7.70 (d, J=8.2 Hz, 1H), 7.62 (t, J=8.5 Hz, 1H), 7.24 (d, J=7.5 Hz, 2H), 7.08 (d, J=7.4 Hz, 2H), 5.38 (s, 2H), 1.42 (s, 6H). MS: [M+H]: m/z=429.1. HPLC: 97.9% (RT-2.36 min), Column: Acquity BEH-C-18, 50×2.1 mm, 1.7 um. Mobile Phase: 0.025% TFA in Water (A), ACN (B), Flow rate: 0.5 ml/min (Gradient).

Tables

In the following tables, if a specific example contains a single value in the column "$R_1$, and $R_{1b}$", then both $R_1$, and $R_{1b}$ (if present) are taken to be this value. If this column contains multiple values separated by a comma, the first value is taken to be $R_1$, and the second to be $R_{1b}$. In the following tables, if a specific example contains multiple instances of $R_2$, they will be separated by commas in the table (e.g. Me, Me or Et, Me). If the $R_2$ column contains a value "-group-" e.g. "-cyclopropyl-", then both $R_2$ values are taken together to be a spiro ring.

In a further aspect the compounds of the disclosure are embodied in with distinct examples listed in the table below taken from Formula (I):

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 1 | A1 | 4-pyridinyl | $OCH_2$ | 2-quinoline | — | — | Me | Me | — |
| 2 | A1 | 4-pyridinyl | $CH_2O$ | 2-quinoline | — | — | Me | Me | — |
| 3 | A3 | 4-pyridinyl | $OCH_2$ | 2-benzimidazole | — | — | — | — | Me |
| 4 | A3 | 4-pyridinyl | $OCH_2$ | 2-tetrahydroisoquinoline | — | — | — | — | Me |
| 5 | A3 | 4-pyridinyl | $OCH_2$ | 2-pyridinyl | — | — | — | — | Me |
| 6 | A3 | 4-pyridinyl | $OCH_2$ | 2-benzoxazole | — | — | — | — | Me |
| 7 | A3 | 4-pyridinyl | $OCH_2$ | 2-benzthiazole | — | — | — | — | Me |
| 8 | A3 | 4-pyridinyl | $OCH_2$ | 2-quinoxaline | — | — | — | — | Me |
| 9 | A3 | 4-pyridinyl | $OCH_2$ | 2-naphthyridine | — | — | — | — | Me |
| 10 | A3 | 4-pyridinyl | $OCH_2$ | 2-quinazoline | — | — | — | — | Me |
| 11 | A3 | 4-pyridinyl | $OCH_2$ | 2-quinoline | — | — | — | — | Me |
| 12 | A3 | 4-pyridinyl | $CH_2O$ | 2-quinoline | — | — | — | — | Me |
| 13 | A4 | 4-pyridinyl | $OCH_2$ | 2-quinoline | — | — | — | — | — |
| 15 | A4 | 4-pyridinyl | $CH_2O$ | 2-quinoline | — | — | — | — | — |
| 17 | A5 | 4-pyridinyl | $OCH_2$ | 2-quinoline | — | — | — | — | H |
| 18 | A5 | 4-pyridinyl | $OCH_2$ | 2-quinoline | — | — | — | — | Me |
| 19 | A5 | 4-pyridinyl | $CH_2O$ | 2-quinoline | — | — | — | — | H |
| 20 | A5 | 4-pyridinyl | $CH_2O$ | 2-quinoline | — | — | — | — | Me |
| 21 | A6 | 4-pyridinyl | $OCH_2$ | 2-quinoline | Me, — | — | — | — | H |
| 22 | A6 | 4-pyridinyl | $CH_2O$ | 2-quinoline | Me, — | — | — | — | H |
| 23 | A7 | 4-pyridinyl | $OCH_2$ | 2-quinoline | — | — | Me | Me | — |
| 24 | A7 | 4-pyridinyl | $CH_2O$ | 2-quinoline | — | — | Me | Me | — |
| 25 | A7 | 4-pyridinyl | $OCH_2$ | 2-quinoline | — | — | Et | Et | — |
| 26 | A7 | 4-pyridinyl | $OCH_2$ | 2-quinoline | — | — | cyclopropyl | | — |
| 27 | A7 | 3-F, 4-OMe phenyl | $OCH_2$ | 2-quinoline | — | — | Me | Me | — |
| 28 | A7 | 3-Cl, 4-OMe phenyl | $OCH_2$ | 2-quinoline | — | — | Me | Me | — |
| 29 | A7 | 3-CN, 4-OMe phenyl | $OCH_2$ | 2-quinoline | — | — | Me | Me | — |
| 30 | A7 | 3-OMe, 4-F phenyl | $OCH_2$ | 2-quinoline | — | — | Me | Me | — |
| 31 | A7 | 3-OMe, 4-Cl phenyl | $OCH_2$ | 2-quinoline | — | — | Me | Me | — |
| 32 | A7 | 3-OMe, 4-CN phenyl | $OCH_2$ | 2-quinoline | — | — | Me | Me | — |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 33 | A7 | 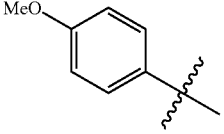 [SMILES: *c1ccc(OC)cc1] MeO-C$_6$H$_4$- | OCH$_2$ | 2-quinoline | — | — | Me | Me | — |
| 34 | A7 | 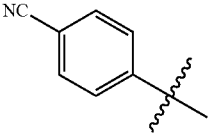 [SMILES: *c1ccc(C#N)cc1] NC-C$_6$H$_4$- | OCH$_2$ | 2-quinoline | — | — | Me | Me | — |
| 35 | A7 | 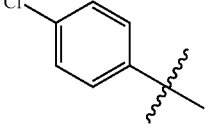 Cl-C$_6$H$_4$- | OCH$_2$ | 2-quinoline | — | — | Me | Me | — |
| 36 | A7 | 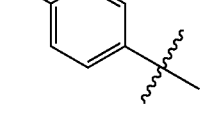 F-C$_6$H$_4$- | OCH$_2$ | 2-quinoline | — | — | Me | Me | — |
| 37 | A7 | 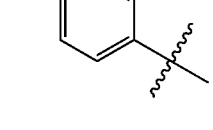 F$_3$C-C$_6$H$_4$- | OCH$_2$ | 2-quinoline | — | — | Me | Me | — |
| 38 | A7 | 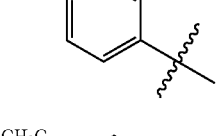 CF$_3$O-C$_6$H$_4$- | OCH$_2$ | 2-quinoline | — | — | Me | Me | — |
| 39 | A7 | 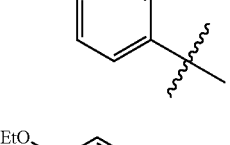 F$_3$CH$_2$C-C$_6$H$_4$- | OCH$_2$ | 2-quinoline | — | — | Me | Me | — |
| 40 | A7 | 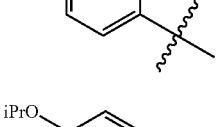 EtO-C$_6$H$_4$- | OCH$_2$ | 2-quinoline | — | — | Me | Me | — |
| 41 | A7 | 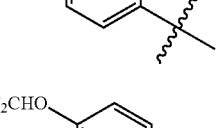 iPrO-C$_6$H$_4$- | OCH$_2$ | 2-quinoline | — | — | Me | Me | — |
| 42 | A7 | 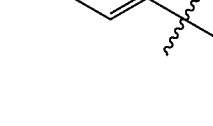 F$_2$CHO-C$_6$H$_4$- | OCH$_2$ | 2-quinoline | — | — | Me | Me | — |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 43 | A7 | 4-(cyclopropyloxy)phenyl | OCH$_2$ | 2-quinoline | — | — | Me | Me | — |
| 44 | A7 | 4-(cyclopropylmethoxy)phenyl | OCH$_2$ | 2-quinoline | — | — | Me | Me | — |
| 45 | A7 | 4-(2,2,2-trifluoroethoxy)phenyl | OCH$_2$ | 2-quinoline | — | — | Me | Me | — |
| 46 | A7 | 4-bromophenyl | OCH$_2$ | 2-quinoline | — | — | Me | Me | — |
| 47 | A7 | 4-nitrophenyl | OCH$_2$ | 2-quinoline | — | — | Me | Me | — |
| 48 | A7 | 4-(difluoromethyl)phenyl | OCH$_2$ | 2-quinoline | — | — | Me | Me | — |
| 49 | A7 | benzo[c][1,2,5]oxadiazol-5-yl | OCH$_2$ | 2-quinoline | — | — | Me | Me | — |
| 50 | A7 | benzo[c][1,2,5]thiadiazol-5-yl | OCH$_2$ | 2-quinoline | — | — | Me | Me | — |
| 51 | A7 | 3-chloro-4-(difluoromethoxy)phenyl | OCH$_2$ | 2-quinoline | — | — | Me | Me | — |

-continued

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 52 | A7 | 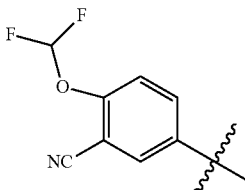 | OCH$_2$ | 2-quinoline | — | — | Me | Me | — |
| 53 | A7 | 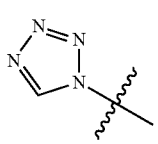 | OCH$_2$ | 2-quinoline | — | — | Me | Me | — |
| 54 | A7 | 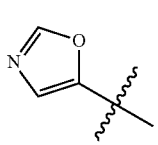 | OCH$_2$ | 2-quinoline | — | — | Me | Me | — |
| 55 | A7 | 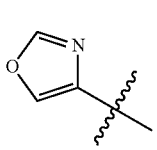 | OCH$_2$ | 2-quinoline | — | — | Me | Me | — |
| 56 | A7 | 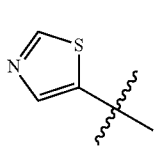 | OCH$_2$ | 2-quinoline | — | — | Me | Me | — |
| 57 | A7 | 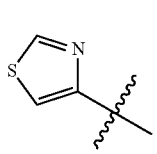 | OCH$_2$ | 2-quinoline | — | — | Me | Me | — |
| 58 | A7 | 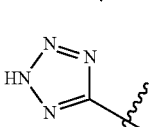 | OCH$_2$ | 2-quinoline | — | — | Me | Me | — |
| 59 | A8 | 4-pyridinyl | OCH$_2$ | 2-quinoline | — | — | cyclopropyl | | H |
| 60 | A8 | 4-pyridinyl | OCH$_2$ | 2-quinoline | — | — | Me | Me | cyclopropyl |
| 61 | A8 | 4-pyridinyl | OCH$_2$ | 2-quinoline | — | — | Et | Et | cyclopropyl |
| 62 | A8 | 4-pyridinyl | OCH$_2$ | 2-quinoline | — | — | cyclopropyl | | cyclopropyl |
| 63 | A8 | 4-pyridinyl | OCH$_2$ | 2-quinoline | — | — | Me | Me | H |
| 64 | A8 | 4-pyridinyl | OCH$_2$ | 2-quinoline | — | — | Me | Me | Me |
| 65 | A8 | 4-pyridinyl | OCH$_2$ | 2-quinoline | — | — | Et | Et | Me |
| 66 | A8 | 4-pyridinyl | OCH$_2$ | 2-quinoline | — | — | cyclopropyl | | Me |
| 67 | A8 | 4-pyridinyl | OCH$_2$ | 2-quinoline | — | — | Me | Me | Et |
| 68 | A8 | 4-pyridinyl | OCH$_2$ | 2-quinoline | — | — | Et | Et | Et |
| 69 | A8 | 4-pyridinyl | OCH$_2$ | 2-quinoline | — | — | cyclopropyl | | Et |
| 70 | A8 | 4-pyridinyl | OCH$_2$ | 2-quinoline | — | — | Me | Me | —CH$_2$CF$_3$ |
| 71 | A8 | 4-pyridinyl | OCH$_2$ | 2-quinoline | — | — | Et | Et | —CH$_2$CF$_3$ |
| 72 | A8 | 4-pyridinyl | OCH$_2$ | 2-quinoline | — | — | cyclopropyl | | —CH$_2$CF$_3$ |

| Ex PCT # | HET | X | Y | Z | R_{1a}, R_{1b} | R_2 | R_3 | R_4 | R_7 |
|---|---|---|---|---|---|---|---|---|---|
| 73 | A8 | 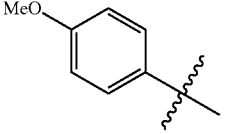 MeO- | OCH_2 | 2-quinoline | — | — | Me | Me | Me |
| 74 | A8 | 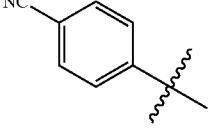 NC- | OCH_2 | 2-quinoline | — | — | Me | Me | Me |
| 75 | A8 | 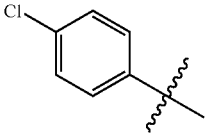 Cl- | OCH_2 | 2-quinoline | — | — | Me | Me | Me |
| 76 | A8 | 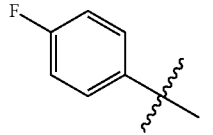 F- | OCH_2 | 2-quinoline | — | — | Me | Me | Me |
| 77 | A8 | 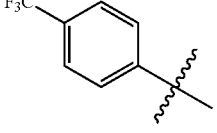 F_3C- | OCH_2 | 2-quinoline | — | — | Me | Me | Me |
| 78 | A8 | 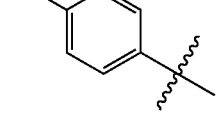 CF_3O- | OCH_2 | 2-quinoline | — | — | Me | Me | Me |
| 79 | A8 | 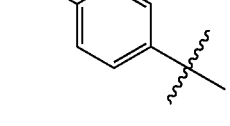 F_3CH_2C- | OCH_2 | 2-quinoline | — | — | Me | Me | Me |
| 80 | A8 | 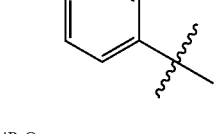 EtO- | OCH_2 | 2-quinoline | — | — | Me | Me | Me |
| 81 | A8 | 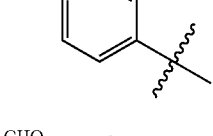 iPrO- | OCH_2 | 2-quinoline | — | — | Me | Me | Me |
| 82 | A8 | 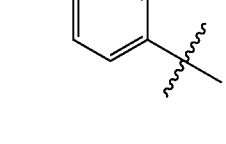 F_2CHO- | OCH_2 | 2-quinoline | — | — | Me | Me | Me |

-continued

| Ex PCT # | HET | X | Y | Z | R_{1a}, R_{1b} | R_2 | R_3 | R_4 | R_7 |
|---|---|---|---|---|---|---|---|---|---|
| 83 | A8 | 4-(cyclopropyloxy)phenyl | OCH$_2$ | 2-quinoline | — | — | Me | Me | Me |
| 84 | A8 | 4-(cyclopropylmethoxy)phenyl | OCH$_2$ | 2-quinoline | — | — | Me | Me | Me |
| 85 | A8 | 4-(2,2,2-trifluoroethoxy)phenyl | OCH$_2$ | 2-quinoline | — | — | Me | Me | Me |
| 86 | A8 | 4-bromophenyl | OCH$_2$ | 2-quinoline | — | — | Me | Me | Me |
| 87 | A8 | 4-nitrophenyl | OCH$_2$ | 2-quinoline | — | — | Me | Me | Me |
| 88 | A8 | 4-(difluoromethyl)phenyl | OCH$_2$ | 2-quinoline | — | — | Me | Me | Me |
| 89 | A8 | benzo[c][1,2,5]oxadiazol-5-yl | OCH$_2$ | 2-quinoline | — | — | Me | Me | Me |
| 90 | A8 | benzo[c][1,2,5]thiadiazol-5-yl | OCH$_2$ | 2-quinoline | — | — | Me | Me | Me |
| 91 | A8 | 3-chloro-4-(difluoromethoxy)phenyl | OCH$_2$ | 2-quinoline | — | — | Me | Me | Me |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 92 | A8 | 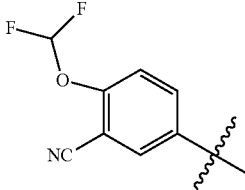 | OCH$_2$ | 2-quinoline | — | — | Me | Me | Me |
| 93 | A8 | 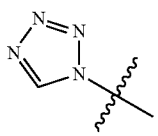 | OCH$_2$ | 2-quinoline | — | — | Me | Me | Me |
| 94 | A8 | 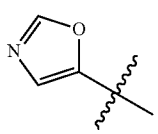 [SMILES: *c1cnco1] | OCH$_2$ | 2-quinoline | — | — | Me | Me | Me |
| 95 | A8 | 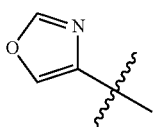 [SMILES: *c1cocn1] | OCH$_2$ | 2-quinoline | — | — | Me | Me | Me |
| 96 | A8 | 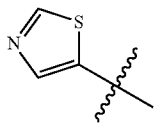 | OCH$_2$ | 2-quinoline | — | — | Me | Me | Me |
| 97 | A8 | 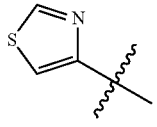 [SMILES: *c1cscn1] | OCH$_2$ | 2-quinoline | — | — | Me | Me | Me |
| 98 | A8 | 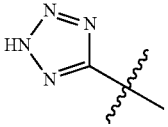 [SMILES: *c1nn[nH]n1] | OCH$_2$ | 2-quinoline | — | — | Me | Me | Me |
| 99 | A9 | 4-pyridinyl | OCH$_2$ | 2-quinoline | — | — | — | — | — |
| 100 | A9 | 4-pyridinyl | OCH$_2$ | 2-quinoline | — | — | — | — | — |
| 101 | A9 | 4-pyridinyl | CH$_2$O | 2-quinoline | — | — | — | — | — |
| 102 | A9 | 4-pyridinyl | CH$_2$O | 2-quinoline | — | — | — | — | — |
| 103 | A10 | 4-pyridinyl | OCH$_2$ | 2-benzimidazole | Me, — | — | — | — | — |
| 104 | A10 | 4-pyridinyl | OCH$_2$ | 2-tetrahydroisoquinoline | Me, — | — | — | — | — |
| 105 | A10 | 4-pyridinyl | OCH$_2$ | 2-pyridinyl | Me, — | — | — | — | — |
| 106 | A10 | 4-pyridinyl | OCH$_2$ | 2-benzoxazole | Me, — | — | — | — | — |
| 107 | A10 | 4-pyridinyl | OCH$_2$ | 2-benzthiazole | Me, — | — | — | — | — |
| 108 | A10 | 4-pyridinyl | OCH$_2$ | 2-quinoxaline | Me, — | — | — | — | — |
| 109 | A10 | 4-pyridinyl | OCH$_2$ | 2-naphthyridine | Me, — | — | — | — | — |
| 110 | A10 | 4-pyridinyl | OCH$_2$ | 2-quinazoline | Me, — | — | — | — | — |
| 111 | A10 | 4-pyridinyl | OCH$_2$ | 2-quinoline | Me, — | — | — | — | — |
| 113 | A11 | 4-pyridinyl | OCH$_2$ | 2-quinoline | Me, — | — | — | — | — |
| 114 | A11 | 4-pyridinyl | CH$_2$O | 2-quinoline | Me, — | — | — | — | — |
| 115 | A12 | 4-pyridinyl | OCH$_2$ | 2-quinoline | Me, — | — | — | — | — |
| 116 | A12 | 4-pyridinyl | CH$_2$O | 2-quinoline | Me, — | — | — | — | — |
| 117 | A13 | 4-pyridinyl | OCH$_2$ | 2-quinoline | Me, Me | — | — | — | — |
| 118 | A13 | 4-pyridinyl | CH$_2$O | 2-quinoline | Me, Me | — | — | — | — |
| 119 | A14 | 4-pyridinyl | OCH$_2$ | 2-quinoline | Me, Me | — | — | — | — |
| 120 | A14 | 4-pyridinyl | CH$_2$O | 2-quinoline | Me, Me | — | — | — | — |
| 121 | A15 | 4-pyridinyl | OCH$_2$ | 2-quinoline | Me, — | — | — | — | — |
| 122 | A15 | 4-pyridinyl | CH$_2$O | 2-quinoline | Me, — | — | — | — | — |

-continued
| Ex PCT # | HET | X | Y | Z | R1a, R1b | R2 | R3 | R4 | R7 |
|---|---|---|---|---|---|---|---|---|---|
| 123 | A25 | 4-pyridinyl | OCH2 | 2-quinoline | — | Me | — | — | — |
| 124 | A25 | 4-pyridinyl | OCH2 | 2-quinoline | — | CH2CF3 | — | — | — |
| 125 | A29 | 4-pyridinyl | OCH2 | 2-quinoline | — | Me, Me | — | — | — |
| 126 | A29 | 4-pyridinyl | OCH2 | 2-quinoline | — | -cyclo-propyl- | — | — | — |
| 127 | A29 | 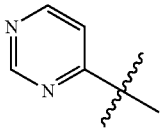 [SMILES: *c1ccncn1] | OCH2 | 2-quinoline | — | Me, Me | — | — | — |
| 128 | A29 | 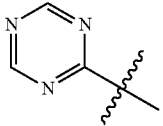 | OCH2 | 2-quinoline | — | Me, Me | — | — | — |
| 129 | A29 | 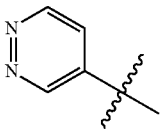 | OCH2 | 2-quinoline | — | Me, Me | — | — | — |
| 130 | A29 | 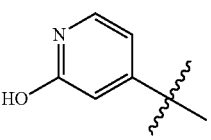 | OCH2 | 2-quinoline | — | Me, Me | — | — | — |
| 131 | A29 | 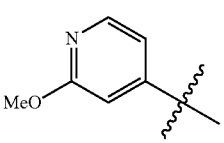 | OCH2 | 2-quinoline | — | Me, Me | — | — | — |
| 132 | A29 | 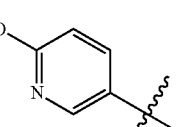 | OCH2 | 2-quinoline | — | Me, Me | — | — | — |
| 133 | A29 | 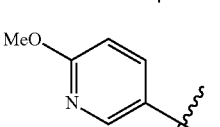 | OCH2 | 2-quinoline | — | Me, Me | — | — | — |
| 134 | A29 | 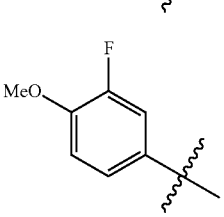 | OCH2 | 2-quinoline | — | Me, Me | — | — | — |
| 135 | A29 | 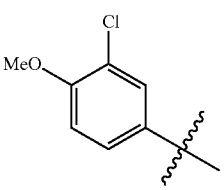 | OCH2 | 2-quinoline | — | Me, Me | — | — | — |

-continued
| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 136 | A29 | 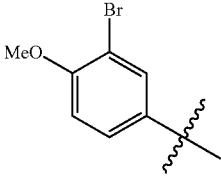 | OCH$_2$ | 2-quinoline | — | Me, Me | — | — | — |
| 137 | A29 | 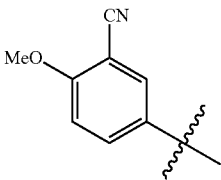 [SMILES: *c1ccc(OC)c(C#N)c1] | OCH$_2$ | 2-quinoline | — | Me, Me | — | — | — |
| 138 | A29 | 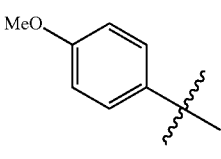 | OCH$_2$ | 2-quinoline | — | Me, Me | — | — | — |
| 139 | A29 | 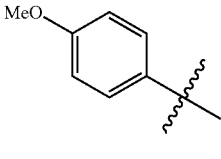 [SMILES: *c1ccc(OC)cc1] | OCH$_2$ | 2-quinoline | — | Me, Et | — | — | — |
| 140 | A29 | 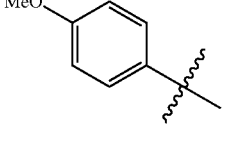 | OCH$_2$ | 2-quinoline | — | Et, Me | — | — | — |
| 141 | A29 | 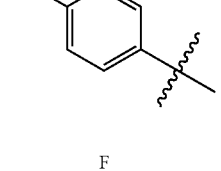 | OCH$_2$ | 2-quinoline | — | Me, Me | — | — | — |
| 142 | A29 | 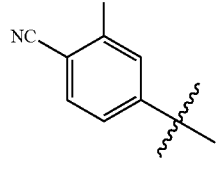 | OCH$_2$ | 2-quinoline | — | Me, Me | — | — | — |
| 143 | A29 | 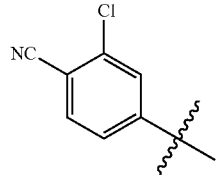 | OCH$_2$ | 2-quinoline | — | Me, Me | — | — | — |

-continued
| Ex PCT # | HET | X | Y | Z | R_{1a}, R_{1b} | R_2 | R_3 | R_4 | R_7 |
|---|---|---|---|---|---|---|---|---|---|
| 144 | A29 | 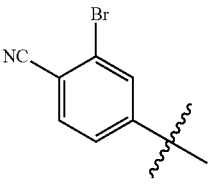 2-Br, 1-CN phenyl | OCH_2 | 2-quinoline | — | Me, Me | — | — | — |
| 145 | A29 | 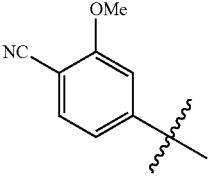 2-OMe, 1-CN phenyl | OCH_2 | 2-quinoline | — | Me, Me | — | — | — |
| 146 | A29 | 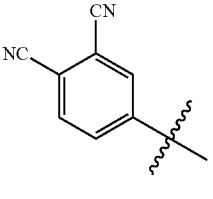 1,2-diCN phenyl | OCH_2 | 2-quinoline | — | Me, Me | — | — | — |
| 147 | A29 | 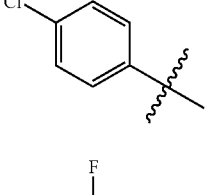 4-Cl phenyl | OCH_2 | 2-quinoline | — | Me, Me | — | — | — |
| 148 | A29 | 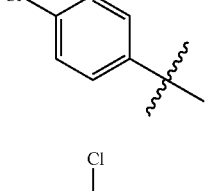 4-Cl, 3-F phenyl | OCH_2 | 2-quinoline | — | Me, Me | — | — | — |
| 149 | A29 | 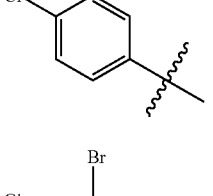 3,4-diCl phenyl | OCH_2 | 2-quinoline | — | Me, Me | — | — | — |
| 150 | A29 | 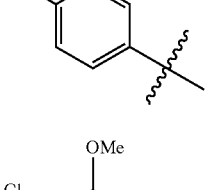 3-Br, 4-Cl phenyl | OCH_2 | 2-quinoline | — | Me, Me | — | — | — |
| 151 | A29 | 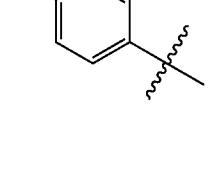 3-OMe, 4-Cl phenyl | OCH_2 | 2-quinoline | — | Me, Me | — | — | — |

-continued
| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 152 | A29 | 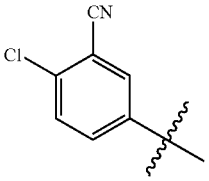 | OCH$_2$ | 2-quinoline | — | Me, Me | — | — | — |
| 153 | A29 | 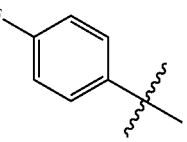 | OCH$_2$ | 2-quinoline | — | Me, Me | — | — | — |
| 154 | A29 | 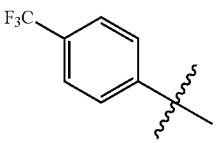 | OCH$_2$ | 2-quinoline | — | Me, Me | — | — | — |
| 155 | A29 | 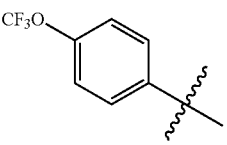 | OCH$_2$ | 2-quinoline | — | Me, Me | — | — | — |
| 156 | A29 | 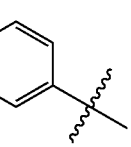 | OCH$_2$ | 2-quinoline | — | Me, Me | — | — | — |
| 157 | A29 | 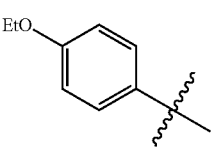 | OCH$_2$ | 2-quinoline | — | Me, Me | — | — | — |
| 158 | A29 | 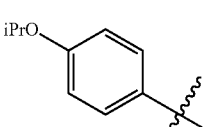 | OCH$_2$ | 2-quinoline | — | Me, Me | — | — | — |
| 159 | A29 | 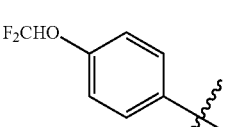 | OCH$_2$ | 2-quinoline | — | Me, Me | — | — | — |
| 160 | A29 | 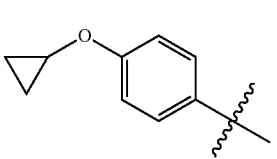 [SMILES: *c1ccc(OC2CC2)cc1] | OCH$_2$ | 2-quinoline | — | Me, Me | — | — | — |

-continued
| Ex PCT # | HET | X | Y | Z | R1a, R1b | R2 | R3 | R4 | R7 |
|---|---|---|---|---|---|---|---|---|---|
| 161 | A29 | 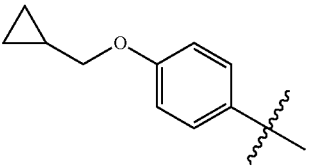 [SMILES: *c1ccc(OCC2CC2)cc1] | OCH2 | 2-quinoline | — | Me, Me | — | — | — |
| 162 | A29 | 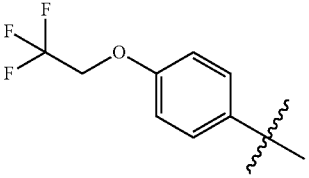 [SMILES: *c1ccc(OCC(F)(F)F)cc1] | OCH2 | 2-quinoline | — | Me, Me | — | — | — |
| 163 | A29 | 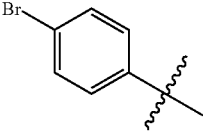 | OCH2 | 2-quinoline | — | Me, Me | — | — | — |
| 164 | A29 | 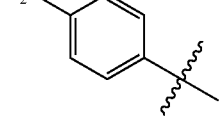 | OCH2 | 2-quinoline | — | Me, Me | — | — | — |
| 165 | A29 | 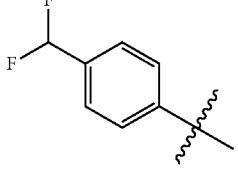 | OCH2 | 2-quinoline | — | Me, Me | — | — | — |
| 166 | A29 | 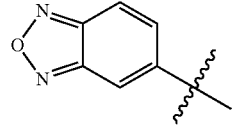 [SMILES: *c1ccc2nonc2c1] | OCH2 | 2-quinoline | — | Me, Me | — | — | — |
| 167 | A29 | 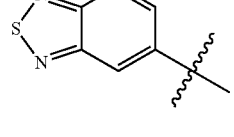 | OCH2 | 2-quinoline | — | Me, Me | — | — | — |
| 168 | A29 | 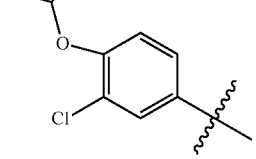 | OCH2 | 2-quinoline | — | Me, Me | — | — | — |

| Ex PCT # | HET | X | Y | Z | R1a, R1b | R2 | R3 | R4 | R7 |
|---|---|---|---|---|---|---|---|---|---|
| 169 | A29 | 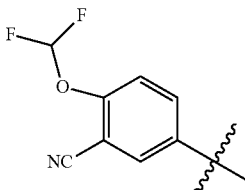 | OCH2 | 2-quinoline | — | Me, Me | — | — | — |
| 170 | A29 | 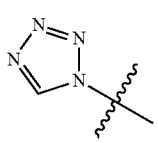 | OCH2 | 2-quinoline | — | Me, Me | — | — | — |
| 171 | A29 | 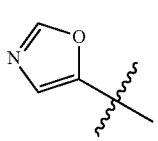 | OCH2 | 2-quinoline | — | Me, Me | — | — | — |
| 172 | A29 | 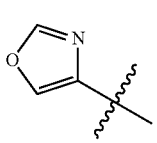 [SMILES: *c1cocn1] | OCH2 | 2-quinoline | — | Me, Me | — | — | — |
| 173 | A29 | 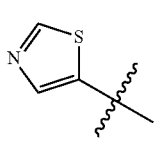 | OCH2 | 2-quinoline | — | Me, Me | — | — | — |
| 174 | A29 | 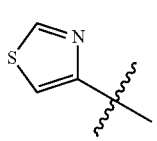 [SMILES: *c1cscn1] | OCH2 | 2-quinoline | — | Me, Me | — | — | — |
| 175 | A29 | 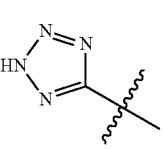 | OCH2 | 2-quinoline | — | Me, Me | — | — | — |
| 176 | A29 | 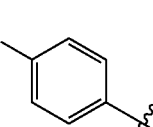 | OCH2 | 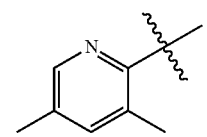 | — | Me, Me | — | — | — |
| 177 | A29 | 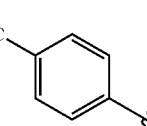 | OCH2 | 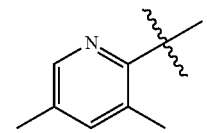 | — | Me, Me | — | — | — |
| 178 | A29 | 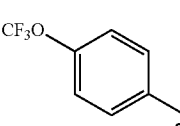 | OCH2 | 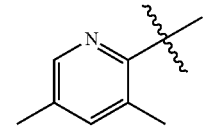 | — | Me, Me | — | — | — |

-continued

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 179 | A29 | F₃CH₂C-C₆H₄- | OCH₂ | 3,5-dimethylpyridin-2-yl | — | Me, Me | — | — | — |
| 180 | A29 | EtO-C₆H₄- | OCH₂ | 3,5-dimethylpyridin-2-yl | — | Me, Me | — | — | — |
| 181 | A29 | iPrO-C₆H₄- | OCH₂ | 3,5-dimethylpyridin-2-yl | — | Me, Me | — | — | — |
| 182 | A29 | CHF₂O-C₆H₄- | OCH₂ | 3,5-dimethylpyridin-2-yl | — | Me, Me | — | — | — |
| 183 | A29 | cyclopropyl-O-C₆H₄- | OCH₂ | 3,5-dimethylpyridin-2-yl | — | Me, Me | — | — | — |
| 184 | A29 | cyclopropyl-CH₂O-C₆H₄- | OCH₂ | 3,5-dimethylpyridin-2-yl | — | Me, Me | — | — | — |
| 185 | A29 | CF₃CH₂O-C₆H₄- | OCH₂ | 3,5-dimethylpyridin-2-yl | — | Me, Me | — | — | — |
| 186 | A29 | Br-C₆H₄- | OCH₂ | 3,5-dimethylpyridin-2-yl | — | Me, Me | — | — | — |
| 187 | A29 | O₂N-C₆H₄- | OCH₂ | 3,5-dimethylpyridin-2-yl | — | Me, Me | — | — | — |

-continued
| Ex PCT # | HET | X | Y | Z | R1a, R1b | R2 | R3 | R4 | R7 |
|---|---|---|---|---|---|---|---|---|---|
| 188 | A29 | 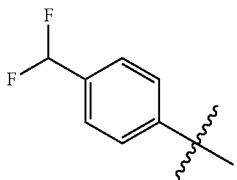 [SMILES: *c1ccc(C(F)F)cc1] | OCH2 | 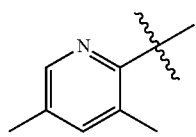 | — | Me, Me | — | — | — |
| 189 | A29 | 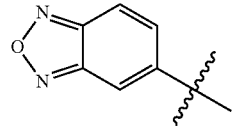 [SMILES: *c1ccc2nonc2c1] | OCH2 | 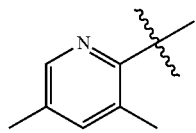 | — | Me, Me | — | — | — |
| 190 | A29 | 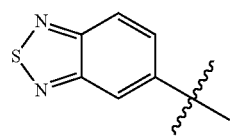 [SMILES: *c1ccc2nsnc2c1] | OCH2 | 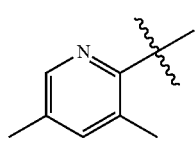 | — | Me, Me | — | — | — |
| 191 | A29 | 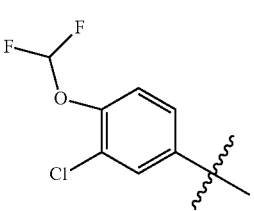 [SMILES: *c1ccc(OC(F)F)c(Cl)c1] | OCH2 | 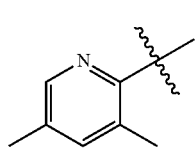 | — | Me, Me | — | — | — |
| 192 | A29 | 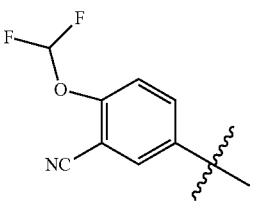 [SMILES: *c1ccc(OC(F)F)c(C#N)c1] | OCH2 | 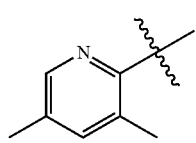 | — | Me, Me | — | — | — |
| 193 | A29 | 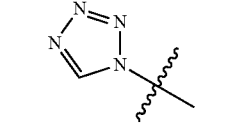 | OCH2 | 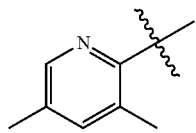 | — | Me, Me | — | — | — |
| 194 | A29 | 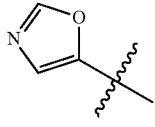 | OCH2 | 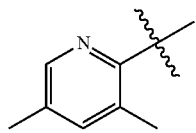 | — | Me, Me | — | — | — |
| 195 | A29 | 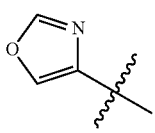 [SMILES: *c1cocn1] | OCH2 | 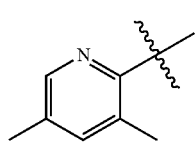 | — | Me, Me | — | — | — |
| 196 | A29 | 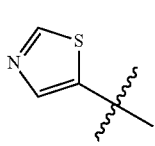 | OCH2 | 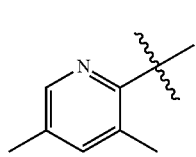 | — | Me, Me | — | — | — |

| Ex PCT # | HET | X | Y | Z | R1a, R1b | R2 | R3 | R4 | R7 |
|---|---|---|---|---|---|---|---|---|---|
| 197 | A29 | 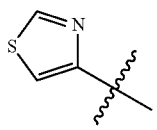 [SMILES: *c1cscn1] | OCH2 | 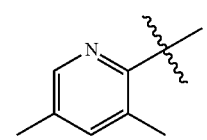 | — | Me, Me | — | — | — |
| 198 | A29 | 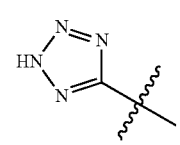 [SMILES: *c1nn[nH]n1] | OCH2 | 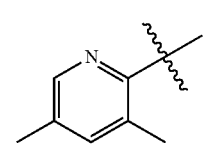 | — | Me, Me | — | — | — |
| 199 | A29 | 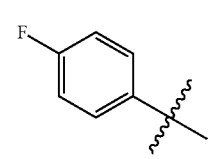 [SMILES: *c1ccc(F)cc1] | OCH2 | 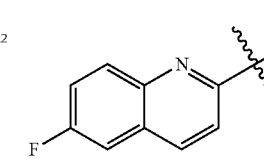 | — | Me, Me | — | — | — |
| 200 | A29 | 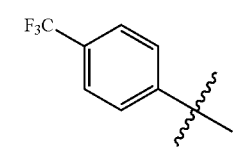 | OCH2 | 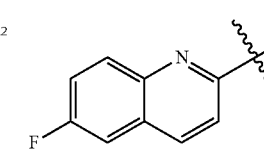 | — | Me, Me | — | — | — |
| 201 | A29 | 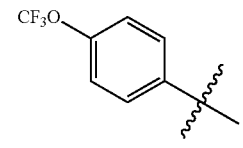 | OCH2 | 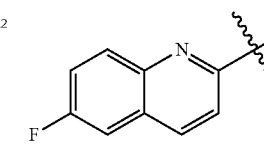 | — | Me, Me | — | — | — |
| 202 | A29 | 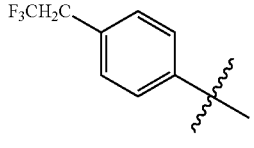 | OCH2 | 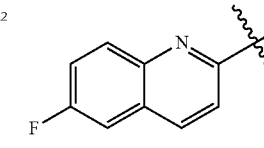 | — | Me, Me | — | — | — |
| 203 | A29 | 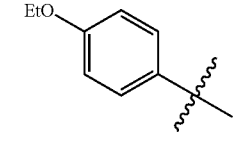 | OCH2 | 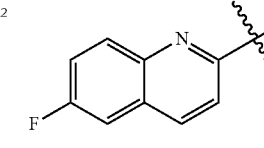 | — | Me, Me | — | — | — |
| 204 | A29 | 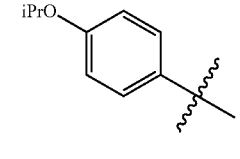 | OCH2 | 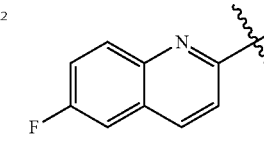 | — | Me, Me | — | — | — |
| 205 | A29 | 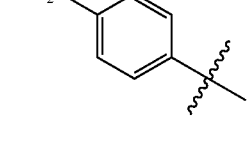 | OCH2 | 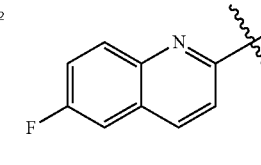 | — | Me, Me | — | — | — |
| 206 | A29 | 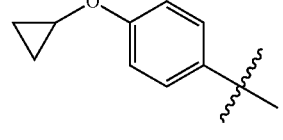 | OCH2 | 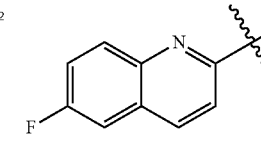 | — | Me, Me | — | — | — |

-continued

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 207 | A29 | cyclopropylmethoxy-phenyl | OCH$_2$ | 6-fluoroquinolin-2-yl | — | Me, Me | — | — | — |
| 208 | A29 | 2,2,2-trifluoroethoxy-phenyl | OCH$_2$ | 6-fluoroquinolin-2-yl | — | Me, Me | — | — | — |
| 209 | A29 | 4-bromophenyl | OCH$_2$ | 6-fluoroquinolin-2-yl | — | Me, Me | — | — | — |
| 210 | A29 | 4-nitrophenyl | OCH$_2$ | 6-fluoroquinolin-2-yl | — | Me, Me | — | — | — |
| 211 | A29 | 4-(difluoromethyl)phenyl | OCH$_2$ | 6-fluoroquinolin-2-yl | — | Me, Me | — | — | — |
| 212 | A29 | benzo[c][1,2,5]oxadiazol-5-yl | OCH$_2$ | 6-fluoroquinolin-2-yl | — | Me, Me | — | — | — |
| 213 | A29 | benzo[c][1,2,5]thiadiazol-5-yl | OCH$_2$ | 6-fluoroquinolin-2-yl | — | Me, Me | — | — | — |
| 214 | A29 | 3-chloro-4-(difluoromethoxy)phenyl | OCH$_2$ | 6-fluoroquinolin-2-yl | — | Me, Me | — | — | — |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 215 | A29 | 2-(difluoromethoxy)-5-cyanophenyl | OCH$_2$ | 6-fluoroquinolin-2-yl | — | Me, Me | — | — | — |
| 216 | A29 | 1H-tetrazol-1-yl | OCH$_2$ | 6-fluoroquinolin-2-yl | — | Me, Me | — | — | — |
| 217 | A29 | oxazol-5-yl | OCH$_2$ | 6-fluoroquinolin-2-yl | — | Me, Me | — | — | — |
| 218 | A29 | oxazol-4-yl | OCH$_2$ | 6-fluoroquinolin-2-yl | — | Me, Me | — | — | — |
| 219 | A29 | thiazol-5-yl | OCH$_2$ | 6-fluoroquinolin-2-yl | — | Me, Me | — | — | — |
| 220 | A29 | thiazol-4-yl | OCH$_2$ | 6-fluoroquinolin-2-yl | — | Me, Me | — | — | — |
| 221 | A29 | 2H-tetrazol-5-yl | OCH$_2$ | 6-fluoroquinolin-2-yl | — | Me, Me | — | — | — |
| 222 | A30 | 4-pyridinyl | OCH$_2$ | 2-quinoline | — | Me, Me | — | — | H |
| 223 | A30 | 4-pyridinyl | OCH$_2$ | 2-quinoline | — | -cyclopropyl- | — | — | H |
| 224 | A30 | 4-pyridinyl | OCH$_2$ | 2-quinoline | — | Me, Me | — | — | Me |
| 225 | A30 | pyrimidinyl | OCH$_2$ | 2-quinoline | — | Me, Me | — | — | Me |
| 226 | A30 | 1,3,5-triazinyl | OCH$_2$ | 2-quinoline | — | Me, Me | — | — | Me |

| Ex PCT # | HET | X | Y | Z | R1a, R1b | R2 | R3 | R4 | R7 |
|---|---|---|---|---|---|---|---|---|---|
| 227 | A30 | 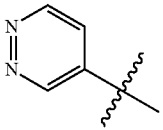 [SMILES: *c1ccnnc1] | OCH₂ | 2-quinoline | — | Me, Me | — | — | Me |
| 228 | A30 | 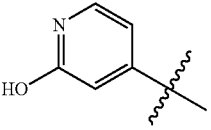 [SMILES: *c1ccnc(O)c1] | OCH₂ | 2-quinoline | — | Me, Me | — | — | Me |
| 229 | A30 | 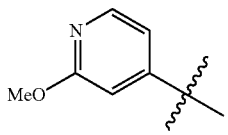 [SMILES: *c1ccnc(OC)c1] | OCH₂ | 2-quinoline | — | Me, Me | — | — | Me |
| 230 | A30 | 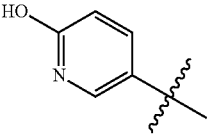 | OCH₂ | 2-quinoline | — | Me, Me | — | — | Me |
| 231 | A30 | 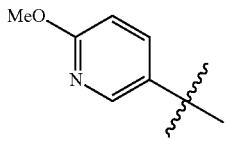 [SMILES: *c1ccc(OC)nc1] | OCH₂ | 2-quinoline | — | Me, Me | — | — | Me |
| 232 | A30 | 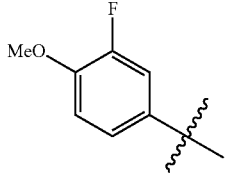 [SMILES: *c1ccc(OC)c(F)c1] | OCH₂ | 2-quinoline | — | Me, Me | — | — | Me |
| 233 | A30 | 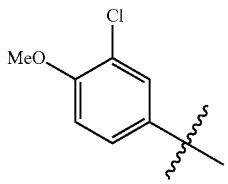 [SMILES: *c1ccc(OC)c(Cl)c1] | OCH₂ | 2-quinoline | — | Me, Me | — | — | Me |
| 234 | A30 | 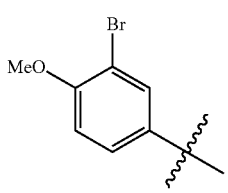 | OCH₂ | 2-quinoline | — | Me, Me | — | — | Me |
| 235 | A30 | 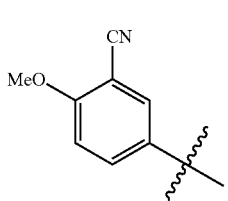 [SMILES: *c1ccc(OC)c(Cl)c1] | OCH₂ | 2-quinoline | — | Me, Me | — | — | Me |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 236 | A30 | 4-MeO-phenyl | OCH$_2$ | 2-quinoline | — | Me, Me | — | — | Me |
| 237 | A30 | 4-NC-phenyl | OCH$_2$ | 2-quinoline | — | Me, Me | — | — | Me |
| 238 | A30 | 4-NC-3-F-phenyl | OCH$_2$ | 2-quinoline | — | Me, Me | — | — | Me |
| 239 | A30 | 4-NC-3-Cl-phenyl | OCH$_2$ | 2-quinoline | — | Me, Me | — | — | Me |
| 240 | A30 | 4-NC-3-Br-phenyl | OCH$_2$ | 2-quinoline | — | Me, Me | — | — | Me |
| 241 | A30 | 4-NC-3-OMe-phenyl | OCH$_2$ | 2-quinoline | — | Me, Me | — | — | Me |
| 242 | A30 | 4-NC-3-CN-phenyl | OCH$_2$ | 2-quinoline | — | Me, Me | — | — | Me |
| 243 | A30 | 4-Cl-phenyl | OCH$_2$ | 2-quinoline | — | Me, Me | — | — | Me |

-continued

| Ex PCT # | HET | X | Y | Z | R₁ₐ, R₁ᵦ | R₂ | R₃ | R₄ | R₇ |
|---|---|---|---|---|---|---|---|---|---|
| 244 | A30 | 4-chloro-3-fluoro-phenyl | OCH₂ | 2-quinoline | — | Me, Me | — | — | Me |
| 245 | A30 | 3,4-dichloro-phenyl | OCH₂ | 2-quinoline | — | Me, Me | — | — | Me |
| 246 | A30 | 3-bromo-4-chloro-phenyl | OCH₂ | 2-quinoline | — | Me, Me | — | — | Me |
| 247 | A30 | 4-chloro-3-methoxy-phenyl | OCH₂ | 2-quinoline | — | Me, Me | — | — | Me |
| 248 | A30 | 4-chloro-3-cyano-phenyl | OCH₂ | 2-quinoline | — | Me, Me | — | — | Me |
| 249 | A31 | 4-pyridinyl | OCH₂ | 2-quinoline | — | Me, Me | — | — | — |
| 250 | A31 | 4-pyridinyl | OCH₂ | 2-quinoline | — | -cyclo-propyl- | — | — | — |
| 251 | A31 | pyrimidinyl | OCH₂ | 2-quinoline | — | Me, Me | — | — | — |
| 252 | A31 | triazinyl | OCH₂ | 2-quinoline | — | Me, Me | — | — | — |
| 253 | A31 | pyridazinyl | OCH₂ | 2-quinoline | — | Me, Me | — | — | — |

-continued

| Ex PCT # | HET | X | Y | Z | R_{1a}, R_{1b} | R_2 | R_3 | R_4 | R_7 |
|---|---|---|---|---|---|---|---|---|---|
| 254 | A31 | 2-hydroxypyridin-4-yl | OCH_2 | 2-quinoline | — | Me, Me | — | — | — |
| 255 | A31 | 2-methoxypyridin-4-yl | OCH_2 | 2-quinoline | — | Me, Me | — | — | — |
| 256 | A31 | 6-hydroxypyridin-3-yl | OCH_2 | 2-quinoline | — | Me, Me | — | — | — |
| 257 | A31 | 6-methoxypyridin-3-yl | OCH_2 | 2-quinoline | — | Me, Me | — | — | — |
| 258 | A31 | 3-fluoro-4-methoxyphenyl | OCH_2 | 2-quinoline | — | Me, Me | — | — | — |
| 259 | A31 | 3-chloro-4-methoxyphenyl | OCH_2 | 2-quinoline | — | Me, Me | — | — | — |
| 260 | A31 | 3-bromo-4-methoxyphenyl | OCH_2 | 2-quinoline | — | Me, Me | — | — | — |
| 261 | A31 | 3-cyano-4-methoxyphenyl | OCH_2 | 2-quinoline | — | Me, Me | — | — | — |
| 262 | A31 | 4-methoxyphenyl | OCH_2 | 2-quinoline | — | Me, Me | — | — | — |

| Ex PCT # | HET | X | Y | Z | R1a, R1b | R2 | R3 | R4 | R7 |
|---|---|---|---|---|---|---|---|---|---|
| 263 | A31 | 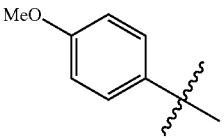 [SMILES: *c1ccc(OC)cc1] | OCH2 | 2-quinoline | — | Me, Et | — | — | — |
| 264 | A31 | 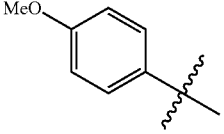 [SMILES: *c1ccc(OC)cc1] | OCH2 | 2-quinoline | — | Et, Me | — | — | — |
| 265 | A31 | 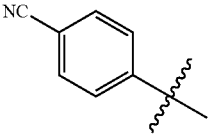 [SMILES: *c1ccc(C#N)cc1] | OCH2 | 2-quinoline | — | Me, Me | — | — | — |
| 266 | A31 | 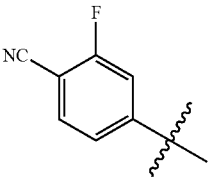 [SMILES: *c1ccc(C#N)c(F)c1] | OCH2 | 2-quinoline | — | Me, Me | — | — | — |
| 267 | A31 | 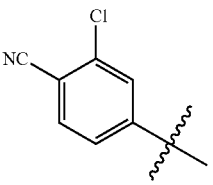 [SMILES: *c1ccc(C#N)c(Cl)c1] | OCH2 | 2-quinoline | — | Me, Me | — | — | — |
| 268 | A31 | 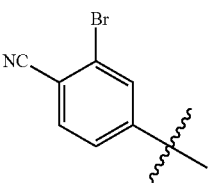 | OCH2 | 2-quinoline | — | Me, Me | — | — | — |
| 269 | A31 | 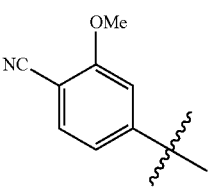 | OCH2 | 2-quinoline | — | Me, Me | — | — | — |
| 270 | A31 | 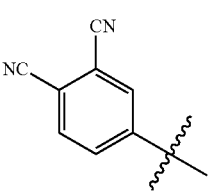 [SMILES: *c1ccc(C#N)c(C#N)c1] | OCH2 | 2-quinoline | — | Me, Me | — | — | — |

-continued

| Ex PCT # | HET | X | Y | Z | $R_{1a}, R_{1b}$ | $R_2$ | $R_3$ | $R_4$ | $R_7$ |
|---|---|---|---|---|---|---|---|---|---|
| 271 | A31 | 4-Cl-phenyl | OCH$_2$ | 2-quinoline | — | Me, Me | — | — | — |
| 272 | A31 | 4-Cl-3-F-phenyl | OCH$_2$ | 2-quinoline | — | Me, Me | — | — | — |
| 273 | A31 | 3,4-diCl-phenyl | OCH$_2$ | 2-quinoline | — | Me, Me | — | — | — |
| 274 | A31 | 3-Br-4-Cl-phenyl | OCH$_2$ | 2-quinoline | — | Me, Me | — | — | — |
| 275 | A31 | 4-Cl-3-OMe-phenyl | OCH$_2$ | 2-quinoline | — | Me, Me | — | — | — |
| 276 | A31 | 4-Cl-3-CN-phenyl | OCH$_2$ | 2-quinoline | — | Me, Me | — | — | — |
| 277 | A31 | 4-F-phenyl | OCH$_2$ | 2-quinoline | — | Me, Me | — | — | — |
| 278 | A31 | 4-CF$_3$-phenyl | OCH$_2$ | 2-quinoline | — | Me, Me | — | — | — |

-continued

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 279 | A31 | 4-CF$_3$O-phenyl | OCH$_2$ | 2-quinoline | — | Me, Me | — | — | — |
| 280 | A31 | 4-(F$_3$CH$_2$C)-phenyl | OCH$_2$ | 2-quinoline | — | Me, Me | — | — | — |
| 281 | A31 | 4-EtO-phenyl | OCH$_2$ | 2-quinoline | — | Me, Me | — | — | — |
| 282 | A31 | 4-iPrO-phenyl | OCH$_2$ | 2-quinoline | — | Me, Me | — | — | — |
| 283 | A31 | 4-F$_2$CHO-phenyl | OCH$_2$ | 2-quinoline | — | Me, Me | — | — | — |
| 284 | A31 | 4-(cyclopropyl-O)-phenyl | OCH$_2$ | 2-quinoline | — | Me, Me | — | — | — |
| 285 | A31 | 4-(cyclopropyl-CH$_2$-O)-phenyl | OCH$_2$ | 2-quinoline | — | Me, Me | — | — | — |
| 286 | A31 | 4-(CF$_3$CH$_2$O)-phenyl | OCH$_2$ | 2-quinoline | — | Me, Me | — | — | — |
| 287 | A31 | 4-Br-phenyl | OCH$_2$ | 2-quinoline | — | Me, Me | — | — | — |

| Ex PCT # | HET | X | Y | Z | R1a, R1b | R2 | R3 | R4 | R7 |
|---|---|---|---|---|---|---|---|---|---|
| 288 | A31 | 4-O2N-C6H4- | OCH2 | 2-quinoline | — | Me, Me | — | — | — |
| 289 | A31 | 4-(CHF2)-C6H4- | OCH2 | 2-quinoline | — | Me, Me | — | — | — |
| 290 | A31 | benzo[1,2,5]oxadiazol-5-yl | OCH2 | 2-quinoline | — | Me, Me | — | — | — |
| 291 | A31 | benzo[1,2,5]thiadiazol-5-yl | OCH2 | 2-quinoline | — | Me, Me | — | — | — |
| 292 | A31 | 3-Cl-4-(OCHF2)-C6H3- | OCH2 | 2-quinoline | — | Me, Me | — | — | — |
| 293 | A31 | 3-CN-4-(OCHF2)-C6H3- | OCH2 | 2-quinoline | — | Me, Me | — | — | — |
| 294 | A31 | tetrazol-1-yl | OCH2 | 2-quinoline | — | Me, Me | — | — | — |
| 295 | A31 | oxazol-5-yl | OCH2 | 2-quinoline | — | Me, Me | — | — | — |
| 296 | A31 | oxazol-4-yl | OCH2 | 2-quinoline | — | Me, Me | — | — | — |

-continued

| Ex PCT # | HET | X | Y | Z | R1a, R1b | R2 | R3 | R4 | R7 |
|---|---|---|---|---|---|---|---|---|---|
| 297 | A31 | thiazol-5-yl | OCH2 | 2-quinoline | — | Me, Me | — | — | — |
| 298 | A31 | thiazol-4-yl | OCH2 | 2-quinoline | — | Me, Me | — | — | — |
| 299 | A31 | 1H-tetrazol-5-yl | OCH2 | 2-quinoline | — | Me, Me | — | — | — |
| 300 | A31 | 4-F-C6H4 | OCH2 | 3,5-dimethylpyridin-2-yl | — | Me, Me | — | — | — |
| 301 | A31 | 4-CF3-C6H4 | OCH2 | 3,5-dimethylpyridin-2-yl | — | Me, Me | — | — | — |
| 302 | A31 | 4-CF3O-C6H4 | OCH2 | 3,5-dimethylpyridin-2-yl | — | Me, Me | — | — | — |
| 303 | A31 | 4-F3CH2C-C6H4 | OCH2 | 3,5-dimethylpyridin-2-yl | — | Me, Me | — | — | — |
| 304 | A31 | 4-EtO-C6H4 | OCH2 | 3,5-dimethylpyridin-2-yl | — | Me, Me | — | — | — |
| 305 | A31 | 4-iPrO-C6H4 | OCH2 | 3,5-dimethylpyridin-2-yl | — | Me, Me | — | — | — |
| 306 | A31 | 4-CHF2O-C6H4 | OCH2 | 3,5-dimethylpyridin-2-yl | — | Me, Me | — | — | — |

-continued

| Ex PCT # | HET | X | Y | Z | R1a, R1b | R2 | R3 | R4 | R7 |
|---|---|---|---|---|---|---|---|---|---|
| 307 | A31 | 4-cyclopropoxyphenyl | OCH2 | 3,5-dimethylpyridin-2-yl | — | Me, Me | — | — | — |
| 308 | A31 | 4-(cyclopropylmethoxy)phenyl | OCH2 | 3,5-dimethylpyridin-2-yl | — | Me, Me | — | — | — |
| 309 | A31 | 4-(2,2,2-trifluoroethoxy)phenyl | OCH2 | 3,5-dimethylpyridin-2-yl | — | Me, Me | — | — | — |
| 310 | A31 | 4-bromophenyl | OCH2 | 3,5-dimethylpyridin-2-yl | — | Me, Me | — | — | — |
| 311 | A31 | 4-nitrophenyl | OCH2 | 3,5-dimethylpyridin-2-yl | — | Me, Me | — | — | — |
| 312 | A31 | 4-(difluoromethyl)phenyl | OCH2 | 3,5-dimethylpyridin-2-yl | — | Me, Me | — | — | — |
| 313 | A31 | benzo[c][1,2,5]oxadiazol-5-yl | OCH2 | 3,5-dimethylpyridin-2-yl | — | Me, Me | — | — | — |
| 314 | A31 | benzo[c][1,2,5]thiadiazol-5-yl | OCH2 | 3,5-dimethylpyridin-2-yl | — | Me, Me | — | — | — |
| 315 | A31 | 3-chloro-4-(difluoromethoxy)phenyl | OCH2 | 3,5-dimethylpyridin-2-yl | — | Me, Me | — | — | — |

-continued
| Ex PCT # | HET | X | Y | Z | R1a, R1b | R2 | R3 | R4 | R7 |
|---|---|---|---|---|---|---|---|---|---|
| 316 | A31 | 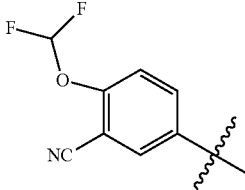 | OCH2 | 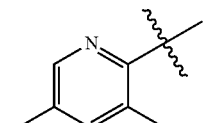 | — | Me, Me | — | — | — |
| 317 | A31 | 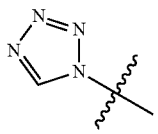 | OCH2 | 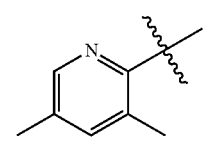 | — | Me, Me | — | — | — |
| 318 | A31 | 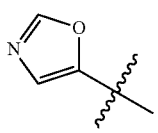 | OCH2 | 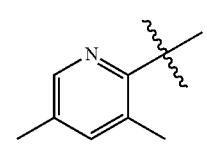 | — | Me, Me | — | — | — |
| 319 | A31 | 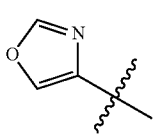 [SMILES: *c1cocn1] | OCH2 | 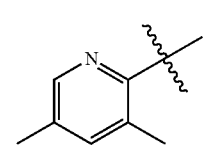 | — | Me, Me | — | — | — |
| 320 | A31 | 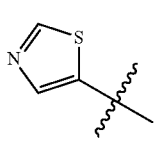 | OCH2 | 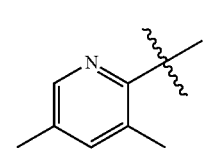 | — | Me, Me | — | — | — |
| 321 | A31 | 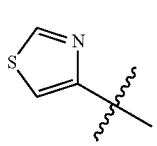 [SMILES: *c1cscn1] | OCH2 | 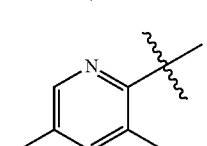 | — | Me, Me | — | — | — |
| 322 | A31 | 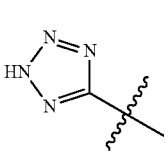 [SMILES: *c1nn[nH]n1] | OCH2 | 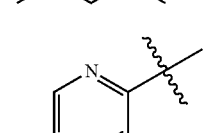 | — | Me, Me | — | — | — |
| 323 | A31 | 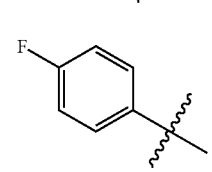 | OCH2 | 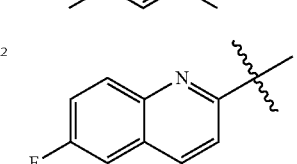 | — | Me, Me | — | — | — |
| 324 | A31 | 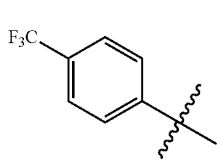 | OCH2 | 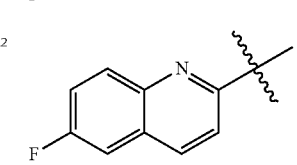 | — | Me, Me | — | — | — |
| 325 | A31 | 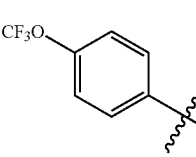 | OCH2 | 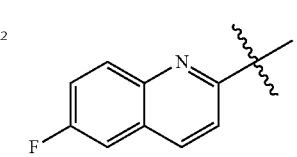 | — | Me, Me | — | — | — |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 326 | A31 | F$_3$CH$_2$C-C$_6$H$_4$- | OCH$_2$ | 6-F-quinolin-2-yl | — | Me, Me | — | — | — |
| 327 | A31 | EtO-C$_6$H$_4$- | OCH$_2$ | 6-F-quinolin-2-yl | — | Me, Me | — | — | — |
| 328 | A31 | iPrO-C$_6$H$_4$- | OCH$_2$ | 6-F-quinolin-2-yl | — | Me, Me | — | — | — |
| 329 | A31 | CHF$_2$O-C$_6$H$_4$- | OCH$_2$ | 6-F-quinolin-2-yl | — | Me, Me | — | — | — |
| 330 | A31 | cyclopropyl-O-C$_6$H$_4$- | OCH$_2$ | 6-F-quinolin-2-yl | — | Me, Me | — | — | — |
| 331 | A31 | cyclopropyl-CH$_2$O-C$_6$H$_4$- | OCH$_2$ | 6-F-quinolin-2-yl | — | Me, Me | — | — | — |
| 332 | A31 | CF$_3$CH$_2$O-C$_6$H$_4$- | OCH$_2$ | 6-F-quinolin-2-yl | — | Me, Me | — | — | — |
| 333 | A31 | Br-C$_6$H$_4$- | OCH$_2$ | 6-F-quinolin-2-yl | — | Me, Me | — | — | — |
| 334 | A31 | O$_2$N-C$_6$H$_4$- | OCH$_2$ | 6-F-quinolin-2-yl | — | Me, Me | — | — | — |

-continued

| Ex PCT # | HET | X | Y | Z | R_{1a}, R_{1b} | R_2 | R_3 | R_4 | R_7 |
|---|---|---|---|---|---|---|---|---|---|
| 335 | A31 | 4-(difluoromethyl)phenyl | OCH_2 | 6-fluoroquinolin-2-yl | — | Me, Me | — | — | — |
| 336 | A31 | benzo[c][1,2,5]oxadiazol-5-yl | OCH_2 | 6-fluoroquinolin-2-yl | — | Me, Me | — | — | — |
| 337 | A31 | benzo[c][1,2,5]thiadiazol-5-yl | OCH_2 | 6-fluoroquinolin-2-yl | — | Me, Me | — | — | — |
| 338 | A31 | 3-chloro-4-(difluoromethoxy)phenyl | OCH_2 | 6-fluoroquinolin-2-yl | — | Me, Me | — | — | — |
| 339 | A31 | 3-cyano-4-(difluoromethoxy)phenyl | OCH_2 | 6-fluoroquinolin-2-yl | — | Me, Me | — | — | — |
| 340 | A31 | 1H-tetrazol-1-yl | OCH_2 | 6-fluoroquinolin-2-yl | — | Me, Me | — | — | — |
| 341 | A31 | oxazol-5-yl | OCH_2 | 6-fluoroquinolin-2-yl | — | Me, Me | — | — | — |
| 342 | A31 | oxazol-4-yl | OCH_2 | 6-fluoroquinolin-2-yl | — | Me, Me | — | — | — |
| 343 | A31 | thiazol-5-yl | OCH_2 | 6-fluoroquinolin-2-yl | — | Me, Me | — | — | — |

| Ex PCT # | HET | X | Y | Z | R1a, R1b | R2 | R3 | R4 | R7 |
|---|---|---|---|---|---|---|---|---|---|
| 344 | A31 | 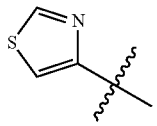 [SMILES: *c1cscn1] | OCH₂ | 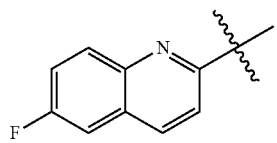 [SMILES: *c1ccc2cc(F)ccc2n1] | — | Me, Me | — | — | — |
| 345 | A31 | 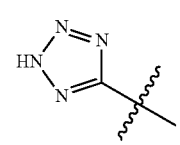 [SMILES: *c1nn[nH]n1] | OCH₂ | 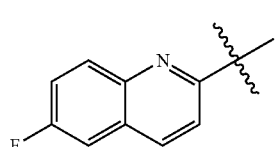 | — | Me, Me | — | — | — |
| 776 | A31 | 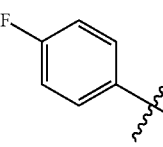 | OCH₂ | 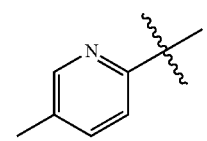 [SMILES: *c1ccc(C)cn1] | — | Me, Me | — | — | — |
| 777 | A31 | 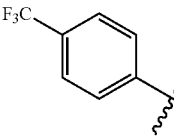 | OCH₂ | 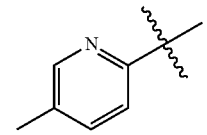 [SMILES: *c1ccc(C)cn1] | — | Me, Me | — | — | — |
| 778 | A31 | 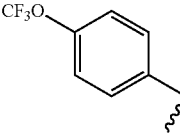 | OCH₂ | 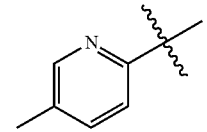 [SMILES: *c1ccc(C)cn1] | — | Me, Me | — | — | — |
| 779 | A31 | 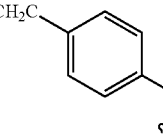 | OCH₂ | 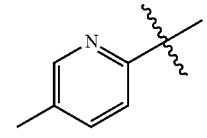 [SMILES: *c1ccc(C)cn1] | — | Me, Me | — | — | — |
| 780 | A31 | 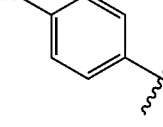 | OCH₂ | 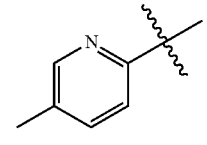 [SMILES: *c1ccc(C)cn1] | — | Me, Me | — | — | — |
| 781 | A31 | 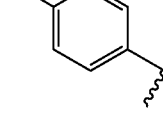 | OCH₂ | 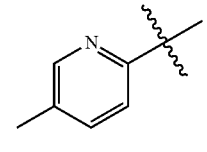 [SMILES: *c1ccc(C)cn1] | — | Me, Me | — | — | — |
| 782 | A31 | 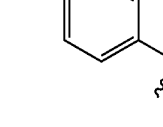 | OCH₂ | 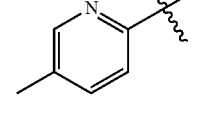 | — | Me, Me | — | — | — |
| 783 | A31 | 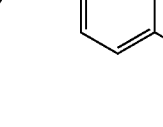 | OCH₂ | 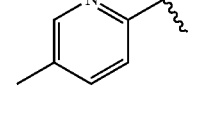 | — | Me, Me | — | — | — |

| Ex PCT # | HET | X | Y | Z | R1a, R1b | R2 | R3 | R4 | R7 |
|---|---|---|---|---|---|---|---|---|---|
| 784 | A31 | cyclopropylmethoxy-phenyl | OCH2 | 5-methylpyridin-2-yl | — | Me, Me | — | — | — |
| 785 | A31 | 2,2,2-trifluoroethoxy-phenyl | OCH2 | 5-methylpyridin-2-yl | — | Me, Me | — | — | — |
| 786 | A31 | 4-bromophenyl | OCH2 | 5-methylpyridin-2-yl | — | Me, Me | — | — | — |
| 787 | A31 | 4-nitrophenyl | OCH2 | 5-methylpyridin-2-yl | — | Me, Me | — | — | — |
| 788 | A31 | 4-(difluoromethyl)phenyl | OCH2 | 5-methylpyridin-2-yl | — | Me, Me | — | — | — |
| 789 | A31 | benzo[c][1,2,5]oxadiazol-5-yl | OCH2 | 5-methylpyridin-2-yl | — | Me, Me | — | — | — |
| 790 | A31 | benzo[c][1,2,5]thiadiazol-5-yl | OCH2 | 5-methylpyridin-2-yl | — | Me, Me | — | — | — |
| 791 | A31 | 3-chloro-4-(difluoromethoxy)phenyl | OCH2 | 5-methylpyridin-2-yl | — | Me, Me | — | — | — |

-continued

| Ex PCT # | HET | X | Y | Z | R1a, R1b | R2 | R3 | R4 | R7 |
|---|---|---|---|---|---|---|---|---|---|
| 792 | A31 | 2-(difluoromethoxy)-5-cyanophenyl | OCH₂ | 5-methylpyridin-2-yl | — | Me, Me | — | — | — |
| 793 | A31 | tetrazol-1-yl | OCH₂ | 5-methylpyridin-2-yl | — | Me, Me | — | — | — |
| 794 | A31 | oxazol-5-yl | OCH₂ | 5-methylpyridin-2-yl | — | Me, Me | — | — | — |
| 795 | A31 | oxazol-4-yl | OCH₂ | 5-methylpyridin-2-yl | — | Me, Me | — | — | — |
| 796 | A31 | thiazol-5-yl | OCH₂ | 5-methylpyridin-2-yl | — | Me, Me | — | — | — |
| 797 | A31 | thiazol-4-yl | OCH₂ | 5-methylpyridin-2-yl | — | Me, Me | — | — | — |
| 798 | A31 | 2H-tetrazol-5-yl | OCH₂ | 5-methylpyridin-2-yl | — | Me, Me | — | — | — |
| 799 | A29 | 4-methoxyphenyl | OCH₂ | 3,5-dimethylpyridin-2-yl | — | Me, Me | — | — | — |
| 800 | A29 | 4-cyanophenyl | OCH₂ | 3,5-dimethylpyridin-2-yl | — | Me, Me | — | — | — |
| 801 | A29 | 4-chlorophenyl | OCH₂ | 3,5-dimethylpyridin-2-yl | — | Me, Me | — | — | — |

-continued
| Ex PCT # | HET | X | Y | Z | R1a, R1b | R2 | R3 | R4 | R7 |
|---|---|---|---|---|---|---|---|---|---|
| 802 | A29 | 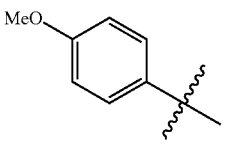 | OCH2 | 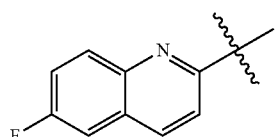 | — | Me, Me | — | — | — |
| 803 | A29 | 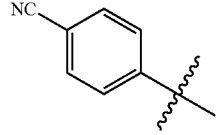 [SMILES: *c1ccc(C#N)cc1] | OCH2 | 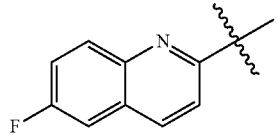 | — | Me, Me | — | — | — |
| 804 | A29 | 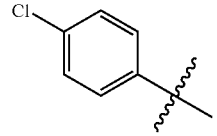 [SMILES: *c1ccc(Cl)cc1] | OCH2 | 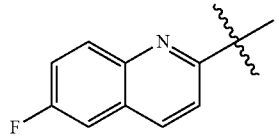 | — | Me, Me | — | — | — |
| 805 | A29 | 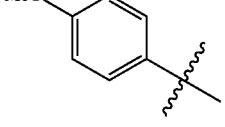 | OCH2 | 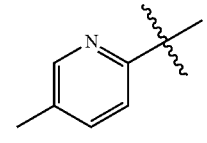 [SMILES: *c1ccc(C)cn1] | — | Me, Me | — | — | — |
| 806 | A29 | 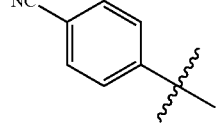 | OCH2 | 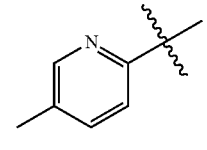 [SMILES: *c1ccc(C)cn1] | — | Me, Me | — | — | — |
| 807 | A29 | 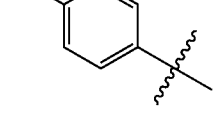 | OCH2 | 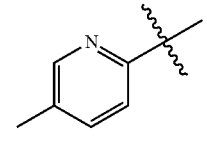 [SMILES: *c1ccc(C)cn1] | — | Me, Me | — | — | — |
| 808 | A29 | 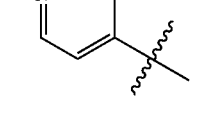 | OCH2 | 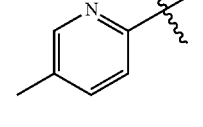 | — | Me, Me | — | — | — |
| 809 | A29 | 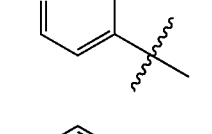 | OCH2 | 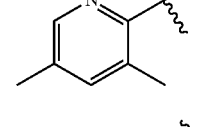 | — | Me, Me | — | — | — |
| 810 | A29 | 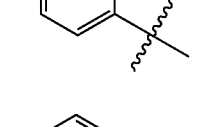 | OCH2 | 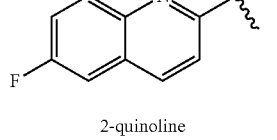 | — | Me, Me | — | — | — |
| 811 | A29 | 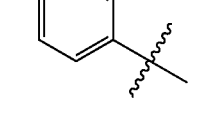 | OCH2 | 2-quinoline | — | Me, Me | — | — | — |

-continued

| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 812 | A3 | morpholine-N-yl | OCH$_2$ | 2-quinoline | — | — | — | — | Me |
| 813 | A29 | 4-hydroxyphenyl | OCH$_2$ | 2-quinoline | — | Me, Me | — | — | — |
| 814 | A29 | 4-acetamidophenyl | OCH$_2$ | 2-quinoline | — | Me, Me | — | — | — |
| 815 | A29 | 4-(methylsulfonamido)phenyl | OCH$_2$ | 2-quinoline | — | Me, Me | — | — | — |
| 817 | A29 | 4-(N,N-dimesyl-amino)phenyl | OCH$_2$ | 2-quinoline | — | Me, Me | — | — | — |
| 818 | A29 | 4-methylphenyl | OCH$_2$ | 2-quinoline | — | Me, Me | — | — | — |
| 819 | A29 | 4-(N,N-diacetyl-amino)phenyl | OCH$_2$ | 2-quinoline | — | Me, Me | — | — | — |
| 820 | A3 | 4-oxopiperidin-1-yl | OCH$_2$ | 2-quinoline | — | — | — | — | Me |
| 821 | A29 | benzoxazol-5-yl | OCH$_2$ | 2-quinoline | — | Me, Me | — | — | — |

-continued
| Ex PCT # | HET | X | Y | Z | R1a, R1b | R2 | R3 | R4 | R7 |
|---|---|---|---|---|---|---|---|---|---|
| 822 | A14 | 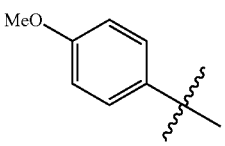 [SMILES: *c1ccc(OC)cc1] | OCH2 | 2-quinoline | Me, Me | — | — | — | — |
| 823 | A8 | 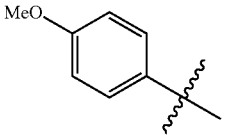 [SMILES: *c1ccc(OC)cc1] | OCH2 | 2-quinoline | — | — | Me | Me | H |
| 824 | A29 | 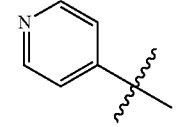 | OCH2 | 2-quinoline | — | -cyclopentyl- | — | — | — |
| 825 | A8 | 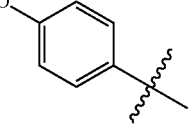 | OCH2 | 2-quinoline | — | — | Me | Me | H |
| 826 | A8 | 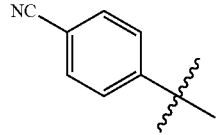 [SMILES: *c1ccc(C#N)cc1] | OCH2 | 2-quinoline | — | — | Me | Me | H |
| 827 | A8 | 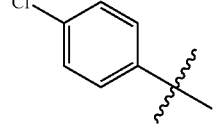 | OCH2 | 2-quinoline | — | — | Me | Me | H |
| 828 | A8 | 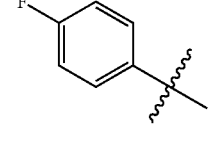 | OCH2 | 2-quinoline | — | — | Me | Me | H |
| 829 | A8 | 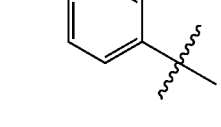 | OCH2 | 2-quinoline | — | — | Me | Me | H |
| 830 | A8 | 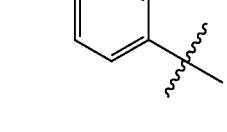 | OCH2 | 2-quinoline | — | — | Me | Me | H |
| 831 | A8 | 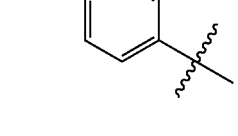 | OCH2 | 2-quinoline | — | — | Me | Me | H |

| Ex PCT # | HET | X | Y | Z | R_{1a}, R_{1b} | R_2 | R_3 | R_4 | R_7 |
|---|---|---|---|---|---|---|---|---|---|
| 832 | A8 | 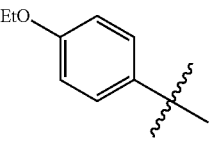 | OCH_2 | 2-quinoline | — | — | Me | Me | H |
| 833 | A8 | 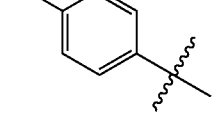 | OCH_2 | 2-quinoline | — | — | Me | Me | H |
| 834 | A8 | 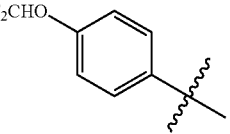 | OCH_2 | 2-quinoline | — | — | Me | Me | H |
| 835 | A8 | 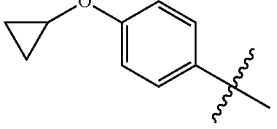 | OCH_2 | 2-quinoline | — | — | Me | Me | H |
| 836 | A8 | 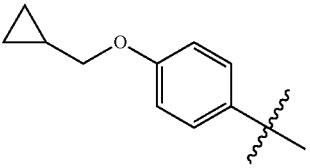 [SMILES: *c1ccc(OCC2CC2)cc1] | OCH_2 | 2-quinoline | — | — | Me | Me | H |
| 837 | A8 | 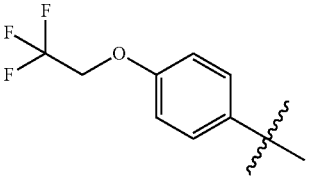 [SMILES: *c1ccc(OCC(F)(F)F)cc1] | OCH_2 | 2-quinoline | — | — | Me | Me | H |
| 838 | A8 | 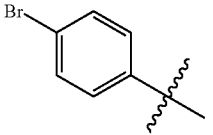 | OCH_2 | 2-quinoline | — | — | Me | Me | H |
| 839 | A8 | 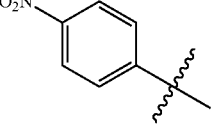 | OCH_2 | 2-quinoline | — | — | Me | Me | H |
| 840 | A8 | 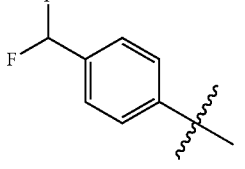 | OCH_2 | 2-quinoline | — | — | Me | Me | H |

-continued

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 841 | A8 | benzofurazan | OCH$_2$ | 2-quinoline | — | — | Me | Me | H |
| 842 | A8 | benzothiadiazole | OCH$_2$ | 2-quinoline | — | — | Me | Me | H |
| 843 | A8 | 3-chloro-4-(difluoromethoxy)phenyl | OCH$_2$ | 2-quinoline | — | — | Me | Me | H |
| 844 | A8 | 3-cyano-4-(difluoromethoxy)phenyl | OCH$_2$ | 2-quinoline | — | — | Me | Me | H |
| 845 | A8 | 1H-tetrazol-1-yl | OCH$_2$ | 2-quinoline | — | — | Me | Me | H |
| 846 | A8 | oxazol-5-yl | OCH$_2$ | 2-quinoline | — | — | Me | Me | H |
| 847 | A8 | oxazol-4-yl | OCH$_2$ | 2-quinoline | — | — | Me | Me | H |
| 848 | A8 | thiazol-5-yl | OCH$_2$ | 2-quinoline | — | — | Me | Me | H |
| 849 | A8 | thiazol-4-yl | OCH$_2$ | 2-quinoline | — | — | Me | Me | H |
| 850 | A8 | 2H-tetrazol-5-yl | OCH$_2$ | 2-quinoline | — | — | Me | Me | H |

-continued

| Ex PCT # | HET | X | Y | Z | R1a, R1b | R2 | R3 | R4 | R7 |
|---|---|---|---|---|---|---|---|---|---|
| 851 | A29 | 4-F-phenyl | OCH2 | 5-Me-pyridin-2-yl | — | Me, Me | — | — | — |
| 852 | A29 | 4-F3C-phenyl | OCH2 | 5-Me-pyridin-2-yl | — | Me, Me | — | — | — |
| 853 | A29 | 4-CF3O-phenyl | OCH2 | 5-Me-pyridin-2-yl | — | Me, Me | — | — | — |
| 854 | A29 | 4-F3CH2C-phenyl | OCH2 | 5-Me-pyridin-2-yl | — | Me, Me | — | — | — |
| 855 | A29 | 4-EtO-phenyl | OCH2 | 5-Me-pyridin-2-yl | — | Me, Me | — | — | — |
| 856 | A29 | 4-iPrO-phenyl | OCH2 | 5-Me-pyridin-2-yl | — | Me, Me | — | — | — |
| 857 | A29 | 4-CHF2O-phenyl | OCH2 | 5-Me-pyridin-2-yl | — | Me, Me | — | — | — |
| 858 | A29 | 4-cyclopropyl-O-phenyl | OCH2 | 5-Me-pyridin-2-yl | — | Me, Me | — | — | — |
| 859 | A29 | 4-(cyclopropylmethoxy)-phenyl | OCH2 | 5-Me-pyridin-2-yl | — | Me, Me | — | — | — |

| Ex PCT # | HET | X | Y | Z | R1a, R1b | R2 | R3 | R4 | R7 |
|---|---|---|---|---|---|---|---|---|---|
| 860 | A29 | 2,2,2-trifluoroethoxy-phenyl | OCH2 | 5-methylpyridin-2-yl | — | Me, Me | — | — | — |
| 861 | A29 | 4-bromophenyl | OCH2 | 5-methylpyridin-2-yl | — | Me, Me | — | — | — |
| 862 | A29 | 4-nitrophenyl | OCH2 | 5-methylpyridin-2-yl | — | Me, Me | — | — | — |
| 863 | A29 | 4-(difluoromethyl)phenyl | OCH2 | 5-methylpyridin-2-yl | — | Me, Me | — | — | — |
| 864 | A29 | benzo[c][1,2,5]oxadiazol-5-yl | OCH2 | 5-methylpyridin-2-yl | — | Me, Me | — | — | — |
| 865 | A29 | benzo[c][1,2,5]thiadiazol-5-yl | OCH2 | 5-methylpyridin-2-yl | — | Me, Me | — | — | — |
| 866 | A29 | 3-chloro-4-(difluoromethoxy)phenyl | OCH2 | 5-methylpyridin-2-yl | — | Me, Me | — | — | — |
| 867 | A29 | 2-(difluoromethoxy)-5-cyanophenyl | OCH2 | 5-methylpyridin-2-yl | — | Me, Me | — | — | — |
| 868 | A29 | 1H-tetrazol-1-yl | OCH2 | 5-methylpyridin-2-yl | — | Me, Me | — | — | — |

-continued
| Ex PCT # | HET | X | Y | Z | R$_{1a}$, R$_{1b}$ | R$_2$ | R$_3$ | R$_4$ | R$_7$ |
|---|---|---|---|---|---|---|---|---|---|
| 869 | A29 | 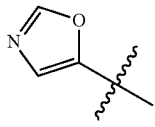 | OCH$_2$ | 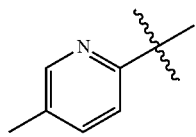 [SMILES: *c1ccc(C)cn1] | — | Me, Me | — | — | — |
| 870 | A29 | 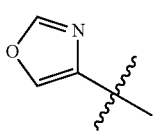 [SMILES: *c1cocn1] | OCH$_2$ | 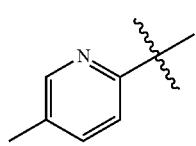 [SMILES: *c1ccc(C)cn1] | — | Me, Me | — | — | — |
| 871 | A29 | 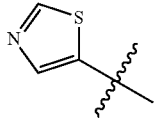 | OCH$_2$ | 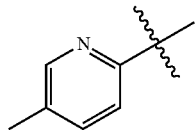 [SMILES: *c1ccc(C)cn1] | — | Me, Me | — | — | — |
| 872 | A29 | 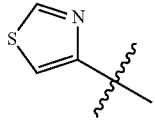 [SMILES: *c1cscn1] | OCH$_2$ | 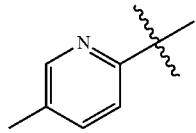 [SMILES: *c1ccc(C)cn1] | — | Me, Me | — | — | — |
| 873 | A29 | 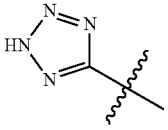 [SMILES: *c1nn[nH]n1] | OCH$_2$ | 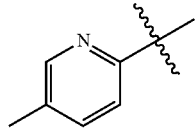 [SMILES: *c1ccc(C)cn1] | — | Me, Me | — | — | — |
| 874 | A29 | 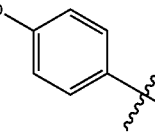 | OCH$_2$ | 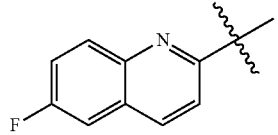 [SMILES: *c1ccc2cc(F)ccc2n1] | — | Me, Me | — | — | — |
| 875 | A29 | 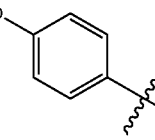 | OCH$_2$ | 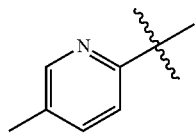 [SMILES: *c1ccc(C)cn1] | — | Me, Me | — | — | — |
| 876 | A29 | 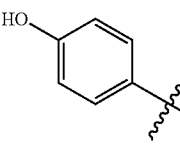 | OCH$_2$ | 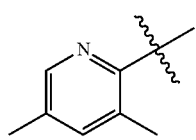 | — | Me, Me | — | — | — |
| 877 | A30 | 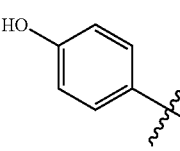 | OCH$_2$ | 2-quinoline | — | Me, Me | — | — | — |
| 878 | A30 | 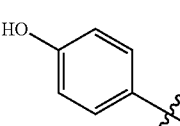 | OCH$_2$ | 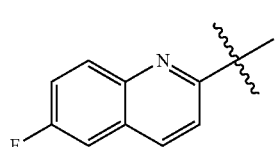 | — | Me, Me | — | — | — |

-continued
| Ex PCT # | HET | X | Y | Z | R1a, R1b | R2 | R3 | R4 | R7 |
|---|---|---|---|---|---|---|---|---|---|
| 879 | A30 | 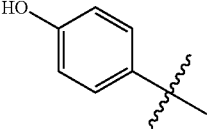 | OCH2 | 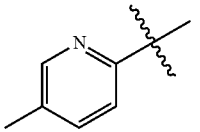 [SMILES: *c1ccc(C)cn1] | — | Me, Me | — | — | — |
| 880 | A30 | 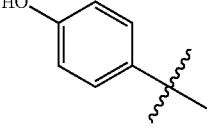 | OCH2 | 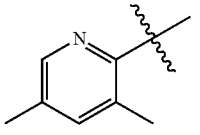 | — | Me, Me | — | — | — |
| 881 | A31 | 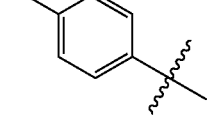 | OCH2 | 2-quinoline | — | Me, Me | — | — | — |
| 882 | A31 | 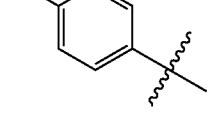 | OCH2 | 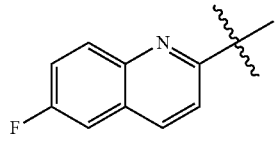 [SMILES: *c1ccc2cc(F)ccc2n1] | — | Me, Me | — | — | — |
| 883 | A31 | 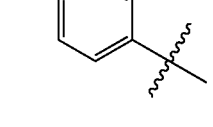 | OCH2 | 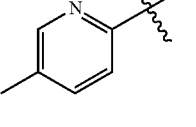 | — | Me, Me | — | — | — |
| 884 | A31 | 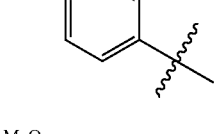 | OCH2 | 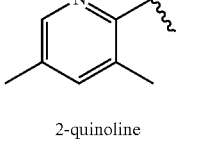 | — | Me, Me | — | — | — |
| 885 | A7 | 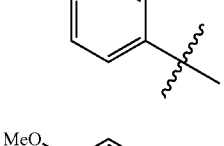 | OCH2 | 2-quinoline | — | — | -cyclo-propyl- | — | — |
| 886 | A39 | 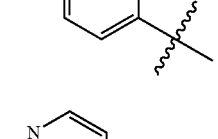 | OCH2 | 2-quinoline | — | — | — | — | — |
| 887 | A39 | 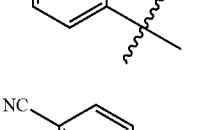 | OCH2 | 2-quinoline | — | — | — | — | — |
| 888 | A39 | 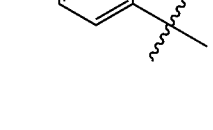 | OCH2 | 2-quinoline | — | — | — | — | — |

| Ex PCT # | HET | X | Y | Z | $R_{1a}$, $R_{1b}$ | $R_2$ | $R_3$ | $R_4$ | $R_7$ |
|---|---|---|---|---|---|---|---|---|---|
| 889 | A39 | 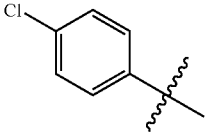 4-Cl-phenyl | $OCH_2$ | 2-quinoline | — | — | — | — | — |
| 890 | A40 | 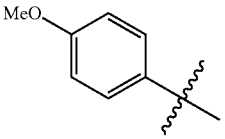 [SMILES: *c1ccc(OC)cc1] 4-MeO-phenyl | $OCH_2$ | 2-quinoline | — | — | — | — | Me |
| 891 | A40 | 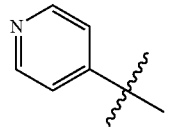 [SMILES: *c1ccncc1] 4-pyridinyl | $OCH_2$ | 2-quinoline | — | — | — | — | Me |
| 892 | A40 | 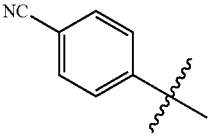 4-NC-phenyl | $OCH_2$ | 2-quinoline | — | — | — | — | Me |
| 893 | A40 | 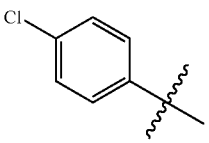 4-Cl-phenyl | $OCH_2$ | 2-quinoline | — | — | — | — | Me |
| 894 | A29 | 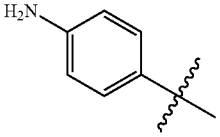 4-$H_2N$-phenyl | $OCH_2$ | 2-quinoline | — | Me, Me | — | — | |

In a further aspect the compounds of the disclosure are embodied in with distinct examples listed in the table below taken from Formula (II):

| Ex PCT # | HET | W | X | Y | Z | $R_{1a}$, $R_{1b}$ | $R_2$ | $R_3$ | $R_4$ | $R_7$ |
|---|---|---|---|---|---|---|---|---|---|---|
| 346 | A2 | Cl | 4-pyridinyl | $OCH_2$ | 2-quinoline | — | — | Me | Me | Me |
| 347 | A2 | Cl | 4-OMe-phenyl | $OCH_2$ | 2-quinoline | — | — | Me | Me | Me |
| 348 | A2 | Cl | 4-pyrazolyl | $OCH_2$ | 2-quinoline | — | — | Me | Me | Me |
| 349 | A2 | Cl | 3-(1-methyl-1H-pyrazolyl) | $OCH_2$ | 2-quinoline | — | — | Me | Me | Me |
| 350 | A2 | Cl | 4-(1-methyl-1H-pyrazolyl) | $OCH_2$ | 2-quinoline | — | — | Me | Me | Me |
| 351 | A2 | Cl | 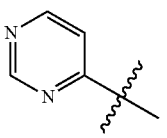 pyrimidinyl | $OCH_2$ | 2-quinoline | — | — | Me | Me | Me |

-continued

| Ex PCT # | HET | W | X | Y | Z | R_{1a}, R_{1b} | R_2 | R_3 | R_4 | R_7 |
|---|---|---|---|---|---|---|---|---|---|---|
| 352 | A2 | Cl | 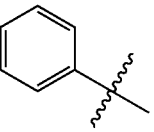 | OCH$_2$ | 2-quinoline | — | — | Me | Me | Me |
| 353 | A2 | Cl | 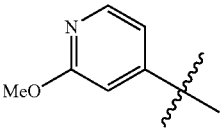 [SMILES: *c1ccnc(OC)c1] | OCH$_2$ | 2-quinoline | — | — | Me | Me | Me |
| 354 | A2 | Cl | 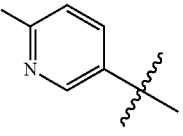 | OCH$_2$ | 2-quinoline | — | — | Me | Me | Me |
| 355 | A2 | Cl | 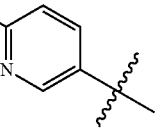 | OCH$_2$ | 2-quinoline | — | — | Me | Me | Me |
| 356 | A2 | Cl | 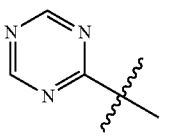 [SMILES: *c1ncncn1] | OCH$_2$ | 2-quinoline | — | — | Me | Me | Me |
| 357 | A2 | Cl | 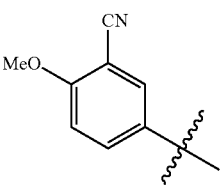 | OCH$_2$ | 2-quinoline | — | — | Me | Me | Me |
| 358 | A2 | Cl | 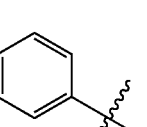 | OCH$_2$ | 2-quinoline | — | — | Me | Me | Me |
| 359 | A5 | Cl | 4-pyridinyl | OCH$_2$ | 2-quinoline | — | — | — | — | H |
| 360 | A5 | Cl | 4-OMe-phenyl | OCH$_2$ | 2-quinoline | — | — | — | — | H |
| 361 | A5 | Cl | 4-pyrazolyl | OCH$_2$ | 2-quinoline | — | — | — | — | H |
| 362 | A5 | Cl | 3-(1-methyl-1H-pyrazolyl) | OCH$_2$ | 2-quinoline | — | — | — | — | H |
| 363 | A5 | Cl | 4-(1-methyl-1H-pyrazolyl) | OCH$_2$ | 2-quinoline | — | — | — | — | H |
| 364 | A5 | Cl | 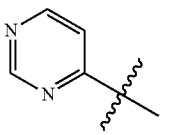 [SMILES: *c1ccncn1] | OCH$_2$ | 2-quinoline | — | — | — | — | H |
| 365 | A5 | Cl | 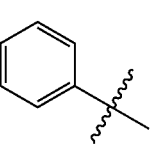 | OCH$_2$ | 2-quinoline | — | — | — | — | H |

| Ex PCT # | HET | W | X | Y | Z | R₁ₐ, R₁ᵦ | R₂ | R₃ | R₄ | R₇ |
|---|---|---|---|---|---|---|---|---|---|---|
| 366 | A5 | Cl | 2-MeO-pyridin-4-yl | OCH₂ | 2-quinoline | — | — | — | — | H |
| 367 | A5 | Cl | 6-MeO-pyridin-3-yl | OCH₂ | 2-quinoline | — | — | — | — | H |
| 368 | A5 | Cl | 6-HO-pyridin-3-yl | OCH₂ | 2-quinoline | — | — | — | — | H |
| 369 | A5 | Cl | 1,3,5-triazin-2-yl | OCH₂ | 2-quinoline | — | — | — | — | H |
| 370 | A5 | Cl | 3-CN-4-MeO-phenyl | OCH₂ | 2-quinoline | — | — | — | — | H |
| 371 | A5 | Cl | 4-Cl-phenyl | OCH₂ | 2-quinoline | — | — | — | — | H |
| 372 | A22 | Cl | 4-pyridinyl | OCH₂ | 2-quinoline | — | Me | — | — | |
| 373 | A22 | Cl | 4-OMe-phenyl | OCH₂ | 2-quinoline | — | Me | — | — | |
| 374 | A22 | Cl | 4-pyrazolyl | OCH₂ | 2-quinoline | — | Me | — | — | |
| 375 | A22 | Cl | 3-(1-methyl-1H-pyrazolyl) | OCH₂ | 2-quinoline | — | Me | — | — | |
| 376 | A22 | Cl | 4-(1-methyl-1H-pyrazolyl) | OCH₂ | 2-quinoline | — | Me | — | — | |
| 377 | A22 | Cl | pyrimidin-4-yl | OCH₂ | 2-quinoline | — | Me | — | — | |
| 378 | A22 | Cl | 4-NC-phenyl | OCH₂ | 2-quinoline | — | Me | — | — | |
| 379 | A22 | Cl | 2-MeO-pyridin-4-yl | OCH₂ | 2-quinoline | — | Me | — | — | |

-continued

| Ex PCT # | HET | W | X | Y | Z | R_{1a}, R_{1b} | R_2 | R_3 | R_4 | R_7 |
|---|---|---|---|---|---|---|---|---|---|---|
| 380 | A22 | Cl | 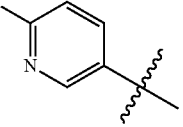 | OCH_2 | 2-quinoline | — | Me | — | — | |
| 381 | A22 | Cl | 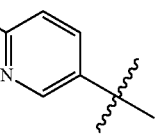 | OCH_2 | 2-quinoline | — | Me | — | — | |
| 382 | A22 | Cl | 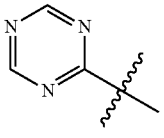 [SMILES: *c1ncncn1] | OCH_2 | 2-quinoline | — | Me | | | |
| 383 | A22 | Cl | 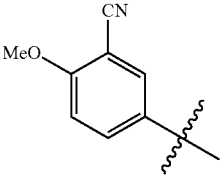 | OCH_2 | 2-quinoline | — | Me | | | |
| 384 | A22 | Cl | 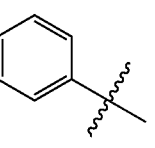 | OCH_2 | 2-quinoline | — | Me | — | — | |
| 385 | A23 | Cl | 4-pyridinyl | OCH_2 | 2-quinoline | — | Me | — | — | |
| 386 | A23 | Cl | 4-OMe-phenyl | OCH_2 | 2-quinoline | — | Me | — | — | |
| 387 | A23 | Cl | 4-pyrazolyl | OCH_2 | 2-quinoline | — | Me | — | — | |
| 388 | A23 | Cl | 3-(1-methyl-1H-pyrazolyl) | OCH_2 | 2-quinoline | — | Me | — | — | |
| 389 | A23 | Cl | 4-(1-methyl-1H-pyrazolyl) | OCH_2 | 2-quinoline | — | Me | | | |
| 390 | A23 | Cl | 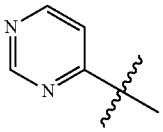 | OCH_2 | 2-quinoline | — | Me | — | — | |
| 391 | A23 | Cl | 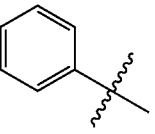 | OCH_2 | 2-quinoline | — | Me | — | — | |
| 392 | A23 | Cl | 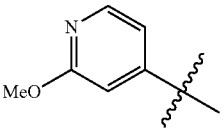 [SMILES: *c1ccnc(OC)c1] | OCH_2 | 2-quinoline | — | Me | — | — | |
| 393 | A23 | Cl | 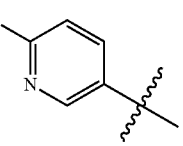 | OCH_2 | 2-quinoline | — | Me | — | — | |

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 394 | A23 | Cl | 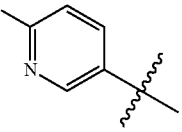 | OCH$_2$ | 2-quinoline | — | Me | — | — | |
| 395 | A23 | Cl | 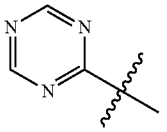 | OCH$_2$ | 2-quinoline | — | Me | — | — | |
| 396 | A23 | Cl | 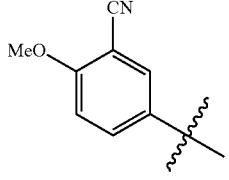 | OCH$_2$ | 2-quinoline | — | Me | — | — | |
| 397 | A23 | Cl | 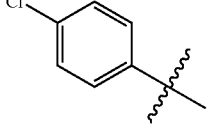 | OCH$_2$ | 2-quinoline | — | Me | — | — | |
| 398 | A26 | Cl | 4-pyridinyl | OCH$_2$ | 2-quinoline | — | Me | — | — | |
| 399 | A26 | Cl | 4-OMe-phenyl | OCH$_2$ | 2-quinoline | — | Me | — | — | |
| 400 | A26 | Cl | 4-pyrazolyl | OCH$_2$ | 2-quinoline | — | Me | — | — | |
| 401 | A26 | Cl | 3-(1-methyl-1H-pyrazolyl) | OCH$_2$ | 2-quinoline | — | Me | — | — | |
| 402 | A26 | Cl | 4-(1-methyl-1H-pyrazolyl) | OCH$_2$ | 2-quinoline | — | Me | — | — | |
| 403 | A26 | Cl | 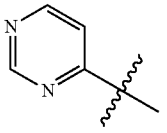 [SMILES: *c1ccncn1] | OCH$_2$ | 2-quinoline | — | Me | — | — | |
| 404 | A26 | Cl | 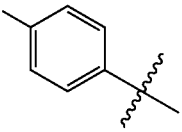 | OCH$_2$ | 2-quinoline | — | Me | — | — | |
| 405 | A26 | Cl | 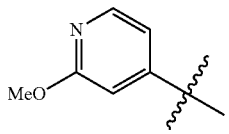 [SMILES: *c1ccnc(OC)c1] | OCH$_2$ | 2-quinoline | — | Me | — | — | |
| 406 | A26 | Cl | 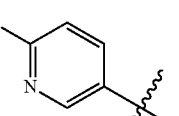 | OCH$_2$ | 2-quinoline | — | Me | — | — | |
| 407 | A26 | Cl | 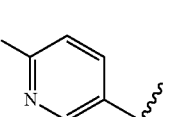 | OCH$_2$ | 2-quinoline | — | Me | — | — | |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 408 | A26 | Cl | 1,3,5-triazin-2-yl | OCH$_2$ | 2-quinoline | — | Me | — | — | |
| 409 | A26 | Cl | 2-MeO-5-CN-phenyl | OCH$_2$ | 2-quinoline | — | Me | — | — | |
| 410 | A26 | Cl | 4-Cl-phenyl | OCH$_2$ | 2-quinoline | — | Me | — | — | |
| 411 | A31 | Cl | 4-pyridinyl | OCH$_2$ | 2-quinoline | — | Me, Me | — | — | |
| 412 | A31 | Cl | 4-OMe-phenyl | OCH$_2$ | 2-quinoline | — | Me, Me | — | — | |
| 413 | A31 | Cl | 4-pyrazolyl | OCH$_2$ | 2-quinoline | — | Me, Me | — | — | |
| 414 | A31 | Cl | 3-(1-methyl-1H-pyrazolyl) | OCH$_2$ | 2-quinoline | — | Me, Me | — | — | |
| 415 | A31 | Cl | 4-(1-methyl-1H-pyrazolyl) | OCH$_2$ | 2-quinoline | — | Me, Me | — | — | |
| 416 | A31 | Cl | 4-pyrimidinyl | OCH$_2$ | 2-quinoline | — | Me, Me | — | — | |
| 417 | A31 | Cl | 4-CN-phenyl | OCH$_2$ | 2-quinoline | — | Me, Me | — | — | |
| 418 | A31 | Cl | 2-MeO-4-pyridinyl | OCH$_2$ | 2-quinoline | — | Me, Me | — | — | |
| 419 | A31 | Cl | 6-MeO-3-pyridinyl | OCH$_2$ | 2-quinoline | — | Me, Me | — | — | |
| 420 | A31 | Cl | 6-HO-3-pyridinyl | OCH$_2$ | 2-quinoline | — | Me, Me | — | — | |
| 421 | A31 | Cl | 1,3,5-triazin-2-yl | OCH$_2$ | 2-quinoline | — | Me, Me | — | — | |

-continued

| Ex PCT # | HET | W | X | Y | Z | $R_{1a}, R_{1b}$ | $R_2$ | $R_3$ | $R_4$ | $R_7$ |
|---|---|---|---|---|---|---|---|---|---|---|
| 422 | A31 | Cl | 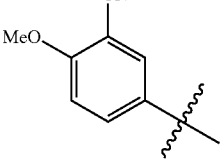 2-CN, 2-MeO-phenyl | OCH$_2$ | 2-quinoline | — | Me, Me | — | — | |
| 423 | A31 | Cl | 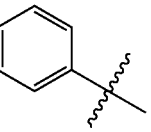 4-Cl-phenyl | OCH$_2$ | 2-quinoline | — | Me, Me | — | — | |
| 424 | A32 | Cl | 4-pyridinyl | OCH$_2$ | 2-quinoline | — | Me, Me | — | — | Me |
| 425 | A32 | Cl | 4-OMe-phenyl | OCH$_2$ | 2-quinoline | — | Me, Me | — | — | Me |
| 426 | A32 | Cl | 4-pyrazolyl | OCH$_2$ | 2-quinoline | — | Me, Me | — | — | Me |
| 427 | A32 | Cl | 3-(1-methyl-1H-pyrazolyl) | OCH$_2$ | 2-quinoline | — | Me, Me | — | — | Me |
| 428 | A32 | Cl | 4-(1-methyl-1H-pyrazolyl) | OCH$_2$ | 2-quinoline | — | Me, Me | — | — | Me |
| 429 | A32 | Cl | 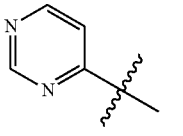 4-pyrimidinyl | OCH$_2$ | 2-quinoline | — | Me, Me | — | — | Me |
| 430 | A32 | Cl | 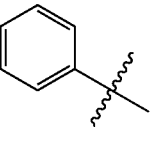 4-CN-phenyl | OCH$_2$ | 2-quinoline | — | Me, Me | — | — | H |
| 431 | A32 | Cl | 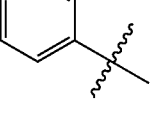 4-CN-phenyl | OCH$_2$ | 2-quinoline | — | Me, Me | — | — | Me |
| 432 | A32 | Cl | 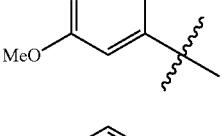 2-MeO-pyridin-4-yl | OCH$_2$ | 2-quinoline | — | Me, Me | — | — | H |
| 433 | A32 | Cl | 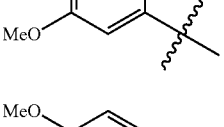 2-MeO-pyridin-4-yl | OCH$_2$ | 2-quinoline | — | Me, Me | — | — | Me |
| 434 | A32 | Cl | 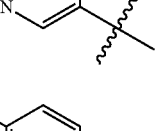 6-MeO-pyridin-3-yl | OCH$_2$ | 2-quinoline | — | Me, Me | — | — | H |
| 435 | A32 | Cl | 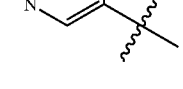 6-MeO-pyridin-3-yl | OCH$_2$ | 2-quinoline | — | Me, Me | — | — | Me |

-continued

| Ex PCT # | HET | W | X | Y | Z | R₁ₐ, R₁ᵦ | R₂ | R₃ | R₄ | R₇ |
|---|---|---|---|---|---|---|---|---|---|---|
| 436 | A32 | Cl | 2-HO-5-pyridinyl | OCH₂ | 2-quinoline | — | Me, Me | — | — | H |
| 437 | A32 | Cl | 2-HO-5-pyridinyl | OCH₂ | 2-quinoline | — | Me, Me | — | — | Me |
| 438 | A32 | Cl | 1,3,5-triazin-2-yl | OCH₂ | 2-quinoline | — | Me, Me | — | — | H |
| 439 | A32 | Cl | 1,3,5-triazin-2-yl | OCH₂ | 2-quinoline | — | Me, Me | — | — | Me |
| 440 | A32 | Cl | 3-CN-4-MeO-phenyl | OCH₂ | 2-quinoline | — | Me, Me | — | — | H |
| 441 | A32 | Cl | 3-CN-4-MeO-phenyl | OCH₂ | 2-quinoline | — | Me, Me | — | — | Me |
| 442 | A32 | Cl | 4-Cl-phenyl | OCH₂ | 2-quinoline | — | Me, Me | — | — | H |
| 443 | A32 | Cl | 4-Cl-phenyl | OCH₂ | 2-quinoline | — | Me, Me | — | — | Me |
| 444 | A35 | Cl | 4-pyridinyl | OCH₂ | 2-quinoline | — | — | — | — | — |
| 445 | A35 | Cl | 4-OMe-phenyl | OCH₂ | 2-quinoline | — | — | — | — | — |
| 446 | A35 | Cl | 4-pyrazolyl | OCH₂ | 2-quinoline | — | — | — | — | — |
| 447 | A35 | Cl | 3-(1-methyl-1H-pyrazolyl) | OCH₂ | 2-quinoline | — | — | — | — | — |
| 448 | A35 | Cl | 4-(1-methyl-1H-pyrazolyl) | OCH₂ | 2-quinoline | — | — | — | — | — |
| 449 | A35 | Cl | 4-pyrimidinyl | OCH₂ | 2-quinoline | — | — | — | — | — |

-continued

| Ex PCT # | HET | W | X | Y | Z | $R_{1a}, R_{1b}$ | $R_2$ | $R_3$ | $R_4$ | $R_7$ |
|---|---|---|---|---|---|---|---|---|---|---|
| 450 | A35 | Cl | 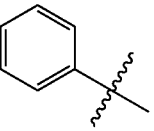 | OCH$_2$ | 2-quinoline | — | — | — | — | — |
| 451 | A35 | Cl | 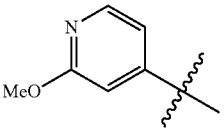 | OCH$_2$ | 2-quinoline | — | — | — | — | — |
| 452 | A35 | Cl | 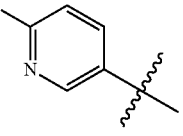 | OCH$_2$ | 2-quinoline | — | — | — | — | — |
| 453 | A35 | Cl | 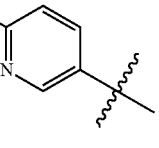 | OCH$_2$ | 2-quinoline | — | — | — | — | — |
| 454 | A35 | Cl | 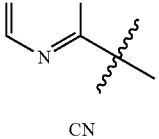 | OCH$_2$ | 2-quinoline | — | — | — | — | — |
| 455 | A35 | Cl | 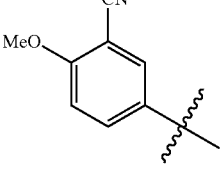 | OCH$_2$ | 2-quinoline | — | — | — | — | — |
| 456 | A35 | Cl | 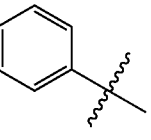 | OCH$_2$ | 2-quinoline | — | — | — | — | — |
| 457 | A2 | CN | 4-pyridinyl | OCH$_2$ | 2-quinoline | — | — | Me | Me | Me |
| 458 | A2 | CN | 4-OMe-phenyl | OCH$_2$ | 2-quinoline | — | — | Me | Me | Me |
| 459 | A2 | CN | 4-pyrazolyl | OCH$_2$ | 2-quinoline | — | — | Me | Me | Me |
| 460 | A2 | CN | 3-(1-methyl-1H-pyrazolyl) | OCH$_2$ | 2-quinoline | — | — | Me | Me | Me |
| 461 | A2 | CN | 4-(1-methyl-1H-pyrazolyl) | OCH$_2$ | 2-quinoline | — | — | Me | Me | Me |
| 462 | A2 | CN | 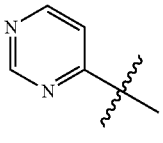 | OCH$_2$ | 2-quinoline | — | — | Me | Me | Me |
| 463 | A2 | CN | 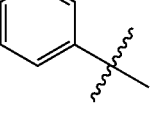 | OCH$_2$ | 2-quinoline | — | — | Me | Me | Me |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 464 | A2 | CN | 2-MeO-pyridin-4-yl | OCH$_2$ | 2-quinoline | — | — | Me | Me | Me |
| 465 | A2 | CN | 6-MeO-pyridin-3-yl | OCH$_2$ | 2-quinoline | — | — | Me | Me | Me |
| 466 | A2 | CN | 6-HO-pyridin-3-yl | OCH$_2$ | 2-quinoline | — | — | Me | Me | Me |
| 467 | A2 | CN | 1,3,5-triazin-2-yl | OCH$_2$ | 2-quinoline | — | — | Me | Me | Me |
| 468 | A2 | CN |  | OCH$_2$ | 2-quinoline | — | — | Me | Me | Me |
| 469 | A2 | CN | 4-Cl-phenyl | OCH$_2$ | 2-quinoline | — | — | Me | Me | Me |
| 470 | A5 | CN | 4-pyridinyl | OCH$_2$ | 2-quinoline | — | — | — | — | H |
| 471 | A5 | CN | 4-OMe-phenyl | OCH$_2$ | 2-quinoline | — | — | — | — | H |
| 472 | A5 | CN | 4-pyrazolyl | OCH$_2$ | 2-quinoline | — | — | — | — | H |
| 473 | A5 | CN | 3-(1-methyl-1H-pyrazolyl) | OCH$_2$ | 2-quinoline | — | — | — | — | H |
| 474 | A5 | CN | 4-(1-methyl-1H-pyrazolyl) | OCH$_2$ | 2-quinoline | — | — | — | — | H |
| 475 | A5 | CN | pyrimidin-4-yl | OCH$_2$ | 2-quinoline | — | — | — | — | H |
| 476 | A5 | CN | 4-NC-phenyl | OCH$_2$ | 2-quinoline | — | — | — | — | H |
| 477 | A5 | CN | 2-MeO-pyridin-4-yl | OCH$_2$ | 2-quinoline | — | — | — | — | H |
| 478 | A5 | CN | 6-MeO-pyridin-3-yl | OCH$_2$ | 2-quinoline | — | — | — | — | H |

-continued

| Ex PCT # | HET | W | X | Y | Z | R_{1a}, R_{1b} | R_2 | R_3 | R_4 | R_7 |
|---|---|---|---|---|---|---|---|---|---|---|
| 479 | A5 | CN | 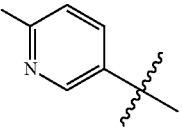 2-hydroxypyridin-5-yl | OCH_2 | 2-quinoline | — | — | — | — | H |
| 480 | A5 | CN | 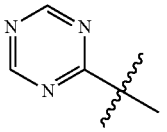 [SMILES: *c1ncncn1] 1,3,5-triazin-2-yl | OCH_2 | 2-quinoline | — | — | — | — | H |
| 481 | A5 | CN |  4-Cl-phenyl | OCH_2 | 2-quinoline | — | — | — | — | H |
| 482 | A5 | CN | 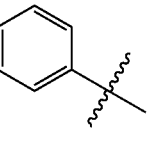 4-Cl-phenyl | OCH_2 | 2-quinoline | — | — | — | — | H |
| 483 | A22 | CN | 4-pyridinyl | OCH_2 | 2-quinoline | — | Me | — | — | — |
| 484 | A22 | CN | 4-OMe-phenyl | OCH_2 | 2-quinoline | — | Me | — | — | — |
| 485 | A22 | CN | 4-pyrazolyl | OCH_2 | 2-quinoline | — | Me | — | — | — |
| 486 | A22 | CN | 3-(1-methyl-1H-pyrazolyl) | OCH_2 | 2-quinoline | — | Me | — | — | — |
| 487 | A22 | CN | 4-(1-methyl-1H-pyrazolyl) | OCH_2 | 2-quinoline | — | Me | — | — | — |
| 488 | A22 | CN | 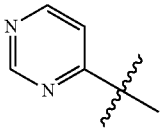 [SMILES: *c1ccncn1] pyrimidin-4-yl | OCH_2 | 2-quinoline | — | Me | — | — | — |
| 489 | A22 | CN | 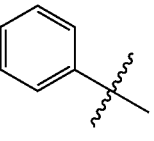 4-CN-phenyl | OCH_2 | 2-quinoline | — | Me | — | — | — |
| 490 | A22 | CN | 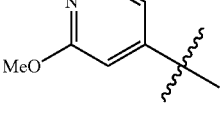 2-MeO-pyridin-4-yl | OCH_2 | 2-quinoline | — | Me | — | — | — |
| 491 | A22 | CN | 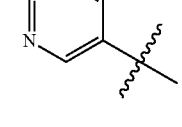 2-MeO-pyridin-5-yl | OCH_2 | 2-quinoline | — | Me | — | — | — |
| 492 | A22 | CN | 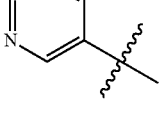 2-HO-pyridin-5-yl | OCH_2 | 2-quinoline | — | Me | — | — | — |

-continued

| Ex PCT # | HET | W | X | Y | Z | $R_{1a}, R_{1b}$ | $R_2$ | $R_3$ | $R_4$ | $R_7$ |
|---|---|---|---|---|---|---|---|---|---|---|
| 493 | A22 | CN | 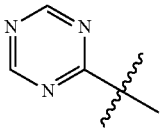 [SMILES: *c1ncncn1] | $OCH_2$ | 2-quinoline | — | Me | — | — | — |
| 494 | A22 | CN | 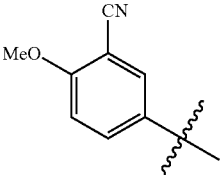 | $OCH_2$ | 2-quinoline | — | Me | — | — | — |
| 495 | A22 | CN | 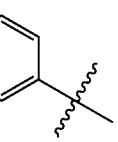 | $OCH_2$ | 2-quinoline | — | Me | — | — | — |
| 496 | A23 | CN | 4-pyridinyl | $OCH_2$ | 2-quinoline | — | Me | — | — | — |
| 497 | A23 | CN | 4-OMe-phenyl | $OCH_2$ | 2-quinoline | — | Me | — | — | — |
| 498 | A23 | CN | 4-pyrazolyl | $OCH_2$ | 2-quinoline | — | Me | — | — | — |
| 499 | A23 | CN | 3-(1-methyl-1H-pyrazolyl) | $OCH_2$ | 2-quinoline | — | Me | — | — | — |
| 500 | A23 | CN | 4-(1-methyl-1H-pyrazolyl) | $OCH_2$ | 2-quinoline | — | Me | — | — | — |
| 501 | A23 | CN | 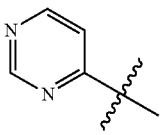 | $OCH_2$ | 2-quinoline | — | Me | — | — | — |
| 502 | A23 | CN | 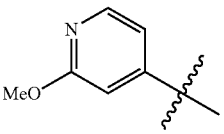 [SMILES: *c1ccnc(OC)c1] | $OCH_2$ | 2-quinoline | — | Me | — | — | — |
| 503 | A23 | CN | 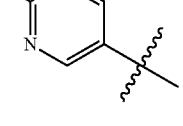 | $OCH_2$ | 2-quinoline | — | Me | — | — | — |
| 504 | A23 | CN | 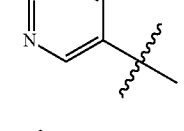 | $OCH_2$ | 2-quinoline | — | Me | — | — | — |
| 505 | A23 | CN | 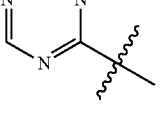 | $OCH_2$ | 2-quinoline | — | Me | — | — | — |
| 506 | A23 | CN |  | $OCH_2$ | 2-quinoline | — | Me | — | — | — |

-continued

| Ex PCT # | HET | W | X | Y | Z | R₁ₐ, R₁ᵦ | R₂ | R₃ | R₄ | R₇ |
|---|---|---|---|---|---|---|---|---|---|---|
| 507 | A23 | CN | 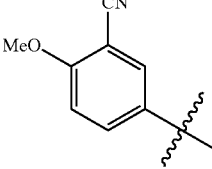 | OCH₂ | 2-quinoline | — | Me | — | — | — |
| 508 | A23 | CN | 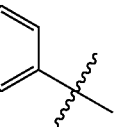 | OCH₂ | 2-quinoline | — | Me | — | — | — |
| 509 | A26 | CN | 4-pyridinyl | OCH₂ | 2-quinoline | — | Me | — | — | — |
| 510 | A26 | CN | 4-OMe-phenyl | OCH₂ | 2-quinoline | — | Me | — | — | — |
| 511 | A26 | CN | 4-pyrazolyl | OCH₂ | 2-quinoline | — | Me | — | — | — |
| 512 | A26 | CN | 3-(1-methyl-1H-pyrazolyl) | OCH₂ | 2-quinoline | — | Me | — | — | — |
| 513 | A26 | CN | 4-(1-methyl-1H-pyrazolyl) | OCH₂ | 2-quinoline | — | Me | — | — | — |
| 514 | A26 | CN | 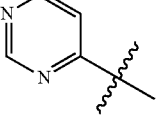 | OCH₂ | 2-quinoline | — | Me | — | — | — |
| 515 | A26 | CN | 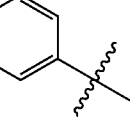 | OCH₂ | 2-quinoline | — | Me | — | — | — |
| 516 | A26 | CN | 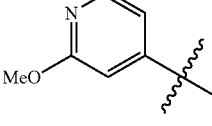 | OCH₂ | 2-quinoline | — | Me | — | — | — |
| 517 | A26 | CN | 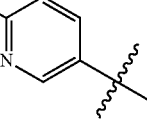 | OCH₂ | 2-quinoline | — | Me | — | — | — |
| 518 | A26 | CN | 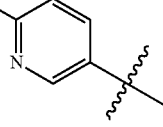 | OCH₂ | 2-quinoline | — | Me | — | — | — |
| 519 | A26 | CN | 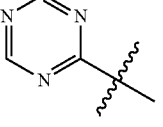 | OCH₂ | 2-quinoline | — | Me | — | — | — |

-continued

| Ex PCT # | HET | W | X | Y | Z | R1a, R1b | R2 | R3 | R4 | R7 |
|---|---|---|---|---|---|---|---|---|---|---|
| 520 | A26 | CN | 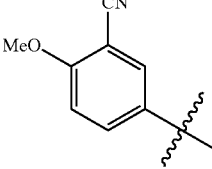 | OCH2 | 2-quinoline | — | Me | — | — | — |
| 521 | A26 | CN | 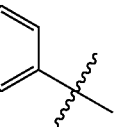 | OCH2 | 2-quinoline | — | Me | — | — | — |
| 522 | A31 | CN | 4-pyridinyl | OCH2 | 2-quinoline | — | Me, Me | — | — | — |
| 523 | A31 | CN | 4-OMe-phenyl | OCH2 | 2-quinoline | — | Me, Me | — | — | — |
| 524 | A31 | CN | 4-pyrazolyl | OCH2 | 2-quinoline | — | Me, Me | — | — | — |
| 525 | A31 | CN | 3-(1-methyl-1H-pyrazolyl) | OCH2 | 2-quinoline | — | Me, Me | — | — | — |
| 526 | A31 | CN | 4-(1-methyl-1H-pyrazolyl) | OCH2 | 2-quinoline | — | Me, Me | — | — | — |
| 527 | A31 | CN | 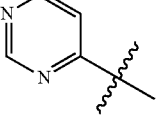 | OCH2 | 2-quinoline | — | Me, Me | — | — | — |
| 528 | A31 | CN | 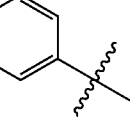 | OCH2 | 2-quinoline | — | Me, Me | — | — | — |
| 529 | A31 | CN | 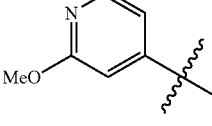 | OCH2 | 2-quinoline | — | Me, Me | — | — | — |
| 530 | A31 | CN | 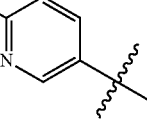 | OCH2 | 2-quinoline | — | Me, Me | — | — | — |
| 531 | A31 | CN | 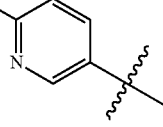 | OCH2 | 2-quinoline | — | Me, Me | — | — | — |
| 532 | A31 | CN | 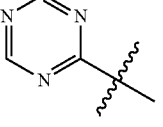 | OCH2 | 2-quinoline | — | Me, Me | — | — | — |

-continued

| Ex PCT # | HET | W | X | Y | Z | R_{1a}, R_{1b} | R_2 | R_3 | R_4 | R_7 |
|---|---|---|---|---|---|---|---|---|---|---|
| 533 | A31 | CN | 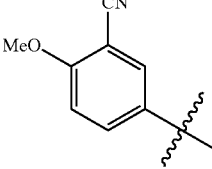 | OCH_2 | 2-quinoline | — | Me, Me | — | — | — |
| 534 | A31 | CN | 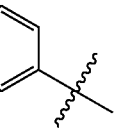 | OCH_2 | 2-quinoline | — | Me, Me | — | — | — |
| 535 | A32 | CN | 4-pyridinyl | OCH_2 | 2-quinoline | — | Me, Me | — | — | Me |
| 536 | A32 | CN | 4-OMe-phenyl | OCH_2 | 2-quinoline | — | Me, Me | — | — | Me |
| 537 | A32 | CN | 4-pyrazolyl | OCH_2 | 2-quinoline | — | Me, Me | — | — | Me |
| 538 | A32 | CN | 3-(1-methyl-1H-pyrazolyl) | OCH_2 | 2-quinoline | — | Me, Me | — | — | Me |
| 539 | A32 | CN | 4-(1-methyl-1H-pyrazolyl) | OCH_2 | 2-quinoline | — | Me, Me | — | — | Me |
| 540 | A32 | CN | 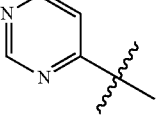 | OCH_2 | 2-quinoline | — | Me, Me | — | — | Me |
| 541 | A32 | CN | 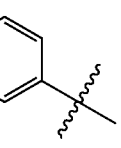 | OCH_2 | 2-quinoline | — | Me, Me | — | — | Me |
| 542 | A32 | CN | 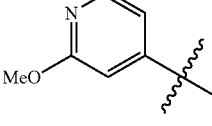 | OCH_2 | 2-quinoline | — | Me, Me | — | — | Me |
| 543 | A32 | CN | 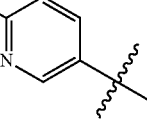 | OCH_2 | 2-quinoline | — | Me, Me | — | — | Me |
| 544 | A32 | CN | 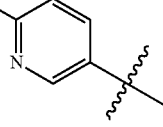 | OCH_2 | 2-quinoline | — | Me, Me | — | — | Me |
| 545 | A32 | CN | 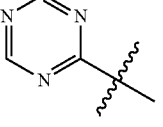 | OCH_2 | 2-quinoline | — | Me, Me | — | — | Me |

-continued
| Ex PCT # | HET | W | X | Y | Z | R_{1a}, R_{1b} | R_2 | R_3 | R_4 | R_7 |
|---|---|---|---|---|---|---|---|---|---|---|
| 546 | A32 | CN | 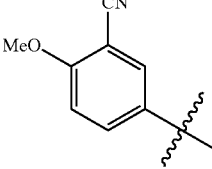 | OCH_2 | 2-quinoline | — | Me, Me | — | — | Me |
| 547 | A32 | CN | 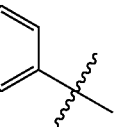 | OCH_2 | 2-quinoline | — | Me, Me | — | — | Me |
| 548 | A35 | CN | 4-pyridinyl | OCH_2 | 2-quinoline | — | — | — | — | — |
| 549 | A35 | CN | 4-OMe-phenyl | OCH_2 | 2-quinoline | — | — | — | — | — |
| 550 | A35 | CN | 4-pyrazolyl | OCH_2 | 2-quinoline | — | — | — | — | — |
| 551 | A35 | CN | 3-(1-methyl-1H-pyrazolyl) | OCH_2 | 2-quinoline | — | — | — | — | — |
| 552 | A35 | CN | 4-(1-methyl-1H-pyrazolyl) | OCH_2 | 2-quinoline | — | — | — | — | — |
| 553 | A35 | CN | 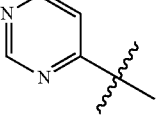 | OCH_2 | 2-quinoline | — | — | — | — | — |
| 554 | A35 | CN | 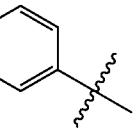 | OCH_2 | 2-quinoline | — | — | — | — | — |
| 555 | A35 | CN | 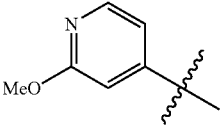 | OCH_2 | 2-quinoline | — | — | — | — | — |
| 556 | A35 | CN | 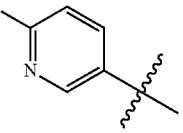 | OCH_2 | 2-quinoline | — | — | — | — | — |
| 557 | A35 | CN | 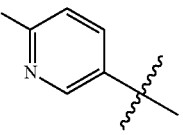 | OCH_2 | 2-quinoline | — | — | — | — | — |
| 558 | A35 | CN | 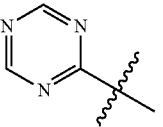 | OCH_2 | 2-quinoline | — | — | — | — | — |

-continued

| Ex PCT # | HET | W | X | Y | Z | $R_{1a}, R_{1b}$ | $R_2$ | $R_3$ | $R_4$ | $R_7$ |
|---|---|---|---|---|---|---|---|---|---|---|
| 559 | A35 | CN | 3-CN-4-OMe-phenyl | $OCH_2$ | 2-quinoline | — | — | — | — | — |
| 560 | A35 | CN | 4-Cl-phenyl | $OCH_2$ | 2-quinoline | — | — | — | — | — |

In a further aspect the compounds of the disclosure are embodied in with distinct examples listed in the table below taken from Formula (III):

| Ex PCT # | HET | W | X | Y | Z | $R_{1a}, R_{1b}$ | $R_2$ | $R_3$ | $R_4$ | $R_7$ |
|---|---|---|---|---|---|---|---|---|---|---|
| 561 | A2 | Cl | 4-pyridinyl | $OCH_2$ | 2-quinoline | — | — | Me | Me | Me |
| 562 | A2 | Cl | 4-OMe-phenyl | $OCH_2$ | 2-quinoline | — | — | Me | Me | Me |
| 563 | A2 | Cl | 4-pyrazolyl | $OCH_2$ | 2-quinoline | — | — | Me | Me | Me |
| 564 | A2 | Cl | 3-(1-methyl-1H-pyrazolyl) | $OCH_2$ | 2-quinoline | — | — | Me | Me | Me |
| 565 | A2 | Cl | 4-(1-methyl-1H-pyrazolyl) | $OCH_2$ | 2-quinoline | — | — | Me | Me | Me |
| 566 | A2 | Cl | pyrimidinyl | $OCH_2$ | 2-quinoline | — | — | Me | Me | Me |
| 567 | A2 | Cl | 4-CN-phenyl | $OCH_2$ | 2-quinoline | — | — | Me | Me | Me |
| 568 | A2 | Cl | 2-OMe-pyridin-4-yl | $OCH_2$ | 2-quinoline | — | — | Me | Me | Me |
| 569 | A2 | Cl | 6-OMe-pyridin-3-yl | $OCH_2$ | 2-quinoline | — | — | Me | Me | Me |
| 570 | A2 | Cl | 6-HO-pyridin-3-yl | $OCH_2$ | 2-quinoline | — | — | Me | Me | Me |

-continued

| Ex PCT # | HET | W | X | Y | Z | R₁ₐ, R₁ᵦ | R₂ | R₃ | R₄ | R₇ |
|---|---|---|---|---|---|---|---|---|---|---|
| 571 | A2 | Cl | (1,3,5-triazin-2-yl) | OCH₂ | 2-quinoline | — | — | Me | Me | Me |
| 572 | A2 | Cl | 3-cyano-2-methoxyphenyl | OCH₂ | 2-quinoline | — | — | Me | Me | Me |
| 573 | A2 | Cl | 4-chlorophenyl | OCH₂ | 2-quinoline | — | — | Me | Me | Me |
| 574 | A5 | Cl | 4-pyridinyl | OCH₂ | 2-quinoline | — | — | — | — | H |
| 575 | A5 | Cl | 4-OMe-phenyl | OCH₂ | 2-quinoline | — | — | — | — | H |
| 576 | A5 | Cl | 4-pyrazolyl | OCH₂ | 2-quinoline | — | — | — | — | H |
| 577 | A5 | Cl | 3-(1-methyl-1H-pyrazolyl) | OCH₂ | 2-quinoline | — | — | — | — | H |
| 578 | A5 | Cl | 4-(1-methyl-1H-pyrazolyl) | OCH₂ | 2-quinoline | — | — | — | — | H |
| 579 | A5 | Cl | pyrimidin-4-yl | OCH₂ | 2-quinoline | — | — | — | — | H |
| 580 | A5 | Cl | 4-cyanophenyl | OCH₂ | 2-quinoline | — | — | — | — | H |
| 581 | A5 | Cl | 2-methoxy-4-pyridinyl | OCH₂ | 2-quinoline | — | — | — | — | H |
| 582 | A5 | Cl | 6-methoxy-3-pyridinyl | OCH₂ | 2-quinoline | — | — | — | — | H |
| 583 | A5 | Cl | 2-hydroxy-5-pyridinyl | OCH₂ | 2-quinoline | — | — | — | — | H |
| 584 | A5 | Cl | (1,3,5-triazin-2-yl) | OCH₂ | 2-quinoline | — | — | — | — | H |

-continued

| Ex PCT # | HET | W | X | Y | Z | R_{1a}, R_{1b} | R_2 | R_3 | R_4 | R_7 |
|---|---|---|---|---|---|---|---|---|---|---|
| 585 | A5 | Cl | 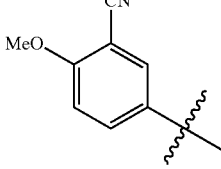 | OCH_2 | 2-quinoline | — | — | — | — | H |
| 586 | A5 | Cl | 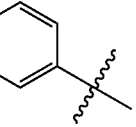 | OCH_2 | 2-quinoline | — | — | — | — | H |
| 587 | A22 | Cl | 4-pyridinyl | OCH_2 | 2-quinoline | — | Me | — | — | |
| 588 | A22 | Cl | 4-OMe-phenyl | OCH_2 | 2-quinoline | — | Me | — | — | |
| 589 | A22 | Cl | 4-pyrazolyl | OCH_2 | 2-quinoline | — | Me | — | — | |
| 590 | A22 | Cl | 3-(1-methyl-1H-pyrazolyl) | OCH_2 | 2-quinoline | — | Me | — | — | |
| 591 | A22 | Cl | 4-(1-methyl-1H-pyrazolyl) | OCH_2 | 2-quinoline | — | Me | — | — | |
| 592 | A22 | Cl | 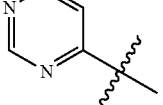 | OCH_2 | 2-quinoline | — | Me | — | — | |
| 593 | A22 | Cl |  | OCH_2 | 2-quinoline | — | Me | — | — | |
| 594 | A22 | Cl | 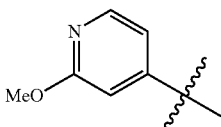 | OCH_2 | 2-quinoline | — | Me | — | — | |
| 595 | A22 | Cl | 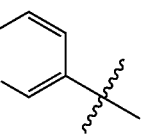 | OCH_2 | 2-quinoline | — | Me | — | — | |
| 596 | A22 | Cl | 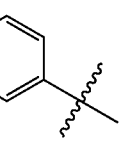 | OCH_2 | 2-quinoline | — | Me | — | — | |
| 597 | A22 | Cl | 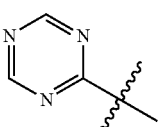 | OCH_2 | 2-quinoline | — | Me | — | — | |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 598 | A22 | Cl | 3-CN-4-OMe-phenyl | OCH$_2$ | 2-quinoline | — | Me | — | — | |
| 599 | A22 | Cl | 4-Cl-phenyl | OCH$_2$ | 2-quinoline | — | Me | — | — | |
| 600 | A23 | Cl | 4-pyridinyl | OCH$_2$ | 2-quinoline | — | Me | — | — | |
| 601 | A23 | Cl | 4-OMe-phenyl | OCH$_2$ | 2-quinoline | — | Me | — | — | |
| 602 | A23 | Cl | 4-pyrazolyl | OCH$_2$ | 2-quinoline | — | Me | — | — | |
| 603 | A23 | Cl | 3-(1-methyl-1H-pyrazolyl) | OCH$_2$ | 2-quinoline | — | Me | — | — | |
| 604 | A23 | Cl | 4-(1-methyl-1H-pyrazolyl) | OCH$_2$ | 2-quinoline | — | Me | — | — | |
| 605 | A23 | Cl | 4-pyrimidinyl | OCH$_2$ | 2-quinoline | — | Me | — | — | |
| 606 | A23 | Cl | 4-CN-phenyl | OCH$_2$ | 2-quinoline | — | Me | — | — | |
| 607 | A23 | Cl | 2-OMe-4-pyridinyl | OCH$_2$ | 2-quinoline | — | Me | — | — | |
| 608 | A23 | Cl | 6-OMe-3-pyridinyl | OCH$_2$ | 2-quinoline | — | Me | — | — | |
| 609 | A23 | Cl | 2-OH-5-pyridinyl | OCH$_2$ | 2-quinoline | — | Me | — | — | |
| 610 | A23 | Cl | 2-(1,3,5-triazinyl) | OCH$_2$ | 2-quinoline | — | Me | — | — | |

-continued

| Ex PCT # | HET | W | X | Y | Z | R1a, R1b | R2 | R3 | R4 | R7 |
|---|---|---|---|---|---|---|---|---|---|---|
| 611 | A23 | Cl | 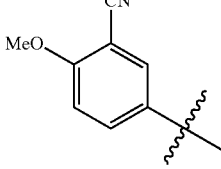 | OCH2 | 2-quinoline | — | Me | — | — | |
| 612 | A23 | Cl | 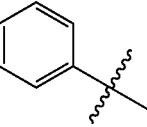 | OCH2 | 2-quinoline | — | Me | — | — | |
| 613 | A26 | Cl | 4-pyridinyl | OCH2 | 2-quinoline | — | Me | — | — | |
| 614 | A26 | Cl | 4-OMe-phenyl | OCH2 | 2-quinoline | — | Me | — | — | |
| 615 | A26 | Cl | 4-pyrazolyl | OCH2 | 2-quinoline | — | Me | — | — | |
| 616 | A26 | Cl | 3-(1-methyl-1H-pyrazolyl) | OCH2 | 2-quinoline | — | Me | — | — | |
| 617 | A26 | Cl | 4-(1-methyl-1H-pyrazolyl) | OCH2 | 2-quinoline | — | Me | — | — | |
| 618 | A26 | Cl | 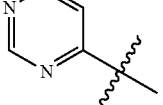 | OCH2 | 2-quinoline | — | Me | — | — | |
| 619 | A26 | Cl |  | OCH2 | 2-quinoline | — | Me | — | — | |
| 620 | A26 | Cl | 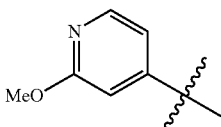 | OCH2 | 2-quinoline | — | Me | — | — | |
| 621 | A26 | Cl | 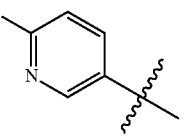 | OCH2 | 2-quinoline | — | Me | — | — | |
| 622 | A26 | Cl | 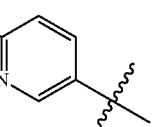 | OCH2 | 2-quinoline | — | Me | — | — | |
| 623 | A26 | Cl | 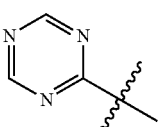 | OCH2 | 2-quinoline | — | Me | — | — | |

-continued

| Ex PCT # | HET | W | X | Y | Z | R<sub>1a</sub>, R<sub>1b</sub> | R<sub>2</sub> | R<sub>3</sub> | R<sub>4</sub> | R<sub>7</sub> |
|---|---|---|---|---|---|---|---|---|---|---|
| 624 | A26 | Cl | 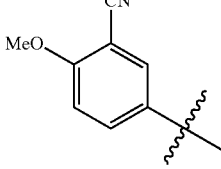 | OCH<sub>2</sub> | 2-quinoline | — | Me | — | — | |
| 625 | A26 | Cl | 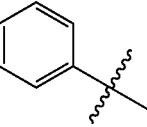 | OCH<sub>2</sub> | 2-quinoline | — | Me | — | — | |
| 626 | A31 | Cl | 4-pyridinyl | OCH<sub>2</sub> | 2-quinoline | — | Me, Me | — | — | |
| 627 | A31 | Cl | 4-OMe-phenyl | OCH<sub>2</sub> | 2-quinoline | — | Me, Me | — | — | |
| 628 | A31 | Cl | 4-pyrazolyl | OCH<sub>2</sub> | 2-quinoline | — | Me, Me | — | — | |
| 629 | A31 | Cl | 3-(1-methyl-1H-pyrazolyl) | OCH<sub>2</sub> | 2-quinoline | — | Me, Me | — | — | |
| 630 | A31 | Cl | 4-(1-methyl-1H-pyrazolyl) | OCH<sub>2</sub> | 2-quinoline | — | Me, Me | — | — | |
| 631 | A31 | Cl | 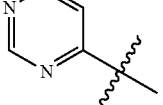 | OCH<sub>2</sub> | 2-quinoline | — | Me, Me | — | — | |
| 632 | A31 | Cl |  | OCH<sub>2</sub> | 2-quinoline | — | Me, Me | — | — | |
| 633 | A31 | Cl | 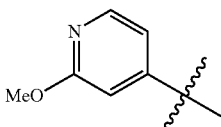 | OCH<sub>2</sub> | 2-quinoline | — | Me, Me | — | — | |
| 634 | A31 | Cl | 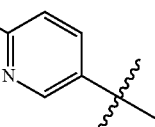 | OCH<sub>2</sub> | 2-quinoline | — | Me, Me | — | — | |
| 635 | A31 | Cl | 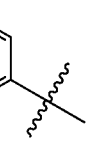 | OCH<sub>2</sub> | 2-quinoline | — | Me, Me | — | — | |
| 636 | A31 | Cl | 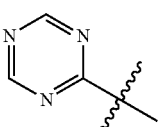 | OCH<sub>2</sub> | 2-quinoline | — | Me, Me | — | — | |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 637 | A31 | Cl | 3-CN-4-MeO-phenyl | OCH$_2$ | 2-quinoline | — | Me, Me | — | — | |
| 638 | A31 | Cl | 3-Cl-phenyl | OCH$_2$ | 2-quinoline | — | Me, Me | — | — | |
| 639 | A32 | Cl | 4-pyridinyl | OCH$_2$ | 2-quinoline | — | Me, Me | — | — | Me |
| 640 | A32 | Cl | 4-OMe-phenyl | OCH$_2$ | 2-quinoline | — | Me, Me | — | — | Me |
| 641 | A32 | Cl | 4-pyrazolyl | OCH$_2$ | 2-quinoline | — | Me, Me | — | — | Me |
| 642 | A32 | Cl | 3-(1-methyl-1H-pyrazolyl) | OCH$_2$ | 2-quinoline | — | Me, Me | — | — | Me |
| 643 | A32 | Cl | 4-(1-methyl-1H-pyrazolyl) | OCH$_2$ | 2-quinoline | — | Me, Me | — | — | Me |
| 644 | A32 | Cl | 4-pyrimidinyl | OCH$_2$ | 2-quinoline | — | Me, Me | — | — | Me |
| 645 | A32 | Cl | 4-CN-phenyl | OCH$_2$ | 2-quinoline | — | Me, Me | — | — | H |
| 646 | A32 | Cl | 4-CN-phenyl | OCH$_2$ | 2-quinoline | — | Me, Me | — | — | Me |
| 647 | A32 | Cl | 2-MeO-4-pyridinyl | OCH$_2$ | 2-quinoline | — | Me, Me | — | — | H |
| 648 | A32 | Cl | 2-MeO-4-pyridinyl | OCH$_2$ | 2-quinoline | — | Me, Me | — | — | Me |
| 649 | A32 | Cl | 6-MeO-3-pyridinyl | OCH$_2$ | 2-quinoline | — | Me, Me | — | — | H |
| 650 | A32 | Cl | 6-MeO-3-pyridinyl | OCH$_2$ | 2-quinoline | — | Me, Me | — | — | Me |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 651 | A32 | Cl | 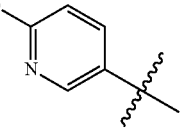 | OCH$_2$ | 2-quinoline | — | Me, Me | — | — | H |
| 652 | A32 | Cl | 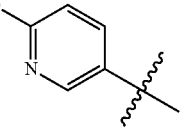 | OCH$_2$ | 2-quinoline | — | Me, Me | — | — | Me |
| 653 | A32 | Cl | 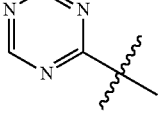 | OCH$_2$ | 2-quinoline | — | Me, Me | — | — | H |
| 654 | A32 | Cl | 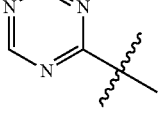 | OCH$_2$ | 2-quinoline | — | Me, Me | — | — | Me |
| 655 | A32 | Cl | 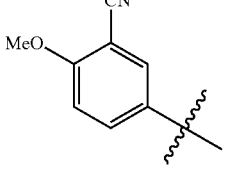 | OCH$_2$ | 2-quinoline | — | Me, Me | — | — | H |
| 656 | A32 | Cl | 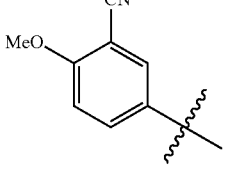 | OCH$_2$ | 2-quinoline | — | Me, Me | — | — | Me |
| 657 | A32 | Cl | 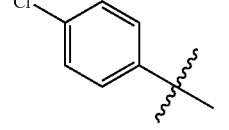 | OCH$_2$ | 2-quinoline | — | Me, Me | — | — | H |
| 658 | A32 | Cl | 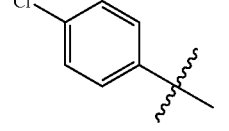 | OCH$_2$ | 2-quinoline | — | Me, Me | — | — | Me |
| 659 | A35 | Cl | 4-pyridinyl | OCH$_2$ | 2-quinoline | — | — | — | — | — |
| 660 | A35 | Cl | 4-OMe-phenyl | OCH$_2$ | 2-quinoline | — | — | — | — | — |
| 661 | A35 | Cl | 4-pyrazolyl | OCH$_2$ | 2-quinoline | — | — | — | — | — |
| 662 | A35 | Cl | 3-(1-methyl-1H-pyrazolyl) | OCH$_2$ | 2-quinoline | — | — | — | — | — |
| 663 | A35 | Cl | 4-(1-methyl-1H-pyrazolyl) | OCH$_2$ | 2-quinoline | — | — | — | — | — |

-continued

| Ex PCT # | HET | W | X | Y | Z | R_{1a}, R_{1b} | R_2 | R_3 | R_4 | R_7 |
|---|---|---|---|---|---|---|---|---|---|---|
| 664 | A35 | Cl | 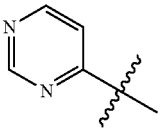 | OCH_2 | 2-quinoline | — | — | — | — | — |
| 665 | A35 | Cl | 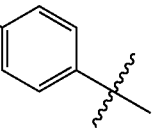 | OCH_2 | 2-quinoline | — | — | — | — | — |
| 666 | A35 | Cl | 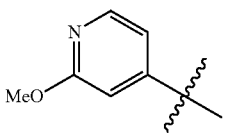 | OCH_2 | 2-quinoline | — | — | — | — | — |
| 667 | A35 | Cl | 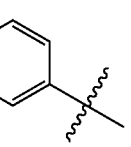 | OCH_2 | 2-quinoline | — | — | — | — | — |
| 668 | A35 | Cl | 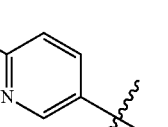 | OCH_2 | 2-quinoline | — | — | — | — | — |
| 669 | A35 | Cl | 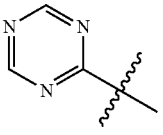 [SMILES: *c1ncncn1] | OCH_2 | 2-quinoline | — | — | — | — | — |
| 670 | A35 | Cl | 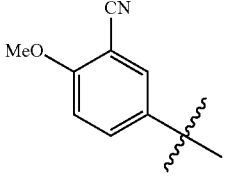 | OCH_2 | 2-quinoline | — | — | — | — | — |
| 671 | A35 | Cl |  | OCH_2 | 2-quinoline | — | — | — | — | — |
| 672 | A2 | CN | 4-pyridinyl | OCH_2 | 2-quinoline | — | — | Me | Me | Me |
| 673 | A2 | CN | 4-OMe-phenyl | OCH_2 | 2-quinoline | — | — | Me | Me | Me |
| 674 | A2 | CN | 4-pyrazolyl | OCH_2 | 2-quinoline | — | — | Me | Me | Me |
| 675 | A2 | CN | 3-(1-methyl-1H-pyrazolyl) | OCH_2 | 2-quinoline | — | — | Me | Me | Me |
| 676 | A2 | CN | 4-(1-methyl-1H-pyrazolyl) | OCH_2 | 2-quinoline | — | — | Me | Me | Me |
| 677 | A2 | CN | 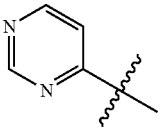 | OCH_2 | 2-quinoline | — | — | Me | Me | Me |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 678 | A2 | CN | 4-cyanophenyl | OCH$_2$ | 2-quinoline | — | — | Me | Me | Me |
| 679 | A2 | CN | 2-methoxypyridin-4-yl | OCH$_2$ | 2-quinoline | — | — | Me | Me | Me |
| 680 | A2 | CN | 6-methoxypyridin-3-yl | OCH$_2$ | 2-quinoline | — | — | Me | Me | Me |
| 681 | A2 | CN | 6-hydroxypyridin-3-yl | OCH$_2$ | 2-quinoline | — | — | Me | Me | Me |
| 682 | A2 | CN | 1,3,5-triazin-2-yl | OCH$_2$ | 2-quinoline | — | — | Me | Me | Me |
| 683 | A2 | CN |  | OCH$_2$ | 2-quinoline | — | — | Me | Me | Me |
| 684 | A2 | CN | 4-chlorophenyl | OCH$_2$ | 2-quinoline | — | — | Me | Me | Me |
| 685 | A5 | CN | 4-pyridinyl | OCH$_2$ | 2-quinoline | — | — | — | — | H |
| 686 | A5 | CN | 4-OMe-phenyl | OCH$_2$ | 2-quinoline | — | — | — | — | H |
| 687 | A5 | CN | 4-pyrazolyl | OCH$_2$ | 2-quinoline | — | — | — | — | H |
| 688 | A5 | CN | 3-(1-methyl-1H-pyrazolyl) | OCH$_2$ | 2-quinoline | — | — | — | — | H |
| 689 | A5 | CN | 4-(1-methyl-1H-pyrazolyl) | OCH$_2$ | 2-quinoline | — | — | — | — | H |
| 690 | A5 | CN | pyrimidin-4-yl | OCH$_2$ | 2-quinoline | — | — | — | — | H |
| 691 | A5 | CN | 4-cyanophenyl | OCH$_2$ | 2-quinoline | — | — | — | — | H |
| 692 | A5 | CN | 2-methoxypyridin-4-yl | OCH$_2$ | 2-quinoline | — | — | — | — | H |

-continued

| Ex PCT # | HET | W | X | Y | Z | R₁ₐ, R₁ᵦ | R₂ | R₃ | R₄ | R₇ |
|---|---|---|---|---|---|---|---|---|---|---|
| 693 | A5 | CN | 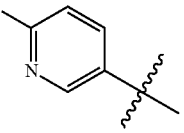 MeO-pyridinyl | OCH₂ | 2-quinoline | — | — | — | — | H |
| 694 | A5 | CN | 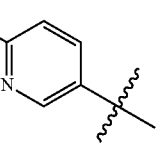 HO-pyridinyl | OCH₂ | 2-quinoline | — | — | — | — | H |
| 695 | A5 | CN | 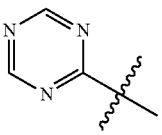 triazinyl | OCH₂ | 2-quinoline | — | — | — | — | H |
| 696 | A5 | CN | 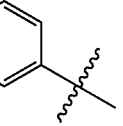 Cl-phenyl | OCH₂ | 2-quinoline | — | — | — | — | H |
| 697 | A5 | CN |  Cl-phenyl | OCH₂ | 2-quinoline | — | — | — | — | H |
| 698 | A22 | CN | 4-pyridinyl | OCH₂ | 2-quinoline | — | Me | — | — | — |
| 699 | A22 | CN | 4-OMe-phenyl | OCH₂ | 2-quinoline | — | Me | — | — | — |
| 700 | A22 | CN | 4-pyrazolyl | OCH₂ | 2-quinoline | — | Me | — | — | — |
| 701 | A22 | CN | 3-(1-methyl-1H-pyrazolyl) | OCH₂ | 2-quinoline | — | Me | — | — | — |
| 702 | A22 | CN | 4-(1-methyl-1H-pyrazolyl) | OCH₂ | 2-quinoline | — | Me | — | — | — |
| 703 | A22 | CN | 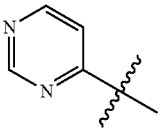 pyrimidinyl | OCH₂ | 2-quinoline | — | Me | — | — | — |
| 704 | A22 | CN |  NC-phenyl | OCH₂ | 2-quinoline | — | Me | — | — | — |
| 705 | A22 | CN | 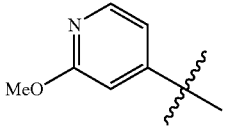 [SMILES: *c1ccnc(OC)c1] MeO-pyridinyl | OCH₂ | 2-quinoline | — | Me | — | — | — |
| 706 | A22 | CN | 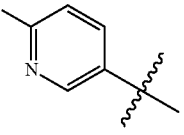 MeO-pyridinyl | OCH₂ | 2-quinoline | — | Me | — | — | — |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 707 | A22 | CN | 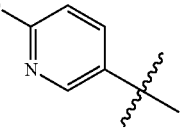 | OCH$_2$ | 2-quinoline | — | Me | — | — | — |
| 708 | A22 | CN | 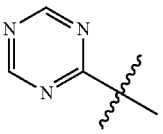 [SMILES: *c1ncncn1] | OCH$_2$ | 2-quinoline | — | Me | — | — | — |
| 709 | A22 | CN | 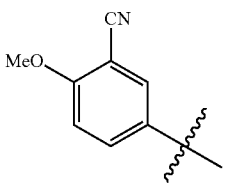 | OCH$_2$ | 2-quinoline | — | Me | — | — | — |
| 710 | A22 | CN | 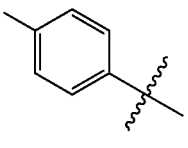 | OCH$_2$ | 2-quinoline | — | Me | — | — | — |
| 711 | A23 | CN | 4-pyridinyl | OCH$_2$ | 2-quinoline | — | Me | — | — | — |
| 712 | A23 | CN | 4-OMe-phenyl | OCH$_2$ | 2-quinoline | — | Me | — | — | — |
| 713 | A23 | CN | 4-pyrazolyl | OCH$_2$ | 2-quinoline | — | Me | — | — | — |
| 714 | A23 | CN | 3-(1-methyl-1H-pyrazolyl) | OCH$_2$ | 2-quinoline | — | Me | — | — | — |
| 715 | A23 | CN | 4-(1-methyl-1H-pyrazolyl) | OCH$_2$ | 2-quinoline | — | Me | — | — | — |
| 716 | A23 | CN | 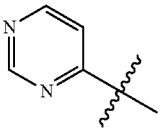 | OCH$_2$ | 2-quinoline | — | Me | — | — | — |
| 717 | A23 | CN | 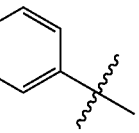 | OCH$_2$ | 2-quinoline | — | Me | — | — | — |
| 718 | A23 | CN | 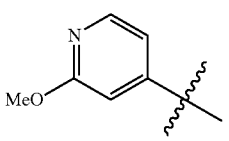 [SMILES: *c1ccnc(OC)c1] | OCH$_2$ | 2-quinoline | — | Me | — | — | — |
| 719 | A23 | CN | 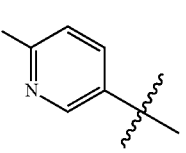 | OCH$_2$ | 2-quinoline | — | Me | — | — | — |
| 720 | A23 | CN | 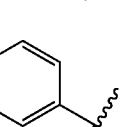 | OCH$_2$ | 2-quinoline | — | Me | — | — | — |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 721 | A23 | CN | pyrimidin-4-yl | OCH$_2$ | 2-quinoline | — | Me | — | — | — |
| 722 | A23 | CN | 2-MeO-5-CN-phenyl | OCH$_2$ | 2-quinoline | — | Me | — | — | — |
| 723 | A23 | CN | 4-Cl-phenyl | OCH$_2$ | 2-quinoline | — | Me | — | — | — |
| 724 | A26 | CN | 4-pyridinyl | OCH$_2$ | 2-quinoline | — | Me | — | — | — |
| 725 | A26 | CN | 4-OMe-phenyl | OCH$_2$ | 2-quinoline | — | Me | — | — | — |
| 726 | A26 | CN | 4-pyrazolyl | OCH$_2$ | 2-quinoline | — | Me | — | — | — |
| 727 | A26 | CN | 3-(1-methyl-1H-pyrazolyl) | OCH$_2$ | 2-quinoline | — | Me | — | — | — |
| 728 | A26 | CN | 4-(1-methyl-1H-pyrazolyl) | OCH$_2$ | 2-quinoline | — | Me | — | — | — |
| 729 | A26 | CN | pyrimidin-4-yl | OCH$_2$ | 2-quinoline | — | Me | — | — | — |
| 730 | A26 | CN | 4-CN-phenyl | OCH$_2$ | 2-quinoline | — | Me | — | — | — |
| 731 | A26 | CN | 2-MeO-pyridin-4-yl | OCH$_2$ | 2-quinoline | — | Me | — | — | — |
| 732 | A26 | CN | 6-MeO-pyridin-3-yl | OCH$_2$ | 2-quinoline | — | Me | — | — | — |
| 733 | A26 | CN | 6-HO-pyridin-3-yl | OCH$_2$ | 2-quinoline | — | Me | — | — | — |
| 734 | A26 | CN | pyrimidin-2-yl | OCH$_2$ | 2-quinoline | — | Me | — | — | — |

-continued

| Ex PCT # | HET | W | X | Y | Z | R_{1a}, R_{1b} | R_2 | R_3 | R_4 | R_7 |
|---|---|---|---|---|---|---|---|---|---|---|
| 735 | A26 | CN | 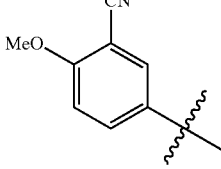 | OCH_2 | 2-quinoline | — | Me | — | — | — |
| 736 | A26 | CN | 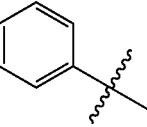 | OCH_2 | 2-quinoline | — | Me | — | — | — |
| 737 | A31 | CN | 4-pyridinyl | OCH_2 | 2-quinoline | — | Me, Me | — | — | — |
| 738 | A31 | CN | 4-OMe-phenyl | OCH_2 | 2-quinoline | — | Me, Me | — | — | — |
| 739 | A31 | CN | 4-pyrazolyl | OCH_2 | 2-quinoline | — | Me, Me | — | — | — |
| 740 | A31 | CN | 3-(1-methyl-1H-pyrazolyl) | OCH_2 | 2-quinoline | — | Me, Me | — | — | — |
| 741 | A31 | CN | 4-(1-methyl-1H-pyrazolyl) | OCH_2 | 2-quinoline | — | Me, Me | — | — | — |
| 742 | A31 | CN | 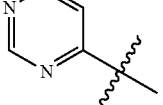 | OCH_2 | 2-quinoline | — | Me, Me | — | — | — |
| 743 | A31 | CN |  | OCH_2 | 2-quinoline | — | Me, Me | — | — | — |
| 744 | A31 | CN | 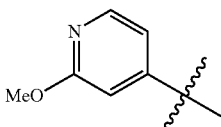 | OCH_2 | 2-quinoline | — | Me, Me | — | — | — |
| 745 | A31 | CN | 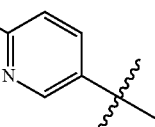 | OCH_2 | 2-quinoline | — | Me, Me | — | — | — |
| 746 | A31 | CN | 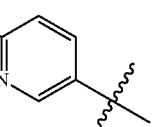 | OCH_2 | 2-quinoline | — | Me, Me | — | — | — |
| 747 | A31 | CN | 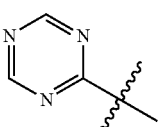 | OCH_2 | 2-quinoline | — | Me, Me | — | — | — |

-continued

| Ex PCT # | HET | W | X | Y | Z | R1a, R1b | R2 | R3 | R4 | R7 |
|---|---|---|---|---|---|---|---|---|---|---|
| 748 | A31 | CN | 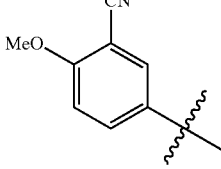 | OCH2 | 2-quinoline | — | Me, Me | — | — | — |
| 749 | A31 | CN | 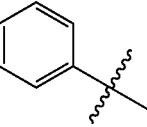 | OCH2 | 2-quinoline | — | Me, Me | — | — | — |
| 750 | A32 | CN | 4-pyridinyl | OCH2 | 2-quinoline | — | Me, Me | — | — | Me |
| 751 | A32 | CN | 4-OMe-phenyl | OCH2 | 2-quinoline | — | Me, Me | — | — | Me |
| 752 | A32 | CN | 4-pyrazolyl | OCH2 | 2-quinoline | — | Me, Me | — | — | Me |
| 753 | A32 | CN | 3-(1-methyl-1H-pyrazolyl) | OCH2 | 2-quinoline | — | Me, Me | — | — | Me |
| 754 | A32 | CN | 4-(1-methyl-1H-pyrazolyl) | OCH2 | 2-quinoline | — | Me, Me | — | — | Me |
| 755 | A32 | CN | 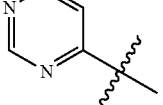 | OCH2 | 2-quinoline | — | Me, Me | — | — | Me |
| 756 | A32 | CN | 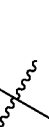 | OCH2 | 2-quinoline | — | Me, Me | — | — | Me |
| 757 | A32 | CN | 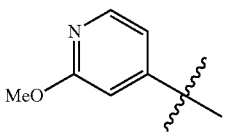 [SMILES: *c1ccnc(OC)c1] | OCH2 | 2-quinoline | — | Me, Me | — | — | Me |
| 758 | A32 | CN | 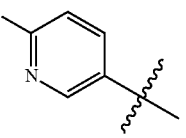 | OCH2 | 2-quinoline | — | Me, Me | — | — | Me |
| 759 | A32 | CN | 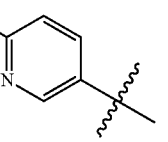 | OCH2 | 2-quinoline | — | Me, Me | — | — | Me |
| 760 | A32 | CN | 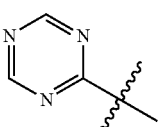 | OCH2 | 2-quinoline | — | Me, Me | — | — | Me |

-continued

| Ex PCT # | HET | W | X | Y | Z | R$_{1a}$, R$_{1b}$ | R$_2$ | R$_3$ | R$_4$ | R$_7$ |
|---|---|---|---|---|---|---|---|---|---|---|
| 761 | A32 | CN | 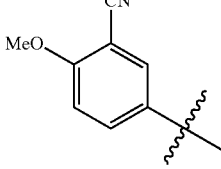 | OCH$_2$ | 2-quinoline | — | Me, Me | — | — | Me |
| 762 | A32 | CN | 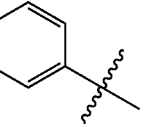 | OCH$_2$ | 2-quinoline | — | Me, Me | — | — | Me |
| 763 | A35 | CN | 4-pyridinyl | OCH$_2$ | 2-quinoline | — | — | — | — | — |
| 764 | A35 | CN | 4-OMe-phenyl | OCH$_2$ | 2-quinoline | — | — | — | — | — |
| 765 | A35 | CN | 4-pyrazolyl | OCH$_2$ | 2-quinoline | — | — | — | — | — |
| 766 | A35 | CN | 3-(1-methyl-1H-pyrazolyl) | OCH$_2$ | 2-quinoline | — | — | — | — | — |
| 767 | A35 | CN | 4-(1-methyl-1H-pyrazolyl) | OCH$_2$ | 2-quinoline | — | — | — | — | — |
| 768 | A35 | CN | 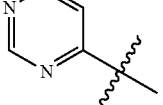 | OCH$_2$ | 2-quinoline | — | — | — | — | — |
| 769 | A35 | CN |  | OCH$_2$ | 2-quinoline | — | — | — | — | — |
| 770 | A35 | CN | 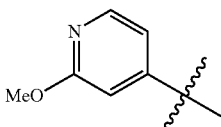 | OCH$_2$ | 2-quinoline | — | — | — | — | — |
| 771 | A35 | CN | 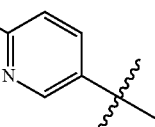 | OCH$_2$ | 2-quinoline | — | — | — | — | — |
| 772 | A35 | CN | 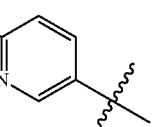 | OCH$_2$ | 2-quinoline | — | — | — | — | — |
| 773 | A35 | CN | 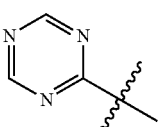 | OCH$_2$ | 2-quinoline | — | — | — | — | — |

-continued

| Ex PCT # | HET | W | X | Y | Z | $R_{1a}, R_{1b}$ | $R_2$ | $R_3$ | $R_4$ | $R_7$ |
|---|---|---|---|---|---|---|---|---|---|---|
| 774 | A35 | CN | MeO-, CN-substituted phenyl | $OCH_2$ | 2-quinoline | — | — | — | — | — |
| 775 | A35 | CN | Cl-substituted phenyl | $OCH_2$ | 2-quinoline | — | — | — | — | — |

Dosage and Administration

The present disclosure includes pharmaceutical composition for treating a subject having a neurological disorder comprising a therapeutically effective amount of a compound of Formulas (I), (II) and (III), a derivative or a pharmaceutically acceptable salt thereof, and a pharmaceutically acceptable excipient, carrier or diluent. The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (IV) administration. The formulations for administration will commonly comprise a solution of the compound of the Formulas (I), (II) and (II) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formulas (I), (II) and (III) in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formulas (I), (II) and (III) can be administered by introduction into the central nervous system of the subject, e.g., into the cerbrospinal fluid of the subject. The formulations for administration will commonly comprise a solution of the compound of Formulas (I), (II) and (III) dissolved in a pharmaceutically acceptable carrier. In certain aspects, the compound of Formulas (I), (II) and (III) is introduced intrathecally, e.g., into a cerebral ventricle, the lumbar area, or the cisterna magna. In another aspect, the compound of Formulas (I), (II) and (III) is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formulas (I), (II) and (III) is administered into a subject intrathecally. As used herein, the term "intrathecal administration" is intended to include delivering a pharmaceutical composition comprising a compound of Formulas (I), (II) and (III) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formulas (I), (II) and (III) to any of the above mentioned sites can be achieved by direct injection of the pharmaceutical composition comprising the compound of Formulas (I), (II)

and (III) or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formulas (I), (II) and (III) is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formulas (I), (II) and (III) with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols. The compounds can be delivered transdermally, by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formulas (I), (II) and (III) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formulas (I), (II) and (III) in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.01 to 100 mg per kilogram body weight of the recipient per day, preferably in the range of 0.1 to 10 mg per kilogram body weight per day. The desired dose is preferably presented once daily, but may be dosed as two, three, four, five, six or more sub-doses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated. Details on techniques for formulation and administration are well described in the scientific and patent literature, see, e.g., the latest edition of Remington's Pharmaceutical Sciences, Maack Publishing Co, Easton Pa. After a pharmaceutical composition has been formulated in an acceptable carrier, it can be placed in an appropriate container and labeled for treatment of an indicated condition. For administration of the compounds of Formulas (I), (II) and (III), such labeling would include, e.g., instructions concerning the amount, frequency and method of administration.

Biological Examples

In Vivo Methods

Subjects:
Male C57BL/6J mice (Charles River; 20-25 g) were used for all assays except prepulse inhibition (PPI) which used male DBA/2N mice (Charles River, 20-25 g). For all studies, animals were housed five/cage on a 12-h light/dark cycle with food and water available ad libitum.

Conditioned Avoidance Responding:
Testing was performed in commercially available avoidance boxes (Kinder Scientific, Poway Calif.). The boxes were divided into two compartments separated by an archway. Each side of the chamber has electronic grid flooring that is equipped to administer footshocks and an overhead light. Training consisted of repeated pairings of the light (conditioned stimulus) followed by a shock (unconditioned stimulus). For each trial the light was presented for 5 sec followed by a 0.5 mA shock that would terminate if the mouse crossed to the other chamber or after 10 seconds. The intertrial interval was set to 20 seconds. Each training and test session consisted a four min habituation period followed by 30 trials. The number of avoidances (mouse crossed to other side during presentation of the light,), escapes (mouse crossed to the other side during presentation of the shock) and failures (mouse did not cross during the entire trial period) were recorded by a computer. For study inclusion an animal had to reach a criterion of at least 80% avoidances for two consecutive test sessions.

PPI:
Mice were individually placed into the test chambers (StartleMonitor, Kinder Scientific, Poway Calif.). The animals were given a five min acclimation period to the test chambers with the background noise level set to 65 decibel (dB) which remained for the entire test session. Following acclimation, four successive trials 120 dB pulse for 40 msec were presented, however these trials were not included in data analysis. The mice were then subjected to five different types of trials in random order: pulse alone (120 dB for 40 msec), no stimulus and three different prepulse+pulse trials with the prepulse set at 67, 69 or 74 dB for 20 msec followed a 100 msec later by a 120 dB pulse for 40 msec. Each animal received 12 trials for each condition for a total of 60 trials with an average intertrial interval of 15 sec. Percent PPI was calculated according to the following formula: (1−(startle response to prepulse+pulse)/startle response to pulse alone))×100.

MK-801-Induced Hyperactivity:
After a 30 min acclimation to the test room mice were individually placed into test cages for a 30 min habituation period. Following habituation to test cages, baseline activity was recorded for 60 min. Mice were then briefly removed and administered test compound and placed immediately back into the test cage. At 5 min prior to test time mice were again briefly removed from test cages and administered MK-801 (0.3 mg/kg, i.p. in 0.9% saline) and then immediately placed back into test cages and activity level recorded 1 hour. Activity level was measured as distance traveled in centimeters (Ethovision tracking software, Noldus Inc. Wageningen, Netherlands).

Catalepsy:
Mice were placed on a wire mesh screen set at a 60 degree angle with their heads facing upwards and the latency to move or break stance was recorded. Animals were given three trials per time point with a 30 sec cut-off per trial.

Data Analysis:

A one-way or two-way ANOVA was used to evaluate overall differences between treatments and a Tukey's post-hoc test or Student's t-test was used to evaluate differences between treatment groups for the one-way ANOVA and a Bonferroni test was used for the two-way ANOVA. The criterion for statistical significance was set to $p \leq 0.05$.

In Vitro Methods hPDE10A1 Enzyme Activity:

50 μl samples of serially diluted Human PDE10A1 enzyme were incubated with 50 μl of [$^3$H]-cAMP for 20 minutes (at 37° C.). Reactions were carried out in Greiner 96 deep well 1 ml master-block. The enzyme was diluted in 20 mM Tris HCl pH7.4 and [$^3$H]-cAMP was diluted in 10 mM $MgCl_2$, 40 mM Tris.HCl pH 7.4. The reaction was terminated by denaturing the PDE enzyme (at 70° C.) after which [$^3$H]-5'-AMP was converted to [$^3$H]-adenosine by adding 25 μl snake venom nucleotidase and incubating for 10 minutes (at 37° C.). Adenosine, being neutral, was separated from charged cAMP or AMP by the addition of 200 μl Dowex resin. Samples were shaken for 20 minutes then centrifuged for 3 minutes at 2,500 r.p.m. 50 μl of supernatant was removed and added to 200 μl of MicroScint-20 in white plates (Greiner 96-well Optiplate) and shaken for 30 minutes before reading on Perkin Elmer TopCount Scintillation Counter.

hPDE10A1 Enzyme Inhibition:

To check inhibition profile 11 μl of serially diluted inhibitor was added to 50 μl of [$^3$H]-cAMP and 50 ul of diluted Human PDE10A1 and assay was carried out as in the enzyme activity assay. Data was analysed using Prism software (GraphPad Inc). Representative compounds of this disclosure are shown in the table below. A compound with the value "A" had an $IC_{50}$ value less than or equal to 50 nM. A compound with the value "B" had an $IC_{50}$ value greater than 50 nM:

| Ex | Name | hPDE10A1 $IC_{50}$ Band |
|---|---|---|
| 11 | 1-methyl-3-(pyridin-4-yl)-4-(4-(quinolin-2-ylmethoxy)phenyl)-1H-pyrrole-2,5-dione | B |
| 23 | 5,5-dimethyl-4-(pyridin-4-yl)-3-(4-(quinolin-2-ylmethoxy)phenyl)furan-2(5H)-one | A |
| 26 | 7-(pyridin-4-yl)-6-(4-(quinolin-2-ylmethoxy)phenyl)-4-oxaspiro[2.4]hept-6-en-5-one | B |
| 33 | 4-(4-methoxyphenyl)-5,5-dimethyl-3-(4-(quinolin-2-ylmethoxy)phenyl)furan-2(5H)-one | A |
| 73 | 4-(4-methoxyphenyl)-1,5,5-trimethyl-3-(4-(quinolin-2-ylmethoxy)phenyl)-1H-pyrrol-2(5H)-one | B |
| 125 | 2,2-dimethyl-5-(pyridin-4-yl)-4-(4-(quinolin-2-ylmethoxy)phenyl)furan-3(2H)-one | A |
| 126 | 7-(4-methoxyphenyl)-6-(4-(quinolin-2-ylmethoxy)phenyl)-4-oxaspiro[2.4]hept-6-en-5-one | A |
| 127 | 2,2-dimethyl-5-(pyrimidin-4-yl)-4-(4-(quinolin-2-ylmethoxy)phenyl)furan-3(2H)-one | B |
| 130 | 5-(2-hydroxypyridin-4-yl)-2,2-dimethyl-4-(4-(quinolin-2-ylmethoxy)phenyl)furan-3(2H)-one | A |
| 131 | 5-(2-methoxypyridin-4-yl)-2,2-dimethyl-4-(4-(quinolin-2-ylmethoxy)phenyl)furan-3(2H)-one | A |
| 132 | 5-(6-hydroxypyridin-3-yl)-2,2-dimethyl-4-(4-(quinolin-2-ylmethoxy)phenyl)furan-3(2H)-one | A |
| 133 | 5-(6-methoxypyridin-3-yl)-2,2-dimethyl-4-(4-(quinolin-2-ylmethoxy)phenyl)furan-3(2H)-one | A |
| 134 | 5-(3-fluoro-4-methoxyphenyl)-2,2-dimethyl-4-(4-(quinolin-2-ylmethoxy)phenyl)furan-3(2H)-one | A |
| 135 | 5-(3-chloro-4-methoxyphenyl)-2,2-dimethyl-4-(4-(quinolin-2-ylmethoxy)phenyl)furan-3(2H)-one | A |
| 137 | 5-(5,5-dimethyl-4-oxo-3-(4-(quinolin-2-ylmethoxy)phenyl)-4,5-dihydrofuran-2-yl)-2-methoxybenzonitrile | A |
| 138 | 5-(4-methoxyphenyl)-2,2-dimethyl-4-(4-(quinolin-2-ylmethoxy)phenyl)furan-3(2H)-one | A |
| 141 | 4-(5,5-dimethyl-4-oxo-3-(4-(quinolin-2-ylmethoxy)phenyl)-4,5-dihydrofuran-2-yl)benzonitrile | A |
| 147 | 5-(4-chlorophenyl)-2,2-dimethyl-4-(4-(quinolin-2-ylmethoxy)phenyl)furan-3(2H)-one | A |
| 153 | 5-(4-fluorophenyl)-2,2-dimethyl-4-(4-(quinolin-2-ylmethoxy)phenyl)furan-3(2H)-one | A |
| 154 | 2,2-dimethyl-4-(4-(quinolin-2-ylmethoxy)phenyl)-5-(4-(trifluoromethyl)phenyl)furan-3(2H)-one | A |
| 155 | 2,2-dimethyl-4-(4-(quinolin-2-ylmethoxy)phenyl)-5-(4-(trifluoromethoxy)phenyl)furan-3(2H)-one | A |
| 156 | 2,2-dimethyl-4-(4-(quinolin-2-ylmethoxy)phenyl)-5-(4-(2,2,2-trifluoroethyl)phenyl)furan-3(2H)-one | A |
| 157 | 5-(4-ethoxyphenyl)-2,2-dimethyl-4-(4-(quinolin-2-ylmethoxy)phenyl)furan-3(2H)-one | A |
| 158 | 5-(4-isopropoxyphenyl)-2,2-dimethyl-4-(4-(quinolin-2-ylmethoxy)phenyl)furan-3(2H)-one | B |
| 159 | 5-(4-(difluoromethoxy)phenyl)-2,2-dimethyl-4-(4-(quinolin-2-ylmethoxy)phenyl)furan-3(2H)-one | A |
| 161 | 5-(4-(cyclopropylmethoxy)phenyl)-2,2-dimethyl-4-(4-(quinolin-2-ylmethoxy)phenyl)furan-3(2H)-one | B |

-continued

| Ex | Name | hPDE10A1 IC$_{50}$ Band |
|---|---|---|
| 162 | 2,2-dimethyl-4-(4-(quinolin-2-ylmethoxy)phenyl)-5-(4-(2,2,2-trifluoroethoxy)phenyl)furan-3(2H)-one | A |
| 166 | 5-(benzo[c][1,2,5]oxadiazol-5-yl)-2,2-dimethyl-4-(4-(quinolin-2-ylmethoxy)phenyl)furan-3(2H)-one | A |
| 167 | 5-(benzo[c][1,2,5]thiadiazol-5-yl)-2,2-dimethyl-4-(4-(quinolin-2-ylmethoxy)phenyl)furan-3(2H)-one | A |
| 169 | 2-(difluoromethoxy)-5-(5,5-dimethyl-4-oxo-3-(4-(quinolin-2-ylmethoxy)phenyl)-4,5-dihydrofuran-2-yl)benzonitrile | A |
| 174 | 2,2-dimethyl-4-(4-(quinolin-2-ylmethoxy)phenyl)-5-(thiazol-4-yl)furan-3(2H)-one | A |
| 164 | 2,2-dimethyl-5-(4-nitrophenyl)-4-(4-(quinolin-2-ylmethoxy)phenyl)furan-3(2H)-one | A |
| 170 | 5-(4-(1H-tetrazol-1-yl)phenyl)-2,2-dimethyl-4-(4-(quinolin-2-ylmethoxy)phenyl)furan-3(2H)-one | A |
| 249 | 2,2-dimethyl-4-(pyridin-4-yl)-5-(4-(quinolin-2-ylmethoxy)phenyl)furan-3(2H)-one | A |
| 262 | 4-(4-methoxyphenyl)-2,2-dimethyl-5-(4-(quinolin-2-ylmethoxy)phenyl)furan-3(2H)-one | A |
| 808 | 2,2-dimethyl-4-(4-((5-methylpyridin-2-yl)methoxy)phenyl)-5-(pyridin-4-yl)furan-3(2H)-one | A |
| 809 | 4-(4-((3,5-dimethylpyridin-2-yl)methoxy)phenyl)-2,2-dimethyl-5-(pyridin-4-yl)furan-3(2H)-one | A |
| 810 | 4-(4-((6-fluoroquinolin-2-yl)methoxy)phenyl)-2,2-dimethyl-5-(pyridin-4-yl)furan-3(2H)-one | A |
| 811 | 2,2-dimethyl-5-phenyl-4-(4-(quinolin-2-ylmethoxy)phenyl)furan-3(2H)-one | A |
| 812 | 1-methyl-3-morpholino-4-(4-(quinolin-2-ylmethoxy)phenyl)-1H-pyrrole-2,5-dione | B |
| 813 | 5-(4-hydroxyphenyl)-2,2-dimethyl-4-(4-(quinolin-2-ylmethoxy)phenyl)furan-3(2H)-one | A |
| 814 | N-(4-(5,5-dimethyl-4-oxo-3-(4-(quinolin-2-ylmethoxy)phenyl)-4,5-dihydrofuran-2-yl)phenyl)acetamide | A |
| 815 | N-(4-(5,5-dimethyl-4-oxo-3-(4-(quinolin-2-ylmethoxy)phenyl)-4,5-dihydrofuran-2-yl)phenyl)methanesulfonamide | A |
| 63 | 5,5-dimethyl-4-(pyridin-4-yl)-3-(4-(quinolin-2-ylmethoxy)phenyl)-1H-pyrrol-2(5H)-one | A |
| 817 | N-(4-(5,5-dimethyl-4-oxo-3-(4-(quinolin-2-ylmethoxy)phenyl)-4,5-dihydrofuran-2-yl)phenyl)-N-(methylsulfonyl)methanesulfonamide | A |
| 818 | 2,2-dimethyl-4-(4-(quinolin-2-ylmethoxy)phenyl)-5-p-tolylfuran-3(2H)-one | A |
| 819 | N-acetyl-N-(4-(5,5-dimethyl-4-oxo-3-(4-(quinolin-2-ylmethoxy)phenyl)-4,5-dihydrofuran-2-yl)phenyl)acetamide | A |
| 820 | 1-methyl-3-(4-oxopiperidin-1-yl)-4-(4-(quinolin-2-ylmethoxy)phenyl)-1H-pyrrole-2,5-dione | B |
| 821 | 5-(benzo[d]oxazol-5-yl)-2,2-dimethyl-4-(4-(quinolin-2-ylmethoxy)phenyl)furan-3(2H)-one | A |
| 822 | 4-(4-methoxyphenyl)-1,3-dimethyl-5-(4-(quinolin-2-ylmethoxy)phenyl)-1H-imidazol-2(3H)-one | B |
| 823 | 4-(4-methoxyphenyl)-5,5-dimethyl-3-(4-(quinolin-2-ylmethoxy)phenyl)-1H-pyrrol-2(5H)-one | A |
| 824 | 2-(pyridin-4-yl)-3-(4-(quinolin-2-ylmethoxy)phenyl)-1-oxaspiro[4.4]non-2-en-4-one | A |

What is claimed is:

1. A compound of Formula (I)

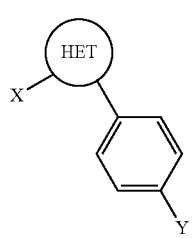

(I)

or pharmaceutically acceptable salt thereof
wherein:
HET is a heterocyclic ring selected from Formulas A1-A26 and A29-A42 below

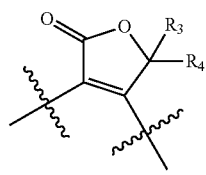

A1

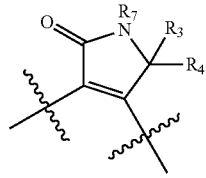

A2

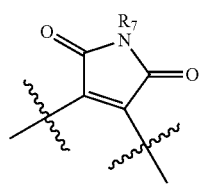 A3
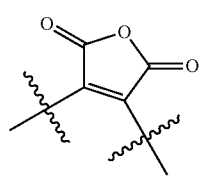 A4
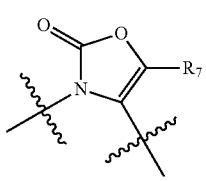 A5
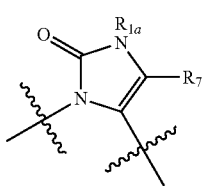 A6
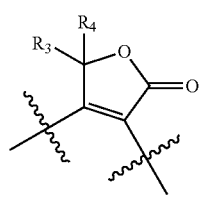 A7
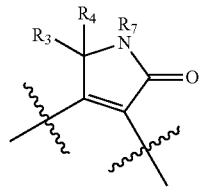 A8
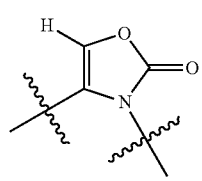 A9
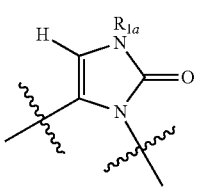 A10
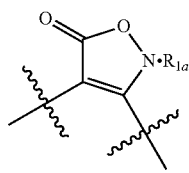 A11
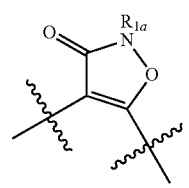 A12
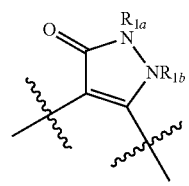 A13
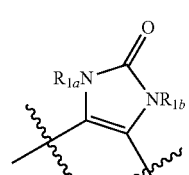 A14
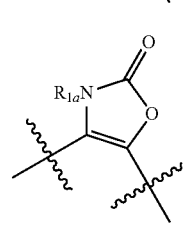 A15
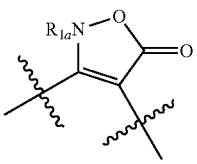 A16
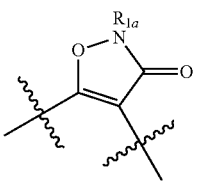 A17
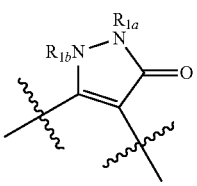 A18

-continued
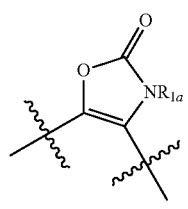
A19
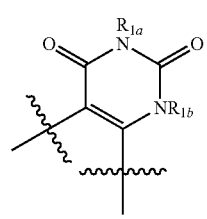
A20
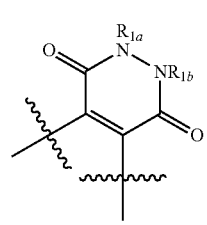
A21
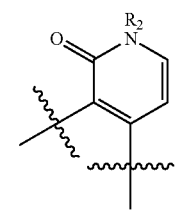
A22
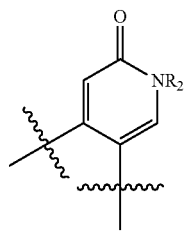
A23
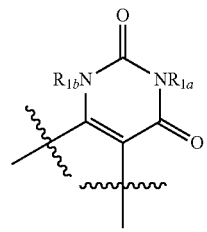
A24
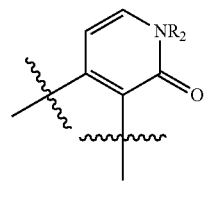
A25
-continued
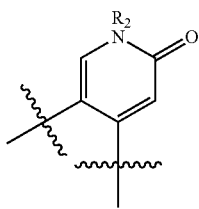
A26
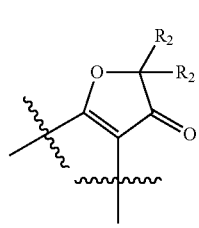
A29
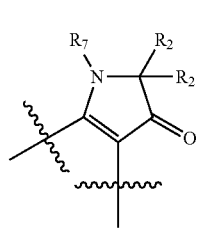
A30
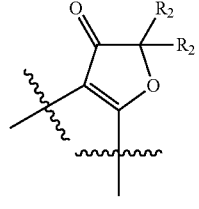
A31
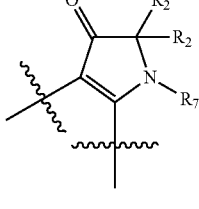
A32
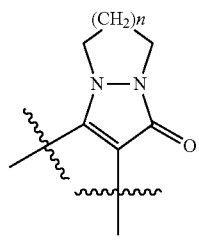
A33
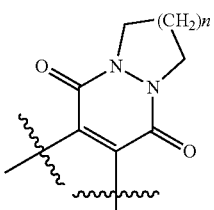
A34

A35 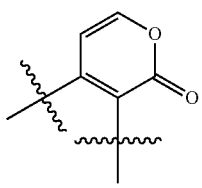

A36 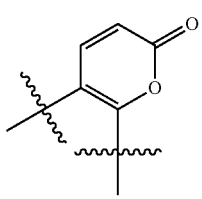

A37 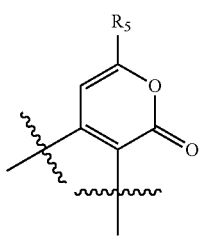

A38 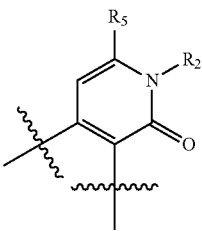

A39 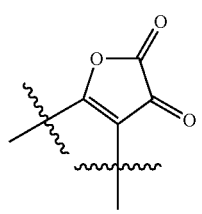

A40 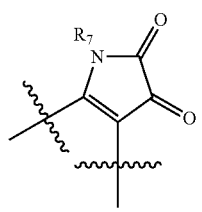

A41 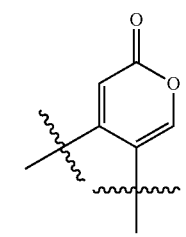

A42 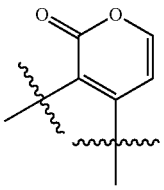

and the left most radical is connected to the X group;

X is selected from $C_3$-$C_8$ alkyl, optionally substituted $C_3$-$C_6$ cycloalkyl, optionally substituted $C_4$-$C_7$ cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl;

Y is a bond or a divalent linker group selected from —$CH_2$—, —O—, —$SO_2$—, —$CH_2O$—, —$OCH_2$— and —$CH_2CH_2$— with the rightmost radical of the Y group connected to the Z substituent;

Z is optionally substituted heteroaryl;

$R_{1a}$ is selected from $C_1$-$C_4$ alkyl, optionally substituted $C_3$-$C_6$ cycloalkyl, optionally substituted $C_4$-$C_7$ cycloalkylalkyl and optionally substituted $C_4$-$C_7$ alkoxyalkyl;

$R_{1b}$ is selected from $C_1$-$C_4$ alkyl, optionally substituted $C_3$-$C_6$ cycloalkyl, optionally substituted $C_4$-$C_7$ cycloalkylalkyl and optionally substituted $C_4$-$C_7$ alkoxyalkyl;

each $R_2$ is independently selected from $C_1$-$C_4$ alkyl, optionally substituted $C_3$-$C_6$ cycloalkyl, optionally substituted $C_4$-$C_7$ cycloalkylalkyl and optionally substituted $C_4$-$C_7$ alkoxyalkyl, or two $R_2$ groups taken together form a 3-6 membered cycloalkyl ring;

$R_3$ and $R_4$ are independently selected from $C_1$-$C_4$ alkyl, $CF_3$, optionally substituted $C_3$-$C_6$ cycloalkyl, or $R_3$ and $R_4$ taken together form a 3-6 membered cycloalkyl ring;

$R_5$ is selected from $C_1$-$C_4$ alkyl, optionally substituted $C_3$-$C_6$ cycloalkyl, optionally substituted $C_4$-$C_7$ cycloalkylalkyl and optionally substituted $C_4$-$C_7$ alkoxyalkyl;

$R_7$ is selected from hydrogen, $C_1$-$C_4$ alkyl, optionally substituted $C_3$-$C_6$ cycloalkyl, optionally substituted $C_4$-$C_7$ cycloalkylalkyl and optionally substituted $C_4$-$C_7$ alkoxyalkyl;

n is independently selected from 1 and 2.

2. The compound of claim 1, wherein HET is a heterocyclic ring of formula selected from the group consisting of A3, A6, A7, A8, A14, A17, A29, A31, A32, A39, and A40;

X is optionally substituted heterocycloalkyl, optionally substituted heterocycloalkylalkyl, optionally substituted aryl or optionally substituted heteroaryl; and Y is —$CH_2O$— or —$OCH_2$—;

or a pharmaceutically acceptable salt thereof.

3. The compound of claim 2, wherein Z is an optionally substituted heteroaryl having only 6 ring atoms or an optionally substituted heterobicyclic ring system;

or a pharmaceutically acceptable salt thereof.

4. The compound of claim 2, wherein Z is an optionally substituted heteroaryl having only 6 ring atoms selected from C and N provided the total number of ring nitrogens is less than or equal to two; said ring is optionally substituted with up to 2 substituents independently selected from the group consisting of $C_1$-$C_4$ alkyl, $C_1$-$C_4$ alkoxy, $C_3$-$C_6$ cycloalkyl, $C_3$-$C_6$ cycloalkyloxy, $C_4$-$C_7$ cycloalkylalkyl, cycloalkylalkoxy, halogen, alkylsulfonyl, cyano and nitro;

or a pharmaceutically acceptable salt thereof.

5. The compound of claim 2, wherein Z is benzimidazolyl, quinolinyl, tetrahydroquinolyl, imidazo[1,2-a]pyridin-2-yl, tetrahydroisoquinolyl, 5-methylpyridin-2-yl, 3,5-dimethylpyridin-2-yl, 6-fluoroquinolyl or isoquinolinyl, each of which is unsubstituted or substituted with up to 3 substituents independently selected from the group consisting of $C_1$-$C_4$ alkyl, $C_1$-$C_4$ alkoxy, $C_3$-$C_6$ cycloalkyl, $C_3$-$C_6$ cycloalkyloxy, $C_4$-$C_7$ cycloalkylalkyl, cycloalkylalkoxy, halogen, alkylsulfonyl, cyano and nitro;

or a pharmaceutically acceptable salt thereof.

6. The compound of claim 2, wherein X is a heterocycloalkyl group having a formula selected form the group consisting of Formulas B1-B16:

wherein $R_6$ is hydrogen, $C_1$-$C_6$ alkyl, $C_3$-$C_6$ cycloalkyl or $C_4$-$C_7$ cycloalkylalkyl;

or a pharmaceutically acceptable salt thereof.

7. The compound of claim 2, wherein X is phenyl, restricted phenyl, or pyridinyl;

or a pharmaceutically acceptable salt thereof.

8. The compound of claim 2, wherein X is benzo[d]oxazoyl, benzo[c][1,2,5]oxadiazyl, benzo[c][1,2,5]thiadiazolyl, benzo[d]isoxazolyl, 1H-benzo[d]imidazoyl, benzo[d]thiazoyl, benzo[c]isothiazolyl, benzo[d]isothiazolyl, benzo[c]isoxazolyl, imidazo[1,2-a]pyridinyl or imidazo[1,5-a]pyridinyl;

or a pharmaceutically acceptable salt thereof.

9. The compound of claim 2, wherein HET is A29;

or a pharmaceutically acceptable salt thereof.

10. The compound of claim 2, wherein HET is A29;
X is optionally substituted heteroaryl;
Y is —OCH$_2$—;
Z is optionally substituted heteroaryl; and
each $R_2$ is independently $C_1$-$C_4$ alkyl;
or a pharmaceutically acceptable salt thereof.

11. The compound of claim 10, wherein X is pyridinyl;
or a pharmaceutically acceptable salt thereof.

12. The compound of claim 2, wherein HET is A29;
X is pyridinyl;
Y is —OCH$_2$—;
Z is heteroaryl; and
each $R_2$ is independently $C_1$-$C_4$ alkyl;
or a pharmaceutically acceptable salt thereof.

13. The compound of claim 2, wherein HET is A29;
X is pyridinyl;
Y is —OCH$_2$—;
Z is heteroaryl; and
each $R_2$ is methyl;
or a pharmaceutically acceptable salt thereof.

14. The compound of claim 2, wherein HET is A29;
X is pyridinyl;
Y is —OCH$_2$—;

Z is a heterobicyclic ring system containing exactly 9 atoms; and each $R_2$ is independently $C_1$-$C_4$ alkyl;

or a pharmaceutically acceptable salt thereof.

15. The compound of claim 2, wherein HET is A29;

X is pyridinyl;

Y is —$OCH_2$—;

Z is a heterobicyclic ring system containing exactly 9 atoms; and each $R_2$ is methyl;

or a pharmaceutically acceptable salt thereof.

16. A pharmaceutical composition comprising the compound of any one of claims 1-15 or a pharmaceutically acceptable salt thereof and a pharmaceutically acceptable carrier or excipient.

* * * * *